US012612669B2

(12) United States Patent
Ryu et al.

(10) Patent No.: US 12,612,669 B2
(45) Date of Patent: Apr. 28, 2026

(54) HIGH-THROUGHPUT METHODS FOR ISOLATING AND CHARACTERIZING AMMONIUM-EXCRETING MUTANT LIBRARIES GENERATED BY CHEMICAL MUTAGENESIS

(71) Applicant: Pivot Bio, Inc., Berkeley, CA (US)

(72) Inventors: Min-Hyung Ryu, Cambridge, MA (US); Bilge Ozaydin Eskiyenturk, Berkeley, CA (US); Alvin Tamsir, Berkeley, CA (US)

(73) Assignee: Pivot Bio, Inc., Berkeley, CA (US)

( * ) Notice: Subject to any disclaimer, the term of this patent is extended or adjusted under 35 U.S.C. 154(b) by 1104 days.

(21) Appl. No.: 17/604,119

(22) PCT Filed: Apr. 24, 2020

(86) PCT No.: PCT/US2020/029831
§ 371 (c)(1),
(2) Date: Oct. 15, 2021

(87) PCT Pub. No.: WO2020/219893
PCT Pub. Date: Oct. 29, 2020

(65) Prior Publication Data
US 2022/0282340 A1 Sep. 8, 2022

Related U.S. Application Data

(60) Provisional application No. 62/838,780, filed on Apr. 25, 2019.

(51) Int. Cl.
| | |
|---|---|
| *C12N 1/20* | (2006.01) |
| *A01N 63/20* | (2020.01) |
| *C12N 1/205* | (2026.01) |
| *C12Q 1/689* | (2018.01) |
| *C12Q 1/6897* | (2018.01) |

(52) U.S. Cl.
CPC .......... *C12Q 1/6897* (2013.01); *A01N 63/20* (2020.01); *C12N 1/205* (2021.05); *C12Q 1/689* (2013.01)

(58) Field of Classification Search
None
See application file for complete search history.

(56) References Cited

U.S. PATENT DOCUMENTS

| | | | |
|---|---|---|---|
| 1,520,545 | A | 12/1924 | Murphy |
| 4,782,022 | A | 11/1988 | Puhler et al. |
| 4,832,728 | A | 5/1989 | Allan et al. |
| 4,970,147 | A | 11/1990 | Huala et al. |
| 5,071,743 | A | 12/1991 | Slilaty et al. |
| 5,116,506 | A | 5/1992 | Williamson et al. |
| 5,188,960 | A | 2/1993 | Payne et al. |
| 5,229,291 | A | 7/1993 | Nielsen et al. |
| 5,354,670 | A | 10/1994 | Nickoloff et al. |
| 5,427,785 | A | 6/1995 | Ronson et al. |
| 5,610,044 | A | 3/1997 | Lam et al. |
| 5,780,270 | A | 7/1998 | Lesley |
| 5,789,166 | A | 8/1998 | Bauer et al. |
| 5,877,012 | A | 3/1999 | Estruch et al. |
| 5,880,275 | A | 3/1999 | Fischhoff et al. |
| 5,916,029 | A | 6/1999 | Smith et al. |
| 6,033,861 | A | 3/2000 | Schafer et al. |
| 6,033,874 | A | 3/2000 | Baum et al. |
| 6,083,499 | A | 7/2000 | Narva et al. |
| 6,107,279 | A | 8/2000 | Estruch et al. |
| 6,114,148 | A | 9/2000 | Seed et al. |
| 6,127,180 | A | 10/2000 | Narva et al. |
| 6,137,033 | A | 10/2000 | Estruch et al. |
| 6,218,188 | B1 | 4/2001 | Cardineau et al. |
| 6,248,535 | B1 | 6/2001 | Danenberg et al. |
| 6,326,351 | B1 | 12/2001 | Donovan et al. |
| 6,340,593 | B1 | 1/2002 | Cardineau et al. |
| 6,391,548 | B1 | 5/2002 | Bauer et al. |
| 6,399,330 | B1 | 6/2002 | Donovan et al. |
| 6,548,289 | B1 | 4/2003 | Beynon et al. |
| 6,548,291 | B1 | 4/2003 | Narva et al. |
| 6,596,509 | B1 | 7/2003 | Bauer et al. |

(Continued)

FOREIGN PATENT DOCUMENTS

| | | |
|---|---|---|
| AU | 636565 B2 | 5/1993 |
| AU | 2022203325 A1 | 6/2022 |

(Continued)

OTHER PUBLICATIONS

US 8,476,226 B2, 07/2013, Lira et al. (withdrawn)
Espin et al. (Mol. Gen. Genet. vol. 184, pp. 213-217, 1981). (Year: 1981).*
USDA Taxon Metakosakonia intestini https://acir.aphis.usda.gov/s/cird-taxon/a0u3d000000BVJOAAO/metakosakonia-intestini, [retrieved Feb. 26, 2025]). (Year: 2025).*
NCBI Taxonomy browser, https://www.ncbi.nlm.nih.gov/Taxonomy/Browser/wwwtax.cgi?id=1898961 [retrieved Feb. 26, 2025]); (Year: 2025).*

(Continued)

*Primary Examiner* — Catherine Konopka
(74) *Attorney, Agent, or Firm* — COOLEY LLP

(57) ABSTRACT

The present disclosure provides high-throughput methods for rapidly mutagenizing, screening, and targeting candidate microbes that are capable of fixing atmospheric nitrogen in the presence of exogenous nitrogen. The methods utilize a microbial biosensor capable of detecting the presence/absence of ammonium and/or glutamine in a composition and signaling with a fluorescent reporter. The present disclosure further utilizes rapid visual detection assays capable of processing thousands of candidate microbes. The disclosed methods and biosensor can be used to identify mutant bacteria with improved nitrogen fixing capabilities. Mutant bacteria with improved nitrogen fixing capabilities are also disclosed, as well as methods of utilizing these novel bacteria to provide fixed nitrogen to a plant.

9 Claims, 13 Drawing Sheets

Specification includes a Sequence Listing.

(56)                References Cited

U.S. PATENT DOCUMENTS

| | | |
|---|---|---|
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Harwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zhang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 11,479,516 B2 | 10/2022 | Voigt et al. |
| 11,565,979 B2 | 1/2023 | Temme et al. |
| 11,678,667 B2 | 6/2023 | Reisinger et al. |
| 11,678,668 B2 | 6/2023 | Reisinger et al. |
| 11,739,032 B2 | 8/2023 | Temme et al. |
| 11,946,162 B2 | 4/2024 | Zhao et al. |
| 11,963,530 B2 | 4/2024 | Reisinger et al. |
| 11,993,778 B2 | 5/2024 | Tamsir et al. |
| 12,151,988 B2 | 11/2024 | Tamsir et al. |
| 12,209,245 B2 | 1/2025 | Mirsky et al. |
| 12,268,212 B2 | 4/2025 | Reisinger et al. |
| 12,281,299 B2 | 4/2025 | Voigt et al. |
| 12,281,980 B2 | 4/2025 | Wood et al. |
| 12,290,074 B2 | 5/2025 | Reisinger et al. |
| 2002/0061579 A1 | 5/2002 | Farrand et al. |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum et al. |
| 2006/0243011 A1 | 11/2006 | Someus |
| 2007/0249018 A1 | 10/2007 | Vemuri et al. |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel et al. |
| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015409 A1 | 1/2012 | Tabata et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener et al. |
| 2012/0266332 A1 | 10/2012 | Kuykendall |
| 2012/0278954 A1 | 11/2012 | Bowen et al. |
| 2012/0284813 A1 | 11/2012 | Olivier et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran et al. |
| 2014/0182018 A1 | 6/2014 | Lang et al. |
| 2014/0196178 A1 | 7/2014 | Zaltsman |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0283569 A1 | 9/2014 | Doty et al. |
| 2014/0301990 A1 | 10/2014 | Gregory et al. |
| 2014/0329326 A1 | 11/2014 | Mirsky et al. |
| 2014/0336050 A1 | 11/2014 | Soto, Sr. et al. |
| 2015/0080261 A1 | 3/2015 | Wigley et al. |
| 2015/0101373 A1 | 4/2015 | Munusamy et al. |
| 2015/0128670 A1 | 5/2015 | Das |
| 2015/0237807 A1 | 8/2015 | Valiquette |

(56) References Cited

U.S. PATENT DOCUMENTS

| | | |
|---|---|---|
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2016/0304842 A1 | 10/2016 | Donovan et al. |
| 2017/0086402 A1 | 3/2017 | Meadows-Smith et al. |
| 2017/0107160 A1 | 4/2017 | Newman et al. |
| 2017/0119690 A1 | 5/2017 | Hansen et al. |
| 2017/0152519 A1 | 6/2017 | Mirsky et al. |
| 2017/0267997 A1 | 9/2017 | Nicol et al. |
| 2017/0367349 A1 | 12/2017 | Gruver et al. |
| 2018/0002243 A1 | 1/2018 | Temme et al. |
| 2018/0020671 A1 | 1/2018 | Wigley et al. |
| 2018/0065896 A1 | 3/2018 | Van Iersel et al. |
| 2018/0073028 A1 | 3/2018 | Mirsky et al. |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1* | 2/2019 | Temme ............... C12N 15/111 |
| 2019/0144352 A1 | 5/2019 | Temme et al. |
| 2019/0339964 A1 | 11/2019 | Young et al. |
| 2020/0087221 A1 | 3/2020 | Temme et al. |
| 2020/0115715 A1 | 4/2020 | Mirsky et al. |
| 2020/0299637 A1 | 9/2020 | Voigt et al. |
| 2020/0308594 A1 | 10/2020 | Tamsir et al. |
| 2020/0331820 A1 | 10/2020 | Tamsir et al. |
| 2021/0009483 A1 | 1/2021 | Temme et al. |
| 2021/0163374 A1 | 6/2021 | Bloch et al. |
| 2021/0214282 A1 | 7/2021 | Temme et al. |
| 2021/0284995 A1 | 9/2021 | Zhao et al. |
| 2021/0315212 A1 | 10/2021 | Rezaei et al. |
| 2021/0345618 A1 | 11/2021 | Bloch et al. |
| 2022/0017911 A1 | 1/2022 | Temme et al. |
| 2022/0079163 A1 | 3/2022 | Reisinger et al. |
| 2022/0090095 A1 | 3/2022 | Higgins et al. |
| 2022/0106238 A1 | 4/2022 | Rezaei et al. |
| 2022/0127627 A1 | 4/2022 | Bloch et al. |
| 2022/0132861 A1 | 5/2022 | Reisinger et al. |
| 2022/0151241 A1 | 5/2022 | Reisinger et al. |
| 2022/0162544 A1 | 5/2022 | Voigt et al. |
| 2022/0211048 A1 | 7/2022 | Temme et al. |
| 2022/0396530 A1 | 12/2022 | Tamsir et al. |
| 2022/0411344 A1 | 12/2022 | Voigt et al. |
| 2023/0019267 A1 | 1/2023 | Hapes et al. |
| 2023/0033451 A1 | 2/2023 | Reisinger et al. |
| 2023/0062568 A1 | 3/2023 | Temme et al. |
| 2023/0148607 A1 | 5/2023 | Rezaei et al. |
| 2023/0175959 A1 | 6/2023 | Wood et al. |
| 2023/0257317 A1 | 8/2023 | Temme et al. |
| 2023/0276807 A1 | 9/2023 | Reisinger et al. |
| 2023/0295559 A1 | 9/2023 | Ozaydin Eskiyenenturk et al. |
| 2024/0010576 A1 | 1/2024 | Temme et al. |
| 2024/0196903 A1 | 6/2024 | Reisinger et al. |
| 2024/0294953 A1 | 9/2024 | Eskiyenenturk et al. |
| 2024/0298647 A1 | 9/2024 | Reisinger et al. |
| 2024/0327851 A1 | 10/2024 | Tamsir et al. |
| 2024/0397955 A1 | 12/2024 | Belcher et al. |
| 2025/0027228 A1 | 1/2025 | Zhao et al. |
| 2025/0075222 A1 | 3/2025 | Bloch et al. |
| 2025/0115529 A1 | 4/2025 | Tamsir et al. |
| 2025/0145544 A1 | 5/2025 | Strobel et al. |
| 2025/0185667 A1 | 6/2025 | Reisinger et al. |

FOREIGN PATENT DOCUMENTS

| | | | |
|---|---|---|---|
| CA | 2051071 A1 | 3/1993 | |
| CA | 2991776 A1 | 1/2017 | |
| CA | 3049258 A1 | 7/2018 | |
| CN | 1289852 A | 4/2001 | |
| CN | 1355293 A | 6/2002 | |
| CN | 1355294 A | 6/2002 | |
| CN | 1421527 A | 6/2003 | |
| CN | 1500801 A | 6/2004 | |
| CN | 1552846 A | 12/2004 | |
| CN | 1746304 A | 3/2006 | |
| CN | 101328477 A | 12/2008 | |
| CN | 101880676 A | 11/2010 | |
| CN | 101899430 A | 12/2010 | |
| CN | 102041241 A | 5/2011 | |
| CN | 102417882 A | 4/2012 | |
| CN | 102690808 A | 9/2012 | |
| CN | 103451130 A | 12/2013 | |
| CN | 103917657 A | 7/2014 | |
| CN | 104136599 A | 11/2014 | |
| CN | 104204211 A | 12/2014 | |
| CN | 104603260 A | 5/2015 | |
| CN | 106086042 A | 11/2016 | |
| CN | 108220215 | 6/2018 | |
| CN | 108602729 A | 9/2018 | |
| CN | 110799474 A | 2/2020 | |
| EP | 0256889 A1 | 2/1988 | |
| EP | 0292984 A2 | 11/1988 | |
| EP | 0339830 A2 | 11/1989 | |
| EP | 1535913 A1 | 6/2005 | |
| EP | 2186890 A1 | 5/2010 | |
| EP | 3231874 A1 | 10/2017 | |
| EP | 3322679 A1 | 5/2018 | |
| FR | 2494297 | 5/1982 | |
| FR | 2910230 A1 | 6/2008 | |
| JP | S63501924 A | 8/1988 | |
| JP | H01225483 A | 9/1989 | |
| JP | H02131581 A | 5/1990 | |
| JP | H07501201 A | 2/1995 | |
| JP | 2009232721 A | 10/2009 | |
| JP | 2014096996 A | 5/2014 | |
| JP | 2015037385 A | 2/2015 | |
| JP | 2015042633 A | 3/2015 | |
| JP | 2015113274 A | 6/2015 | |
| JP | 2015518023 A | 6/2015 | |
| JP | 2015519352 A | 7/2015 | |
| JP | 2015173652 A | 10/2015 | |
| JP | 2017513480 A | 6/2017 | |
| RU | 94045882 A | 9/1996 | |
| WO | WO-8704182 A1 | 7/1987 | |
| WO | WO-9305154 A1 | 3/1993 | |
| WO | WO-9320685 A1 | 10/1993 | |
| WO | WO-9801088 A1 | 1/1998 | |
| WO | WO-9810088 A1 | 3/1998 | |
| WO | WO-9909834 A2 | 3/1999 | |
| WO | WO-0057183 A1 | 9/2000 | |
| WO | WO-0107567 A1 | 2/2001 | |
| WO | WO-03089640 A2 | 10/2003 | |
| WO | WO-2004074462 A2 | 9/2004 | |
| WO | WO-2005021585 A2 | 3/2005 | |
| WO | WO-2005038032 A1 | 4/2005 | |
| WO | WO-2006005100 A1 | 1/2006 | |
| WO | WO-2006098225 A1 | 9/2006 | |
| WO | WO-2006083891 A3 | 11/2006 | |
| WO | WO-2006119457 A1 | 11/2006 | |
| WO | WO-2007027776 A3 | 8/2007 | |
| WO | WO-2009060012 A2 | 5/2009 | |
| WO | WO-2009091557 A1 | 7/2009 | |
| WO | WO-2010080184 A1 | 7/2010 | |
| WO | WO-2010105226 A2 | 9/2010 | |
| WO | WO-2011099019 A1 | 8/2011 | |
| WO | WO-2011099024 A1 | 8/2011 | |
| WO | WO-2011103247 A2 | 8/2011 | |
| WO | WO-2011103248 A2 | 8/2011 | |
| WO | WO-2011154960 A1 | 12/2011 | |
| WO | WO-2012139004 A2 | 10/2012 | |
| WO | WO-2012154651 A2 | 11/2012 | |
| WO | WO-2012174271 A2 | 12/2012 | |
| WO | WO-2012174646 A1 | 12/2012 | |
| WO | WO-2013076687 A2 | 5/2013 | |
| WO | WO-2013132518 A1 | 9/2013 | |
| WO | WO-2014042517 A2 | 3/2014 | |
| WO | WO-2014071182 A1 | 5/2014 | |
| WO | WO-2014201044 A2 | 12/2014 | |
| WO | WO-2015158403 A1 | 10/2015 | |
| WO | WO-2015179825 A1 | 11/2015 | |
| WO | WO-2016016629 A1 | 2/2016 | |

(56) References Cited

FOREIGN PATENT DOCUMENTS

| WO | WO-2016016630 A1 | 2/2016 |
| WO | WO-2016100727 A1 | 6/2016 |
| WO | WO-2016146955 A1 | 9/2016 |
| WO | WO-2016172655 A1 | 10/2016 |
| WO | WO-2016178580 A2 | 11/2016 |
| WO | WO-2016179046 A1 | 11/2016 |
| WO | WO-2016181228 A2 | 11/2016 |
| WO | WO-2016191828 A1 | 12/2016 |
| WO | WO-2017011602 A1 | 1/2017 |
| WO | WO-2017042833 A1 | 3/2017 |
| WO | WO-2017062412 A1 | 4/2017 |
| WO | WO-2017069717 A1 | 4/2017 |
| WO | WO-2017085235 A1 | 5/2017 |
| WO | WO-2017112827 A1 | 6/2017 |
| WO | WO-2017203440 A1 | 11/2017 |
| WO | WO-2018081543 A1 | 5/2018 |
| WO | WO-2018093331 A1 | 5/2018 |
| WO | WO-2018132774 A1 | 7/2018 |
| WO | WO-2018133774 A1 | 7/2018 |
| WO | WO-2019032926 A1 | 2/2019 |
| WO | WO-2019084059 A2 | 5/2019 |
| WO | WO-2019084342 A1 | 5/2019 |
| WO | WO-2019140125 A1 | 7/2019 |
| WO | WO-2020006064 A2 | 1/2020 |
| WO | WO-2020006246 A1 | 1/2020 |
| WO | WO-2020014498 A1 | 1/2020 |
| WO | WO-2020023630 A1 | 1/2020 |
| WO | WO-2020061363 A1 | 3/2020 |
| WO | WO-2020092940 A1 | 5/2020 |
| WO | WO-2020118111 A1 | 6/2020 |
| WO | WO-2020132632 A2 | 6/2020 |
| WO | WO-2020146372 A1 | 7/2020 |
| WO | WO-2020163251 A1 | 8/2020 |
| WO | WO-2020190363 A1 | 9/2020 |
| WO | WO-2020191201 A1 | 9/2020 |
| WO | WO-2020219893 A2 | 10/2020 |
| WO | WO-2020219932 A1 | 10/2020 |
| WO | WO-2021113352 A1 | 6/2021 |
| WO | WO-2021146209 A1 | 7/2021 |
| WO | WO-2021221689 A1 | 11/2021 |
| WO | WO-2021221690 A1 | 11/2021 |
| WO | WO-2021222567 A2 | 11/2021 |
| WO | WO-2021222643 A1 | 11/2021 |
| WO | WO-2021231449 A2 | 11/2021 |
| WO | WO-2022029661 A1 | 2/2022 |
| WO | WO-2022140656 A1 | 6/2022 |
| WO | WO-2022260676 A1 | 12/2022 |
| WO | WO-2022261433 A1 | 12/2022 |
| WO | WO-2023278804 A1 | 1/2023 |
| WO | WO-2023147050 A1 | 8/2023 |
| WO | WO-2023154805 A2 | 8/2023 |
| WO | WO-2024006524 A1 | 1/2024 |
| WO | WO-2024015230 A1 | 1/2024 |
| WO | WO-2024137259 A1 | 6/2024 |
| WO | WO-2025/024750 A2 | 1/2025 |

OTHER PUBLICATIONS

Sharma et al., Diversity and Evolution of Nitrogen-fixing bacteria. N. K. Singh et al. (eds.), Sustainable Agriculture Reviews 60., pp. 95-120 (Year: 2023).*

KEGG Enzyme: 6.3.1.2, https://www.genome.jp/dbget-bin/www_bget?ec:6.3.1.2 [retrieved Feb. 25, 2025] (Year: 2025).*

Fisher and Wray, Feedback-Resistant Mutations in Bacillus subtilis Glutamine Synthetase Are Clustered in the Active Site. Journal of Bacteriology (2006), 188: 5966-5974 (Year: 2006).*

Fernandes et al., Glutamine synthetase stabilizes the binding of GlnR to nitrogen fixation gene operators. FEBS Journal (2017), 284: 903-918 (Year: 2017).*

Fisher et al., Mutations in Bacillus subtilis glutamine synthetase that block its interaction with transcription factor TnrA. Molecular Microbiology (2002); 45: 627-635 (Year: 2002).*

Wray and Fisher, A feedback-resistant mutant of Bacillus subtilis glutamine synthetase with pleiotropic defects in nitrogen-regulated gene expression, Journal of Biological Chemistry (2005), 280: 33298-33304 (Year: 2005).*

Fisher and Wray, Bacillus subtilis glutamine synthetase regulates its own synthesis by acting as a chaperone to stabilize GlnR-DNA complexes. PNAS (2008), 105: 1014-1019 (Year: 2008).*

Wray and Fisher, Functional Roles of the Conserved Glu304 Loop of Bacillus subtilis Glutamine Synthetase. Journal of Bacteriology (2010), 192: 5018-5025 (Year: 2010).*

Batista et al., Manipulating nitrogen regulation in diazotrophic bacteria for agronomic benefit. Biochemical Society Transactions (2019), 47 603-614 (Year: 2019).*

Ambrosio et al., Metabolic engineering of a diazotrophic bacterium improves ammonium release and biofertilization of plants and microalgae. Metabolic Engineering, (2017) 40: 59-68 (Year: 2017).*

Farmer et al., Altered residues in key proteins influence the expression and activity of the nitrogenase complex in an adaptive CO2 fixation-deficient mutant strain of Rhodobacter sphaeroides. Microbiology (2014), 160: 198-208 (Year: 2014).*

CAM3815164.1, Type I glutamate-ammonia ligase [Cereibacter sphaeroides], https://www.ncbi.nlm.nih.gov/protein/CAM3815164.1, [retrieved Feb. 24, 2025] (Year: 2025).*

Cereibacter sphaeroides Taxonomy Browser, https://www.ncbi.nlm.nih.gov/Taxonomy/Browser/wwwtax.cgi?mode=info&id=1063, [retrieved Feb. 24, 2025] (Year: 2025).*

TAH83087.1, type I glutamate—ammonia ligase [Bacillus subtilis], https://www.ncbi.nlm.nih.gov/protein/TAH83087.1, [retrieved Feb. 26, 2025] (Year: 2019).*

NZ_AGBD01001514.1, Paenibacillus riograndensis SBR5 Contig541c, whole genome shotgun sequence, https://www.ncbi.nlm.nih.gov/nuccore/NZ_AGBD01001514.1, [retrieved Feb. 26, 2025] (Year: 2019).*

CCZ99900.1 glutamine synthetase [Klebsiella variicola] https://www.ncbi.nlm.nih.gov/protein/CCZ99900.1, [retrieved Feb. 26, 2025] (Year: 2013).*

Lin et al., Complete genome sequence of endophytic nitrogen-fixing Klebsiella variicola strain DX120E. Standards in Genomic Sciences (2015), 10:22, 1-7 (Year: 2015).*

CP009274.2, Klebsiella variicola strain DX120E, complete genome, https://www.ncbi.nlm.nih.gov/nuccore/CP009274, [retrieved Feb. 26, 2025], nucleotides 5430000-5433000 shown (Year: 2016).*

Bolay et al., The Distinctive Regulation of Cyanobacterial Glutamine Synthetase. Life (2018), 8:52; doi: 10.3390/life8040052 (Year: 2018).*

Interview Summary, dated Dec. 9, 2024, for U.S. Appl. No. 18/345,783, 3 pages.

Krishnan, H. B., et al., "Citrate Synthase Mutants of Sinorhizobium fredii USDA257 Form Ineffective Nodules with Aberrant Ultrastructure," Applied and Environmental Microbiology, Jun. 2003, vol. 69, No. 6, pp. 3561-3568.

Non-Final Office Action, dated Dec. 16, 2024, for U.S. Appl. No. 17/605,374, 11 pages.

Notice of Allowance, dated Dec. 17, 2024, for Chinese Patent Application No. 201880082093.3, 5 pages.

Notice of Allowance, dated Sep. 16, 2024, for U.S. Appl. No. 16/671,036, 9 pages.

Office Action for Australian Patent Application No. 2019293248 dated Dec. 19, 2024, 7 pages.

Restriction Requirement, dated Dec. 4, 2024, for U.S. Appl. No. 17/822,740, 8 pages.

40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010), 3 pages.

Abd-Elhafeez, E., et al., "Isolation and Characterization of Enterobacter Strains Causing Potato Soft Rot Disease in Egypt," Minia Science Bulletin, Botany Section, Mar. 2018, 29(1), pp. 1-13.

Adhikary, H., et al. "Artificial Citrate Operon Confers Mineral Phosphate Solubilization Ability to Diverse Fluorescent Pseudomonads", Plos One, Sep. 2014, vol. 9, No. 9, p. e107554, 12 total pages.

Aita, T.; Husimi, Y., "Adaptive walks by the fittest among finite random mutants on a Mt. Fugi-type fitness landscape," J. Theor. Biol. 193:383-405 (1998).

(56) References Cited

OTHER PUBLICATIONS

Alper, et al., "Tuning genetic control through promoter engineering". Proc Natl Acad Sci U S A. (Sep. 6, 2005); 102(36): 12678-12683, and erratum. Epub Aug. 25, 2005.

Altschul, S. F., et al., "Basic local alignment search tool", Journal of Molecular Biology (1990); 215(3): 403-410.

Altschul, S. F., et al., "Gapped BLAST and PSI-BLAST: a new generation of protein database search programs", Nucleic Acids Research (1997); 25(17): 3389-3402.

Ambrosio, et al. "Metabolic engineering of a diazotrophic bacterium improves ammonium release and biofertilization of plants and microalgae"; Metabolic Engineering (2017), vol. 40, pp. 59-68, DOI: 10.1016/j.ymben.2017.01.002.

An, Q., et al. "Constitutive expression of the nifA gene activates associative nitrogen fixation of Enterobacter gergoviae 57-7, an opportunistic endophytic diazotroph". Journal of Applied Microbiology, Sep. 2007, vol. 103, No. 3, pp. 613-620, doi: 10.1111/j.1365-2672.2007.03289.

Andersen, et al. Energetics of biological nitrogen fixation: determination of the ratio of formation of H2 to NH4+ catalysed by nitrogenase of Klebsiella pneumoniae in vivo. J Gen Microbiol. Nov. 1977;103(1):107-22.

Andersen et al., Herpesvirus-Mediated Gene Delivery into the Rat Brain: Specificity and Efficiency of the Neuron-Specific Enolase Promoter, Cell. Mol. Neurobiol., 13:503-15 (1993).

Anderson, J.C., et al. "BglBricks: A flexible standard for biological part assembly," Journal of Biological Engineering, 2010, 4:1, 12 pages.

Andrews et al. Use of Nitrogen Fixing Bacteria Inoculants as a Substitute for Nitrogen Fertiliser for Dryland Graminaceous Crops: Progress Made, Mechanisms of Action and Future Potential. Symbiosis 34 (2003). 21 pages.

Andrianantoandro E, et al., "Synthetic biology: new engineering rules for an emerging discipline," Mol Syst Biol 2:2006.0028, 14 pages (2006).

Arbuthnot et al. "In vitro and in vivo hepatoma cell-specific expression of a gene transferred with an adenoviral vector," Hum Gene Ther., 1996, 7(13):1503-1514.

Arnold et al., "Nucleotide sequence of a 24,206-base-pair DNA fragment carrying the entire nitrogen fixation gene cluster of Klebsiella pneumonia", J. Mol. Biol. (1988) 203, pp. 715-738.

Arriel-Elias, M.T., et al., "Shelf life enhancement of plant growth promoting rhizobacteria using a simple formulation screening method," African Journal of Microbiology Research, Feb. 7, 2018, vol. 12(5), pp. 115-126, DOI: 10.5897/AJMR2017.8787.

Arsene, F., et al., "Modulation of NifA activity by PII in Azospirillum brasilense: Evidence for a Regulatory role of the NifA N-Terminal Domain," Journal of Bacteriology, Aug. 1996, vol. 178, No. 16, p. 4830-4838.

Austin et al. "Characterisation of the Klebsiella pneumoniae nitrogen-fixation regulatory proteins NIFA and NIFL in vitro," Eur J Biochem., 1990, 187(2):353-360.

Ausubel, et al., "Glutamine Synthetase Mutations Which Affect Expression of Nitrogen Fixation Genes in Klebsiella pneumoniae", Journal of Bacteriology, 1979, vol. 140(2), pp. 597-606.

Bageshwar, et al. An Environmentally Friendly Engineered Azotobacter Strain That Replaces a Substantial Amount of Urea Fertilizer while Sustaining the Same Wheat Yield. Appl Environ Microbial. Aug. 1, 2017; 83(15): e00590-17, 14 pages.

Bali, A. et al., "Excretion of ammonium by a nifL mutant of Azotobacter vinelandii fixing nitrogen," Appl Environ Microbiol, May 1992, vol. 58, No. 5, pp. 1711-1718.

Balota, E. L., et al., "Occurrence of Diazotrophic Bateria and Arbuscular Mycorrhizal Fungi on the Cassava Crop," Pesq. Agropec. Bras, Brasilia, v. 34, n. 7, pp. 1265-1276, Jul. 1999, English abstract only.

Barney et al., "Gene deletions resulting in increased nitrogen release by azotobacter vinelandii: application of a novel nitrogen biosensor," Applied and Environmental Microbiology, Jul. 2015, 81(13), pp. 4316-4328. Published online Apr. 17, 2015.

Barney, et al., Transcriptional analysis of an Ammonium-excreting stain of azotobacter vinelandii deregulated for nitrogen fixation. Appl. Environ. Microbiol. 2017; 83(20): 1-22.

Barrangou R., Exploiting CRISPR-Cas immune systems for genome editing in bacteria. Curr. Opin. Biotechnol. 2016; 37:61-68.

Batista et al. "Manipulating nitrogen regulation in diazotrophic bacteria for agronomic benefit," Biochemical Society Transactions 2019, vol. 47, pp. 603-614, doi: 10.1042/BST20180342.

Batzer, M. et al., "Enhanced evolutionary PCR using oligonucleotides with inosine at the 3'-terminus," Nucleic Acid Res, vol. 19:5081-5082 (1991).

Baum, et al. "Control of coleopteran insect pests through RNA interference." Nat Biotechnol. Nov. 2007;25(11):1322-6. doi: 10.1038/nbtl359.

Bayer TS et al., "Synthesis of Methyl Halides from Biomass Using Engineered Microbes", JAm Chem Soc, (20090000), vol. 131, No. 18, pp. 6508-6515.

Becker, M., et al., "Comparative Genomics Reveal a Flagellar System, a Type VI Secretion System and Plant Growth-Promoting Gene Clusters Unique to the Endophytic Bacterium Kosakonia radicincitans," Frontiers in Microbiology, Aug. 2018, vol. 9, Art. 1997, 22 pages, doi: 10.3389/fmicb.2018.01997.

Bender, et al., "Regulatory mutations in the Klebsiella aerogenes structural gene for glutamine synthetase", Journal of Bacteriology, Oct. 1977, vol. 132, No. 1, pp. 100-105.

Bender R., "A NAC for Regulating Metabolism: the Nitrogen Assimilation Control Protein(NAC) from Klebsiella pneumoniae", J. Bacteriol., 192(19), pp. 4801-4811, Jul. 30, 2010.

Berge, O., et al., "Rahnella aquatilis, a nitrogen-fixing enteric bacterium associated with the rhizosphere of wheat and maize," Canadian Journal of Microbiology (1991), vol. 37(3) : 195-203.

Berger, B., et al., "The plant growth-promoting bacterium Kosakonia radicincitans improves fruit yield and quality of *Solanum lycopersicum*," J Sci Food Agric 2017, 7 pages, DOI 10.1002/jsfa.8357.

Berger, B., et al., "Successful Formulation and Application of Plant Growth-Promoting Kosakonia radicincitans in Maize Cultivation," BioMed Research International, vol. 2018, Art. 6439481, 8 pages, published Mar. 28, 2018, https://doi.org/10.1155/2018/6439481.

Beringer et al., Genetic engineering and nitrogen fixation. Biotech. Gen. Eng. Rev. 1984; 1(1):65-88.

Berninger et al., "Maintenance and Assessment of Cell Viability in Formulation of Non-Sporulating Bacterial Inoculants," Microbial Biotechnology, Mar. 2018, 11(2): 277-301.

Beynon J, Cannon M, Buchanan-Wollaston V, & Cannon F (1983) The nifpromoters of Klebsiella pneumoniae have a characteristic primary structure. Cell 34(2):665-671.

Bhattacharjee, R. B., et al., "Use of Nitrogen-Fixing Bacteria as Biofertiliser for non-legumes; prospects and challenges," Applied Microbiology and Biotechnology, 80:199-209 (2008).

Biggins JB, Liu, X., Feng, Z., Brady, S.F. (2011) Metabolites from the induced expression of cryptic single operons found in the genome of Burkolderia pseudomallei. JACS 133:1638-1641.

Bikard et al., "The synthetic integron: an in vivo genetic shuffling device," Nucleic Acids Res., 2010, 38(15): e153, 7 pages, doi:10.1093/nar/gkq511. Epub Jun. 9, 2010.

Bilitchenko, AI., "Eugene—a domain specific language for specifying and constraining synthetic biological parts, devices, and systems." Plos One (2011); 6.4: e18882, Apr. 29;6(4): doi: 10.1371/journal.pone.0018882. 12 pages.

Bittner, M., et al., "RpoS and RpoN are involved in the growth-dependent regulation of rfaH transcription and O antigen expression in *Salmonella enterica* serovar typhi," Microbial Pathogenesis 2004, vol. 36, No. 1, pp. 19-24.

Blanco, G. et al., "Sequence and molecular analysis of the nifL gene of Azotobacter vinelandii," Mol Microbiol, 9(4):869-879 (1993). doi: 10.1111/j.1365-2958.1993.tb01745.x.

Blast. Basic local alignment search tool. Available at http://blast.ncbi.nlm.nih.gov/Blast.cgi. Accessed on Oct. 10, 2023, 10 pages.

Bloch, S. E., et al., Biological nitrogen fixation in maize: optimizing nitrogenase expression in a root-associated diazotroph, Journal of Experimental Botany 2020, vol. 71, No. 15, pp. 4591-4603, doi: 10.1093/jxb/eraa176.

(56) References Cited

OTHER PUBLICATIONS

Bonde et al., "MODEST: a web-based design tool for oligonucleotide-mediated genome engineering and recombineering," Nucleic Acids Res., 2014, 42(W1):W408- W415.

Boris Magasanik, "Genetic Control of Nitrogen Assimilation in Bacteria," Ann. Rev. Genet 1982. 16:135-68 (Year: 1982).

Boshart et al., A very strong enhancer is located upstream of an immediate early gene of human cytomegalovirus, Cell, Jun. 1985, pp. 521-530.

Bosmans, F., et al.; "Sea anemone venom as a source of insecticidal peptides acting on voltage-gated Na+ channels," Toxicon; 49(4):550-560 (2007).

Bosworth, et al. Alfalfa yield response to inoculation with recombinant strains of Rhizobium meliloti with an extra dctABD and/or modified nifA expression. Appl Environ Microbiol. Oct. 1994;60(10):3815-32.

Boyle et al. "Tools for genome-wide strain design and construction," Curr Opin Biotechnol., 2012, 23(5):666-671. doi: 10.1016/j.copbio.2012.01.012.

Brady, C., et al., "Taxonomic evaluation of the genus Enterobacter based on multilocus sequence analysis (MLSA)," Systemic and Applied Microbiology 36 (2013), pp. 309-319, https://doi.org/10.1016/j.syapm.2013.03.005.

Brandl et al., "*Salmonella* interactions with plants and their associated microbiota," Phytopathology, 2013, 103:316-325.

Brewin, et al., The Basis of Ammonium release in nifL Mutants of Azotobacter vinelandii. Journal of Bacteriology, Dec. 1999; 181(23): p. 7356-7362.

Buchanan-Wollaston et al., "Role of the nifA gene product in the regulation of nif expression in Klebsiella pneumoniae," Nature, vol. 294, pp. 776-778 (Dec. 1981).

Buck, M. and Cannon, W. (1987) Frameshifts close to the Klebsiella pneumoniae nifH promoter prevent multicopy inhibition by hybrid nifH plasmids. Mal Gen Genet 207(2-3):492-498.

Buckley Lab NifH database, retrieved via WayBack Machine from URL web.archive.org/web/20180110043803/https:/ /blogs.cornell.edu/buckley/nifh-sequence-database/, available on or before Jan. 10, 2018, 2 pages.

Buddrus-Schiemann, et al. Root colonization by Pseudomonas sp. DSMZ 13134 and impact on the indigenous rhizosphere bacterial community of barley. Microb Ecol. Aug. 2010;60(2):381-93. doi: 10.1007/s00248-010-9720-8. Epub Jul. 20, 2010.

Burgmann et al., Effects of model root exudates on structure and activity of a soil diazotroph community. Environmental Microbiology (2005), 7: 1711-1724 (Year: 2005).

Burris et al., "Nitrogenases," J Biol Chem., 266(15):9339-9342. (May 25, 1991).

Calcagno et al., Adaptation of the Yeast URA3 Selection System to Gram-Negative Bacteria and Generation of a ΔbetCDE Pseudomonas putida Strain. Applied and Environmental Microbiology (2005), 71: 883-892 (Year: 2005).

Cardinale, S., & Arkin, A.P. Contextualizing context for synthetic biology identifying causes of failure of synthetic biological systems. Biotechnol. J. 7:856-866 (2012).

Carr et al., "Enhanced multiplex genome engineering through co-operative oligonucleotide co-selection," Nucleic Acids Res., 2012, 40(17):e132, 11 pages.

Cera. "GM Crop Database. Center for Environmental Risk Assessment (CERA)", ILSI Research Foundation, at cera-gmc.org/index.php?action=gm_crop_database, 1 page (2010).

Chakroun, et al. "Bacterial Vegetative Insecticidal Proteins (Vip) from Entomopathogenic Bacteria." Microbial Mal Biol Rev. Mar. 2, 2016;80(2):329-50. doi: 10.1 128/MMBR.00060-15.

Chan et al., "Refactoring bacteriophage T7," Molecular Systems Biology, 2005, vol. 1, No. 1, pp. E1-E10, doi: 10.1038/msb4100025.

Chen, et al., "Characterization of 582 natural and synthetic terminators and quantification of their design constraints". Nat Methods. (Jul. 2013); 10(7): 659-664. Epub Jun. 2, 2013.

Chen, et al. "Expression of rat bone sialoprotein promoter in transgenic mice." J Bone Miner Res., May 1996, 11(5): 654-64.

Chen, M., et al., "Complete genome sequence of Kosakonia sacchari type strain SP1T," Standards in Genomic Sciences 2014, 9:1311-1318, DOI: 10.4056/sigs.5779977.

Chen, X., et al., Common Knowledge Evidence 1, Plant Physiology and Molecular Biology, 3rd Edition, Higher Education Press, Jun. 2007, 3rd edition, pp. 261-267, with English translation, 18 pages.

Chiang, et al. "Mutagenic oligonucleotide-directed PCR amplification (Mod-PCR): an efficient method for generating random base substitution mutations in a DNA sequence element." PCR Methods Annl. Feb. 1993;2(3):210-7. doi: 10.1101/gr.2.3.210.

Chin JW "Programming and engineering biological networks," Curr Opin Struct Biol 16: 551-556 (2006).

Choi, et al. A Tn7-based broad-range bacterial cloning and expression system. Nat Methods. Jun. 2005;2(6):443-8.

Choudhary, et al. Interactions of Bacillus spp. and Plants—With Special Reference to Induced Systemic Resistance (ISR). Microbiological Research. 2009, vol. 164, No. 5; pp. 493-513.

Clancy, P., et al., "The domains carrying the opposing activities in adenylyl transferase are separated by a central regulatory domain," FEBS Journal (2007), 274:2865-2877.

Cobb et al., Directed evolution: an evolving and enabling synthetic biology tool. Curr Opin Chem Biol. Aug. 2012;16(3-4):285-91, doi:10.1016/j.cbpa.2012.05.186. Epub Jun. 4, 2012.

Cohen, J.D., In vitro Tomato Fruit Cultures Demonstrate a Role for Indole-3-acetic Acid in Regulating Fruit Ripening. J. Amer. Soc. Hort. Sci. 121(3):520-524. 1996.

Colby, R.S., "Calculating Synergistic and Antagonistic Responses of Herbicide Combinations," Weeds. vol. 15, pp. 20-22 (1967).

Colebatch et al. "Symbiotic nitrogen fixation research in the postgenomics era," New Phytologist., 2002, 153(1):37-42 doi:10.1046/j.0028-646X.2001.00304.x.

Colnaghi, R., et al., "Lethality of glnD null mutations in Azotobacter vinelandii is suppressible by prevention of glutamine synthetase adenylylation," Microbiology, May 2001; 147(Pt 5):1267-1276.

Colnaghi, R. et al., Strategies for increased ammonium production in free-living or plant associated nitrogen fixing bacteria. Plant and Soil, 1997; 194: 145-154.

Communication pursuant to Article 94(3) EPC, dated Jun. 25, 2021, for European Patent Application No. 16825147.8 (7 total pages).

Communication pursuant to Article 94(3) EPC, dated Mar. 23, 2022, for European Patent Application No. 19186353.9 (6 total pages).

Compant, S., et al., "A review on the plant microbiome: Ecology, functions, and emerging trends in microbial application," Journal of Advanced Research 19 (2019), pp. 29-37, https://doi.org/10.1016/j.jare.2019.03.004.

Conniff, R., Microbes help grow better crops. Scientific american. http://www.scientificamerican.com/article/microbes-help-grow-better-crops/ Sep. 2013, 7 pages.

Contreras, et al. The product of the nitrogen fixation regulatory gene nfrX of Azotobacter vinelandii is functionally and structurally homologous to the uridylyltransferase encoded by glnD in enteric bacteria. J Bacteriol. Dec. 1991; 173(24): 7741-7749.

Cornelis et al., "The type III secretion injectisome," Nature Reviews Mocrobilogy, 2006, 4(11):811-825.

Costerton, J. W., et al., "Microbial Biofilms," Annu. Rev. Microbiol. 1995, 49:711-745.

Crameri, et al., "Molecular evolution of an arsenate detoxification pathway by DNA shuffling." Nature Biotechnology (May 1997); 15(5): 436-438.

Crickmore, et al. "Bacillus thuringiensis toxin nomenclature." Web page, https://web.archive.org/web/20161110143346/http://www.btnomenclature.info/, 2016, 1 page, retrieved from internet on Nov. 30, 2022.

Crickmore N, Baum J, Bravo A, Lereclus D, Narva K, Sampson K, Schnepf E, Sun M, Zeigler DR (2016) Bacillus thuringiensis toxin nomenclature, 3 pages, http://www.btnomenclature.info.

Crickmore, N., et al.; "Revision of the nomenclature for the Bacillus thuringiensis pesticidal crystal proteins," Microbiol Mol Biol Rev. (1998); 62(3):807-813.

(56) References Cited

OTHER PUBLICATIONS

Crook, N.C., et al., "Re-engineering multicloning sites for function and convenience," Nucl. Acids Res. 2011, vol. 39, No. 14, e92, 10 pages.

Curatti, et al., Genes required for rapid expression of nitrogenase activity in Azotobacter vinelandii. PNAS 2005; 102(18): 6291-6296.

Czar, et al. "Gene synthesis demystified." Trends in Biotechnology (Feb. 2009); 27(2): 63-72. Epub Dec. 26, 2008.

Da Silva, M. F., et al., "Survival of endophytic bacteria in polymer-based inoculants and efficiency of their application to sugarcane," Plant and Soil 356, pp. 231-243 (2012), https://doi.org/10.1007/s11104-012-1242-3.

Dandekar, T., Snel, B., Huynen, M., & Bork, P. Conservation of gene order: a fingerprint of proteins that physically interact. Trends Biochem. Sci. 23:324-328 (1998).

Das, H. K., et al, "Azotobacters as biofertilizer," Advances in Applied Microbiology 2019, vol. 108, pp. 1-43, doi: 10.1016/bs.aambs.2019.07.001.

Das, S. & De, T. K., "Microbial assay of N2 fixation rate, a simple alternate for acetylene reduction assay," MethodsX 5 (2018), p. 909-914, doi: 10.1016/j.mex.2017.11.010.

Dash, N., et al., "Functionalities of Phosphate-Solubilizing-Bacteria of Rice Rhizosphere: Techniques and Perspectives," Recent Advances in Applied Microbiology, 2017, 151-163, DOI 10.1007/978-981-10-5275-0_7.

Database WPI, 0, Derwent World Patents Index, vol. 1989, No. 42, Database accession No. 1989-304907 & JPH01225483 A 19890908 (Kyowa Hakko Kogyo KK), abstract, 2 pages.

Database WPI, 0, Derwent World Patents Index, vol. 2015, No. 20, Database accession No. 2015-165987, JP2015042633 A 2015/03/05 (Maekawa Seisakusho KK) [Y] 1-18, 8 pages.

Datsenko and Wanner, "One-step inactivation of chromosomal genes in Escherichia coli K-12 using PCR products". PNAS (Jun. 6, 2000); 97(12): 6640-6645.

Davin-Regli et al. "Enterobacter aerogenes and Enterobacter cloacae; versatile bacterial pathogens confronting antibiotic treatment," Front Microbiol, May 2015, vol. 6, 392:1-10.

De Freitas, J.R., "Yield and N assimilation of winter wheat (Triticum aestivum L., var. Norstar) inoculated with rhizobacteria", Pedobiologia 2000, vol. 44, pp. 97-104, doi:10.1078/S0031-4056(04)70031-1.

De Raad, M., et al. "A solid-phase platform for combinatorial and scarless multipart gene assembly". ACS Synth. Biol. 2:316-326 (2013).

De Werra, P., et al., "Role of Gluconic Acid Production in the Regulation of Biocontrol traits of Pseudomonas fluorescens CHA0," Applied and Environmental Microbiology, Jun. 2009, 75(12): 4162-4174, doi:10.1128/AEM.00295-09.

Debruijn, F.J., et al., The Cloning and characterization of the glnF (ntrA) Gene of Klebsiella pneumoniae: Role of glnF (ntrA) in the Regulation of Nitrogen Fixation (nif) and other Nitrogen assimilation genes. Mol. Gen. Genet. 1983; 192:342-353.

Decision of Final Rejection, dated Jun. 1, 2023, for Japanese Patent Application No. 2021-135296 (8 total pages).

Decision of Refusal, dated Apr. 27, 2023, for Japanese Patent Application No. 2020- 524148 (12 total pages).

Decision of Rejection, dated Apr. 23, 2021, for Japanese Patent Application No. 2018- 536712 (8 total pages).

Decision on grant of patent for invention, dated Apr. 3, 2023, for Russian Patent Application No. 2019125282 (16 total pages).

Decision on grant of patent for invention, dated Feb. 8, 2022, for Russian Patent Application No. 2018105055 (15 total pages).

Decision on grant of patent for invention, dated Feb. 9, 2023, for Russian Patent Application No. 2020116780 (15 total pages).

Delaux, et al., Tracing the evolutionary path to nitrogen-fixing crops. Curr. Opin. Plant Biol. 2015; 26:95-99.

Dent, et al., Establishing symbiotic nitrogen fixation in cereals and other non-legume crops: The greener nitrogen revolution. Agric & Food Secur 2017; 6(7): 1-9.

Desnoues, N. et al., Nitrogen fixation genetics and regulation in a Pseudomonas stutzeri strain associated with rice. Microbiology, 2003; 149:2251-2262.

Dixon et al. "Characterisation of the Klebsiella pneumoniae nitrogen-fixation regulatory proteins NIFA and NIFL in vitro". (1990) Eur. J. Biochem. 187: 353-360. (Year: 1990).

Dixon, R. et al. "Genetic regulation of biological nitrogen fixation," Nature Reviews Microbiology, Aug. 2004, vol. 2, pp. 621-631.

Dixon, R. et al. "Genetic transfer of nitrogen fixation from Klebsiella pneumoniae to Escherichia coli," Nature (1972), 237(5350):102-103.

Dong, et al. Kinetics and Strain Specificity of Rhizosphere and Endophytic Colonization by Enteric Bacteria on Seedlings of Medicago sativa and Medicago truncatula. Appl Environ Microbial. Mar. 2003; 69(3): 1783-1790.

Doroshchuk, N. A., "Regulation of Nitrogen Metabolism in Gram-Positive Bacteria," Molecular Biology 2006, vol. 40, No. 5, pp. 829-836.

Dos Santos, P. C. et al. "Distribution of nitrogen fixation and nitrogenase-like sequences amongst microbial genomes". BMC Genomics, 2012; (13)162: 1-12.

Drummond et al., "Expression from the nifB promoter of Azotobacter vinelandii can be activated by NifA, VnfA, or AnfA transcriptional activators", Journal of bacteriology, Feb. 1996, vol. 178, No. 3., pp. 788-792.

Du et al., Customized optimization of metabolic pathways by combinatorial transcriptional engineering. Nucleic Acids Res. 2012;40(18):e142, 10 pages.

Duca Daiana et al: "Indole-3-acetic acid 15 in plant-microbe interactions", Antonie Van Leeuwenhoek, Springer, Dordrecht; Nl, vol. 106, No. 1, Jan. 21, 2014 (Jan. 21, 2014), pp. 85-125, ISSN: 0003-6072, DOI: 10.1007/S10482-013-0095-Y [retrieved on Jan. 21, 2014].

Dunican, L. K. et al, "Genetic Transfer of Nitrogen Fixation from Rhizobium Trifolii to Klebsiella Aerogenes," Biochemical and Biophysical Research Communications, vol. 57, No. 1, pp. 62-72 (1974).

Dykxhoorn et al., (1996) A set of compatible tac promoter expression vectors. Gene 177(1-2):133-136.

Easter, et al., "Role of the parCBA Operon of the Broad-Host-Range Plasmid RK2 in Stable Plasmid Maintenance," Journal of Bacteriology, 1998, 180(22):6023-6030.

Eberhart et al., A methodology for markerless genetic modifications in Azotobacter vinelandii. Journal of Applied Microbiology (2016), 120: 1595-1604 (Year: 2016).

Egener, et al., Identification of NifL-like protein in a diazotroph of the b-subgroup of the proteobacteria, azoarcus sp. strain BH72, Microbiology 2002; 148: 3203-3212.

Emboss Needle: Pairwise Sequence Alignment. Retrieved on Oct. 31, 2023. Retrieved from https://www.ebi.ac.uk/Tools/psa/emboss_needle/, 2 pages.

Endy et al., "Foundations for engineering biology," Nature, 2005, 438:449-453.

Engler, Carola, et al., "A One Pot, One Step, Precision Cloning Method with High Throughput Capability." Plos One (Nov. 2008); 3.11: e3647, pp. 1-7. Epub Nov. 5, 2008.

Engler, et al., "Golden Gate Shuffling: A One-Pot DNA Shuffling Method Based on Type IIs Restriction Enzymes". PLoS One (2009); 4(5): e5553, 9 pages. Epub May 14, 2009.

Enkh-Amgalan, et al., "Molecular evolution of the nif gene cluster carrying nifI1 and nifI2 genes in the Gram-positive phototrophic bacterium Heliobacterium chlorum," International Journal of Systematic and Evolutionary Microbiology, 2006, 56:65-74.

EP Extended European Search Report in European Application No. 16854192.8, dated Feb. 20, 2019, 11 pages.

Estrem, et al., "Identification of an UP element consensus sequence for bacterial promoters," PNAS, 95 (11): 9761-9766 (1998).

Examination Report, dated Aug. 17, 2022, for Canadian Patent Application No. 2,991,776 (5 total pages).

Examination Report, dated Aug. 22, 2022, for Russian Patent Application No. 2019125282 (15 total pages).

Examination Report, dated Dec. 12, 2022, for Canadian Patent Application No. 3,001,001 (7 total pages).

(56)        References Cited

OTHER PUBLICATIONS

Examination Report, dated Dec. 16, 2020, for Indian Patent Application No. 201817001025 (7 total pages).
Examination Report, dated Feb. 15, 2023, for Australian Application No. 2018207204, 2 pages.
Examination Report, dated Feb. 24, 2022, for Argentina Patent Application No. 20180100082 (7 total pages).
Examination Report, dated Feb. 8, 2023, for Brazilan Patent Application No. BR122022025322-9 (26 total pages).
Examination Report, dated Feb. 8, 2023, for Brazilian Patent Application No. BR112018006800-4, 26 total pages.
Examination Report, dated Jan. 31, 2022, for Philippines Patent Application No. Jan. 2018/500103 (5 total pages).
Examination Report, dated Jan. 5, 2023, for Canadian Patent Application No. 2,991,776 (6 total pages).
Examination Report, dated Jul. 17, 2023, for Canadian Patent Application No. 3,104,531 (6 total pages).
Examination Report, dated Jun. 13, 2023, for Canadian Patent Application No. 2,991,776 (5 total pages).
Examination Report, dated Jun. 14, 2022, for Brazilian Patent Application No. BR112019014378-5 (8 total pages).
Examination Report, dated Jun. 17, 2022, for Indian Patent Application No. 201817011738 (7 total pages).
Examination Report, dated Jun. 26, 2023, for Brazilian Application No. 112018006800-4, 12 pages.
Examination Report, dated Jun. 27, 2023, for Brazilian Application No. 122022025322-9, 9 pages.
Examination Report, dated Jun. 28, 2022, for Brazilian Patent Application No. BR122020010314-0, 9 pages.
Examination Report, dated Jun. 29, 2023, for Canadian Patent Application No. 3,049,258 (7 total pages).
Examination Report, dated Jun. 30, 2023, for Canadian Patent Application No. 3,129,539 (5 total pages).
Examination Report, dated Jun. 8, 2021, for Bangladesh Application No. 113/2020 (1 total page).
Examination Report, dated Mar. 6, 2023, for Australian Application No. 2022271476 (5 total pages).
Examination Report, dated May 10, 2022, for Brazilian Patent Application No. BR112018000729-3 (7 total pages).
Examination Report, dated May 20, 2021, for Philippines Patent Application No. Jan. 2018/500103 (4 total pages).
Examination Report, dated May 24, 2023, for Canadian Patent Application No. 3,137,739 (4 total pages).
Examination Report, dated May 31, 2022, for Brazilian Patent Application No. BR112020008002-0 (7 total pages).
Examination Report, dated May 9, 2023, for Canadian Patent Application No. 3,079,955 (5 total pages).
Examination Report, dated Nov. 18, 2021, for Australian Patent Application No. 2016336328, 5 pages.
Examination Report, dated Nov. 25, 2022, for Brazilian Patent Application No. BR122020010314-0 (7 total pages).
Examination Report, dated Nov. 6, 2023, for Canadian Patent Application No. 2,991,776 (5 total pages).
Examination Report, dated Oct. 20, 2023, for Brazilian Patent Application No. BR122020010314- 0 (20 total pages).
Examination Report, dated Oct. 23, 2023, for Brazilian Application No. BR112018006800-4 (14 total pages).
Examination Report, dated Oct. 23, 2023, for Brazilian Application No. BR122022025322-9 (14 total pages).
Examination Report, dated Sep. 21, 2023, for Australian Application No. 2018354338, 2 pages.
Examination Report dated Sep. 7, 2022, for Australian Application No. 2016336328, 6 pages.
Examination Report, for Pakistan Patent Application No. 264/2020 (1 total page).
Examination Report with Search Report, dated Jul. 27, 2023, for Russian Patent Application No. 2023103521 (25 total pages).
Examination Report with Search Report, dated Mar. 27, 2023, for Russian Patent Application No. 2021101586, 18 pages.

Examination Report, with Search Report dated Mar. 3, 2020, for Brazilian Patent Application No. 112018006800-4 (7 total pages).
Examination Report with Search Report, dated May 31, 2022, for Russian Patent Application No. 2020116780 (15 total pages).
Examination Report with Search Report, dated Oct. 17, 2023, for Russian Patent Application No. 2021134059 (22 total pages).
Extended European Search Report and Search Opinion, dated Feb. 1, 2021, for European Patent Application No. 18739050.5 (20 total pages).
Extended European Search Report and Search Opinion, dated May 22, 2023, for European Patent Application No. 20795673.1 (9 total pages).
Extended European Search Report, dated Mar. 14, 2022, for European Application No. 19833252.0 (6 total pages).
Extended European Search Report for EP16825147.8, dated Jun. 6, 2019, 19 pages.
Extended European Search Report for European Application No. 12800054.4, mailed Dec. 19, 2014, 8 Pages.
Extended European Search Report for European Application No. 19186353.9, mailed Nov. 13, 2019, 9 Pages.
Extended European Search Report for European Application No. 19826654.6, mailed Jul. 4, 2022, 16 Pages.
Extended European Search Report in European Application No. 18870036.3, dated Dec. 14, 2021, 26 pages.
Extended Search Report and Search Opinion, dated Jul. 22, 2021, for European Patent Application No. 18843845.1 (18 total pages).
Extended Search Report and Search Opinion, dated Jul. 22, 2021, for European Patent Application No. 18870346.6 (5 total pages).
Eyraud, V., et al.; "Expression and biological activity of the cystine knot bioinsecticide PA1b (Pea Albumin 1 Subunit b)," PLoS One; 8(12):e81619; 9 pages (2013); doi: 10.1371/journal.pone.0081619.
Fani et al., "Molecular evolution of nitrogen fixation: the evolutionary history of the nilD, nifK, nifE, and nifN gene," J Mo/ Evol., 2000, 51(1): 1-11.
Feher, et al. In the fast lane: large-scale bacterial genome engineering. J Biotechnol. Jul. 31, 2012 ;160(1-2):72-9.
Fernandes, G. et al., Glutamine synthetase stabilizes the binding of GlnR to nitrogen fixation gene operators, The FEBS Journal 2017, vol. 284, No. 6, pp. 903-918.
Ferrieres, et al., "The yjbEFGH locus in *Escherichia coli* K-12 is an operon encoding proteins involved in exopolysaccharide production," Microbiology, Apr. 2007, 153(4):1070-80.
Final Office Action, dated Apr. 11, 2024, for U.S. Appl. No. 17/027,030, 35 pages.
Final Office Action, dated Dec. 7, 2023, for U.S. Appl. No. 17/255,304 (13 total pages).
Final Office Action, dated Feb. 2, 2021, for U.S. Appl. No. 15/766,122 (19 total pages).
Final Office Action, dated Jul. 21, 2020, for U.S. Appl. No. 16/192,738 (7 total pages).
Fischbach, et al., The evolution of gene collectives: how natural selection drives chemical innovation. Proc. Natl. Acad. Sci. USA 105:4601-4608 (2008).
Fisher, et al., "Mutations in the Bacillus subtilis glnRA operon that cause nitrogen source-dependent defects in regulation of TnrA activity", Journal of bacteriology, Aug. 15, 2002, vol. 184, No. 16, pp. 4636-4639.
Fisher, et al., "Novel trans-acting Bacillus subtilis glnA mutations that derepress glnRA expression", Journal of bacteriology, Apr. 15, 2009, vol. 191, No. 8, pp. 2485-2492.
Flores-Núñez, V. M., et al., "Functional Signatures of the Epiphytic Prokaryotic Microbiome of Agaves and Cacti," Frontiers in Microbiology, Jan. 2020, vol. 10, Art. 3044, 13 pages, doi: 10.3389/fmicb.2019.03044.
Fontana, W., et al., RNA folding and combinatory landscapes. Phys. Rev. E. 47:2083-2099 (1993).
Forner, A., et al., "Treatment of hepatocellular carcinoma," Critical Reviews in Oncology/Hematology 60, Nov. 2006, pp. 89-98, doi:10.1016/j.critrevonc.2006.06.001.
Fox, et al., Major cereal crops benefit from biological nitrogen fixation when inoculated with the nitrogen-fixing bacterium Pseudomonas protegens Pf-5 X940. Environmental Microbiology 2016; 18(10):3522-3534.

(56)                References Cited

OTHER PUBLICATIONS

Frasch et al., Design-based re-engineering of biosynthetic gene clusters: plug-and-play in practice. Curr Opin Biotechnol. Dec. 2013;24(6):1144-50, . doi: 10.1016/j.copbio.2013.03.006. Epub Mar. 27, 2013.

Gaby, et al. "A comprehensive aligned nifH gene database: a multipurpose tool for studies of nitrogen-fixing bacteria." Database (Oxford). Feb. 5, 2014;2014:bau001, 8 pages, doi: 10.1093/database/bau001.

Gamer, et al. A T7 RNA polymerase-dependent gene expression system for Bacillus megaterium. Appl Micro biol Biotechnol. Apr. 2009; 82(6):1195-203.

Gao, Y., et al., "Groundwater Nitrogen Pollution and Assessment of Its Health Risks: A Case Sutdy of a Typical Village in Rural-Urban Continuum, China," PLoS ONE, Apr. 2012, vol. 7, Issue 4, e33982, 8 pages.

Gebeyehu, G. et al., 1987, Novel biotinylated nucleotide-analogs for labeling and colorimetric detection of DNA, Nucl Acids Res., 15(11):4513-4534.

Geddes, B.A., Use of plant colonizing bacteria as chassis for transfer of N2-fixation to cereals. Curr. Opin. Biotechnol. 2015; 32:216-222.

GenBank: CP007215.3. Kosakonia sacchari SP1 chromosome, complete genome. Sep. 19, 2017, 805 pages.

"Genbank", Database accession No. X 13303.1. Apr. 18, 2005. 17 pages.

GenBank submission CP016337, Jul. 11, 2016 [online]. Retrieved on Feb. 21, 2022. Retrieved from the internet https://https://www.ncbi.nlm.nih.gov/protein/1043189580, 3 pages.

Georg, J. et al. "cis-Antisense RNA, another level of gene regulation in bacteria". Microbiol Mol Biol Rev. (2011). 75(2):286-300.

Gibson, A. H., "Physical Environment and Symbiotic Nitrogen Fixation," Australian Journal of Biological Sciences. 1963; 16, 28-42.

Gibson, et al., Chemical synthesis of the mouse mitochondrial genome. Nat. Methods 7, 901-903 (2010).

Gibson, et al., "Enzymatic assembly of DNA molecules up to several hundred kilobases." Nature Methods (Apr. 12, 2009); 6(5): 343-345.

Giri, K., et al., "The First Report of Indigenous Free-Living Diazotroph Kosakonia sacchari Isolated from Himalayan Alder-Based Shifting Cultivation System in Nagaland, India," Journal of Soil Science and Plant Nutrition (2019), 19:574-579, https://doi.org/10.1007/s42729-019-00056-5.

Global Agricultural Inoculants Market Research Report—Industry Analysis, Size, Share, Growth, Trends and Forecast 2015-2022, ReportBuyer, PreNewsWire.com, Dec. 8, 2016, 4 pages.

Gosink, M. M., et al, "The product of the Klebsiella pneumoniae nifX gene is a negative regulator of the nitrogen fixation (nif) regulon," J. Bacteriology, 1990, 172(3):1441-1447.

Gossen and Bujard, "Tight control of gene expression in mammalian cells by tetracycline-responsive promoters". Proc Natl Acad Sci U S A, Jun. 15, 1992; 89(12): 5547-5551.

Gossen, M. et al. (Jun. 23, 1995) "Transcriptional activation by tetracyclkines in mammalian cells" Science, 268(5218):1766-1769.

Gottelt et al., (2010) Deletion of a regulatory gene within the cpk gene cluster reveals novel antibacterial activity in Streptomyces coelicolor A3(2). Microbiology 156:2343-2353.

Govantes, et al. Mechanism of coordinated synthesis of the antagonistic regulatory proteins NifL and NifA of Klebsiella pneumoniae. J Bacteriol. Dec. 1996; 178(23): 6817-6823.

Gruber, et al., "Versatile plasmid-based expression systems for Gram-negative bacteria—General essentials exemplified with the bacterium Ralstonia eutropha H16," New Biotechnology, Dec. 2015, vol. 32, No. 6, 552-558.

Gruber, T. M. et al. "Multiple Sigma Subunits and the Partitioning of Bacterial Transcription Space". Annu. Rev. Microbiol., (2003), vol. 57, pp. 441-466.

Gu, C. T., et al., "Enterobacter xiangfangensis sp. nov., isolated from Chinese traditional sourdough, and reclassification of Enterobacter sacchari Zhu et al. 2013 as Kosakonia sacchari comb. nov.," International Journal of Systematic and Evolutionary Microbiology (2014), 64, 2650-2656, DOI: 10.1099/js.0.064709-0.

Guell et al., "Bacterial transcriptomics: what is beyond the RNA horiz-ome?" Nature reviews. Microbiology. (2011). 9(9):658-669.

Guell, et al. "Transcriptome complexity in a genome-reduced bacterium". Science. (2009). 326:1268-1271.

Guo et al., Discovery of Reactive Microbiota-Derived Metabolites that Inhibit Host Proteases. Cell. Jan. 26, 2017;168(3):517-526.e18.

Haapalainen, et al., Soluble plant cell signals induce the expression of the type ILL secretion system of Pseudomonas syringae and upregulate the production of pilus protein HrpA. Mol. Plant Microbe Interact. 22, 282-290 (2009).

Hale, et al., An efficient stress-free strategy to displace stable bacterial plasmids. Bio Techniques 2010; 48:223-228.

Hansal, et al. Cutting Edge: Induction of antigen-specific hyporesponsiveness by transplantation of hemopoietic cells containing an MHC class I transgene regulated by a lymphocyte-specific promoter. J Immunol. Aug. 1, 1998 ;161(3):1063-8.

Harvey et al., Inducible control of gene expression: prospects for gene therapy, Curr. Opin. Chem. Biol., 2:512-518 (1998).

Hearing Notice, dated Dec. 1, 2023, for Indian Patent Application No. 201817001025, 4 pages.

Hearing Notice, dated Dec. 26, 2023, for Indian Patent Application No. 201817001025, 4 pages.

Hearing Notice, dated Feb. 14, 2023, for Indian Patent Application No. 201817011738 (2 total pages).

Hearing Notice, dated Jan. 8, 2024, for Indian Patent Application No. 201917031229. 3 pages.

Henikoff et al., "Amino acid substitution matrices from protein blocks," Proc. Natl. Acad. Sci. U.S.A., Nov. 1992, 89: 10915-10919.

Herlache, et al. Characterization of the Agrobacterium vitis pehA gene and comparison of the encoded polygalacturonase with the homologous enzymes from Erwinia carotovora and Ralstonia solanacearum. Appl Environ Microbial. Jan. 1997; 63(1): 338-346.

Hernandez, J.A., et al. "Biochemical analysis of the recombinant Fur (ferric uptake regulator) protein from Anabaena PCC 7119: factors affecting its oligomerization state," Biochem J., 2002, 366:315-322.

Hesketh, A. et al, "The GlnD and GlnK homologues of Streptomyces coelicolor A3(2) are functionally dissimilar to their nitrogen regulatory system counterparts from enteric bacteria," Molecular Microbiology (2002) (2), 319- 330.

Hett,, E. C., et al., "Bacterial Growth and Cell Division: a Mycobacterial Perspective," Microbiology and Molecular Biology Reviews, vol. 72, Issue 1, Mar. 2008, pp. 126-156, https://doi.org/10.1128/MMBR.00028-07 (61 total pages).

Hidaka, M. et al., "Promotion of the Growth of Rice by Inoculation of Nitrogen-Fixing-Activity-Enhanced Bacteria to the Rhizosphere," Nitrogen Fixation: From Molecules to Crop Productivity, Current Plant Science and Biotechnology in Agriculture, vol. 38, p. 445 (2002).

Higdon, S. M., et al., "Genomic characterization of a diazotrophic microbiota associated with maize aerial root mucilage," PLoS ONE, 15(9): e0239677, Sep. 2020, 26 pages, https://doi.org/10.1371/journal.pone.0239677.

Hoeschle-Zeledon, I., et al.; "Regulatory challenges for biological control," The CGIAR Systemwide Program on Integrated Pest Management, Jan. 2013; SP-IPM Secretariat, International Institute of Tropical Agriculture (IITA), Ibadan, Nigeria; 53 pages.

Holden, et al. Colonization outwith the colon: plants as an alternative environmental reservoir for human pathogenic enterobacteria. FEMS Microbiol. Rev. 33, 689-703 (2009).

Hosseini-Abari, A., et al., "LC/MS detection of oligogalacturonic acids obtained from tragacanth degradation by pectinase producing bacteria," Journal of Basic Microbiology, 2019, 59:249-255, DOI: 10.1002/jobm.201800332.

Hu et al., (2008) Assembly of nitrogenase MoFe protein. Biochemistry 47(13):3973-3981.

Hu, L., et al., "Application of bryophyte rhizoid-associated bacteria increases silicon accumulation and growth in maize (Zea mays L.)

(56) References Cited

OTHER PUBLICATIONS seedlings," App. Ecol. Env. Res., 2019, 17(6):13423-13433, DOI: http://dx.doi.org/10.15666/aeer/1706_1342313433.

Hunter, P., "Genetically Modified Lite" placates public but not activists. EMBO Reports 2014; 15(2): 138-141.

Huynen, et al., Smoothness within ruggedness: the role of neutrality in adaptation. Proc. Natl. Acad. Sci. USA 93:397-401 (1996).

Iber, D. A quantitative study of the benefits of co-regulation using the spollA operon as an example. Mol. Sys. Biol. 2, 1-6 (2006).

Idalia, V. N. et al., "*Escherichia coli* as a model organism and its application in biotechnology," Recent Advances on Physiology, Pathogenesis, and Biotechnological Applications, Chapter 13, 2017, pp. 253-274.

Iltis H. H., et al., "Zea diploperennis (Gramineae): A New Teosinte from Mexico" Science, vol. 203, Jan. 12, 1979, pp. 186-188.

Iniguez, A. L., et al., "Regulation of Enteric Endophytic Bacterial Colonization by Plant Defenses," MPMI (2005), vol. 18, No. 2, pp. 169-178, DOI: 10.1094/MPMI-18-0169.

Iniguez, et al., Nitrogen Fixation in Wheat Provided by Klebsiella pneumoniae 342. MPMI vol. 17, No. 10, 2004, pp. 1078-1085.

International Preliminary Report on Patentability dated Apr. 19, 2018 for International Application No. PCT/US2016/055429, 12 pages.

International Preliminary Report on Patentability dated Jul. 16, 2019 for International Application No. PCT/US2018/013671, 6 pages.

International Preliminary Report on Patentability dated May 14, 2015 for International Application No. PCT/US2013/068055, 11 pages.

International Preliminary Report on Patentability for International Application No. PCT/US2012/042502, mailed Jan. 3, 2014, 9 Pages.

International Preliminary Report on Patentability for International Application No. PCT/US2019/039528, mailed Jan. 7, 2021, 15 Pages.

International Preliminary Report on Patentability in International Application No. PCT/US2021/029895, dated Nov. 10, 2022 (14 total pages).

International Preliminary Report on Patentability in International Application No. PCT/US2021/031808, dated Nov. 24, 2022 (17 total pages).

International Preliminary Report on Patentability in International Appln. No. PCT/US2016/042170, dated Jan. 16, 2018, 19 pages.

International Preliminary Report on Patentability in International Appln. No. PCT/US2018/046148, dated Feb. 11, 2020, 12 pages.

International Preliminary Report on Patentability in International Appln. No. PCT/US2018/057174, dated Apr. 28, 2020, 5 pages.

International Preliminary Report on Patentability in International Appln. No. PCT/US2018/057613, dated Apr. 28, 2020, 8 pages.

International Preliminary Report on Patentability, mailed Apr. 1, 2021, for International Application No. PCT/US2019/052003 (10 total pages).

International Preliminary Report on Patentability, mailed Jul. 1, 2021, for International Application No. PCT/US2019/068152 (12 pages).

International Preliminary Report on Patentability, mailed Nov. 10, 2022, for International Application No. PCT/US2020/031201 (17 total pages).

International Preliminary Report on Patentability, mailed Nov. 4, 2021, for International Application No. PCT/US2020/029831 (8 pages).

International Preliminary Report on Patentability, mailed, Nov. 4, 2021, for International Application No. PCT/US2020/029894, 13 pages.

International Search Report and Written Opinion dated Mar. 22, 2018, for International Application No. PCT/US2018/013671, 8 pages.

International Search Report and Written Opinion for International Application No. PCT/US2012/042502, mailed Jan. 31, 2013, 11 Pages.

International Search Report and Written Opinion for International Application No. PCT/US2013/068055, mailed Feb. 18, 2014, 16 Pages.

International Search Report and Written Opinion for International Application No. PCT/US2019/039528, mailed Nov. 6, 2019, 20 Pages.

International Search Report and Written Opinion for International Application No. PCT/US2020/029831, mailed Nov. 16, 2020, 12 pages.

International Search Report and Written Opinion for International Application No. PCT/US2021/055858 dated Mar. 25, 2022, 16 pages.

International Search Report and Written Opinion for PCT/US2020/014083, mailed on Jul. 20, 2020, 20 pages.

International Search Report and Written Opinion in International Appln. No. PCT/US2016/042170, dated Dec. 2, 2016, 26 pages.

International Search Report and Written Opinion in International Appln. No. PCT/US2016/055429, dated Dec. 30, 2016, 16 pages.

International Search Report and Written Opinion in International Appln. No. PCT/US2018/046148, dated Dec. 3, 2018, 6 pages.

International Search Report and Written Opinion in International Appln. No. PCT/US2018/057613, dated Mar. 5, 2019, 11 pages.

International Search Report and Written Opinion in International Appln. No. PCT/US2019/068152, dated Jun. 25, 2020, 21 pages.

International Search Report and Written Opinion in International Appln. No. PCT/US2020/031201, dated Mar. 18, 2021, 23 pages.

International Search Report and Written Opinion in PCT International Application No. PCT/US2019/052003, Jan. 9, 2020, 15 pages.

International Search Report and Written Opinion in PCT International Application No. PCT/US2020/029894, mailed Aug. 31, 2020, 18 pages.

International Search Report and Written Opinion mailed Apr. 16, 2020 for International Application No. PCT/US2019/064782, 13 pages.

International Search Report and Written Opinion, mailed Dec. 21, 2022, for International Application No. PCT/US2022/035873 (27 total pages).

International Search Report and Written Opinion, mailed Dec. 3, 2019, for International Application No. PCT/US2019/041429 (19 total pages).

International Search Report and Written Opinion, mailed Mar. 10, 2020, for International Appl. No. PCT/US2019/059450, 20 pages.

International Search Report and Written Opinion mailed Mar. 9, 2022 for International Application No. PCT/US2021/031808 (24 total pages).

International Search Report and Written Opinion, mailed Nov. 19, 2019, for International Application No. PCT/US2019/039217, 13 pages.

International Search Report and Written Opinion, mailed Sep. 15, 2021, for International Application No. PCT/US2021/029993, 11 pages.

International Search Report and Written Opinion, mailed Sep. 24, 2021, for International Application No. PCT/US2021/029895 (20 total pages).

Invitation to Pay Additional Fees and, Where Applicable, Protest Fee, dated Jan. 27, 2021, for International Application No. PCT/US2020/031201 (11 total pages).

Invitation to Pay Additional Fees, and Where Applicable, Protest Fee, dated Sep. 26, 2016, for International Application No. PCT/US2016/042170 (2 total pages).

Invitation to Pay Additional Fees, and Where Applicable, Protest Fee, dated Sep. 4, 2019, for International Application No. PCT/US2019/039528 (3 total pages).

Invitation to Pay Additional Fees and, Where Applicable, Protest Fee, dated Sep. 9, 2020, for International Application No. PCT/US2020/029831 (4 total pages).

Ishihama A, "Prokaryotic genome regulation: multifactor promoters, multitarget regulators and hierarchic networks", FEMS Microbiol Rev, (2010), vol. 34, No. 5, pp. 628-645.

Ivanova et al. "Artificial Regulation of Genes, of the coding proteins of the nitrogenase complex Rhizobial bacteria," Natural Sciences, 2014, 13(174):36-39 (English Machine Translation).

(56)        References Cited

OTHER PUBLICATIONS

Izquierdo et al., "Distribution of Extensive nifH Gene Diversity Across Physical Soil Microenvironments," Microbial Ecology, 2006, 51(4):441-452.

Jacob et al., (1987) Solid-state NMR studies of Klebsiella pneumoniae grown under nitrogen-fixing conditions. J Biol Chem 262(1):254-259.

Jacoby et al., "The Role of Soil Microorganisms in Plant Mineral Nutrition-Current Knowledge and Future Directions," Frontiers in Plant Science, 2017, 8(19):1-19.

Jahn, A. & Nielsen, P. H., "Extraction of Extracellular Polymeric Substances (EPS) from Biofilms Using a Cation Exchange Resin," Wat. Sci. Tech., 32(8):157-164 (1995).

Janczarek, M., et al., "Multiple copies of rosR and pssA genes enhance exopolysaccharide production, symbiotic competitveness and clover nodulation in Rhizobium leguminosarum bv. trifolii," Antonie Van Leeuwenhoek (2009), vol. 96, pp. 471-486, published online Jul. 9, 2009, DOI: 10.1007/S10482-009-9362-3.

Jan-Philip Schluter et al: "Global mapping of transcription start sites and promoter motifs in the symbiotic [alpha]-proteobacterium Sinorhizobium meliloti", BMC Genomics, Biomed Central Ltd, London, UK, vol. 14, No. 1, Mar. 7, 2013 (Mar. 7, 2013), p. 156, ISSN: 1471-2164, DOI: 10.1186/1471-2164-14-156.

Jaschke, et al. A fully decompressed synthetic bacteriophage 0X174 genome assembled and archived in yeast. Virology 434, 278-284 (2012).

Jayaraman, R., et al., "Strain Improvement of Phosphate Solubilizing Fungal Strains," Journal of Ecobiotechnology, 2010, 2(5):65-70.

Jensen, K.F. The Escherichia coli K-12 "wild types" W3110 and MG1655 have an rph frameshift mutation that leads to pyrimidine starvation due to low pyre expression levels. J. Bacteriol. 175:3401-3407 (1993).

Johnson, Z. I. et al. "Properties of overlapping genes are conserved across microbial genomes". Genome Res. (2004). 14(11):2268-2272.

Joseph R.C., et al., "Recent Development of the Synthetic Biology Toolkit for Clostridium", Frontiers in Microbiology, vol. 9, pp. 1-13, 2018.

Kabaluk, J. Todd, et al., ed. 2010, The use and regulation of microbial pesticides in representative jurisdictions worldwide. International Organization for Biological Control of Noxious Animals and Plants (IOBC), 99 pp. (108 total pages).

Kalir S, et al. (2001) Ordering genes in a flagella pathway by analysis of expression kinetics from living bacteria. Science 292(5524):2080-2083.

Kaneko, T., et al. Complete genomic structure of the cultivated rice endophyte Azospirillum sp. B510. DNA Res. 17:37-50 (2010).

Kant, et al. "Understanding plant response to nitrogen limitation for the improvement of crop nitrogen use efficiency." J Exp Bot. Feb. 2011;62(4):1499-509. doi: 10.1093/jxb/erq297.

Karlin et al. "Applications and statistics for multiple high-scoring segments in molecular sequences" Proceedings of the National Academy of Sciences (1993); 90(12):5873-5877.

Karlin, S., et al.; "Methods for assessing the statistical significance of molecular sequence features by using general scoring schemes," PNAS USA; 87(6):2264-2268 (1990).

Katsnelson, A., et al., "Engineered bacteria could boost com yields: Gene-edited microbe offer continuous nitrogen fixation," Chemical & Engineering News, Dec. 28, 2021, retrieved from https://cen.acs.org/food/agriculture/Engineered-bacteria-boost-corn-yields/99/web/2021/12, 2 pages.

Kececiglu, J., et al., "Of mice and men: Algorithms for evolutionary distances between genomes with translocation," SODA: Proceedings of the sixth annual ACM-SIA symposium on Discrete algorithms, 1995, 10 pages.

Kelly, J.R., et al. "Measuring the activity of BioBrick promoters using an in vivo reference standard". J Biol Eng. (2009). 3:4. 13 pages.

Kent et al., "A Transposable Partitioning Locus Used to Stabilize Plasmid-Borne Hydrogen Oxidation and Trifolitoxin Production Genes in a Sinorhizobium Strain," Appl. Environ. Microbiol., 1998, 64(5):1657-1662.

Kerby, et al. Photoproduction of ammonium by immobilized mutant strains of Anabaena variabilis. Applied Microbiology and Biotechnology. Apr. 1986, vol. 24, Issue 1, pp. 42-46.

Khandeparker, R. D. S., et al., "Extracellular polymeric substances of the marine fouling diatom amphora rostrata Wm.Sm," Biofouling (2001), 17(2):117-127, DOI: 10.1080/08927010109378471.

Kim, Y., et al., "A 20 nucleotide upstream element is essentail for the nopaline synthase (nos) promoter activity," Plant Molecular Biology 24: 105-117 (1994).

Kim, Y. et al., "Constitutive expression of nitrogenase system in Klebsiella oxytoca by gene targeting mutation to the chromosomal nifLA operon," Journal of Biotechnology, 10(3-4):293-301 (1989).

King, et al. "Spider-venom peptides: structure, pharmacology, and potential for control of insect pests." Annu Rev Entomol. 2013;58:475-96. doi: 10.1146/ammrev-ento-120811-153650.

Kingsford et al., "Rapid, accurate, computational discovery of Rho-independent transcription terminators illuminates their relationship to DNA uptake," Genome Bio. 2007, 8(2):R22, 12 pages.

Kitano, H. "Systems biology: a brief overview". Science. (2002). 295(5560): 1662-1664.

Klose, K., et al., "Glutamate at the Site of Phosphorylation of Nitrogen-regulatory Protein NTRC Mimics Aspartyl-Phosphate and Activates the Protein," Journal of Molecular Biology (1993), vol. 232, pp. 67-78.

Knight, T., "Idempotent Vector Design for Standard Assembly of Biobricks," MIT Artificial Intelligence Laboratory, The TTL Data Book for Design Engineers, 2003, 11 pages.

Knight, T.K. et al. "Cellular Gate Technology". Unconventional Models of Computation. (1997). pp. 257-272.

Kou, W., et al., "Identification of bacterial communities in sediments of Poyang Lake, the largest freshwater lake in China," SpringerPlus (2016), 5:401, pp. 1-9, DOI 10.1186/s40064-016-2026-7.

Kovacs et al., "Stochasticity in protein levels drives colinearity of gene order in metabolic operons of Escherichia coli." PLoS Biol. (2009). 7(5):e1000115. pp. 1-9.

Kranz, R. G., et al, "Ammonia-constitutive nitrogen fixation mutants of rhodobacter capsulatus," Gene, (1988), vol. 71, pp. 65-74, doi: 10.1016/0378-1119(88)90078-9.

Kumar, R., et al., "Metabolic regulation of Escherichia coli and its gdhA, glnL, gltB, D mutants under different carbon and nitrogen limitations in the continuous culture," Microbial Cell Factories 2010, vol. 9, No. 8, pp. 1-17.

Kumar, V., et al., "Establishment of phosphate-solubilizing strains of Azotobacter chroococcum in the rhizosphere and their effect on wheat cultivars under green house conditions," Microbiological Research (2001), 156:87-93.

Kurzweil, A. Plant Bacteria breakthrough enables crops worldwide to take nitrogen from the air. Aug. 1, 2013. http://www.kurzweilai.net/plant-bacteria-breakthrough-enables-crops-worldwide-to-take-nitrogen-from- the-air. 4 Pages.

Kutter et al. Colonization of barley (Hordeum vulgare) with Salmonella enterica and Listeria spp. FEMS Microbial. Ecol. 56, 262-271 (2006).

Lauber, C. L., et al., "Pyrosequencing-Based Assessment of Soil pH as a Predictor of Soil Bacterial Community Structure at the Continental Scale," Environmental Microbiology, Aug. 2009, vol. 75, Issue 15, https://doi.org/10.1128/AEM.00335-09 (18 total pages).

Lauritsen, et al., "A versatile one-step CRISPR-Cas9 based approach to plasmid-curing". Microb Cell Fact (2017); 16:135, 10 pages.

Leang, C. et al. "Genome-wide analysis of the RpoN regulon in Geobacter sulfurreducens," BMC Genomics. Jul. 22, 2009; 10:331, 19 pages.

Lee et al., "The class IId bacteriocin thuricin-17 increases plant growth," Planta, 2009, 229:747-755.

Leigh, J. A., et al., "Nitrogen Regulation in Bacteria and Archaea," Annu. Rev. Microbiol. 2007, 61:349-77.

(56)     References Cited

OTHER PUBLICATIONS

Lenski, R. E., et al., "Effects of Segregation and Selection on Instability of Plasmid pACYC184 in *Escherichia coli* B," Journal of Bacteriology, Nov. 1987, 169(11):5314-5316.

Leo Daniel, Amalraj E et al., "Effect of Polymeric Additives, Adjuvants, Surfactants on Survival, Stability and Plant Growth Promoting Ability of Liquid Bioinoculants," J Plant Physiol Pathol 2013, 1:2, 5 pages; http://dx.doi.org/10.4172/jppp.1000105.

Levican et al, "Comparative genomic analysis of carbon and nitrogen assimilation mechanisms in three indigenous bioleaching bacteria: predictions and validations" BMC Genomics 2008, 9:581, 19 pages (Year: 2008).

Levin-Karp, A., et al. Quantifying translational coupling in *E. coli* synthetic operons using RBS modulation and fluorescent reporters. ACS Synth. Biol. 2:327-336 (2013).

Li, S., et al., "Human Enhancers are Fragile and Prone to Deactivating Mutations," Molecular Biology and Evolution, 2015, 32(8):2161-2180, Advance access publication May 14, 2015, doi: 10.1093/molbev/msv118.

Liang, L. W. et al., "Minimal effect of gene clustering on expression in *Escherichia coli*". Genetics. Feb. 2013;193(2):453-65. doi:10.1534/genetics.112.147199. Epub Dec. 5, 2012.

Lim et al., Fundamental relationship between operon organization and gene expression. Proc Natl Acad Sci U S A. Jun. 28, 2011;108(26):10626-31. doi:10.1073/pnas.1105692108. Epub Jun. 13, 2011.

Lin, P., et al.; "PC, a Novel Oral Insecticidal Toxin from Bacillus bombysepticus Involved in Host Lethality via APN and BtR-175," Sci. Rep.; 5:11101, 14 pages; doi:10.1038/srep11101 (2015).

Lindström, E. S., et al., "Distribution of Typical Freshwater Bacterial Groups Is Associated with pH, Temperature, and Lake Water Rentention Time," Microbial Ecology, Dec. 2005, vol. 71, Issue 12, https://doi.org/10.1128/AEM.71.12.8201-8206.2005 (13 total pages).

Lindström, E. S., "Investigating Influential Factors on Bacterioplankton Community Composition: Results from a Field Study of Five Mesotrophic Lakes," Microbial Ecology (2001), 42:598-605, DOI: 10.1007/s00248-001-0031-y.

Liu, et al. Whole genome analysis of halotolerant and alkalotolerant plant growth-promoting rhizobacterium *Klebsiella* sp. D5A. Sci Rep. May 24, 2016; 6: 1-10.

Liu, H.-M., et al., "Phenazine-1-carboxylic acid biosynthesis in Pseudomonas Chlororaphis GP72 is positively regulated by the sigma factor RpoN," World Journal of Microbiology and Biotechnology (2008), vol. 24. pp. 1961-1966, DOI 10.1007/s11274-008-9655-0.

Liu, L. et al., "Development of an engineered soil bacterium enabling to convert both insoluble inorganic and organic phosphate into plant available phosphate and its use as a biofertilizer," Molecular Biotechnology 2015, 57:419-429, DOI 10.1007/s12033-014-9834-1.

Lombo et al., (1999) The mithramycin gene cluster of *Streptomyces argillaceus* contains a positive regulatory gene and two repeated DNA sequences that are located at both ends of the cluster. J. Bacterial. 181:642-647.

Lucks et al., Toward scalable parts families for predictable design of biological circuits. Curr. Opin. Microbiol. 11, 567-573 (2008).

Lugtenberg, B. J. J., et al., "Molecular determinants of rhizosphere colonization by Pseudomonas," Annu. Rev. Phytopathol. 2001, 39, 461-90, doi:10.1146/annurev.phyto.39.1.461.

Ma et al., "Effect of nicotine from tobacco root exudates on chemotaxis, growth, biocontrol efficiency, and colonization byPseudomonas aeruginosaNXHG29," Antonie van Leeuwenhoek, 2018, 111(7):1237-1257.

Mabrouk, Y. et al., "Chapter 6: Potential of Rhizobia in Improving Nitrogen Fixation and Yields of Legumes," Symbiosis, IntechOpen, pp. 1-16, (May 2018) https://www.intechopen.com/books/symbiosis/potential-of-rhizobia-in-improving- nitrogen-fixation-and-yields-of-legumes (15 total pages).

Machado, H. B., et al., "Excretion of ammonium by Azospirillum brasilense mutants resistant to ethylenediamine," Can. J Microbio. 1991, 37, pp. 549-553 (including Abstract, 2 pages).

MacNeil, et al. Fine-structure mapping and complementation analysis of nif (nitrogen fixation) genes in *Klebsiella* pneumoniae. J Bacteriol. Oct. 1978; 136(1): 253-266.

MacNeil, et al. Mutations in nif genes that cause *Klebsiella* pneumoniae to be derepressed for nitrogenase synthesis in the presence of ammonium. J Bacteriol. Nov. 1980; 144(2): 744-751.

Maduro M (2011) Random DNA Generator, retrieved from URL http://www.faculty.ucr.edu/ljfmmaduro/random.htm, 1 page.

Magari et al., Pharmacologic control of a Humanized Gene Therapy System Implanted into Nude Mice, J. Clin. Invest., 100:2865-2872 (1997).

Mandal M. and Breaker R. R., "Gene regulation by riboswitches", Nat Rev Mol Cell Biol, vol. 5, pp. 451-463, Jun. 2004, doi: 10.1038/nrm1403.

Mao, et al. "Silencing a cotton bollworm P450 monooxygenase gene by plant-mediated RNAi impairs larval tolerance of gossypol," Nature Biotechnology (2007); 25(11): 1307-1313. Epub Nov. 4, 2007.

Marroqui et al. "Enhanced Symbiotic Performance by Rhizobium tropici Glycogen Synthase Mutants," Journal of Bacteriology, Feb. 1, 2001, vol. 183, No. 3, pp. 854-864.

Martinez, M., et al., "Symbiotic Autoregulation of nifA Expression in Rhizobium leguminosarum bv. viciae," Journal of Bacteriology, Oct. 2004, vol. 186, No. 19, pp. 6586-6594, DOI: 10.1128/JB.186.19.6586-6594.2004.

Martinez-Argudo, I., et al., "The NifL-NifA System: a Multidomain Transcriptional Regulatory Complex that Integrates Environmental Signals," Journal of Bacteriology, Feb. 2004, vol. 186, No. 3, pp. 601-610, DOI: 10.1128/JB.186.3.601-610.2004.

Martinez-Noel et al., NifB and NifEN protein levels are regulated by ClpX2 under nitrogen fixation conditions in Azotobacter vinelandii. Mol Microbiol. Mar. 2011;79(5):1182-93, doi: 10.1111/j.I365-2958.2011.07540.x. Epub Jan. 25, 2011.

Marx, C. J., et al., "Broad-Host-Range cre-lox System for Antibiotic Marker Recycling in Gram-Negative Bacteria," Biotechniques, 33:1062-1067 (Nov. 2002).

Masepohl, et al., Organization and regulation of genes encoding the molybdenum nitrogenase and the alternative nitrogenase in Rhodobacter capsulatus. Arch. Microbiol. 1996;165:80-90.

Mason C. A. & Hamer G. (1987) Cryptic Growth in Klebsiella-Pneumoniae. Appl Microbiol Biotechnol 25:577-584.

Matsubayashi, et al. Peptide hormones in plants. Annu Rev Plant Biol. 2006; 57:649-74.

Medema et al., Computational tools for the synthetic design of biochemical pathways. Nat Rev Microbiol. Jan. 23, 2012; 10(3):191-202, doi: 10.1038/nrmicro2717.

Medema M. H. et al., "Exploiting plug-and-play synthetic biology for drug discovery and production in microorganisms", Nature reviews. Microbiology, vol. 9, pp. 131-137, Feb. 2011, doi: 10.1038/nrmicro2478.

Medema M. H. et al., "Synthetic biology in Steptomyces bacteria", Methods Enzymol, (2011), vol. 497, pp. 485-502.

Meng, X., et al., "Draft Genome Sequence of Rice Endophyte-Associated Isolate Kosakonia oryzae KO348," Genome Announcements, May'Jun. 2015, vol. 3, Issue 3, e00594-15, 1 page.

Mengel, D., "Roots, Growth and Nutrient Uptake," Dept. of Agronomy publication #AGRY-95-08 (Rev. May 95), 8 pages.

Merriam-Webster. "Originate", accessed Jul. 7, 2020 (Year: 2020). 13 pages.

Merrick, M., et al., "Repressor Properties of the nifL Gene Product in Klebsiella pneumonaie," Mol Gen Genet, 185, pp. 75-81 (1982).

Merrick, M. J., et al., "Nitrogen control of the nif regulon in Klebsiella pneumoniae: involvement of the ntrA gene and analogies between ntrC and nifA," The EMBO Journal (1983), vol. 2, No. 1, pp. 39-44.

(56)     References Cited

OTHER PUBLICATIONS

Michael Fischbach et al, "Prokaryotic gene clusters: A rich toolbox for synthetic biology", Biotechnology Journal, (Dec. 10, 2010), vol. 5, No. 12, doi:10.1002/biot.201000181, ISSN 1860-6768, pp. 1277-1296.

Miller S. H., et al., "Biochemical and genomic comparison of inorganic phosphate solubilization in Pseudomonas species," Environmental Microbiology Reports (2010), 2(3):403-411, doi:10.1111/j.1758-2229.2009.00105.x.

Mirsky, Ethan M., Refactoring the *Salmonella* Type ILL Secretion System. (Doctoral Dissertation) Apr. 12, 2012, 60 pages.

Mirzahoseini, et al., "Heterologous Proteins Production in *Escherichia coli*: An Investigation on the Effect of Codon Usage and Expression Host Optimization," Cell Journal (Yakhteh), 12(4), Winter 2011, pp. 453-458, 2011.

Mitra, Ranjana. Regulation of nifLA operon in Azotobacter vinelandii. Thesis submitted to the Jawaharlal Nehru University, New Delhi, for the degree of doctor of philosophy. 2000. 153 pages.

Miyazaki K, "Creating random mutagenesis libraries by megaprimer PCR of whole plasmid (MEGAWHOP)", Methods Mol Biol, (2003), vol. 231, pp. 23-28.

Montanez, A., et al., "Biological nitrogen fixation maize (*Zea mays* L.) by 15N isotope-dilution and identification of associated culturable diazotrophs," Biol Fertil Soils 2009, 45, pp. 253-263, DOI 10.1007/s00374-008-0322-2.

Moon et al., Genetic programs constructed from layered logic gates in single cells. Nature. Nov. 8, 2012; 491(7423):249-53, doi: 10.1038/nature11516. Epub Oct. 7, 2012.

Mosquito, S., et al., "In Planta Colonization and Role of T6SS in Two Rice Kosakonia Endophytes," MPMI 2020, vol. 33, No. 2, pp. 349-363, https://doi.org/10.1094/MPMI-09-19-0256-R.

Mueller, et al. Closing yield gaps through nutrient and water management. Nature 490, 254-257 (2012).

Murphy, J., et al., "A modified single solution method for the determination of phosphate in natural waters," Analytica Chimica Acta, 27 (1962), pp. 31-36.

Mus, F., et al., "Diazotrophic Growth Allows Azotobacter vinelandii to Overcome the Deleterious Effects of a glnE Deletion," Applied and Environmental Microbiology, Jul. 2017, vol. 83, No. 13, e00808-17, 13 pages, DOI: 10.1128/AEM.00808-17.

Mus, F., et al. Symbiotic Nitrogen Fixation and the Challenges to Its Extension to Nonlegumes. Appl. Environ. Microbiol., Jul. 2016, 82(13):3698-3710.

Muse, W. B., et al., "The nac (Nitrogen Assimilation Control) Gene from *Escherichia coli*," Journal of Bacteriology, Mar. 1998, vol. 180, No. 5, pp. 1166-1173.

Mutalik, V.K., et al. Quantitative estimation of activity and quality for collections of functional genetic elements. Nat. Methods 10:347-353 (2013).

Nagy, Zs. K., et al., "Nanofibrous solid dosage form of living bacteria prepared by electrospinning," eXPRESS Polymer Letters, (2014), vol. 8, No. 5, pp. 352-361, DOI: 10.3144/expresspolymlett.2014.39.

Naimov, et al. "Solubilization, activation, and insecticidal activity of Bacillus thuringiensis serovar thompsoni HD542 crystal proteins." Appl Environ Microbiol. Dec. 2008;74(23):7145-51. doi: 10.1128/AEM.00752-08.

Nassar et al. Promotion of plant growth by an auxin-producing isolate of the yeast *Williopsis saturnus* endophytic in maize (*Zea mays* L.) roots. Biology and Fertility of Soils, 2005, 42:97-108.

Nelissen, et al., Translational research: from pot to plot. Plant Biotechnology Journal 2014, 12:277-285.

Nestmann, et al. "Mutagenesis by nitrosoguanidine, ethyl methanesulfonate, and mutator gene mutH in continuous cultures of *Escherichia coli*." Mutat Res. Jun. 1975;28(3):323-30. doi: 10.1016/00275107(75)90226-2.

Newton, R. J., et al., "A Guide to the Natural History of Freshwater Lake Bacteria," Microbiology and Molecular Biology Reviews, Mar. 2011, vol. 75, No. 1, pp. 14-49, doi:10.1128/MMBR.00028-10.

Nichkawade, Anuradha. "Studies on upstream regulatory sequence of the nifLA promoter of Klebsiella pnuemoniae", Thesis submitted to the Jawaharlal Nehru University, New Delhi, for the degree of Doctor of Philosophy. 1996. 166 pages.

Nielsen, H., et al., "Extraction of EPS," Wingender et al. (eds.), Microbial Extracellular Polymeric Substances, 1999, Chapter 3, 24 pages.

Nielsen, K.M., Transgenic organisms—time for conceptual diversification? Nature Biotechnology 2003; 21: 227-228.

Nielsen, P. H. et al., "Conceptual model for production and composition of exopolymers in biofilms," Wat. Sci. Tech., vol. 36, No. 1, pp. 11-19 (1997).

Nita, P. et al., "Liquid formulations of Acetobacter diazotrophicus L1 and Herbaspirillum seropedicae J24 and their field trials on wheat," International Journal of Environmental Science, 2012, 3(3):1116-1129, DOI: 10.6088/ijes.2012030133019.

No., et al., "Ecdysone-inducible gene expression in mammalian cells and transgenic mice" Proc. Natl. Acad. Sci. USA vol. 93, Issue 8, pp. 3346-3351, Apr. 1996.

Noindorf, L., et al., "Role of PII proteins in nitrogen fixation control of Herbaspirillum seropedicae strain SmR1," BMC Microbiology 2011, vol. 11:8, pp. 1-8, http://www.biomedcentral.com/1471-2180/11/8.

Non-Final Office Action, dated Dec. 11, 2023, for U.S. Appl. No. 16/759,212, 11 pages.

Non-Final Office Action, dated Dec. 18, 2017, for U.S. Appl. No. 15/636,595 (10 pages).

Non-Final Office Action, dated Dec. 22, 2022, for U.S. Appl. No. 16/759,231 (12 total pages).

Non-Final Office Action, dated Dec. 30, 2019, for U.S. Appl. No. 15/766,122 (15 total pages).

Non-Final Office Action, dated Feb. 1, 2022, for U.S. Appl. No. 16/192,738 (8 total pages).

Non-Final Office Action, dated Jan. 10, 2020, for U.S. Appl. No. 16/192,738 (8 total pages).

Non-Final Office Action, dated Jan. 24, 2024, for U.S. Appl. No. 16/759,231, 11 pages.

Non-Final Office Action, dated Jan. 7, 2021, for U.S. Appl. No. 16/192,738 (17 total pages).

Non-Final Office Action, dated Jul. 8, 2020, for U.S. Appl. No. 15/766,122 (16 total pages).

Non-Final Office Action, dated Jul. 9, 2021, for U.S. Appl. No. 16/192,738 (8 total pages).

Non-Final Office Action, dated Jun. 21, 2023, for U.S. Appl. No. 16/759,231 (11 total pages).

Non-Final Office Action, dated Jun. 24, 2021, for U.S. Appl. No. 15/766,122 (30 total pages).

Non-Final Office Action, dated Mar. 8, 2019, for U.S. Appl. No. 16/159,542 (33 pages).

Non-Final Office Action, dated May 11, 2023, for U.S. Appl. No. 17/027,030 (30 total pages).

Non-Final Office Action, dated May 26, 2020, for U.S. Appl. No. 16/685,997 (16 total pages).

Non-Final Office Action for U.S. Appl. No. 17/255,304 dated Jul. 13, 2023, 19 pages.

Noskov, V.N. et al. Assembly of large, high G+C bacterial DNA fragments in yeast. ACS Synth. Biol. 1:267-273 (2012).

Notice of Acceptance, dated Dec. 29, 2021, for Bangladesh Application No. 113/2020 (1 total pages).

Notice of Acceptance, dated Jan. 29, 2020, for Australian Patent Application No. 2016294506 (3 total pages).

Notice of Acceptance, dated Nov. 21, 2023, for Australian Patent Application No. 2018207204, 4 pages.

Notice of Acceptance, dated Oct. 12, 2023, for Australian Patent Application No. 2022271476 (3 total pages).

Notice of Acceptance, dated Oct. 13, 2023, for Australian Patent Application No. 2018354338 (3 total pages).

Notice of Allowance, dated Apr. 10, 2023, for Japanese Patent Application No. 2020-189397 (6 total pages).

Notice of Allowance, dated Apr. 4, 2024, for U.S. Appl. No. 16/759,212, 5 pages.

Notice of Allowance, dated Apr. 5, 2023, for U.S. Appl. No. 17/148,173 (8 total pages).

(56) References Cited

OTHER PUBLICATIONS

Notice of Allowance, dated Dec. 27, 2023, for Japanese Patent Application No. 2020-524148, 6 pages.

Notice of Allowance, dated Feb. 16, 2022, for U.S. Appl. No. 15/766,122 (8 total pages).

Notice of Allowance, dated Feb. 7, 2023, for Japanese Patent Application No. 2022-068364, 6 pages.

Notice of Allowance, dated Jan. 25, 2023, for Japanese Patent Application No. 2019-537786, 8 total pages.

Notice of Allowance, dated Jan. 6, 2021, for U.S. Appl. No. 16/685,997 (12 total pages).

Notice of Allowance, dated Jul. 16, 2024, for U.S. Appl. No. 16/759,231, 10 pages.

Notice of Allowance, dated Jul. 20, 2023, for Korean Patent Application No. 10-2022-7037148 (8 total pages).

Notice of Allowance, dated Jul. 25, 2022, for Indonesian Patent Application No. PID201906965 (4 total pages).

Notice of Allowance, dated Jul. 27, 2022, for Korean Patent Application No. 10-2020-7036413 (6 total pages).

Notice of Allowance, dated Jun. 9, 2022, for U.S. Appl. No. 15/766,122 (8 total pages).

Notice of Allowance, dated Mar. 29, 2024, for U.S. Appl. No. 16/759,212, 8 pages.

Notice of Allowance, dated Mar. 30, 2018, for U.S. Appl. No. 15/636,595 (24 pages).

Notice of Allowance, dated May 28, 2024, for Korean Patent Application No. 10-2019-7023576, 9 pages.

Notice of Allowance, dated May 4, 2023, for Canadian Patent Application No. 2,838,955 (1 total pages).

Notice of Allowance, dated Oct. 16, 2020. for Japanese Patent Application No. 2018-502160 (6 total pages).

Notice of Allowance, dated Oct. 23, 2020, for U.S. Appl. No. 16/685,997 (11 total pages).

Notice of Allowance, dated Sep. 8, 2022, for U.S. Appl. No. 16/192,738 (8 total pages).

Notice of Final Rejection, mailed Dec. 21, 2023, for Japanese Patent Application No. 2020-573030, 13 pages.

Notice of Opinion, dated Sep. 27, 2023, for Korean Patent Application No. 10- 2020-7014831 (20 total pages).

Notice of Opinion, dated Sep. 28, 2023, for Korean Patent Application No. 10- 2020-7014678 (11 total pages).

Notice of Panel Decision from Pre-Appeal Brief Review, dated May 7, 2024, for U.S. Appl. No. 16/759,231, 2 pages.

Notice of Reasons for Refusal, dated Mar. 8, 2023, for Japanese Patent Application No. 2018-536712 (15 total pages).

Notice of Reasons for Rejection, dated Feb. 4, 2022, for Japanese Patent Application No. 2020-189397 (9 total pages).

Notice of Reasons for Rejection, dated Jan. 7, 2020, for Japanese Patent Application No. 2018-502160 (18 pages).

Notice of Reasons for Rejection, dated May 11, 2020, for Japanese Patent Application No. 2018-502160 (10 total pages).

Notice of Reasons for Rejection, dated May 24, 2023, for Japanese Patent Application No. 2020-573030 (12 total pages).

Notice of Reasons for Rejection, dated Nov. 21, 2022, for Japanese Patent Application No. 2020-524160 (14 total pages).

Notification of Decision to Grant or Register with Search Report, dated May 24, 2021, for ARIPO Patent Application No. AP/P/2018/010427 (6 total pages).

Notification of Decision to Grant or Register with Search Report, dated Nov. 16, 2022, for ARIPO Patent Application No. AP/P/2020/012402 (6 total pages).

Notification of Decision to Grant or Register with Search Report, dated Sep. 5, 2022, for ARIPO Patent Application No. AP/P/2020/012401 (5 total pages).

Notification of Grant of Patent for Invention, mailed Nov. 4, 2022, for Chinese Patent Application No. 201680064863.2 (4 total pages).

Notification of Non-Compliance and Search Report, dated Nov. 26, 2020, for ARIPO Patent Application No. AP/P/2018/010427 (6 total pages).

Notification of Non-Compliance with Substantive Requirements and Invitation to Submit Observations and/or Amended Application, dated Apr. 28, 2022, for ARIPO Application No. AP/P/2020/012245 (5 total pages).

Notification of Non-Compliance with Substantive Requirements and Invitation to Submit Observations and/or Amended Application with Search Report, dated Feb. 15, 2022, for ARIPO Patent Application No. AP/P/2020/012402 (5 total pages).

Notification of Non-Compliance with Substantive Requirements and Invitation to Submit Observations and/or Amended Application with Search Report, dated Feb. 8, 2022, for ARIPO Patent Application No. AP/P/2020/012401 (4 total pages).

Notification of Provisional Rejection, mailed Aug. 1, 2023, for Korean Patent Application No. 10-2020-7006825 (5 total pages).

Notification of Reasons for Refusal (1st Office Action), dated Jul. 31, 2020, for Japanese Patent Application No. 2018-536712 (9 total pages).

Notification of Reasons for Refusal (1st Office Action), dated Sep. 5, 2022, for Japanese Application No. 2021-135296, 8 pages.

Notification of Reasons for Refusal (1st Office Action from the Board of Appeal), dated Aug. 19, 2022, for Japanese Application No. 2018-536712, 18 pages.

Notification of Reasons for Refusal, dated Jun. 28, 2022, for Japanese Patent Application No. 2019-537786, 6 pages.

Notification on violation of the unity requirement, mailed Nov. 25, 2022, for Russian Application No. 2021101586 (11 pages).

O'Brien, F. J. M., et al., "Soil Salinity and pH Drive Soil Bacterial Community Composition and Diversity Along a Lateritic Slope in the Avon River Critical Zone Observatory, Western, Australia," Frontiers in Microbiology, Jul. 2019, vol. 10, Art. 1486, pp. 1-20, doi: 10.3389/fmicb.2019.01486.

Office Action and Search report for Chinese Application No. CN202080031072.6 dated Nov. 8, 2023, 18 pages.

Office Action, dated Apr. 24, 2022, for Chinese Patent Application No. 201680064863.2 (13 total pages).

Office Action, dated Apr. 8, 2024, for Japanese Patent Application No. 2021-563211, 12 pages.

Office Action, dated Aug. 1, 2024, for Japanese Patent Application No. 2023- 069005, 11 pages.

Office Action, dated Aug. 18, 2022, for Indonesia Patent Application No. P00202100102 (4 total pages).

Office Action, dated Aug. 19, 2023, for Ukraine Patent Application No. a201908538 (13 total pages).

Office Action, dated Aug. 25, 2023, for Mexican Patent Application No. MX/A/2020/001599 (20 total pages).

Office Action, dated Aug. 30, 2023, for Vietnam Application No. 1-2020-02899 (4 total pages).

Office Action, dated Dec. 1, 2023, for Brazilian Patent Application No. BR122022018729-3, 18 pages.

Office Action, dated Dec. 15, 2021, for Chinese Patent Application No. 2016800527106 (8 total pages).

Office Action, dated Dec. 27, 2023, for Korean Patent Application No. 10-2019- 7023576, 10 pages.

Office Action, dated Dec. 8, 2021, for Chinese Patent Application No. 201680064863.2 (12 total pages).

Office Action, dated Feb. 14, 2022, for Turkish Patent Application No. 2018/00432 (7 total pages).

Office Action, dated Feb. 6, 2024, for European Patent Application No. 19186353.9, 6 pages.

Office Action, dated Feb. 8, 2022, for Indian Patent Application No. 201917031229, 10 pages.

Office Action, dated Jan. 12, 2022, for Ukraine Patent Application No. a201801310 (15 total pages).

Office Action, dated Jan. 30, 2023, for Indonesian Patent Application No. P00202003665 (6 total pages).

Office Action, dated Jul. 15, 2024, for Mexican Patent Application No. MX/a/2020/012304, 6 pages.

Office Action, dated Jul. 26, 2024, for Korean Patent Application No. 10-2020-7014831, 9 pages.

Office Action, dated Jul. 30, 2024, for Mexican Patent Application No. MX/a/2020/004343, 10 pages.

Office Action, dated Jun. 27, 2023, for Korean Patent Application No. 10-2019-7023576 (11 total pages).

(56)     References Cited

OTHER PUBLICATIONS

Office Action, dated Jun. 27, 2024, for Korean Patent Application No. 10-2020-7014678, 9 pages.
Office Action, dated Jun. 10, 2021, for Russian Patent Application No. 2018105055 (11 total pages).
Office Action, dated Mar. 12, 2024, for Japanese Patent Application No. 2023-008125, 8 pages.
Office Action, dated Mar. 15, 2024, for Japanese Patent Application No. 2023-036406, 7 pages.
Office Action, dated Mar. 23, 2022, for Russian Patent Application No. 2019125282 (15 total pages).
Office Action, dated Mar. 29, 2024, for Chinese Patent Application No. 202080030837.4, 19 pages.
Office Action, dated May 10, 2024, for Korean Patent Application No. 10-2023-7036383, 10 pages.
Office Action, dated May 12, 2020, for Indonesia Patent Application No. PID201800905 (6 total pages).
Office Action, dated May 13, 2022, for Mexican Patent Application No. MX/a/2019/008285 (10 total pages).
Office Action, dated May 23, 2023, for Indonesian Patent Application No. P00202108852 (8 total pages).
Office Action, dated May 26, 2021, for Russian Patent Application No. 2019125282 (21 total pages).
Office Action, dated Nov. 11, 2022, for Russian Patent Application No. 2020116764 (6 total pages).
Office Action, dated Nov. 21, 2023, for Ukraine Patent Application No. 202001335, 18 pages.
Office Action, dated Nov. 24, 2022, for Pakistan Patent Application No. 354/2021 (1 total page).
Office Action, dated Nov. 27, 2023, for Japanese Patent Application No. 2020-524148, 11 pages.
Office Action, dated Nov. 4, 2022, for Pakistan Patent Application No. 336/2021 (1 total page).
Office Action, dated Oct. 1, 2024, for Japanese Patent Application No. 2023-137168, 7 pages.
Office Action, dated Oct. 16, 2019 for European Application No. 16854192.8, 8 pages.
Office Action, dated Oct. 24, 2022, for Japanese Application No. 2020-524148, 15 pages.
Office Action, dated Oct. 30, 2023, for Mexican Patent Application No. MX/A/2020/004344, 12 pages.
Office Action, dated Sep. 12, 2024, for Japanese Patent Application No. 2023-008125, 11 pages.
Office Action, dated Sep. 15, 2020, for Indonesia Patent Application No. PID201800905 (24 pages).
Office Action, dated Sep. 19, 2024, for Chinese Patent Application No. 202080030837.4, 12 pages.
Office Action, dated Sep. 2, 2022, for Mexican Patent Application No. MX/A/2019/008285, dated Sep. 2, 2022, 16 pages.
Office Action, dated Sep. 24, 2024, for Chinese Patent Application No. 202210708554.1, 16 pages.
Office Action, dated Sep. 27, 2023, for Vietnam Application No. 1-2020-02898 (4 total pages).
Office Action, dated Sep. 29, 2023, for Vietnam Patent Application No. 1-2019-04336 (4 total pages).
Office Action, dated Sep. 4, 2021, for Indonesian Patent Application No. PID201906965 (6 total pages).
Office Action for Australian Patent Application No. 2018354221, dated Apr. 19, 2024, 5 pages.
Office Action for Australian Patent Application No. 2018354221, dated Nov. 6, 2024, 5 pages.
Office Action for Australian Patent Application No. 2022203325, dated Jan. 24, 2024, 3 pages.
Office Action for Brazilan Patent Application No. BR112019014378-5 dated May 15, 2024, 12 pages.
Office Action for Brazilian Patent Application No. BR112018006800-4 dated Apr. 30, 2024, 27 pages.
Office Action for Brazilian Patent Application No. BR112019014378-5 dated Feb. 6, 2024, 17 pages.

Office Action for Brazilian Patent Application No. BR112020008035-7 dated Jul. 29, 2024, 7 pages.
Office Action for Brazilian Patent Application No. BR122022018729-3, dated Apr. 17, 2024, 22 pages.
Office Action for Brazilian Patent Application No. BR122022025322-9 dated Apr. 30, 2024, 29 pages.
Office Action for Brazilian Patent Application No. BR122024009210-7 dated May 21, 2024, 2 pages.
Office Action for Canadian Patent Application No. 2,991,776 dated Apr. 8, 2024, 10 pages.
Office Action for Canadian Patent Application No. 3,001,001 dated Apr. 16, 2024, 7 pages.
Office Action for Canadian Patent Application No. 3,049,258, dated Sep. 4, 2024, 4 pages.
Office Action for Canadian Patent Application No. 3,104,531, dated Oct. 24, 2024, 4 pages.
Office Action for Canadian Patent Application No. 3, 137,739 dated Aug. 15, 2024, 5 pages.
Office Action for Canadian Patent Application No. 3, 172,322, dated Jan. 11, 2024, 7 pages.
Office Action for Canadian Patent Application No. 3,172,323 dated Nov. 8, 2023, 3 pages.
Office Action for Chinese Application No. 201880081988.5, dated Jul. 26, 2023, 17 pages.
Office Action for Chinese Application No. 201880081988.5, dated Dec. 7, 2022, 9 pages.
Office Action for Chinese Application No. 201880082093.3, dated Aug. 16, 2022, 11 pages.
Office Action for Chinese Application No. 201880082093.3, dated Dec. 19, 2023, 12 pages.
Office Action for Chinese Application No. 201880082093.3, dated May 10, 2023, 8 pages.
Office Action for Chinese Application No. 201980053945.0 dated Feb. 22, 2023, 11 pages.
Office Action for Chinese Application No. 201980053945.0 dated Jun. 14, 2022, 14 pages.
Office Action for Chinese Patent Application No. 201680052710.6, dated Jun. 28, 2021, 8 pages.
Office Action for Chinese Patent Application No. 201880082093.3 dated Jun. 21, 2024, 10 pages.
Office Action for Thailand Patent Application No. 1901004319 dated Dec. 18, 2023, 7 pages.
Office Action for Thailand Patent Application No. 2001002304, dated Dec. 18, 2023, 7 pages.
Office Action, mailed Aug. 26, 2024, for Korean Patent Application No. 10-2021-7002488, 7 pages.
Office Action with Search Report, dated Dec. 3, 2020, for Chinese Patent Application No. 201680064863.2 (23 total pages).
Office Action with Search Report, dated Nov. 7, 2023, for ARIPO Patent Application No. AP/P/2021/013636, 5 pages.
Office Action with Search Report, dated Oct. 26, 2020, for Chinese Patent Application No. 201680052710.6 (15 total pages).
Office Action with Search Report, dated Sep. 15, 2023, for Paraguay Patent Application No. 1801672 (6 total pages).
Office Action with Search Report for Brazilian Patent Application No. BR112018000729-3, dated Jan. 27, 2020, 10 pages.
Office Action with Search Report for Brazilian Patent Application No. BR112020002654-9, dated May 24, 2022, 8 pages.
Office Action with Search Report for Chinese Application No. 2022107085541 dated Jan. 6, 2024, 17 pages.
Oh, et al., "Organization of nif gene cluster in Frankia sp. EulK1 strain, a symbiont of Elaeagnus umbellata," Arch Microbiol., 2012, 194:29-34.
Ohta et al., "Associative N2-fixation of Rice with Soil Microorganisms", Soil and Microorganisms 1985, 27:17-27 (English abstract only).
Ohtsuka, E. et al., "An alternative approach to deoxyoligonucleotides as hybridization probes by insertion of deoxyinosine at ambiguous codon positions," JBC, 260(5):2605-2608 (1985).
Okubo et al. Effects of Elevated Carbon Dioxide, Elevated Temperature, and Rice Growth Stage on the Community Structure of Rice Root-Associated Bacteria. Microbes Environ. 2014; 29(2):184-190. Published online May 31, 2014.doi: 10.1264/jsme2.ME14011.

(56) References Cited

OTHER PUBLICATIONS

Opposition—Statement of Grounds and Particulars, dated Aug. 18, 2022, for Australian Patent Application No. 2020203002 (29 total pages).

Orme-Johnson WH, "Molecular basis of biological nitrogen fixation", Annu Rev Biophys Biophys Chem, (1985), vol. 14, pp. 419-459.

Ortiz-Marquez, et al., "Association with an Ammonium-excreting bacterium allows diazotrophic culture of oil-rich Eukaryotic microalgae," Applied and Environmental Microbiology 2012, 78(7), pp. 2345-2352.

Ortiz-Marquez, J. C., et al., "Metabolic engineering of ammonium release for nitrogen-fixing multispecies microbial cell-factories," Metabolic Engineering 23 (2014), pp. 154-164.

Pakula, A. A., et al., "Genetic Analysis of Protein Stability and Function," Annu. Rev. Genet. 1989, 23: 289-310.

Pankievicz, V. C. S., et al., "Robust biological nitrogen fixation in a model grass-bacterial association," The Plant Journal (2015), 81, pp. 907-919, doi: 10.1111/tpj.12777.

Parker, M.W., et al.; "Pore-forming protein toxins: from structure to function," Prog Biophys Mol Biol.; 88(1):91-142; doi: 10.1016/j.pbiomolbio.2004.01.009 (2005).

Parsons, R., "Physiological Regulation of Nitrogen Fixation in Soybean Root Nodules," The Australian National University, Sep. 1989, ProQuest No. 28831644, 173 pages.

Partial Supplementary European Search Report, dated Oct. 27, 2020, for European Application No. 18739050.5, 19 pages.

Partial Supplementary European Search Report for European Patent Application No. 16825147.8, dated Mar. 4, 2019, 21 pages.

Partial Supplementary European Search Report for European Patent Application No. 19826654.6, dated Mar. 17, 2022, 11 Pages.

Partial Supplementary European Search Report in European Application No. 18843845.1, dated Apr. 12, 2021, 14 pages.

Partial Supplementary European Search Report in European Appln. No. 18870036.3, dated Aug. 19, 2021, 16 pages.

Pedrosa, F. O., et al., "Regulation of Nitrogen Fixation and Ammonium Assimilation in Associative and Endophytic Nitrogen Fixing Bacteria," Chapter 3, C. Elmerich and W. E. Newton (eds.), Associative and Endophytic Nitrogen-fixing Bacteria and Cyanobacterial Associations, pp. 41-71 (2007).

Pfleger et al., "Combinatorial engineering of intergenic regions in operons tunes expression of multiple genes"; Nature Biotechnology; 24(8):1027-1031 (2006).

Philippe N. et al., "Improvement of pCVD442, a suicide plasmid for gene allele exchange in bacteria", Plasmid, vol. 51, 2004, pp. 246-255.

Piccioli et al., "Neuroantibodies: Ectopic Expression of a Recombinant Anti-Substance P Antibody in the Central Nervous System of Transgenic Mice", Neuron, 15:373-84 (1995).

Piccioli, et al. Neuroantibodies: molecular cloning of a monoclonal antibody against substance P for expression in the central nervous system. Proc Natl Acad Sci USA. Jul. 1, 1991; 88(13): 5611-5615.

Pickens, L.B., et al., "Metabolic engineering for the production of natural products," Annu. Rev. Chem. Biomol. Eng. 2011, 2:211-236, 29 pages.

Plotnikova, et a. Pathogenesis of the human opportunistic pathogen Pseudomonas aeruginosa PA14 in *Arabidopsis*. Plant Physiol. 124, 1766-1774 (2000).

Poliner, E., et al., "Nontransgenic Marker-Free Gene Disruption by an Episomal CRISPR System in the Oleaginous Microalga, Nannochloropsis oceanica CCMP1779," ACS Synthetic. Biology, 2018, 7, pp. 962-968, published Mar. 8, 2018, DOI: 10.1021/acssynbio.7b00362.

Price, M. N., et al., "Operon formation is driven by co-regulation and not by horizontal gene transfer," Genome Research, 15, 809-819 (2005).

Price, M. N. et al. "The life-cycle of operons". PLoS Genet. Jun. 2006; 2(6):e96, 15 pages, doi: 10.1371/journal.pgen.0020096. Epub Jun. 23, 2006.

Priyanka J., et al., "Diversity Study of Nitrate Reducing Bacteria from Soil Samples—A Metagenomics Approach," Journal of Computer Science & Systems Biology 2015, vol. 8(4), pp. 191-198, DOI: 10.4172/jcsb.1000188.

Purcell, et al. "Cholesterol oxidase: a potent insecticidal protein active against boll weevil larvae." Biochem Biophys Res Commun. Nov. 15, 1993;196(3):1406-13. doi: 10.1006/bbrc.1993.2409.

Purnick PE & Weiss R (2009) The second wave of synthetic biology: from modules to systems. Nat Rev Mol Cell Biol 10(6):410-422.

Pyne, M. E., et al., "Coupling the CRISPR/Cas9 System with Lambda Red Recombineering Enables Simplified Chromosomal Gene Replacement in *Escherichia coli*," Applied and Environmental Microbiology, Aug. 2015, vol. 81, No. 15, pp. 5103-5114, doi: 10.1128/AEM.01248-15.

Qaim, M., et al.; "Yield effects of genetically modified crops in developing countries," Science; 299(5608):900-902 (2003); 10.1126/science.1080609.

Qiu, D.-Y. & Shen, B.-F., "Construction of Genetically Engineered Strains of Enterobacter Cloacae (nifL-Ac)," Acta Phytophysiologica Sinica, 25(3):269-273 (1999). English translation.

Rajput, M. S., et al., "Derepression of Mineral Phosphate Solubilization Phenotype by Insertional Inactivation of icIR in Klebsiella pneumoniae," PLoS One, Sep. 18, 2015, 10(9):e0138235, pp. 1-15, doi:10.1371/journal.pone.0138235.

Ramirez, M. D. A., et al., "Burkholderia and Paraburkholderia are Predominant Soybean Rhizobial Genera in Venezuela Soils in Different Climatic and Topographical Regions," Microbes and Environments, 2019, vol. 34, No. 1, 43-58, doi: 10:1264/jsme2. ME18076.

Ramon and Smith, "Single-step linker-based combinatorial assembly of promoter and gene cassettes for pathway engineering". Biotechnology Letters (Mar. 2011); 33(3): 549-555. Epub Nov. 24, 2010.

Ran et al., "Genome erosion in a nitrogen-fixing vertically transmitted endosymbiotic multicellular cyanobacterium", PLoS One, vol. 5, Issue 7, e11486, pp. 1-11, Jul. 2010, doi: 10.1371/journal.pone.0011486. Erratum in: PLoS One. 2010;5(9) doi: 10.1371/annotation/835c5766-5128-41c4-b636-adfe0c503103.

Resendis-Antonio et al. "Systems biology of bacterial nitrogen fixation: High-throughput technology and its integrative description with constraint-based modeling", BMC Syst Biol. 2011; 5:120. pp. 1-15.

Restriction Requirement, dated Apr. 14, 2022, for U.S. Appl. No. 16/637,565 (8 total pages).

Restriction Requirement, dated Aug. 14, 2023, for Philippines Application No. 1-2020-552234, 4 pages.

Restriction Requirement, dated Aug. 19, 2024, for U.S. Appl. No. 17/605,374, 8 pages.

Restriction Requirement, dated Jul. 17, 2023, for U.S. Appl. No. 16/759,212 (11 total pages).

Restriction Requirement, dated Mar. 30, 2023, for U.S. Appl. No. 17/255,304 (9 total pages).

Restriction Requirement, dated Nov. 21, 2023, for U.S. Appl. No. 17/027,030, 6 pages.

Reyes, I, et al., "Characteristics of phosphate solubilization by an isolate of a tropical Penicillium rugulosum and two UV-induced mutants," FEMS Microbiology Ecology 28 (1999), pp. 291-295.

Riedel et al., (1983) Nitrogen fixation by Klebsiella pneumoniae is inhibited by certain multicopy hybrid nif plasmids. J Bacterial 153(1):45-56.

Riggs, P. J., et al., "Enhance maize productivity by inoculation with diazotrophic bacteria," Australian Journal of Plant Physiology, 2001, 28, pp. 829-836.

Rivarez, M. P. S., et al., "Defense Biopriming and Antimicrobial Activity of Endophytic Bacteria and Associated *Bacillus* Species Contribute to Bacterial Crown Rot Tolerance in Papaya," bioRxiv 2019, 24 pages, doi: https://doi.org/10.1101/2019.12.22.886341.

Roberts et al. (1978) Regulation and Characterization of Protein Products Coded by the nif (Nitrogen Fixation) Genes of Kelbsiella pneumoniae. J. Bacteriol. 136(1): 267-279. (Year: 1978).

Robledo, M. et al., "Rhizobium cellulase CelC2 is essential for primary symbiotic infection of legume host roots,," Proceedings of

(56) References Cited

OTHER PUBLICATIONS the National Academy of Sciences, May 13, 2008, vol. 105, No. 19, pp. 7064-7069, doi: 10.1073/pnas.0802547105.

Robledo, M. et al., "Role of Rhizobium endoglucanase CelC2 in cellulose biosynthesis and biofilm formation on plant roots and abiotic surfaces," Microbial Cell Factories 2012, 11:125, pp. 1-12, http://www.microbialcellfactories.com/content/11/1/125.

Robson et al., Azotobacter Genomes: The Genome of Azotobacter chroococcum NCIMB 8003 (ATCC 4412). PLOS One (2015), 10 (6): e0127997. doi:10.1371/journal.pone.0127997.

Rodriguez, H. et al., "Genetics of phosphate solubilization and its potential applications for improving plant growth-promoting bacteria," Plant and Soil (2006), 287:15-21, DOI 10.1007/s11104-006-9056-9.

Rogers, et al., Synthetic biology approaches to engineering the nitrogen symbiosis in cereals. Journal of Experimental Botany, 2014; 65(8):1939-1946.

Rojas-Tapias, D. et al., "Preservation of Azotobacter chroococcum vegetative cells in dry polymers," Univ. Sci. 2015, vol. 20(2): 201-207, doi: 10.11144/Javeriana.SC20-2.pacv.

Rommens, et al. Intergeneric transfer and functional expression of the tomato disease resistance gene PTO. Plant Cell. Oct. 1995; 7(10): 1537-1544.

Roncato-Maccari, et al., Endophytic Herbaspirillum seropedicae expresses nif genes in gramineous plants. FEMS Microbiology Ecology. 2003; 45: 39-47.

Rong et al., "Promoter specificity determinants of T7 RNA polymerase," Proc. Natl. Acad. Sci. USA, 95(2):515-519 (1998).

Rosenblueth et al., Bacterial Endophytes and Their Interaction with Hosts. Mol Plant Microbe Interact. Aug. 2006;19(8):827-37.

Rosenblueth et al. Nitrogen Fixation in Cereals. Frontiers in Microbiology, vol. 9, Article 1794. (Aug. 9, 2018). 13 pages.

Rossolini et al., "Use of Deoxyinosine-Containing Primers vs Degenerate Primers for Polymerase Chain Reaction Based on Ambiguous Sequence Information" Mol. Cell. Probes 8:91-98 (1994).

Rubio, L. M. et al., "Maturation of Nitrogenase: a Biochemical Puzzle", J. Bacteriology, 2005, 187(2):405-414.

Saikia, et al., Biological nitrogen fixation with non-legumes: An achievable target or a dogma? Curr. Sci. 2007; 92(3): 317-322.

Saleh, S. S., et al., "Involvement of gacS and rpoS in enhancement of the plant growth-promoting capabilities of Enterobacter cloacae CAL2 and UW4," Canadian Journal of Microbiology (2001), 47:698-705, DOI: 10.1139/cjm-47-8-698.

Salis, et al., "Automated Design of Synthetic Ribosome Binding Sites to Precisely Control Protein Expression". Nat Biotechnol. (Oct. 2009); 27(10): 946-950. Epub Oct. 4, 2009.

Sanahuja, et al. "Bacillus thuringiensis: a century of research, development and commercial applications." Plant Biotechnol J. Apr. 2011;9(3):283-300. doi: 10.1111/j.1467-7652.2011.00595.x.

Sandoval, et al. Strategy for directing combinatorial genome engineering in *Escherichia coli*. Proc Natl Acad Sci USA. Jun. 26, 2012; 109(26):10540-5.

Sanjuan and Olivares, "Multicopy plasmids carrying the Klebsiella pneumoniae nifA gene enhance Rhizobium meliloti nodulation competitiveness on alfalfa," Molecular Plant-Microbe Interactions, 1991, 4(4):365-369.

Santi et al., Biological nitrogen fixation in non-legume plants. Annals of Botany 2013; 111: 743-767.

Sanyal, A. J., et al., "The Etiology of Hepatocellular Carcinoma and Consequences for Treatment," The Oncologist 2010, 15(Suppl 4):14-22, doi: 10.1634/theoncologist.2010-S4-14.

Schmidt-Dannert et al., Molecular breeding of carotenoid biosynthetic pathways. Nat. Biotechnol. 18:750-753 (2000).

Schmitz, et al. Iron is required to relieve inhibitory effects on NifL on transcriptional activation by NifA in Klebsiella pneumoniae. J Bacteriol. Aug. 1996; 178(15): 4679-4687.

Schouten, et al., Do cisgenic plants warrant less stringent oversight? Nature Biotechnology vol. 24, No. 7, Jul. 2006, p. 753.

Schreier, et al., "Bacillus subtilis glnR mutants defective in regulation", Gene, vol. 161, No. 1., pp. 51-56 (1995).

Schreier, H. J., et al., "Altered Regulation of the glnA Gene in Glutamine Synthetase Mutants of Bacillus subtilis," Journal of Bacteriology, Jul. 1986, vol. 167, No. 1, pp. 35-43.

Schuler, et al., "Insect-resistant transgenic plants," Trends Biotechnol., Apr. 1998, vol. 16, pp. 168-175.

Schuler, et al. "Potential side effects of insect-resistant transgenic plants on arthropod natural enemies." Trends Biotechnol. May 1999; 17(5):210-6. doi: 10.1016/S0167-7799(98)01298-0.

Science Council of Japan, New breeding technology in plants (NPBT: New Plant Breeding Techniques) current situation and issues, Aug. 26, 2014, retrieved Nov. 2, 2023, retrieved from URL https://www.scj.go.jp/ja/info/kohyo/pdf/kohyo-22-h140826.pdf, 82 pages.

Search Report, dated Nov. 4, 2020, for Chinese Patent Application No. 201680064863.2 (2 total pages).

Service, R. Genetically engineered microbes make their own fertilizer, could feed the world's poorest. Science Apr. 2017, 2 pages, doi:10.1126/science.aal1000.

Setten, L., et al., Engineering Pseudomonas protegens Pf-5 for Nitrogen Fixation and its Application to Improve Plant Growth under Nitrogen-Deficient Conditions, PLOS One, May 2013, vol. 8, No. 5, e63666, 14 pages, doi: 10.1371/journal.pone.0063666, including Correction in PLOS One, published Oct. 30, 2013, 2 pages, https://doi.org/10.1371/annotation/279fe0d7-d9b1-4d05-a45a-5ff00b4606b7.

Shahid, M., et al., "Colonization of Vigna radiata by a halotolerant bacterium Kosakonia sacchari improves the ionic balance, stressor metabolites, antioxidant status and yield under NaCl stress," Applied Soil Ecology 2021, vol. 158, 103809, 14 pages, https://doi.org/10.1016/j.apsoil.2020.103809.

Shamseldin, A., "The Role of Different Genes Involved in Symbiotic Nitrogen Fixation—Review," Global Journal of Biotechnology & Biochemistry 8(4): 84-94, 2013.

Sheety et al., Engineering BioBrick vectors from BioBrick parts, J Biol Eng 2008, 2:5, 12 pages.

Shinjo, R., et al., "Complete Genome Sequence of Kosakonia sacchari Strain BO-1, an Endophytic Diazotroph Isolated from a Sweet Potato," Genome Announcements, Sep./Oct. 2016, vol. 4, Issue 5, e00868-16, 2 pages.

Shulse, C. N., et al., "Engineered Root Bacteria Release Plant-Available Phosphate from Phytate," Applied and Environmental Microbiology, Sep. 2019, vol. 85, Issue 18, e01210-19, 11 pages, https://doi.org/10.1128/AEM.01210-19.

Sibold et al., "A nif mutant of Klebsiella pneumoniae fixing nitrogen in the presence of ammonia," FEMS Microbiology Letters 10, pp. 37-41 (1981).

Sibold et al. Constitutive expression of nitrogen fixation (nif) genes of Klebsiella pneumoniae due to a DNA duplication. EMBO J. 1982;1(12):1551-8.

Siddavattam, et al., Regulation of nif Gene expression in Enterobacter agglomerans: Nucleotide sequence of the nifLA operon and influence of temperature and ammonium on its transcription. Molecular and general genetics. Dec. 20, 1995; 249(6): 629-636.

Simon et al., (1996) Perturbation of niff expression in Klebsiella pneumoniae has limited effect on nitrogen fixation. J Bacteriol 178(10):2975-2977.

Singer, M. et al., "Genes and Genomes: A Changing Perspective", University Science Books (1998); Moscow, MIR, vol. 1, pp. 63-64 (with English machine translation), 10 total pages.

Singh, et al. An L-methionine-D, L-sulfoximine-resistant mutant of the cyanobacterium Nostoc muscorum showing inhibitor—resistant ?-glutamyl-transferase, defective glutamine synthetase and producing extracellular ammonia during N2 fixation. FEBS Letters. vol. 154, Issue 1, Apr. 5, 1983, pp. 10-14.

Sivaraman et al., "Codon choice in genes depends on flanking sequence information—implications for theoretical reverse translation," Nucleic Acids Research, vol. 36, No. 3, e16, pp. 1-8 (2008).

Sleight, S.C., & Sauro, H.M. Randomized BioBrick assembly: a novel DNA assembly method for randomizing and optimizing genetic circuits and metabolic pathways. ACS Synth. Biol., 2013, 2(9):506-518.

(56) References Cited

OTHER PUBLICATIONS

Sleight, SC et al., "Designing and engineering evolutionary robust genetic circuits", Journal of Biological Engineering, 2010, vol. 4, No. 12, pp. 1-20.

Smanski et al., "Engineered Streptomyces platensis strains that overproduce antibiotics platensimycin and platencin," Antimicrob. Agents Chemother., 2009, 53:1299-12304.

Smanski, et al., "Functional optimization of gene clusters by combinatorial design and assembly." Nature Biotechnology, Dec. 2014, vol. 32, No. 12, pp. 1241-1249, including Online Methods 3 pages, doi: 10.1038/nbt.3063. Epub Nov. 24, 2014.

Smanski et al., Synthetic biology to access and expand nature's chemical diversity. Nat Rev Microbial. Mar. 2016;14(3): 135-49, doi: 10.1038/nrmicro.2015.24.

Sorek and Cossart, Prokaryotic transcriptomics: a new view on regulation, physiology, and pathogenicity. Nat. Rev. Genet. 11:9-16 (2010).

Souza et al., "The N-Terminus of the NIFA protein of herbaspirillum seropedicae is probably involved in sensing of ammonia." In Tikhonovich et al. (Eds.) Proceedings of the 10th International Congress on Nitrogen Fixation, St. Petersburg, Russia, May 28-Jun. 3, 1995 (p. 260) Dordrecht: Kluwer.

Spiller et al. Isolation and characterization of nitrogenase-derepressed mutant strains of cyanobacterium Anabaena variabilis. J Bacterial. Feb. 1986, 165(2):412-419.

Staron et al., "The Third Pillar of Bacterial Signal Transduction: Classification of the Extracytoplasmic Function (ECF) Sigma Factor Protein Family," Mol Microbiol 14(3): 557-81 (2009).

Steenhoudt et al., "Azospirillum, a free-living nitrogen-fixing bacterium closely associated with grasses: genetic, biochemical and ecological aspects." FEMS Microbial. Rev. 2000; 24:487-506.

Stein et al. The osteocalcin gene: a model for multiple parameters of skeletal-specific transcriptional control. Mol Biol Rep. Aug. 1997;24(3):185-96.

Stemmer, "DNA shuffling by random fragmentation and reassembly: in vitro recombination for molecular evolution." Proc Natl Acad Sci U S A. Oct. 25, 1994;91(22):10747-51. doi: 10.1073/pnas. 91.22.10747.

Stemple, "Tilling—a high-throughput harvest for functional genomics." Nat Rev Genet. Feb. 2004;5(2):145-50. doi: 10.1038/nrg1273.

Stephanopoulos, G., "Challenges in engineering microbes for biofuels production," Science. Feb. 9, 2007;315(5813):801-4.

Stewart et al., (1967) In situ studies on nitrogen fixation with the acetylene reduction technique. Science, vol. 158(3800), p. 536.

Streicher, S. L., et al., "Genetic Control of Glutamine Synthetase in Klebsiella aerogenes," Journal of Bacteriology, Jan. 1975, vol. 121, No. 1, pp. 320-331.

Stucken, K., et al. The smallest known genomes of multicellular and toxic cyanobacteria: comparison, minimal gene sets for linked traits and the evolutionary implications. PLoS ONE, Feb. 2010, vol. 5, Issue 2, e9235, pp. 1-15.

Subtil, et al. Secretion of Predicted Inc Proteins of Chlamydia pneumoniae by a Heterologous Type III Machinery. Molecular Microbiology. Feb. 2001, vol. 39, No. 3; pp. 792-800.

Suh, et al., Functional expression of the FeMo-cofactor-specific biosynthetic genes nifEN as a NifE-N fusion protein synthesizing unit in Azotobacter vinelandii. Biochem. Biophys. Res. Comm. 299:233-240 (2002).

Suzuki, S, et al., "Immune-mediated motor polyneuropathy after hematopoietic stem cell transplantation," Bone Marrow Transplantation 2007, vol. 40, pp. 289-291, published online May 14, 2007, doi: 10.1038/sj.bmt.1705716.

Swain et al., "Nitrogen fixation and its improvement through genetic engineering." J. Global Biosciences, 2013, 2(5): 98-112.

Tamsir, A et al., "Robust multicellular computing using genetically encoded NOR gates and chemical wires", Nature, 2011, vol. 469, No. 7329, pp. 212-215, 9 pages, doi:10.1038/nature09565.

Tan C, "A synthetic biology challenge: making cells compute," Mol Biosyst 3: 343-353 (2007).

Tang, H., et al., "Biology of Nitrogen-fixing Organisms", Northeast Forestry University Press, First Edition, Jun. 2009, pp. 172-183, with English translation, 26 pages.

Temme et al., Modular control of multiple pathways using engineered orthogonal T7 polymerases. Nucleic Acids Res. 2012, vol. 40(17):8773-8781, Epub Jun. 28, 2012.

Temme et al., "Refactoring the nitrogen fixation gene cluster from Klebsiella oxytoca," Proc. Natl. Acad. Sci. USA, May 2012, 109(18):7085-7090.

Temme K, et al. "Induction and relaxation dynamics of the regulatory network controlling the type III secretion system encoded within Salmonella Pathogenicity Island 1," J Mol Biol 2008, 377(1):47-61, 27 pages.

Temme K. L., "Designing and Engineering Complex Behavior in Living Machines", University of California, San Francisco Dissertation. Doctor of Philosophy in Bioengineering, Electronic Thesis and Dissertation, (Oct. 1, 2011), URL: https://escholarship.org/uc/item/1r41x99s.pdf, (Nov. 28, 2014), 75 pages.

Terpolilli, J. J. et al., "What Determines the Efficiency of N2-Fixing Rhizobium-Legume Symbioses?," Advances in Microbial Physiology 2012, vol. 60, pp. 325-389, DOI: 10.1016/B978-0-12-398264-3.00005-X.

Thiel, T., et al., Characterization of genes for a second Mo-dependent nitrogenase in the cyanobacterium Anabaena variabilis. J. Bact. 179:5222-5225 (1997).

Thomas, et al. Ammonium Excretion by an L-Methionine-DL-Sulfoximine-Resistant Mutant of the Rice Field Cyanobacterium Anabaena siamensis. Appl Environ Microbiol. Nov. 1990; 56(11):3499-3504.

Tian, H., et al., "Six New Families of Aerobic Arsenate Reducing Bacteria: Leclercia, Raoultella, Kosakonia, Lelliottia, Yokenella, and Kluyvera," Geomicrobiology Journal 2019, vol. 36, No. 4, 339-347, https://doi.org/10.1080/01490451.2018.1554726.

Tijssen, P., "Overview of principles of hybridization and the strategy of nucleic acid probe assay," Part 1, Chapter 2, Hybridization with Nucleic Acid Probes, Laboratory Techniques in Biochemistry and Molecular Biology, Department for Physiological Chemistry, University of Utrecht, Utrecht, The Netherlands, vol. 24 (1993) 65 pages.

Tilman, et al. "Global food demand and the sustainable intensification of agriculture." PNAS 108:20260-20264 (2011).

Travis, B. A., et al., "Molecular dissection of the glutamine synthetase-GlnR nitrogen regulatory circuitry in Gram-positive bacteria," Nature Communications 2022, 13:3793, 15 pages, https://doi.org/10.1038.s41467-022-31573-0.

Triplett, E.W. Diazotrophic endophytes: progress and prospects for nitrogen fixation in monocots. Plant and Soil 1996; 186: 29-38.

Tritt, et al., "An Integrated Pipeline for de Novo Assembly of Microbial Genomes". Sep. 13, 2012. PLOS one. https://doi.org/10.1371/journal.pone.0042304. 9 pages.

Troisfontaines, P., et al., "Type III Secretion: More Systems Than You Think," Physiology, vol. 20, Oct. 2005, pp. 326-339, doi: 10.1152/physiol.00011.2005.

Tyler, H. L. et al., "Plants as a habitat for Beneficial and/or Human Pathogenic Bacteria," Annu. Rev. Phytopathol. 2008, 46:53-73, doi: 10/1146/annurev.phyto.011708.103102 (23 total pages).

Ueda et al., Remarkable N2-Fixing Bacterial Diversity Detected in Rice Roots by Molecular Evolutionary Analysis of nifH Gene Sequences. Journal of Bacteriology, Mar. 1995, p. 1414-1417.

Uozumi, T., et al, "Cloning and Expression of the nif A Gene of Klebsiella oxytoca in K. pneumoniae and Azospirillum lipoferum", Agricultural and Biological Chemistry, 1986, 50(6):1539-1544.

Van Dongen, S., "Performance criteria for graph clustering and Markov cluster experiments," CWI, 2000, 36 pages.

Van Heeswijk et al. "Nitrogen Assimilation in Escherichia coli: Putting Molecular Data into a Systems Perspective," Microbiology and Molecular Biology Reviews 2013, vol. 77 No. 4, p. 628-695, doi: 10.1128/MMBR.00025-13.

Vernon, et al., "Analysis of 16S rRNA gene sequences and circulating cell-free DNA from plasma of chronic fatigue syndrome and non-fatigued subjects". BMC Microbiology 2002; 2:39. pp. 1-6.

(56) References Cited

OTHER PUBLICATIONS

Vick, J. E., et al., "Optimized compatible set of BioBrickTM vectors for metabolic pathway engineering," Appl Microbiol Biotechnol (2011), 92:1275-1286, DOI 10.1007/s00253-011-3633-4.

Villa et al., Azotobacter vinelandii siderophore can provide nitrogen to support the culture of the green algae neochloris oleoabundans and scenedesmus. FEMS Microbial. Lett. 2014; 351(1): 70-77.

Villalobos, A. et al. "Gene Designer: a synthetic biology tool for constructing artificial DNA segments", BMC Bioinformatics, 2006, vol. 7:285, pp. 1-8, doi: 10.1186/1471-2105-7-285.

Voigt, C. A., "Gaining Access: Rebuilding Genetics from the Ground Up", Institute of Medicine Board on Global Health Forum on Microbial Threats, Mar. 2011, 20 pages.

Voigt et al., "Genetic parts to program bacteria", Current Opinion In Biotechnology, 2006, vol. 17, pp. 548-557, doi: 10.1016/J.COPBIO. 2006.09.001.

Wagh, J., et al., "Heterologous expression of pyrroloquinoline quinone (pqq) gene cluster confers mineral phosphate solubilization ability to Herbaspirillum seropedicae Z67," Applied Microbiology and Biotechnology (2014), 98:5117-5129, DOI 10.1007/s00253-014-5610-1.

Wang, C., et al., "*Kosakonia quasisacchari* sp. nov. recovered from human wound secretion in China," International Journal of Systemic and Evolutionary Microbiology, 2019, 69:3155-3160, DOI 10.1099/ijsem.0.003606.

Wang, C., et al., "Roles of poly-3-hydroxybutyrate (PHB) and glycogen in symbiosis of Sinorhizobium meliloti with *Medicago* sp.," Microbiology (2007), 153, pp. 388-398, DOI: 10.1099/mic.0. 29214-0.

Wang, D. et al., "Biofilm formation enables free-living nitrogen-fixing rhizobacteria to fix nitrogen under aerobic conditions," The ISME Journal 2017, vol. 11, No. 7, pp. 1602-1613, published online Mar. 24, 2017, doi: 10.1038/ismej.2017.30.

Wang et al. Ligand-inducible and liver-specific target gene expression in transgenic mice. Nat Biotechnol. Mar. 1997; 15(3):239-43.

Wang et al., Positive and negative regulation of gene expression in eukaryotic cells with an inducible transcriptional regulator. Gene Ther., 4.5 (May 1997): 432-441.

Wang, et al., "Programming cells by multiplex genome engineering and accelerated evolution". Nature (Aug. 13, 2009); 460(7257): 894-898. Epub Jul. 26, 2009, 14 pages.

Wang et al., Using Synthetic biology to distinguish and overcome regulatory and functional barriers related to nitrogen fixation. PLoS One. 2013;8(7):e68677. 11 pages.

Wang, L., et al., "A minimal nitrogen fixation gene cluster from *Paenibacillus* sp. WLY78 enables expression of active nitrogenase in *Escherichia coli*," PLoS Genetics, Oct. 2013; 9(10), e1003865, pp. 1-11, DOI: 10.1371/journal.pgen.1003865.

Wang, P., et al., "High Throughput sequencing analysis of bacterial communities in soils of a typical Poyang Lake Wetland," ACTA Ecologica Sinica, vol. 37, No. 5, Mar. 2017, pp. 1-9, DOI: 10.5846/stxb201510052000 (English Abstract).

Wang, T. et al., "Positive and negative regulation of transferred nif genes mediated by indigenous GlnR in Gram-positive Paenibacillus polymyxa," PLpS Genetics, vol. 14, No. 9, e1007629, Sep. 2018, https://doi.org/10.1371/journal.pgen.1007629 (15 total pages).

Wang, W. et al., "Screening, Identification and Growth Promotion Ability of Phosphate Solubilizing Bacteria from Soybean Rhizosphere under Maize-Soybean Intercropping Systems," bioRxiv 2020, 25 pages, doi: https://doi.org/10.1101/2020.12.15.422997.

Wang, X., et al., "Emergence of a novel mobile colistin resistance gene, mcr-8, in NDM-producing Klebsiella pneumoniae," Emerging Microbes & Infections 2018, 7:122, 10 pages, DOI 10.1038/s41426-018-0124-z.

Watanabe et al., (2006) Total biosynthesis of antitumor nonribosomal peptides in *Escherichia coli*. Nature Chemical Biology, 2:423-428.

Watanabe et al., Chapter 15. Plasmid-borne gene cluster assemblage and heterologous biosynthesis of nonribosomal peptides in *Escherichia coli*. Methods Enzymol. 2009;458:379-99. doi:10.1016/S0076-6879(09)04815-0.

Weber, et al., "A Modular Cloning System for Standardized Assembly of Multigene Constructs". PLoS One, Feb. 2011, 6(2): e16765, 11 pages, doi: 10.1371/journal.pone.0016765.

Wei, C. et al. "Endophytic nitrogen-fixing Klebsiella variicola strain DX120E promotes sugarcane growth", Biol Fertil Soils. 2014. 50:657-666.

Welch et al., "Design Parameters to Control Synthetic Gene Expression in *Escherichia coli*," PLoS One, Sep. 2009, vol. 4, Issue 9, e7002, 10 pages.

Wells, James A, "Additivity of mutational effects in proteins", Biochemistry (1990); 29(37): 8509-8517.

Wen, A., et al., "Enabling Biological Nitrogen Fixation for Cereal Crops in Fertilized Fields," ACS Synth. Biol. 2021, 10, 3264-3277, published Dec. 1, 2021, https://doi.org/10.1021/acssynbio.1c00049.

Wenzel S. C. & Muller R., Recent developments towards the heterologous expression of complex bacterial natural product biosynthetic pathways. Curr Opin Biotechnol 2005, 16(6):594-606.

Werner et al., Fast track assembly of multigene constructs using Golden Gate cloning and the MoClo system. Bioeng Bugs. Jan. 1, 2012 ;3(1):38-43, doi: 10.1371/journal.pone.0016765. Epub Jan. 1, 2012.

Widmaier, et al. Engineering the *Salmonella* type III secretion system to export spider silk monomers. Mol. Syst. Biol. 5, No. 309, pp. 1-9 (2009), doi:10.1038/msb.2009.62.

Willardson, B. M., et al., "Development and Testing of a Bacterial Biosensor for Toluene-Based Environmental Contaminants," Applied and Environmental Microbiology, Mar. 1998, vol. 64, No. 3, pp. 1006-1012.

Wimpenny, J. et al., "An overview of biofilms as functional communities," Community structure and co-operation in biofilms, 59th Symposium of the Society for General Microbiology, D.G. Allison, P. Gilbert, H.M. Lappin-Scott and M. Wilson, Eds., 2000, 28 pages.

Witkowski, A. et al., "Conversion of a β-Ketoacyl Synthase to a Malonyl Decarboxylase by Replacement of the Active-Site Cysteine with Glutamine," Biochemistry 1999, 38, pp. 11643-11650.

Woolbright, B. L, et al., "Novel insight into mechanisms of cholestatic liver injury," World Journal of Gastroenterology, Sep. 28, 2012, 18(36): 4985-4993, doi:10.3748/wjg.v18.i36.4985.

Wootton et al. Statistics of local complexity in amino acid sequences and sequence databases. Computers & Chemistry. vol. 17, Issue 2, Jun. 1993, pp. 149-163.

Written Opinion, dated, Jan. 4, 2019, for International Application No. PCT/US2018/057174, 3 pages.

Wu, et al., "Effects of different amendments on contents of phenolic acids and specific microbes in rhizo-sphere of Pseudostellaria heterophylla," Chinese Journal of Applied Ecology, Nov. 2016, 27(11): 3623-3630, DOI: 10.13287/j. 1001-9332.201611.004 (English abstract only).

Wu, et al., "Mixed Phenolic Acids Mediated Proliferation of Pathogens Talaromyces helicus and Kosakonia sacchari in Continuously Monocultured Radix pseudostellariae Rhizosphere Soil," Frontiers in Microbiology, Mar. 2016, vol. 7, Article 335, 14 pages, doi: 10.3389/fmicb.2016.00335.

Wu et al., "Root exudates from two tobacco cultivars affect colonization of Ralstonia solanacearum and the disease index," European Journal of Plant Pathology, 2014, 141(4):667-677.

Wu, H., et al., "Insights into the Mechanism of Proliferation on the Special Microbes Mediated by Phenolic Acids in the Radix pseudostellariae Rhizosphere under Continuous Monoculture Regimes," Frontiers in Plant Science, May 2017, vol. 8, Article 659, 15 pages, DOI: 10.3389/fpls.2017.00659.

Wu, H., et al., "The role of organic acids on microbial deterioration in the Radix pseudostellariae rhizosphere under continuous monoculture regimes," Scientific Reports, 7:3497, 13 pages, published online Jun. 14, 2017, doi: 10.1038/s41598-017-03793-8.

Wu, J., et al. Multivariate modular metabolic engineering of *Escherichia coli* to produce resveratrol from L-tyrosine. J. Biotechnol. (2013), 167:404-411.

Wu, S. C., et al., "Effects of biofertilizer containing N-fixer, P and K solubilizers and AM fungi on maize growth: a greenhouse trial," Geoderma 125 (2005), pp. 155-166, doi:10.1016/j.geoderma.2004. 07.003.

(56) References Cited

OTHER PUBLICATIONS

Xiao, Y., et al., "Developing a Genetically Encoded, Cross-Species Biosensor for Detecting Ammonium and Regulating Biosynthesis of Cyanophycin," ACS Synthetic Biology 2017, 6, 1807-1815, published Jul. 6, 2017, DOI: 10.1021/acssynbio.7b00069.

Xie, Z., et al., "Interaction between NifL and NifA in the nitrogen-fixing Pseudomonas stutzeri A1501," Microbiology (2006), 152, pp. 3535-3542, DOI 10.1099/mic.0.29171-0.

Xu, et al., ePathBrick: a synthetic biology platform for engineering metabolic pathways in E. coli. ACS Synth. Biol., 1:256-266 (2012).

Xu Ye et al., "Advance of Study on Nitrogenase", Journal of Biology, vol. 28, No. 4, Aug. 2011, pp. 61-64 (English abstract only).

Yan, N., et al., "Influence of salinity and water content on soil microorganisms," International Soil and Water Conservation Research 3 (2015), pp. 316-323, https://doi.org/10.1016/j.iswcr.2015.11.003.

Yan, Y., et al., "Global transcriptional analysis of nitrogen fixation and ammonium repression in root-associated Pseudomonas stutzeri A1501," Bmc Genomics 2010, 11:11, pp. 1-13, http://www.biomedcentral.com/1471-2164/11/11.

Yao et al., "Complementation analysis of heterologous nifA genes to nifA mutants of Sinorhizobium pallida," Chinese Science Bulletin, Oct. 2006, 51(19):2258-2264, 9 pages (English abstract only).

Yarza et al., "Uniting the classification of cultured and uncultured bacteria and archaea using 16S rRNA gene sequences," Nature Rev. Micro. 12:635-645 (2014).

Ye, J., et al., "Primer-BLAST: A tool to design target-specific primers for polymerase chain reaction," BMC Bioinformatics, 2012, 13: 134, 11 pages.

Yokobayashi et al, (2002) Directed evolution of a genetic circuit. Proc Natl Acad Sci USA 99(26):16587-16591.

Yoshida et al., Atmospheric dinitrogen fixation in the flooded rice rhizosphere as determined by the N-15 isotope technique. Soil Science and Plant Nutrition, Dec. 1980, 26(4):551-559.

Young, C. and Pratt-Szeliga, A., Ceres Trust. 2012. https://cerestrust.org/wp-content/uploads/NitrogenFixingBacteriaCorn.pdf, 9 pages.

Yurgel S. N. et al., "A mutant GlnD nitrogen sensor protein leads to a nitrogen-fixing but ineffective Sinorhizobium meliloti symbiosis with alfalfa," PNAS, Dec. 2, 2008, vol. 105, No. 48, pp. 18958-18963, https://doi.org/10.1073/pnas.0808048105.

Zaller, J. G., et al., "Editorial: Non-target Effects of Pesticides on Organisms Inhabiting Agroecosystems," Frontiers in Environmental Science, May 2019, vol. 7, Article 75, pp. 1-3, doi: 10.3389/fenvs.2019.00075.

Zaslaver et al., (2006) Optimal gene partition into operons correlates with gene functional order. Phys Biol 3(3): 183-189.

Zazopoulos E, et al., "A genomics-guided approach for discovering and expressing cryptic metabolic pathways," Nat Biotechnol 21(2):187-190, Feb. 2003, doi: 10.1038/nbt784.

Zehr, et al. New Nitrogen-Fixing Microorganisms Detected in Oligotrophic Oceans by Amplification of Nitrogenase (nifH) Genes. Appl Environ Microbiol. Sep. 1998; 64(9): 3444-3450.

Zehr lab NifH database, retrieved from URL https://wwwzehr.pmc.ucsc.edu/nifH_Database_Public/, Apr. 4, 2014, 1 page.

Zhang et al., Influence of different factors on the nitrogenase activity of the engineered Escherichia coli 78-7, World Journal of Microbiology and Biotechnology 31, pp. 921-927, published online Apr. 8, 2015, doi: 10.1007/s11274-015-1846-x.

Zhang et al., "Mutagenesis and functional characterization of the four domains of GlnD, a bifunctional nitrogen sensor protein," Journal of Bacteriology, Jun. 2010, 192(11):2711-2721.

Zhang, L., et al., "Expression of the N2 fixation gene operon of Paenibacillus sp. WLY78 under the control of the T7 promoter in Escherichia coli BL21," Biotechnol Lett., 2015, 37: 1999-2004, epub Jun. 9, 2015, DOI: 10.1007/s10529-015-1874-5.

Zhang, T., et al., "Involvement of the ammonium transporter AmtB in nitrogenase regulation and ammonium excretion in Pseudomonas stutzeri A1501," Research in Microbiology 163 (2012), pp. 332-339, doi:10.1016/j.resmic.2012.05.002.

Zhang, Y., et al., "GlnD Is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum," Journal of Bacteriology, Feb. 2005, 187(4), pp. 1254-1265, doi: 10.1128/JB.187.4.1254-1265.2005.

Zhang, Y., et al., "Mutagenesis and Functional Characterization of the glnB, glnA, and nifA Genes from the Photosynthetic Bacterium Rhodospirillum rubrum," Journal of Bacteriology, Feb. 2000, vol. 182, No. 4, pp. 983-992.

Zhao et al., "Evidence for nifU and nifS participation in the biosynthesis of the iron-molybdenum cofactor of nitrogenase," J. Biol. Chem., 2007, 282(51):37016-37025.

Zhao, Z., et al., "Soil bacterial community composition in rice-fish integrated farming systems with different planting years," Scientific Reports (2021), 11:10855, pp. 1-10, https://doi.org/10.1038/s41598-021-90370-9.

Zhu, B., et al., "Enterobacter sacchari sp. nov., a nitrogen-fixing bacterium associated with sugar cane (Saccharum officinarum L.)," International Journal of Systemic and Evolutionary Microbiology (2013), 63, 2577-2582, DOI 10.1099/ijs.0.045500-0.

Zhu, B., et al., "Genome Sequence of Enterobacter sp. Strain SP1, an Endophytic Nitrogen-Fixing Bacterium Isolated from Sugar-cane," J. Bacterial., Dec. 2012, vol. 194, No. 24, pp. 6963-6964, doi: 10.1128/JB.01933-12.

Zomer, A. L. (2011) PPP: Perform Promoter Prediction, retrieved from URL web.archive.org/web/20141018000631/http://bioinformatics.biol.rug.nl/websoftware/ppp/ppp_start.php, 2 pages.

Ambrosio R., et al., Competitive fitness and stability of ammonium-excreting Azotobacter vinelandii strains in the soil, Applied Microbiology and Biotechnology 2024, 108:378, pp. 1-16, Published online Jun. 18, 2024, doi: 10.1007/s00253/024-13231-1.

Ayres Sia, E., et al., "Different Relative Importances of the par Operons and the Effect of Conjugal Transfer on the Maintenance of Intact Promiscuous Plasmid RK2," Journal of Bacteriology, May 1995, vol. 177, No. 10, pp. 2789-2797.

Bageshwar, U. K., "Studies on Some Nitrogen Fixing Genes of Azotobacter Vinelandii," Thesis submitted to the Jamia Millia Islamia for the award of Degree of Doctor of Philosophy, Department of Biosciences, Faculty of Natural Sciences, Jamia Millia Islamia, New Delhi, Aug. 1994, 254 pages.

Biology 2e, OpenStax, https://openstax.org/books/biology-2e/pages/18-key-terms, retrieved Apr. 3, 2025.

Chaurasia, A. K., et al., "Improved Eco-Friendly Recombinant Anabaena sp. Strain PCC7120 with Enhanced Nitrogen Biofertilizer Potential," Applied and Environmental Microbiology, Jan. 2011, vol. 77, No. 2, pp. 395-399, doi:10.1128/AEM.01714-10.

Grant, Kyle C., "Engineering Rhizobacteria as Synthetic Biology Chassis," Thesis, University of Oxford, 2018, 372 pages.

Hearing adjournment notice, dated Feb. 25, 2025, for Indian Patent Application No. 201917031229, 3 pages.

Non-Final Office Action, dated Jan. 30, 2025, for U.S. Appl. No. 17/027,030, 38 pages.

Non-Final Office Action, dated Apr. 4, 2025, for U.S. Appl. No. 18/345,783, 58 pages.

Non-Final Office Action for U.S. Appl. No. 18/607,210 dated Apr. 9, 2025, 16 pages.

Non-Final Office Action, dated Apr. 23, 2025, for U.S. Appl. No. 17/822,740, 15 pages.

Notice of Acceptance, dated Jan. 16, 2025, for Australian Patent Application No. 2022203325, 3 pages.

Notice of Acceptance, dated Apr. 8, 2025, for Australian Patent Application No. 2018354221, 3 pages.

Notice of Allowance, dated Mar. 25, 2025, for Canadian Patent Application No. 3,080,172, 1 page.

Notice of Allowance, dated Apr. 30, 2025, for Mexican Patent Application No. MX/a/2020/014295, with English translation, 8 pages.

Notice of Allowance, dated Dec. 13, 2024, for Ukraine Patent Application No. a201908538, with English translation, 15 pages.

Notice of Allowance, dated Jan. 30, 2025, for Korean Patent Application No. 10-2023-7036383, with English translation, 8 pages.

(56)　　　　　References Cited

OTHER PUBLICATIONS

Office Action for Australian Patent Application No. 2020261427, dated Mar. 7, 2025, 6 pages.

Office Action, dated Jan. 10, 2025, for Chinese Patent Application No. 202210708554.1, with English translation, 18 pages.

Office Action, dated Jan. 21, 2025, for Japanese Patent Application No. 2021- 563211, with English translation, 6 pages.

Office Action, dated Feb. 4, 2025, for Japanese Patent Application No. 2023-171070, with English translation, 8 pages.

Office Action, dated Jan. 26, 2025, for Chinese Patent Application No. 202080030837.4, with English translation, 14 pages.

Office Action, dated Mar. 27, 2025, for Chinese Patent Application No. 202210708554.1, with English translation, 14 pages.

Office Action for Brazilian Patent Application No. BR122020010314-0 dated Feb. 11, 2025, with English translation, 10 pages.

Office Action for Brazilian Patent Application No. BR122024009210-7 dated Mar. 11, 2025, with English translation, 17 pages.

Office Action for European Application No. 19826654.6 dated Jun. 24, 2025, 7 pages.

Office Action for Mexican Patent Application No. MX/a/2020/014295 dated Feb. 4, 2025, with English translation, 28 pages.

Office Action, dated Apr. 3, 2025, for Mexican Patent Application No. MX/a/2021/012909, with English translation, 11 pages.

Peralta, H., et al., "Engineering the nifH Promoter Region and Abolishing Poly-β-Hydroxybutyrate Accumulation in Rhizobium etli Enhance Nitrogen Fixation in Symbiosis with Phaseolus vulgaris," Applied and Environmental Microbiology, Jun. 2004, vol. 70, No. 6, pp. 3272-3281.

Restriction Requirement, dated Jan. 8, 2025, for U.S. Appl. No. 17/924,916, 11 pages.

Restriction Requirement, dated Jan. 15, 2025, for U.S. Appl. No. 18/607,210, 8 pages.

Simon, H. M., et al., "Importance of cis Determinants and Nitrogenase Activity in Regulated Stability of the Klebsiella pneumoniae Nitrogenase Structural Gene mRNA," Journal of Bacteriology, Jun. 1999, vol. 181, No. 12, pp. 3751-3760.

* cited by examiner

Klebsiella variicola    Cl137

Kosakonia sacchari    Cl6

Metakosakonia intestini    Cl910

Paraburkholderia tropica    Cl8

FIG. 11

SEQUENCE LISTING

```
<160> NUMBER OF SEQ ID NOS: 46

<210> SEQ ID NO 1
<211> LENGTH: 1410
<212> TYPE: DNA
<213> ORGANISM: Klebsiella variicola

<400> SEQUENCE: 1
atgtccgctg aacacgtttt gacgatgctg aacgagcacg aagtgaagtt tgtcgatctg        60
cgcttcaccg ataccaaagg taaagaacag cacgtcacga ttccgtctca tcaggtaaat       120
gccgaattct tcgaagaagg caaaatgttt gatggctcct cgatcggtgg ctggaaaggt       180
atcaacgaat ctgacatggt cctgatgccg gacgcttcca ccgcggtcat tgacccgttc       240
tacgaagaac cgaccctgat catccgctgc gatatcctcg agccaggcac cctgcagggc       300
tatgaccgtg acccgcgctc catcgcgaaa cgcgctgaag agtacctgcg cgccaccggc       360
atcgctgaca ccgtcctgtt cgggccagaa ccagaattct tcctgttcga cgacatccgt       420
tttggcgcct ctatctccgg ctcccatgtc gcgatcgatg acatcgaagg tgcgtggaac       480
tcctccacca aatacgaagg cggtaacaaa ggtcaccgtc cgggcgtgaa agggggttac       540
ttcccggttc cgccagtaga ctcttctcag gatatccgtt ccaccatgtg tatgatcatg       600
gaagagatgg gcctggttgt tgaagctcac caccacgaag tggctaccgc aggtcagaac       660
gaagtggcaa cccgcttcaa caccatgacc aaaaaagcgg acgaaattca gatttacaaa       720
tacgttgttc acaacgtcgc tcaccgcttc ggtaaaaccg cgacctttat gccgaaacca       780
atgttcggcg ataacggctc cggcatgcac tgccatatgt ctctggcgaa aaacgggact       840
```

```
aacctgttct ccggcgacaa atacgcaggt ctgtctgagc aggcgctgtt ctacatcggc        900
ggcgtaatca aacacgctaa agctatcaac gccctggcga acccgaccac caactcctac        960
aagcgtctgg tcccgggtta cgaagcgccg gttatgctgg cttactctgc gcgtaaccgc       1020
tctgcctcca tccgtattcc ggtggtgacc tctccgaaag cgcgtcgtat cgaagtgcgc       1080
ttcccggacc cggctgccaa cccgtacctg tgctttgcgg cgctgctgat ggctggcctt       1140
gatggtatca agaacaaaat ccatccgggc gaagcaatgg acaaaaacct gtatgacctg       1200
ccgccggaag aagcgaaaga gatcccgcag gttgcaggct ctctggaaga agccctgcag       1260
gccctggatg ctgaccgcga gttcctgacg gctggcggcg tgttcaccaa tgacgctatc       1320
gatgcttaca tcgccctgcg tctggaagag aacgaccgcg tacgcatgac tccgcatccg       1380
gttgagttcg aactgtacta cagcgtctaa                                        1410
```

<210> SEQ ID NO 2
<211> LENGTH: 1410
<212> TYPE: DNA
<213> ORGANISM: Kosakonia sacchari

<400> SEQUENCE: 2

```
atgtccgctg aacacgtttt gacgatgctg aatgagcacg aagtgaagtt tgtcgatctg         60
cgcttcaccg ataccaaagg taaagaacag cacgtcacta tcccagccca tcaagtaaac        120
gctgacttct ttgaagaagg taaaatgttt gatggttctt cgattggtgg ctggaaaggc        180
atcaacgaat cagacatggt gctgatgccg gacgcgacta ccgctgtcat tgacccgttc        240
tacgaagagt ctacgctgat cattcgttgc gatatcctcg aaccaggcac catgcagggc        300
tacgatcgtg acccgcgctc catcgctaaa cgcgctgaag aatacctgcg ctccaccggt        360
ctggcagaca ccgttctgtt tgggccagag ccggaattct tcctgttcga cgacgtgcgc        420
ttcggcagct ccatttccgg ttccagcgtc gctatcgacg atatcgaagg cgcatggaac        480
acctccacca aatacgaagg tggtaacaaa ggtcaccgtc cggcagtgaa aggcggttac        540
ttcccggttc cgccggtcga ttcatcacag gatctgcgtt ccaccatgtg tctggtgatg        600
gaagagatgg gcctggttgt tgaagctcac caccacgaag tggcaacggc tggtcagaac        660
gaagtggcta cccgcttcaa caccatgacc aaaaaagcgg acgaaattca gatttacaaa        720
tacgtggtgc acaacgttgc tcaccgcttt ggtaaaaccg cgacctttat gccgaaaccg        780
atgttcggtg ataacggttc cggtatgcac tgccacatgt ctctgtccaa gaacggtacc        840
aacctgttct ctggcgacaa atacgctggc ctgtctgaaa tggcgctgta ctacattggc        900
ggcgtaatca aacacgcaaa agcgatcaac gccctgtcta acccgaccac caactcctac        960
aagcgtctgg tcccgggtta tgaagcgccg gtaatgctgg cttactctgc acgtaaccgt       1020
tctgcatcta tccgtattcc ggtagtggct tctccgaaag cgcgtcgtat cgaagtgcgc       1080
ttcccggacc cggctgctaa cccgtatctg tgcttcgcag cgctgttgat ggctggtctg       1140
gatggcatta aaaacaaaat ccacccgggc gaagcgatgg acaaaaacct gtatgacctg       1200
ccggctgaag aagcgaaaga aatcccgcag gttgcaggct ctctggaaga agcgctcaac       1260
gcgctggatg ctgaccgcga gttcctgact gctggtggcg tattcaccga cgacgctatc       1320
gatgcttaca tcgcgctgcg tatcgaagag aacgaccgtg ttcgcatgac gccgcacccg       1380
gtagagttcg aactgtacta cagcgtttaa                                        1410
```

<210> SEQ ID NO 3
<211> LENGTH: 1410

```
<212> TYPE: DNA
<213> ORGANISM: Metakosakonia intestini

<400> SEQUENCE: 3
atgtccgctg aacacgtttt gacgatgctg aacgagcacg aagtcaagtt tgttgatttg      60
cgcttcaccg acactaaagg taaagagcag cacgtcacga tcccagctca tcaggtaaat     120
gctgacttct ttgaagaagg caaaatgttt gatggctcct cgattggtgg ctggaaaggc     180
attaacgaat ctgacatggt actgatgccg dacgcctcta ccgctgtcat tgacccgttc     240
tacgaagaac cgactctgat catccgttgc gatatcctcg agccgggcac tatgcagggc     300
tacgatcgcg acccgcgctc catcgcaaaa cgcgctgaag aatacctgcg cgcaacaggc     360
atcgcagaca ccgttctgtt cgggcctgag ccagagttct tcctgttcga cgacgtacgt     420
ttcggcagct ctatttccgg ttcccacgtc gctatcgatg atatcgaagg cgcatggaac     480
tcctccacca aatacgaagg cggtaacaaa ggtcaccgtc cggctgttaa aggtggttac     540
ttcccggttc cgccagtgga ctccgcacaa gacctgcgtt ccactatgtg tctggtaatg     600
gaagagatgg gcctggttgt tgaagctcat caccacgaag ttgcaactgc tggtcagaac     660
gaagtggcaa cccgcttcaa taccatgacc aaaaaagcag acgaaattca gatctacaaa     720
tatgtggttc acaacgttgc tcaccgcttc ggtaaaaccg caacctttat gccaaaaccg     780
atgttcggtg ataacggttc cggtatgcac tgccacatgt ctctgtccaa gaacggcgta     840
aacctgttct ctggcgacaa atatgctggt ctgtctgagc aggcgctgta ctacatcggc     900
ggcgttatta aacacgctaa agcgatcaac gccctgtcca acccgactac caactcctac     960
aaacgtctgg tcccgggtta cgaagcaccg gtcatgctgg cttactctgc ccgtaaccgt    1020
tcagcttcca tccgtattcc ggtggttgca tctccgaaag cgcgtcgtat tgaagtgcgt    1080
ttcccggacc cggctgctaa cccgtacctg tgcttcgcag cgctgctgat ggctggtctt    1140
gatggcatca agaacaaaat ccatccgggc gaagcgatgg acaaaaacct gtatgacctg    1200
ccagctgaag aagcgaaaga aatcccgcag gttgcaggct ctctggaaga agcactgaac    1260
tgcctgaacg aagaccgcga gttcctgact gcgggtggcg tattcaccga cgacgcaatt    1320
gatgcttaca tcgctctgcg tatcgaagaa aacgaccgcg tacgcatgac gccgcacccg    1380
gtagagttcg agctgtacta cagcgtttaa                                     1410

<210> SEQ ID NO 4
<211> LENGTH: 1416
<212> TYPE: DNA
<213> ORGANISM: Paraburkholderia tropica

<400> SEQUENCE: 4
atgagtaaat ccgtggccga cgtcatgcaa ctcgtcaagg acgaagacgt caagtttgtc      60
gacttccgct ttaccgacac gcgcggcaag gagcaacacg tctcggttcc gctgtcgcac     120
ttcgacgaag acaagttcga gtcgggtcat gcatttgacg gttcgtcgat cgccggctgg     180
aagggcatcg aagcctcgga catgctgctc gttccggatg cgaacacggc cttcatcgac     240
ccgttctacg aagagtcgac gctggttctg acctgcgacg tggtcgagcc ggctgacggc     300
aagggctacg agcgcgaccc gcgctcgctc gccaagcgcg ctgaagcgta cctgaagagc     360
acgggcctcg cgacacggc cttcttcggt ccggaacccg aattcttcat tttcgactcg     420
gtccagtgga acacggacat gtcgggctcg ttcgtcaaga tcggctcgga agaagcaccg     480
tggtcgtcga gcaaggaatt cgaaggcggc aacacgggtc accgtccggg cgtcaagggc     540
```

-continued

```
ggctacttcc cggtcgcgcc ggtcgacacg ttccaggaca tccgttcgga aatgtgtctg      600
ctgctcgaac agatcggcat cccggtcgaa gtgcaccacc acgaagtcgc tggccagggc      660
cagaacgaaa tcggcacgaa gttctcgacg ctggttcagc gcgcggactg gacgcagcag      720
atgaagtaca tcatccataa cgtggcgcac acgtatggca agacggcgac gttcatgccg      780
aagccgatcg ttggcgacaa cggttcgggc atgcacgttc accagtcgat ctggaaggac      840
ggccagaacc tgttcgcagg caacggctac gcaggtctgt cggaattcgc gctgttctac      900
atcggcggca tcatcaagca cgctcgcgcg ctgaacgcca tcacgaaccc gtcgacgaac      960
tcgtacaagc gtctggttcc gcacttcgaa gcaccggtca agctggctta ctcggcacgc     1020
aaccgttcgg cgtcgatccg tattccgcac gtctcgaacc cgaagggtcg ccgtatcgaa     1080
acgcgcttcc cggacccgat ggccaacccg tacctgtgct tctcggcact gatgatggca     1140
ggtctggacg gcgtgcagaa caagatccat ccgggcgaag ccgccgacaa gaacctgtac     1200
gacctgccgc cggaagagga tgcaaagatc ccgaccgttt gcgccggcct cgaccaggct     1260
ctggaagcgc ttgacaagga tcgcgagttc ctgacgcgcg gtggcgtgtt cacggattcg     1320
atgatcgacg cctacctcgc actgaaggaa ggcgaactgc aacgcgtgcg catgacgacg     1380
cacccggtcg agttcgaact gtactactcg ctgtaa                              1416

<210> SEQ ID NO 5
<211> LENGTH: 2838
<212> TYPE: DNA
<213> ORGANISM: Klebsiella variicola

<400> SEQUENCE: 5
atgatgccgc tttctccgca attacagcag cactggcaga cggtcgctga ccgtctgcca       60
gcggattttc ccattgccga actgagccca caggccaggt cggtcatggc gttcagcgat      120
tttgtcgaac agagtgtgat cgcccagccg ggctggctga atgagcttgc ggactcctcg      180
ccggaggcga aagagtggcg gcattacgag gcctggctgc aggatcgcct gcaggccgtc      240
actgacgaag cggggttgat gcgagagctg cgtctcttcc gccgccagat gatggtccgc      300
atcgcctggg cgcaggcgct gtcgctggtg agcgaagaag agactctgca gcagctgagc      360
gtcctggcgg agaccctgat tgtcgccgcc cgcgactggc tgtacgccgc ctgctgtaag      420
gagtggggaa cgccatgcaa tgccgagggc cagccgcagc cgctgctgat cctcgggatg      480
ggaaagctgg cgggcggcga gctgaacttc tcttccgata tcgatctgat ctttgcctgg      540
cctgagcatg cgccacccg cggcggccgc cgcgagctgg ataacgccca gttctttacc      600
cgtctggggc agcggctgat caaggccctt gaccagccga cgcaggacgg ctttgtctat      660
cgggttgaca tgcgcctgcg gccgtttggc gacagtgggc cgctggtact cagttttgcg      720
gcgctggaag attattacca ggagcagggt cgggactggg aacgctatgc gatggtgaaa      780
gcgcggatca tgggcgataa cgacggcgtg tacgccagcg agttgcgcgc gatgctccgt      840
cctttcgtct tccgccgtta tatcgacttc agcgtgatcc agtcgctgcg taacatgaaa      900
ggcatgatcg cccgcgaagt gcggcgtcgc gggctgaaag acaacatcaa gctcggcgcc      960
ggcgggatcc gtgaaattga gtttatcgtt caggtctttc aactgatccg cggtggtcgc     1020
gaacctgcac tgcagcagcg cgccctgctg ccgacgctgg cggcgattga tgagctacat     1080
ctgctgccgg aaggcgacgc ggcgctgctg cgcgaggcct atctgttcct cgcgccggctg    1140 gaaaacctgc tgcaaagcat caacgatgag cagacccaga ccctgccgca ggatgaactt     1200
aaccgcgcca ggctggcgtg ggggatgcat accgaagact gggagacgct gagcgcgcag     1260
```

-continued

```
ctggcgagcc agatggccaa cgtgcggcga gtgtttaatg aactgatcgg cgatgatgag      1320
gatcagtccc cggatgagca actggccgag tactggcgcg agctgtggca ggatgcgctg      1380
gaagaagatg acgccagccc ggcgctggcg catttaaacg ataccgaccg ccgtagcgtg      1440
ctggcgctga ttgccgattt tcgtaaagag ctggatcggc gcaccatcgg cccgcgcggc      1500
cgccaggtgc tggatcagct gatgccgcat ctgctgagcg aaatctgctc gcgcgccgat      1560
gcgccgctgc ctctggcgcg gatcacgccg ctgttgaccg ggatcgtcac ccgtaccacc      1620
tatcttgagc tgctgagcga attccccggc gcgctgaagc acctgatcac gctctgcgcg      1680
gcgtcgccga tggtcgccag ccagctggcg cgccacccgc tgctgctgga tgagctgctg      1740
gatcccaaca ccctctatca gccgacggcg accgatgcct atcgcgacga gctgcgccag      1800
tacctgctgc gcgtgccgga agaggatgaa gagcagcagc tggaggcgtt gcgccagttt      1860
aagcaggcgc agcagctgca tatcgcggcg gcggatatcg ctggtaccct gccggtgatg      1920
aaggtcagcg atcacttaac ctggcttgcc gaagcgatcc tcgacgcggt ggtgcagcag      1980
gcatgggggc agatggtcgc tcgctacggc cagccgaccc acctgcacga tcgccagggt      2040
cgcggcttcg ccgtcgtcgg ctacggtaag cttggcggct gggagctggg ctacagctcc      2100
gatctcgatc tggtgttcct ccatgactgc ccggcggagg tgatgaccga cggcgagcgg      2160
gagattgacg gccgtcagtt ctacctgcgg ctggcccagc ggatcatgca cctgttcagc      2220
acccgcacct cgtccggtat tctctacgaa gtggacgccc ggctgcgtcc ttctggcgcg      2280
gcggggatgc tggtcaccac cgccgacgcg tttgctgact atcagcagaa cgaagcctgg      2340
acgtgggaac atcaggcgct ggtgcgcgcc cgcgtggtct atggcgaccc ggcgctgcag      2400
gcgcgctttg acgccattcg tcgcgatatc ctgaccaccc cgcgggaggg gatgaccctg      2460
cagaccgagg ttcgcgagat gcgcgagaag atgcgcgccc accttggcaa caaacatccc      2520
gatcgttttg atatcaaagc cgatgccggc gggatcaccg atattgaatt tattactcag      2580
tatctggtcc tacgctatgc cagtgacaag ccgaagctga cccgctggtc tgacaacgtg      2640
cgtattcttg agctgctggc gcagaacgac atcatggacg aggaggaggc gcgcgcctta      2700
acgcatgcgt acaccaccct tgcgtgatgcg ctccatcacc tggccctgca ggagcagccg      2760
ggacacgtgg cgccagaggc cttcagccgg gagcgtcagc aggtcagcgc cagctggcag      2820
aagtggctga tggcttaa                                                    2838
```

<210> SEQ ID NO 6
<211> LENGTH: 1410
<212> TYPE: DNA
<213> ORGANISM: Klebsiella variicola

<400> SEQUENCE: 6

```
atgtccgctg aacacgtttt gacgatgctg aacgagcacg aagtgaagtt tgtcgatctg        60
cgcttcaccg ataccaaagg taaagaacag cacgtcacga ttccgtctca tcaggtaaat       120
gccgaattct tcgaagaagg caaaatgttt gatggctcct cgatcggtgg ctggaaaggt       180
atcaacgaat ctgacatagt cctgatgccg gacgcttcca ccgcggtcat tgacccgttc       240
tacgaagaac cgaccctgat catccgctgc gatatcctcg agccaggcac cctgcagggc       300
tatgaccgtg acccgcgctc catcgcgaaa cgcgctgaag agtacctgcg cgccaccggc       360
atcgctgaca ccgtcctgtt cgggccagaa ccagaattct tcctgttcga cgacatccgt       420
tttggcgcct ctatctccgg ctcccatgtc gcgatcgatg acatcgaagg tgcgtggaac       480
```
tcctccacca aatacgaagg cggtaacaaa ggtcaccgtc cgggcgtgaa agggggttac          540
ttcccggttc cgccagtaga ctcttctcag gatatccgtt ccaccatgtg tatgatcatg          600
gaagagatgg gcctggttgt tgaagctcac caccacgaag tggctaccgc aggtcagaac          660
gaagtggcaa cccgcttcaa caccatgacc aaaaaagcgg acgaaattca gatttacaaa          720
tacgttgttc acaacgtcgc tcaccgcttc ggtaaaaccg cgacctttat gccgaaacca          780
atgttcggcg ataacggctc cggcatgcac tgccatatgt ctctggcgaa aaacgggact          840
aacctgttct ccggcgacaa atacgcaggt ctgtctgagc aggcgctgtt ctacatcggc          900
ggcgtaatca aacacgctaa agctatcaac gccctggcga acccgaccac caactcctac          960
aagcgtctgg tcccgggtta cgaagcgccg gttatgctgg cttactctgc gcgtaaccgc         1020
tctgcctcca tccgtattcc ggtggtgacc tctccgaaag cgcgtcgtat cgaagtgcgc         1080
ttcccggacc cggctgccaa cccgtacctg tgctttgcgg cgctgctgat ggctggcctt         1140
gatggtatca agaacaaaat ccatccgggc gaagcaatgg acaaaaacct gtatgacctg         1200
ccgccggaag aagcgaaaga gatcccgcag gttgcaggct ctctggaaga gcccctgcag         1260
gccctggatg ctgaccgcga gttcctgacg gctggcggcg tgttcaccaa tgacgctatc         1320
gatgcttaca tcgccctgcg tctggaagag aacgaccgcg tacgcatgac tccgcatccg         1380
gttgagttcg aactgtacta cagcgtctaa                                          1410

<210> SEQ ID NO 7
<211> LENGTH: 1410
<212> TYPE: DNA
<213> ORGANISM: Klebsiella variicola

<400> SEQUENCE: 7
atgtccgctg aacacgtttt gacgatgctg aacgagcacg aagtgaagtt tgtcgatctg           60
cgcttcaccg ataccaaagg taaagaacag cacgtcacga ttccgtctca tcaggtaaat          120
gccgaattct tcgaagaagg caaaatgttt gatggctcct cgatcggtgg ctggaaaggt          180
atcaacgaat ctgacgtggt cctgatgccg gacgcttcca ccgcggtcat tgacccgttc          240
tacgaagaac cgaccctgat catccgctgc gatatcctcg agccaggcac cctgcagggc          300
tatgaccgtg acccgcgctc catcgcgaaa cgcgctgaag agtacctgcg cgccaccggc          360
atcgctgaca ccgtcctgtt cgggccagaa ccagaattct tcctgttcga cgacatccgt          420
tttggcgcct ctatctccgg ctcccatgtc gcgatcgatg acatcgaagg tgcgtggaac          480
tcctccacca aatacgaagg cggtaacaaa ggtcaccgtc cgggcgtgaa agggggttac          540
ttcccggttc cgccagtaga ctcttctcag gatatccgtt ccaccatgtg tatgatcatg          600
gaagagatgg gcctggttgt tgaagctcac caccacgaag tggctaccgc aggtcagaac          660
gaagtggcaa cccgcttcaa caccatgacc aaaaaagcgg acgaaattca gatttacaaa          720
tacgttgttc acaacgtcgc tcaccgcttc ggtaaaaccg cgacctttat gccgaaacca          780
atgttcggcg ataacggctc cggcatgcac tgccatatgt ctctggcgaa aaacgggact          840
aacctgttct ccggcgacaa atacgcaggt ctgtctgagc aggcgctgtt ctacatcggc          900
ggcgtaatca aacacgctaa agctatcaac gccctggcga acccgaccac caactcctac          960
aagcgtctgg tcccgggtta cgaagcgccg gttatgctgg cttactctgc gcgtaaccgc         1020
tctgcctcca tccgtattcc ggtggtgacc tctccgaaag cgcgtcgtat cgaagtgcgc         1080
ttcccggacc cggctgccaa cccgtacctg tgctttgcgg cgctgctgat ggctggcctt         1140
gatggtatca agaacaaaat ccatccgggc gaagcaatgg acaaaaacct gtatgacctg         1200

-continued

```
ccgccggaag aagcgaaaga gatcccgcag gttgcaggct ctctggaaga agccctgcag        1260
gccctggatg ctgaccgcga gttcctgacg gctggcggcg tgttcaccaa tgacgctatc        1320
gatgcttaca tcgccctgcg tctggaagag aacgaccgcg tacgcatgac tccgcatccg        1380
gttgagttcg aactgtacta cagcgtctaa                                        1410

<210> SEQ ID NO 8
<211> LENGTH: 1410
<212> TYPE: DNA
<213> ORGANISM: Klebsiella variicola

<400> SEQUENCE: 8
atgtccgctg aacacgtttt gacgatgctg aacgagcacg aagtgaagtt tgtcgatctg         60
cgcttcaccg ataccaaagg taaagaacag cacgtcacga ttccgtctca tcaggtaaat        120
gccgaattct tcgaagaagg caaaatgttt gatggctcct cgatcggtgg ctggaaaggt        180
atcaacgaat ctgacatggt cctgatgccg gacgcttcca ccgcggtcat tgacccgttc        240
tacgaagaac cgaccctgat catccgctgc gatatcctcg agccaggcac cctgcagggc        300
tatgaccgtg acccgcgctc catcgcgaaa cgcgctgaag agtacctgcg cgccaccggc        360
atcgctgaca ccgtcctgtt cgggccagaa ccagaattct tcctgttcga cgacatccgt        420
tttggcgcct ctatctccgg ctcccatgtc gcgatcgatg acatcgaatg tgcgtggaac        480
tcctccacca aatacgaagg cggtaacaaa ggtcaccgtc cgggcgtgaa aggggggttac        540 ttcccggttc cgccagtaga ctcttctcag gatatccgtt ccaccatgtg tatgatcatg        600
gaagagatgg gcctggttgt tgaagctcac caccacgaag tggctaccgc aggtcagaac        660
gaagtggcaa cccgcttcaa caccatgacc aaaaaagcgg acgaaattca gatttacaaa        720
tacgttgttc acaacgtcgc tcaccgcttc ggtaaaaccg cgacctttat gccgaaacca        780
atgttcggcg ataacggctc cggcatgcac tgccatatgt ctctggcgaa aaacgggact        840
aacctgttct ccggcgacaa atacgcaggt ctgtctgagc aggcgctgtt ctacatcggc        900
ggcgtaatca aacacgctaa agctatcaac gccctggcga acccgaccac caactcctac        960
aagcgtctgg tcccgggtta cgaagcgccg gttatgctgg cttactctgc gcgtaaccgc       1020
tctgcctcca tccgtattcc ggtggtgacc tctccgaaag cgcgtcgtat cgaagtgcgc       1080
ttcccggacc cggctgccaa cccgtacctg tgctttgcgg cgctgctgat ggctggcctt       1140
gatggtatca agaacaaaat ccatccgggc gaagcaatgg acaaaaacct gtatgacctg       1200
ccgccggaag aagcgaaaga gatcccgcag gttgcaggct ctctggaaga agccctgcag       1260
gccctggatg ctgaccgcga gttcctgacg gctggcggcg tgttcaccaa tgacgctatc       1320
gatgcttaca tcgccctgcg tctggaagag aacgaccgcg tacgcatgac tccgcatccg       1380
gttgagttcg aactgtacta cagcgtctaa                                       1410

<210> SEQ ID NO 9
<211> LENGTH: 1410
<212> TYPE: DNA
<213> ORGANISM: Klebsiella variicola

<400> SEQUENCE: 9
atgtccgctg aacacgtttt gacgatgctg aacgagcacg aagtgaagtt tgtcgatctg         60
cgcttcaccg ataccaaagg taaagaacag cacgtcacga ttccgtctca tcaggtaaat        120
gccgaattct tcgaagaagg caaaatgttt gatggctcct cgatcggtgg ctggaaaggt        180
```

```
atcaacgaat ctgacatggt cctgatgccg gacgcttcca ccgcggtcat tgacccgttc      240
tacgaagaac cgaccctgat catccgctgc gatatcctcg agccaggcac cctgcagggc      300
tatgaccgtg acccgcgctc catcgcgaaa cgcgctgaag agtacctgcg cgccaccggc      360
atcgctgaca ccgtcctgtt cgggccagaa ccagaattct tcctgttcga cgacatccgt      420
tttggcgcct ctatctccgg ctcccatgtc gcgatcgatg acatcgaagg tgcgtggaac      480
tcctccacca aatacgaagg cggtaacaaa ggtcaccgtc tgggcgtgaa aggggggttac      540 ttcccggttc cgccagtaga ctcttctcag gatatccgtt ccaccatgtg tatgatcatg      600
gaagagatgg gcctggttgt tgaagctcac caccacgaag tggctaccgc aggtcagaac      660
gaagtggcaa cccgcttcaa caccatgacc aaaaaagcgg acgaaattca gatttacaaa      720
tacgttgttc acaacgtcgc tcaccgcttc ggtaaaaccg cgacctttat gccgaaacca      780
atgttcggcg ataacggctc cggcatgcac tgccatatgt ctctggcgaa aaacgggact      840
aacctgttct ccggcgacaa atacgcaggt ctgtctgagc aggcgctgtt ctacatcggc      900
ggcgtaatca aacacgctaa agctatcaac gccctggcga acccgaccac caactcctac      960
aagcgtctgg tcccgggtta cgaagcgccg gttatgctgg cttactctgc gcgtaaccgc     1020
tctgcctcca tccgtattcc ggtggtgacc tctccgaaag cgcgtcgtat cgaagtgcgc     1080
ttcccggacc cggctgccaa cccgtacctg tgctttgcgg cgctgctgat ggctggcctt     1140
gatggtatca agaacaaaat ccatccgggc gaagcaatgg acaaaaacct gtatgacctg     1200
ccgccggaag aagcgaaaga gatcccgcag gttgcaggct ctctggaaga agccctgcag     1260
gccctggatg ctgaccgcga gttcctgacg gctggcggcg tgttcaccaa tgacgctatc     1320
gatgcttaca tcgccctgcg tctggaagag aacgaccgcg tacgcatgac tccgcatccg     1380
gttgagttcg aactgtacta cagcgtctaa                                       1410

<210> SEQ ID NO 10
<211> LENGTH: 1410
<212> TYPE: DNA
<213> ORGANISM: Klebsiella variicola

<400> SEQUENCE: 10
atgtccgctg aacacgtttt gacgatgctg aacgagcacg aagtgaagtt tgtcgatctg       60
cgcttcaccg ataccaaagg taaagaacag cacgtcacga ttccgtctca tcaggtaaat      120
gccgaattct tcgaagaagg caaaatgttt gatggctcct cgatcggtgg ctggaaaggt      180
atcaacgaat ctgacatggt cctgatgccg gacgcttcca ccgcggtcat tgacccgttc      240
tacgaagaac cgaccctgat catccgctgc gatatcctcg agccaggcac cctgcagggc      300
tatgaccgtg acccgcgctc catcgcgaaa cgcgctgaag agtacctgcg cgccaccggc      360
atcgctgaca ccgtcctgtt cgggccagaa ccagaattct tcctgttcga cgacatccgt      420
tttggcgcct ctatctccgg ctcccatgtc gcgatcgatg acatcgaagg tgcgtggaac      480
tcctccacca aatacgaagg cggtaacaaa ggtcaccgtc cgggcgtgaa aggggggttac      540 ttcccggttc cgccagtaga ctcttttcag gatatccgtt ccaccatgtg tatgatcatg      600
gaagagatgg gcctggttgt tgaagctcac caccacgaag tggctaccgc aggtcagaac      660
gaagtggcaa cccgcttcaa caccatgacc aaaaaagcgg acgaaattca gatttacaaa      720
tacgttgttc acaacgtcgc tcaccgcttc ggtaaaaccg cgacctttat gccgaaacca      780
atgttcggcg ataacggctc cggcatgcac tgccatatgt ctctggcgaa aaacgggact      840
aacctgttct ccggcgacaa atacgcaggt ctgtctgagc aggcgctgtt ctacatcggc      900
```

-continued

```
ggcgtaatca aacacgctaa agctatcaac gccctggcga acccgaccac caactcctac      960
aagcgtctgg tcccgggtta cgaagcgccg gttatgctgg cttactctgc gcgtaaccgc     1020
tctgcctcca tccgtattcc ggtggtgacc tctccgaaag cgcgtcgtat cgaagtgcgc     1080
ttcccggacc cggctgccaa cccgtacctg tgctttgcgg cgctgctgat ggctggcctt     1140
gatggtatca agaacaaaat ccatccgggc gaagcaatgg acaaaaacct gtatgacctg     1200
ccgccggaag aagcgaaaga gatcccgcag gttgcaggct ctctggaaga agccctgcag     1260
gccctggatg ctgaccgcga gttcctgacg gctggcggcg tgttcaccaa tgacgctatc     1320
gatgcttaca tcgccctgcg tctggaagag aacgaccgcg tacgcatgac tccgcatccg     1380
gttgagttcg aactgtacta cagcgtctaa                                      1410
```

```
<210> SEQ ID NO 11
<211> LENGTH: 1410
<212> TYPE: DNA
<213> ORGANISM: Klebsiella variicola

<400> SEQUENCE: 11
```

```
atgtccgctg aacacgtttt gacgatgctg aacgagcacg aagtgaagtt tgtcgatctg       60
cgcttcaccg ataccaaagg taaagaacag cacgtcacga ttccgtctca tcaggtaaat      120
gccgaattct tcgaagaagg caaaatgttt gatggctcct cgatcggtgg ctggaaaggt      180
atcaacgaat ctgacatggt cctgatgccg gacgcttcca ccgcggtcat tgacccgttc      240
tacgaagaac cgaccctgat catccgctgc gatatcctcg agccaggcac cctgcagggc      300
tatgaccgtg acccgcgctc catcgcgaaa cgcgctgaag agtacctgcg cgccaccggc      360
atcgctgaca ccgtcctgtt cgggccagaa ccagaattct tcctgttcga cgacatccgt      420
tttggcgcct ctatctccgg ctcccatgtc gcgatcgatg acatcgaagg tgcgtggaac      480
tcctccacca aatacgaagg cggtaacaaa ggtcaccgtc cgggcgtgaa agggggttac      540
ttcccggttc cgccagtaga ctcttctcag gatatccgtt ccaccatgtg tatgatcatg      600
gaagagatgg gcctggttgt taaagctcac caccacgaag tggctaccgc aggtcagaac      660
gaagtggcaa cccgcttcaa caccatgacc aaaaaagcgg acgaaattca gatttacaaa      720
tacgttgttc acaacgtcgc tcaccgcttc ggtaaaaccg cgacctttat gccgaaacca      780
atgttcggcg ataacggctc cggcatgcac tgccatatgt ctctggcgaa aaacgggact      840
aacctgttct ccggcgacaa atacgcaggt ctgtctgagc aggcgctgtt ctacatcggc      900
ggcgtaatca aacacgctaa agctatcaac gccctggcga acccgaccac caactcctac      960
aagcgtctgg tcccgggtta cgaagcgccg gttatgctgg cttactctgc gcgtaaccgc     1020
tctgcctcca tccgtattcc ggtggtgacc tctccgaaag cgcgtcgtat cgaagtgcgc     1080
ttcccggacc cggctgccaa cccgtacctg tgctttgcgg cgctgctgat ggctggcctt     1140
gatggtatca agaacaaaat ccatccgggc gaagcaatgg acaaaaacct gtatgacctg     1200
ccgccggaag aagcgaaaga gatcccgcag gttgcaggct ctctggaaga agccctgcag     1260
gccctggatg ctgaccgcga gttcctgacg gctggcggcg tgttcaccaa tgacgctatc     1320
gatgcttaca tcgccctgcg tctggaagag aacgaccgcg tacgcatgac tccgcatccg     1380
gttgagttcg aactgtacta cagcgtctaa                                      1410
```

```
<210> SEQ ID NO 12
<211> LENGTH: 1410
<212> TYPE: DNA
```

<213> ORGANISM: Klebsiella variicola

<400> SEQUENCE: 12

```
atgtccgctg aacacgtttt gacgatgctg aacgagcacg aagtgaagtt tgtcgatctg        60
cgcttcaccg ataccaaagg taaagaacag cacgtcacga ttccgtctca tcaggtaaat       120
gccgaattct tcgaagaagg caaaatgttt gatggctcct cgatcggtgg ctggaaaggt       180
atcaacgaat ctgacatggt cctgatgccg gacgcttcca ccgcggtcat tgacccgttc       240
tacgaagaac cgaccctgat catccgctgc gatatcctcg agccaggcac cctgcagggc       300
tatgaccgtg acccgcgctc catcgcgaaa cgcgctgaag agtacctgcg cgccaccggc       360
atcgctgaca ccgtcctgtt cgggccagaa ccagaattct tcctgttcga cgacatccgt       420
tttggcgcct ctatctccgg ctcccatgtc gcgatcgatg acatcgaagg tgcgtggaac       480
tcctccacca aatacgaagg cggtaacaaa ggtcaccgtc cgggcgtgaa aggggggttac       540 ttcccggttc cgccagtaga ctcttctcag gatatccgtt ccaccatgtg tatgatcatg       600
gaagagatgg gcctggttgt tgaagctcac caccacgaag tggctaccgc aggtcagaac       660
gaagtggcaa cccgcttcaa caccatgacc aaaaaagcgg acgaaattca gatttacaaa       720
tacgttgttc acaacgtcgc tcaccgcttc ggtaaaaccg cgacctttat gccgaaacca       780
atgttcggcg ataacggctc cagcatgcac tgccatatgt ctctggcgaa aaacgggact       840
aacctgttct ccggcgacaa atacgcaggt ctgtctgagc aggcgctgtt ctacatcggc       900
ggcgtaatca aacacgctaa agctatcaac gccctggcga acccgaccac caactcctac       960
aagcgtctgg tcccggggtta cgaagcgccg gttatgctgg cttactctgc gcgtaaccgc      1020
tctgcctcca tccgtattcc ggtggtgacc tctccgaaag cgcgtcgtat cgaagtgcgc      1080
ttcccggacc cggctgccaa cccgtacctg tgctttgcgg cgctgctgat ggctggcctt      1140
gatggtatca agaacaaaat ccatccgggc gaagcaatgg acaaaaacct gtatgacctg      1200
ccgccggaag aagcgaaaga gatcccgcag gttgcaggct ctctggaaga gccctgcag      1260 gccctggatg ctgaccgcga gttcctgacg gctggcggcg tgttcaccaa tgacgctatc      1320
gatgcttaca tcgccctgcg tctggaagag aacgaccgcg tacgcatgac tccgcatccg      1380
gttgagttcg aactgtacta cagcgtctaa                                       1410
```

<210> SEQ ID NO 13
<211> LENGTH: 1410
<212> TYPE: DNA
<213> ORGANISM: Klebsiella variicola

<400> SEQUENCE: 13

```
atgtccgctg aacacgtttt gacgatgctg aacgagcacg aagtgaagtt tgtcgatctg        60
cgcttcaccg ataccaaagg taaagaacag cacgtcacga ttccgtctca tcaggtaaat       120
gccgaattct tcgaagaagg caaaatgttt gatggctcct cgatcggtgg ctggaaaggt       180
atcaacgaat ctgacatggt cctgatgccg gacgcttcca ccgcggtcat tgacccgttc       240
tacgaagaac cgaccctgat catccgctgc gatatcctcg agccaggcac cctgcagggc       300
tatgaccgtg acccgcgctc catcgcgaaa cgcgctgaag agtacctgcg cgccaccggc       360
atcgctgaca ccgtcctgtt cgggccagaa ccagaattct tcctgttcga cgacatccgt       420
tttggcgcct ctatctccgg ctcccatgtc gcgatcgatg acatcgaagg tgcgtggaac       480
tcctccacca aatacgaagg cggtaacaaa ggtcaccgtc cgggcgtgaa aggggggttac       540 ttcccggttc cgccagtaga ctcttctcag gatatccgtt ccaccatgtg tatgatcatg       600
```

```
gaagagatgg gcctggttgt tgaagctcac caccacgaag tggctaccgc aggtcagaac      660
gaagtggcaa cccgcttcaa caccatgacc aaaaaagcgg acgaaattca gatttacaaa      720
tacgttgttc acaacgtcgc tcaccgcttc ggtaaaaccg cgacctttat gccgaaacca      780
atgttcggcg ataacggctc cggcatgcac tgccatatgt ctctggcgaa aaacgggact      840
aacctgttct ccggcgacaa atacgcaggt ctgtctgagc aggcgctgtt ctacatcggc      900
ggcgtaatca aacacgctaa agctatcaac gccctggcga acccgaccac caactcctac      960
aagcgtctgg tcccgggtta cgaagcgccg gttatgctgg cttactctgc gcgtgaccgc     1020
tctgcctcca tccgtattcc ggtggtgacc tctccgaaag cgcgtcgtat cgaagtgcgc     1080
ttcccggacc cggctgccaa cccgtacctg tgctttgcgg cgctgctgat ggctggcctt     1140
gatggtatca agaacaaaat ccatccgggc gaagcaatgg acaaaaacct gtatgacctg     1200
ccgccggaag aagcgaaaga gatcccgcag gttgcaggct ctctggaaga agccctgcag     1260
gccctggatg ctgaccgcga gttcctgacg gctggcggcg tgttcaccaa tgacgctatc     1320
gatgcttaca tcgccctgcg tctggaagag aacgaccgcg tacgcatgac tccgcatccg     1380
gttgagttcg aactgtacta cagcgtctaa                                      1410

<210> SEQ ID NO 14
<211> LENGTH: 2838
<212> TYPE: DNA
<213> ORGANISM: Klebsiella variicola

<400> SEQUENCE: 14
atgatgccgc tttctccgca attacagcag cactggcaga cggtcgctga ccgtctgcca       60
gcggattttc ccattgccga actgagccca caggccaggt cggtcatggc gttcagcgat      120
tttgtcgaac agagtgtgat cgcccagccg ggctggctga atgagcttgc ggactcctcg      180
ccggaggcgg aagagtggcg gcattacgag gcctggctgc aggatcgcct gcaggccgtc      240
actgacgaag cggggttgat gcgagagctg cgtctcttcc gccgccagat gatggtccgc      300
atcgcctggg cgcaggcgct gtcgctggtg agcgaagaag agactctgca gcagctgagc      360
gtcctggcgg agaccctgat tgtcgccgcc cgcgactggc tgtacgccgc ctgctgtaag      420 gagtgggga  cgccatgcaa tgccgagggc cagccgcagc cgctgctgat cctcgggatg      480
ggaaagctgg gcggcggcga gctgaacttc tcttccgata tcgatctgat ctttgcctgg      540
cctgagcatg cgccaccccg cggcggccgc cgcgagctgg ataacgccca gttctttacc      600 cgtctgggc  agcggctgat caaggccctt gaccagccga cgcaggacgg ctttgtctat      660
cgggttgaca tgcgcctgcg gccgtttggc gacagtgggc cgctggtact cagtttttgcg      720 gcgctggaag attattacca ggagcagggt cgggactggg aacgctatgc gatggtgaaa      780
gcgcggatca tgggcgataa cgacggcgtg tacgccagcg agttgcgcgc gatgctccgt      840
cctttcgtct tccgccgtta tatcgacttc agcgtgatcc agtcgctgcg taacatgaaa      900
ggcatgatcg cccgcgaagt gcggcgtcgc gggctgaaag acaacatcaa gctcggcgcc      960
ggcgagatcc gtgaaattga gtttatcgtt caggtctttc aactgatccg cggtggtcgc     1020
gaacctgcac tgcagcagcg cgccctgctg ccgacgctgg cggcgattga tgagctacat     1080
ctgctgccgg aaggcgacgc ggcgctgctg cgcgaggcct atctgttcct gcgccggctg     1140
gaaaacctgc tgcaaagcat caacgatgag cagacccaga ccctgccgca ggatgaactt     1200
aaccgcgcca ggctggcgtg ggggatgcat accgaagact gggagacgct gagcgcgcag     1260
```

-continued

```
ctggcgagcc agatggccaa cgtgcggcga gtgtttaatg aactgatcgg cgatgatgag      1320
gatcagtccc cggatgagca actggccgag tactggcgcg agctgtggca ggatgcgctg      1380
gaagaagatg acgccagccc ggcgctggcg catttaaacg ataccgaccg ccgtagcgtg      1440
ctggcgctga ttgccgattt tcgtaaagag ctggatcggc gcaccatcgg cccgcgcggc      1500
cgccaggtgc tggatcagct gatgccgcat ctgctgagcg aaatctgctc gcgcgccgat      1560
gcgccgctgc ctctggcgcg gatcacgccg ctgttgaccg ggatcgtcac ccgtaccacc      1620
tatcttgagc tgctgagcga attccccggc gcgctgaagc acctgatcac gctctgcgcg      1680
gcgtcgccga tggtcgccag ccagctggcg cgccacccgc tgctgctgga tgagctgctg      1740
gatcccaaca ccctctatca gccgacggcg accgatgcct atcgcgacga gctgcgccag      1800
tacctgctgc gcgtgccgga agaggatgaa gagcagcagc tggaggcgtt gcgccagttt      1860
aagcaggcgc agcagctgca tatcgcggcg gcggatatcg ctggtaccct gccggtgatg      1920
aaggtcagcg atcacttaac ctggcttgcc gaagcgatcc tcgacgcggt ggtgcagcag      1980
gcatgggggc agatggtcgc tcgctacggc cagccgaccc acctgcacga tcgccagggt      2040
cgcggcttcg ccgtcgtcgg ctacggtaag cttggcggct gggagctggg ctacagctcc      2100
gatctcgatc tggtgttcct ccatgactgc ccggcggagg tgatgaccga cggcgagcgg      2160
gagattgacg gccgtcagtt ctacctgcgg ctggcccagc ggatcatgca cctgttcagc      2220
acccgcacct cgtccgatat tctctacgaa gtggacgccc ggctgcgtcc ttctggcgcg      2280
gcggggatgc tggtcaccac cgccgacgcg tttgctgact atcagcagaa cgaagcctgg      2340
acgtgggaac atcaggcgct ggtgcgcgcc cgcgtggtct atggcgaccc ggcgctgcag      2400
gcgcgctttg acgccattcg tcgcgatatc ctgaccaccc cgcgggaggg gatgaccctg      2460
cagaccgagg ttcgcgagat gcgcgagaag atgcgcgccc accttggcaa caaacatccc      2520
gatcgttttg atatcaaagc cgatgccggc gggatcaccg atattgaatt tattactcag      2580
tatctggtcc tacgctatgc cagtgacaag ccgaagctga cccgctggtc tgacaacgtg      2640
cgtattcttg agctgctggc gcagaacgac atcatggacg aggaggaggc gcgcgcctta      2700
acgcatgcgt acaccacctt gcgtgatgcg ctccatcacc tggccctgca ggagcagccg      2760
ggacacgtgg cgccagaggc cttcagccgg gagcgtcagc aggtcagcgc cagctggcag      2820
aagtggctga tggcttaa                                                    2838
```

<210> SEQ ID NO 15
<211> LENGTH: 1410
<212> TYPE: DNA
<213> ORGANISM: Kosakonia sacchari

<400> SEQUENCE: 15

```
atgtccgctg aacacgtttt gacgatgctg aatgagcacg aagtgaagtt tgtcgatctg        60
cgcttcaccg ataccaaagg taaagaacag cacgtcacta tcccagccca tcaagtaaac      120
gctgacttct ttgaagaagg taaaatgttt gatggttctt cgattggtgg ctggaaaggc      180
atcaacgaat cagacatagt gctgatgccg gacgcgacta ccgctgtcat tgacccgttc      240
tacgaagagt ctacgctgat cattcgttgc gatatcctcg aaccaggcac catgcagggc      300
tacgatcgtg acccgcgctc catcgctaaa cgcgctgaag aatacctgcg ctccaccggt      360
ctggcagaca ccgttctgtt tgggccagag ccggaattct tcctgttcga cgacgtgcgc      420
ttcggcagct ccatttccgg ttccagcgtc gctatcgacg atatcgaagg cgcatggaac      480
acctccacca aatacgaagg tggtaacaaa ggtcaccgtc cggcagtgaa aggcggttac      540
```

-continued

```
ttcccggttc cgccggtcga ttcatcacag gatctgcgtt ccaccatgtg tctggtgatg      600
gaagagatgg gcctggttgt tgaagctcac caccacgaag tggcaacggc tggtcagaac      660
gaagtggcta cccgcttcaa caccatgacc aaaaaagcgg acgaaattca gatttacaaa      720
tacgtggtgc acaacgttgc tcaccgcttt ggtaaaaccg cgacctttat gccgaaaccg      780
atgttcggtg ataacggttc cggtatgcac tgccacatgt ctctgtccaa gaacggtacc      840
aacctgttct ctggcgacaa atacgctggc ctgtctgaaa tggcgctgta ctacattggc      900
ggcgtaatca aacacgcaaa agcgatcaac gccctgtcta acccgaccac caactcctac      960
aagcgtctgg tcccgggtta tgaagcgccg gtaatgctgg cttactctgc acgtaaccgt     1020
tctgcatcta tccgtattcc ggtagtggct tctccgaaag cgcgtcgtat cgaagtgcgc     1080
ttcccggacc cggctgctaa cccgtatctg tgcttcgcag cgctgttgat ggctggtctg     1140
gatggcatta aaaacaaaat ccacccgggc gaagcgatgg acaaaaacct gtatgacctg     1200
ccggctgaag aagcgaaaga aatcccgcag gttgcaggct ctctggaaga agcgctcaac     1260
gcgctggatg ctgaccgcga gttcctgact gctggtggcg tattcaccga cgacgctatc     1320
gatgcttaca tcgcgctgcg tatcgaagag aacgaccgtg ttcgcatgac gccgcacccg     1380
gtagagttcg aactgtacta cagcgtttaa                                     1410
```

```
<210> SEQ ID NO 16
<211> LENGTH: 1410
<212> TYPE: DNA
<213> ORGANISM: Metakosakonia intestini

<400> SEQUENCE: 16
```

```
atgtccgctg aacacgtttt gacgatgctg aacgagcacg aagtcaagtt tgttgatttg       60
cgcttcaccg acactaaagg taaagagcag cacgtcacga tcccagctca tcaggtaaat      120
gctgacttct ttgaagaagg caaaatgttt gatggctcct cgattggtgg ctggaaaggc      180
attaacgaat ctgacatggt actgatgccg gacgcctcta ccgctgtcat tgacccgttc      240
tacgaagaac cgactctgat catccgttgc gatatcctcg agccgggcac tatgcagggc      300
tacgatcgcg acccgcgctc catcgcaaaa cgcgctgaag aatacctgcg cgcaacaggc      360
atcgcagaca ccgttctgtt cgggcctgag ccagagttct tcctgttcga cgacgtacgt      420
ttcggcagct ctatttccgg ttcccacgtc gctatcgatg atatcgaagg cgcatggaac      480
tcctccacca aatacgaagg cggtaacaaa ggtctccgtc cggctgttaa aggtggttac      540
ttcccggttc cgccagtgga ctccgcacaa gacctgcgtt ccactatgtg tctggtaatg      600
gaagagatgg gcctggttgt tgaagctcat caccacgaag ttgcaactgc tggtcagaac      660
gaagtggcaa cccgcttcaa taccatgacc aaaaaagcag acgaaattca gatctacaaa      720
tatgtggttc acaacgttgc tcaccgcttc ggtaaaaccg caacctttat gccaaaaccg      780
atgttcggtg ataacggttc cggtatgcac tgccacatgt ctctgtccaa gaacggcgta      840
aacctgttct ctggcgacaa atatgctggt ctgtctgagc aggcgctgta ctacatcggc      900
ggcgttatta aacacgctaa agcgatcaac gccctgtcca acccgactac caactcctac      960
aaacgtctgg tcccgggtta cgaagcaccg gtcatgctgg cttactctgc ccgtaaccgt     1020
tcagcttcca tccgtattcc ggtggttgca tctccgaaag cgcgtcgtat tgaagtgcgt     1080
ttcccggacc cggctgctaa cccgtacctg tgcttcgcag cgctgctgat ggctggtctt     1140
gatggcatca agaacaaaat ccatccgggc gaagcgatgg acaaaaacct gtatgacctg     1200
```

```
ccagctgaag aagcgaaaga atcccgcag gttgcaggct ctctggaaga agcactgaac     1260
tgcctgaacg aagaccgcga gttcctgact gcgggtggcg tattcaccga cgacgcaatt     1320
gatgcttaca tcgctctgcg tatcgaagaa aacgaccgcg tacgcatgac gccgcacccg     1380
gtagagttcg agctgtacta cagcgtttaa                                     1410
```

```
<210> SEQ ID NO 17
<211> LENGTH: 1410
<212> TYPE: DNA
<213> ORGANISM: Metakosakonia intestini

<400> SEQUENCE: 17
atgtccgctg aacacgtttt gacgatgctg aacgagcacg aagtcaagtt tgttgatttg      60
cgcttcaccg acactaaagg taaagagcag cacgtcacga tcccagctca tcaggtaaat     120
gctgacttct ttgaagaagg caaaatgttt gatggctcct cgattggtgg ctggaaaggc     180
attaacgaat ctgacatggt actgatgccg gacgcctcta ccgctgtcat tgacccgttc     240
tacgaagaac cgactctgat catccgttgc gatatcctcg agccgggcac tatgcagggc     300
tacgatcgcg accgcgctc catcgcaaaa cgcgctgaag aatacctgcg cgcaacaggc     360
atcgcagaca ccgttctgtt cgggcctgag ccagagttct tcctgttcga cgacgtacgt     420
ttcggcagct ctatttccgg ttcccacgtc gctatcgatg atatcgaagg cgcatggaac     480
tcctccacca aatacgaagg cggtaacaaa ggtcaccgtc cggctgttaa aggtggttac     540
ttcccggttc cgccagtgga ctccgcacaa gacctgcgtt ccactatgtg tctggtaatg     600
gaagagatgg gcctggttgt tgaagctcat caccacgaag ttgcaactgc tagtcagaac     660
gaagtggcaa cccgcttcaa taccatgacc aaaaaagcag acgaaattca gatctacaaa     720
tatgtggttc acaacgttgc tcaccgcttc ggtaaaaccg caacctttat gccaaaaccg     780
atgttcggtg ataacggttc cggtatgcac tgccacatgt ctctgtccaa gaacggcgta     840
aacctgttct ctggcgacaa atatgctggt ctgtctgagc aggcgctgta ctacatcggc     900
ggcgttatta aacacgctaa agcgatcaac gccctgtcca acccgactac caactcctac     960
aaacgtctgg tcccgggtta cgaagcaccg gtcatgctgg cttactctgc ccgtaaccgt    1020
tcagcttcca tccgtattcc ggtggttgca tctccgaaag cgcgtcgtat tgaagtgcgt    1080
ttcccggacc cggctgctaa cccgtacctg tgcttcgcag cgctgctgat ggctggtctt    1140
gatggcatca gaacaaaat ccatccgggc gaagcgatgg acaaaaacct gtatgacctg    1200
ccagctgaag aagcgaaaga atcccgcag gttgcaggct ctctggaaga agcactgaac    1260
tgcctgaacg aagaccgcga gttcctgact gcgggtggcg tattcaccga cgacgcaatt    1320
gatgcttaca tcgctctgcg tatcgaagaa aacgaccgcg tacgcatgac gccgcacccg    1380
gtagagttcg agctgtacta cagcgtttaa                                     1410
```

```
<210> SEQ ID NO 18
<211> LENGTH: 1410
<212> TYPE: DNA
<213> ORGANISM: Metakosakonia intestini

<400> SEQUENCE: 18
atgtccgctg aacacgtttt gacgatgctg aacgagcacg aagtcaagtt tgttgatttg      60
cgcttcaccg acactaaagg taaagagcag cacgtcacga tcccagctca tcaggtaaat     120
gctgacttct ttgaagaagg caaaatgttt gatggctcct cgattggtgg ctggaaaggc     180
attaacgaat ctgacatggt actgatgccg gacgcctcta ccgctgtcat tgacccgttc     240
```

```
tacgaagaac cgactctgat catccgttgc gatatcctcg agccgggcac tatgcagggc    300
tacgatcgcg acccgcgctc catcgcaaaa cgcgctgaag aatacctgcg cgcaacaggc    360
atcgcagaca ccgttctgtt cgggcctgag ccagagttct tcctgttcga cgacgtacgt    420
ttcggcagct ctatttccgg ttcccacgtc gctatcgatg atatcgaagg cgcatggaac    480
tcctccacca aatacgaagg cggtaacaaa ggtcaccgtc cggctgttaa aggtggttac    540
ttcccggttc cgccagtgga ctccgcacaa gacctgcgtt ccactatgtg tctggtaatg    600
gaagagatgg gcctggttgt tgaagctcat caccacgaag ttgcaactgc tggtcagaac    660
gaagtggcaa cccgcttcaa taccatgacc aaaaaagcag acgaaattca gatctacaaa    720
tatgtggttc acaacgttgc tcaccgcttc ggtaaaaccg caatctttat gccaaaaccg    780
atgttcggtg ataacggttc cggtatgcac tgccacatgt ctctgtccaa gaacggcgta    840
aacctgttct ctggcgacaa atatgctggt ctgtctgagc aggcgctgta ctacatcggc    900
ggcgttatta aacacgctaa agcgatcaac gccctgtcca acccgactac caactcctac    960
aaacgtctgg tcccgggtta cgaagcaccg gtcatgctgg cttactctgc ccgtaaccgt    1020
tcagcttcca tccgtattcc ggtggttgca tctccgaaag cgcgtcgtat tgaagtgcgt    1080
ttcccggacc cggctgctaa cccgtacctg tgcttcgcag cgctgctgat ggctggtctt    1140
gatggcatca gaacaaaat ccatccgggc gaagcgatgg acaaaaacct gtatgacctg    1200
ccagctgaag aagcgaaaga aatcccgcag gttgcaggct ctctggaaga agcactgaac    1260
tgcctgaacg aagaccgcga gttcctgact gcgggtggcg tattcaccga cgacgcaatt    1320
gatgcttaca tcgctctgcg tatcgaagaa aacgaccgcg tacgcatgac gccgcacccg    1380
gtagagttcg agctgtacta cagcgtttaa                                     1410
```

<210> SEQ ID NO 19
<211> LENGTH: 1410
<212> TYPE: DNA
<213> ORGANISM: Metakosakonia intestini

<400> SEQUENCE: 19

```
atgtccgctg aacacgtttt gacgatgctg aacgagcacg aagtcaagtt tgttgatttg     60
cgcttcaccg acactaaagg taaagagcag cacgtcacga tcccagctca tcaggtaaat    120
gctgacttct ttgaagaagg caaaatgttt gatggctcct cgattggtgg ctggaaaggc    180
attaacgaat ctgacatggt actgatgccg gacgcctcta ccgctgtcat tgacccgttc    240
tacgaagaac cgactctgat catccgttgc gatatcctcg agccgggcac tatgcagggc    300
tacgatcgcg acccgcgctc catcgcaaaa cgcgctgaag aatacctgcg cgcaacaggc    360
atcgcagaca ccgttctgtt cgggcctgag ccagagttct tcctgttcga cgacgtacgt    420
ttcggcagct ctatttccgg ttcccacgtc gctatcgatg atatcgaagg cgcatggaac    480
tcctccacca aatacgaagg cggtaacaaa ggtcaccgtc cggctgttaa aggtggttac    540
ttcccggttc cgccagtgga ctccgcacaa gacctgcgtt ccactatgtg tctggtaatg    600
gaagagatgg gcctggttgt tgaagctcat caccacgaag ttgcaactgc tggtcagaac    660
gaagtggcaa cccgcttcaa taccatgacc aaaaaagcag acgaaattca gatctacaaa    720
tatgtggttc acaacgttgc tcaccgcttc ggtaaaaccg caaccttat gccaaaaccg     780 atgttcggtg ataacggttc cggtatgcac tgccacatgt ctctgtccaa gaacggcgta    840
aacctgttct ctggcgacaa atatgctggt ctgtctgagc aggcgctgta ctacatcggc    900
```

-continued

```
ggcgttatta aacacgctaa agcgatcaac gccctgtcca acccgactac caactcctac      960
aaacgtctgg tcccgggtta cgaagtaccg gtcatgctgg cttactctgc ccgtaaccgt     1020
tcagcttcca tccgtattcc ggtggttgca tctccgaaag cgcgtcgtat tgaagtgcgt     1080
ttcccggacc cggctgctaa cccgtacctg tgcttcgcag cgctgctgat ggctggtctt     1140
gatggcatca agaacaaaat ccatccgggc gaagcgatgg acaaaaacct gtatgacctg     1200
ccagctgaag aagcgaaaga aatcccgcag gttgcaggct ctctggaaga agcactgaac     1260
tgcctgaacg aagaccgcga gttcctgact gcgggtggcg tattcaccga cgacgcaatt     1320
gatgcttaca tcgctctgcg tatcgaagaa aacgaccgcg tacgcatgac gccgcacccg     1380
gtagagttcg agctgtacta cagcgtttaa                                      1410
```

```
<210> SEQ ID NO 20
<211> LENGTH: 1416
<212> TYPE: DNA
<213> ORGANISM: Paraburkholderia tropica

<400> SEQUENCE: 20
atgagtaaat ccgtggccga cgtcatgcaa ctcgtcaagg acgaagacgt caagtttgtc       60
gacttccgct ttaccgacac gcgcggcaag gagcaacacg tctcggttcc gctgtcgcac      120
ttcgacgaag acaagttcga gtcgggtcat gcatttgacg gttcgtcgat cgccggctgg      180
aagggcatcg aagcctcgga catgctgctc gttccggatg cgaacacggc cttcatcgac      240
ccgttctacg aagagtcgac gctggttctg acctgcgacg tggtcgagcc ggctgacggc      300
aagggctgcg agcgcgaccc gcgctcgctc gccaagcgcg ctgaagcgta cctgaagagc      360
acgggcctcg gcgacacggc cttcttcggt ccggaacccg aattcttcat tttcgactcg      420
gtccagtgga acacggacat gtcgggctcg ttcgtcaaga tcggctcgga agaagcaccg      480
tggtcgtcga gcaaggaatt cgaaggcggc aacacgggtc accgtccggg cgtcaagggc      540
ggctacttcc cggtcgcgcc ggtcgacacg ttccaggaca tccgttcgga aatgtgtctg      600
ctgctcgaac agatcggcat cccggtcgaa gtgcaccacc acgaagtcgc tggccagggc      660
cagaacgaaa tcggcacgaa gttctcgacg ctggttcagc gcgcggactg gacgcagcag      720
atgaagtaca tcatccataa cgtggcgcac acgtatggca agacggcgac gttcatgccg      780
aagccgatcg ttggcgacaa cggttcgggc atgcacgttc accagtcgat ctggaaggac      840
ggccagaacc tgttcgcagg caacggctac gcaggtctgt cggaattcgc gctgttctac      900
atcggcggca tcatcaagca cgctcgcgcg ctgaacgcca tcacgaaccc gtcgacgaac      960
tcgtacaagc gtctggttcc gcacttcgaa gcaccggtca agctggctta ctcggcacgc     1020
aaccgttcgg cgtcgatccg tattccgcac gtctcgaacc cgaagggtcg ccgtatcgaa     1080
acgcgcttcc cggacccgat ggccaacccg tacctgtgct ctcggcact gatgatggca      1140 ggtctggacg gcgtgcagaa caagatccat ccgggcgaag ccgccgacaa gaacctgtac     1200
gacctgccgc cggaagagga tgcaaagatc ccgaccgttt cgcgccggcct cgaccaggct    1260 ctggaagcgc ttgacaagga tcgcgagttc ctgacgcgcg gtggcgtgtt cacggattcg     1320
atgatcgacg cctacctcgc actgaaggaa ggcgaactgc aacgcgtgcg catgacgacg     1380
cacccggtcg agttcgaact gtactactcg ctgtaa                               1416
```

```
<210> SEQ ID NO 21
<211> LENGTH: 1416
<212> TYPE: DNA
<213> ORGANISM: Paraburkholderia tropica
```

```
<400> SEQUENCE: 21
atgagtaaat ccgtggccga cgtcatgcaa ctcgtcaagg acgaagacgt caagtttgtc      60
gacttccgct ttaccgacac gcgcggcaag gagcaacacg tctcggttcc gctgtcgcac     120
ttcgacgaag acaagttcga gtcgggtcat gcatttgacg gttcgtcgat cgccggctgg     180
aagggcatcg aagcctcgga catgctgctc gttccggatg cgaacacggc cttcatcgac     240
ccgttctacg aagagtcgac gctggttctg acctgcgacg tggtcgagcc ggctgacggc     300
aagggctacg agcgcgaccc gcgctcgctc gccaagcgcg ctgaagcgta cctgaagagc     360
acgggcctcg gcgacacggc cttcttcggt ccggaacccg aattcttcat tttcgactcg     420
gtccagtgga acacggacat gtcgggctcg ttcgtcaaga tcggctcgga agaagcaccg     480
tggtcgccga gcaaggaatt cgaaggcggc aacacgggtc accgtccggg cgtcaagggc     540
ggctacttcc cggtcgcgcc ggtcgacacg ttccaggaca tccgttcgga aatgtgtctg     600
ctgctcgaac agatcggcat cccggtcgaa gtgcaccacc acgaagtcgc tggccagggc     660
cagaacgaaa tcggcacgaa gttctcgacg ctggttcagc gcgcggactg gacgcagcag     720
atgaagtaca tcatccataa cgtggcgcac acgtatggca agacggcgac gttcatgccg     780
aagccgatcg ttggcgacaa cggttcgggc atgcacgttc accagtcgat ctggaaggac     840
ggccagaacc tgttcgcagg caacggctac gcaggtctgt cggaattcgc gctgttctac     900
atcggcggca tcatcaagca cgctcgcgcg ctgaacgcca tcacgaaccc gtcgacgaac     960
tcgtacaagc gtctggttcc gcacttcgaa gcaccggtca agctggctta tcggcacgc    1020 aaccgttcgg cgtcgatccg tattccgcac gtctcgaacc cgaagggtcg ccgtatcgaa    1080
acgcgcttcc cggacccgat ggccaacccg tacctgtgct tctcggcact gatgatggca    1140
ggtctggacg gcgtgcagaa caagatccat ccgggcgaag ccgccgacaa gaacctgtac    1200
gacctgccgc cggaagagga tgcaaagatc ccgaccgttt gcgccggcct cgaccaggct    1260
ctggaagcgc ttgacaagga tcgcgagttc ctgacgcgcg gtggcgtgtt cacggattcg    1320
atgatcgacg cctacctcgc actgaaggaa ggcgaactgc aacgcgtgcg catgacgacg    1380
cacccggtcg agttcgaact gtactactcg ctgtaa                             1416

<210> SEQ ID NO 22
<211> LENGTH: 1416
<212> TYPE: DNA
<213> ORGANISM: Paraburkholderia tropica

<400> SEQUENCE: 22
atgagtaaat ccgtggccga cgtcatgcaa ctcgtcaagg acgaagacgt caagtttgtc      60
gacttccgct ttaccgacac gcgcggcaag gagcaacacg tctcggttcc gctgtcgcac     120
ttcgacgaag acaagttcga gtcgggtcat gcatttgacg gttcgtcgat cgccggctgg     180
aagggcatcg aagcctcgga catgctgctc gttccggatg cgaacacggc cttcatcgac     240
ccgttctacg aagagtcgac gctggttctg acctgcgacg tggtcgagcc ggctgacggc     300
aagggctacg agcgcgaccc gcgctcgctc gccaagcgcg ctgaagcgta cctgaagagc     360
acgggcctcg gcgacacggc cttcttcggt ccggaacccg aattcttcat tttcgactcg     420
gtccagtgga acacggacat gtcgggctcg ttcgtcaaga tcggctcgga agaagcaccg     480
tggtcgtcga gcaaggaatt cgaaggcggc gacacgggtc accgtccggg cgtcaagggc     540
ggctacttcc cggtcgcgcc ggtcgacacg ttccaggaca tccgttcgga aatgtgtctg     600
```

```
ctgctcgaac agatcggcat cccggtcgaa gtgcaccacc acgaagtcgc tggccagggc         660
cagaacgaaa tcggcacgaa gttctcgacg ctggttcagc gcgcggactg gacgcagcag         720
atgaagtaca tcatccataa cgtggcgcac acgtatggca agacggcgac gttcatgccg         780
aagccgatcg ttggcgacaa cggttcgggc atgcacgttc accagtcgat ctggaaggac         840
ggccagaacc tgttcgcagg caacggctac gcaggtctgt cggaattcgc gctgttctac         900
atcggcggca tcatcaagca cgctcgcgcg ctgaacgcca tcacgaaccc gtcgacgaac         960
tcgtacaagc gtctggttcc gcacttcgaa gcaccggtca agctggctta ctcggcacgc        1020
aaccgttcgg cgtcgatccg tattccgcac gtctcgaacc cgaagggtcg ccgtatcgaa        1080
acgcgcttcc cggacccgat ggccaacccg tacctgtgct tctcggcact gatgatggca        1140
ggtctggacg gcgtgcagaa caagatccat ccgggcgaag ccgccgacaa gaacctgtac        1200
gacctgccgc cggaagagga tgcaaagatc ccgaccgttt gcgccggcct cgaccaggct        1260
ctggaagcgc ttgacaagga tcgcgagttc ctgacgcgcg gtggcgtgtt cacggattcg        1320
atgatcgacg cctacctcgc actgaaggaa ggcgaactgc aacgcgtgcg catgacgacg        1380
cacccggtcg agttcgaact gtactactcg ctgtaa                                   1416

<210> SEQ ID NO 23
<211> LENGTH: 1416
<212> TYPE: DNA
<213> ORGANISM: Paraburkholderia tropica

<400> SEQUENCE: 23
atgagtaaat ccgtggccga cgtcatgcaa ctcgtcaagg acgaagacgt caagtttgtc          60
gacttccgct ttaccgacac gcgcggcaag gagcaacacg tctcggttcc gctgtcgcac         120
ttcgacgaag acaagttcga gtcgggtcat gcatttgacg gttcgtcgat cgccggctgg         180
aagggcatcg aagcctcgga catgctgctc gttccggatg cgaacacggc cttcatcgac         240
ccgttctacg aagagtcgac gctggttctg acctgcgacg tggtcgagcc ggctgacggc         300
aagggctacg agcgcgaccc gcgctcgctc gccaagcgcg ctgaagcgta cctgaagagc         360
acgggcctcg gcgacacggc cttcttcggt ccggaacccg aattcttcat tttcgactcg         420
gtccagtgga acacggacat gtcgggctcg ttcgtcaaga tcggctcgga agaagcaccg         480
tggtcgtcga gcaaggaatt cgaaggcggc aacacgggtc accgtccggg cgtcaagggc         540
ggctacttcc cggtcgcgcc ggtcgacacg ttccaggaca tccgttcgga aatgtgtctg         600
ctgctcgaac agatcggcat cccggtcgaa gtgcaccacc acgaagtcgc tggccacggc         660
cagaacgaaa tcggcacgaa gttctcgacg ctggttcagc gcgcggactg gacgcagcag         720
atgaagtaca tcatccataa cgtggcgcac acgtatggca agacggcgac gttcatgccg         780
aagccgatcg ttggcgacaa cggttcgggc atgcacgttc accagtcgat ctggaaggac         840
ggccagaacc tgttcgcagg caacggctac gcaggtctgt cggaattcgc gctgttctac         900
atcggcggca tcatcaagca cgctcgcgcg ctgaacgcca tcacgaaccc gtcgacgaac         960
tcgtacaagc gtctggttcc gcacttcgaa gcaccggtca agctggctta ctcggcacgc        1020
aaccgttcgg cgtcgatccg tattccgcac gtctcgaacc cgaagggtcg ccgtatcgaa        1080
acgcgcttcc cggacccgat ggccaacccg tacctgtgct tctcggcact gatgatggca        1140
ggtctggacg gcgtgcagaa caagatccat ccgggcgaag ccgccgacaa gaacctgtac        1200
gacctgccgc cggaagagga tgcaaagatc ccgaccgttt gcgccggcct cgaccaggct        1260
ctggaagcgc ttgacaagga tcgcgagttc ctgacgcgcg gtggcgtgtt cacggattcg        1320
```
atgatcgacg cctacctcgc actgaaggaa ggcgaactgc aacgcgtgcg catgacgacg          1380
cacccggtcg agttcgaact gtactactcg ctgtaa          1416

<210> SEQ ID NO 24
<211> LENGTH: 469
<212> TYPE: PRT
<213> ORGANISM: Klebsiella variicola

<400> SEQUENCE: 24

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ser His Gln Val Asn Ala Glu Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
            100                 105                 110

Glu Glu Tyr Leu Arg Ala Thr Gly Ile Ala Asp Thr Val Leu Phe Gly
            115                 120                 125

Pro Glu Pro Glu Phe Phe Leu Phe Asp Asp Ile Arg Phe Gly Ala Ser
        130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Pro Gly Val
                165                 170                 175

Lys Gly Gly Tyr Phe Pro Val Pro Pro Val Asp Ser Ser Gln Asp Ile
            180                 185                 190

Arg Ser Thr Met Cys Met Ile Met Glu Glu Met Gly Leu Val Val Glu
            195                 200                 205

Ala His His His Glu Val Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ala Lys Asn Gly Thr Asn Leu Phe Ser Gly Asp Lys Tyr
            275                 280                 285

Ala Gly Leu Ser Glu Gln Ala Leu Phe Tyr Ile Gly Gly Val Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Thr Ser Pro
            340                 345                 350

```
Lys Ala Arg Arg Ile Glu Val Arg Phe Pro Asp Pro Ala Ala Asn Pro
        355                 360                 365

Tyr Leu Cys Phe Ala Ala Leu Leu Met Ala Gly Leu Asp Gly Ile Lys
        370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                405                 410                 415

Glu Ala Leu Gln Ala Leu Asp Ala Asp Arg Glu Phe Leu Thr Ala Gly
                420                 425                 430

Gly Val Phe Thr Asn Asp Ala Ile Asp Ala Tyr Ile Ala Leu Arg Leu
            435                 440                 445

Glu Glu Asn Asp Arg Val Arg Met Thr Pro His Pro Val Glu Phe Glu
        450                 455                 460

Leu Tyr Tyr Ser Val
465
```

```
<210> SEQ ID NO 25
<211> LENGTH: 469
<212> TYPE: PRT
<213> ORGANISM: Kosakonia sacchari

<400> SEQUENCE: 25

Met Ser Ala Glu His Val Leu Thr Met Leu Asn Glu His Glu Val Lys
1                 5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
        50                  55                  60

Asp Met Val Leu Met Pro Asp Ala Thr Thr Ala Val Ile Asp Pro Phe
65                  70                  75                  80

Tyr Glu Glu Ser Thr Leu Ile Ile Arg Cys Asp Ile Leu Glu Pro Gly
            85                  90                  95

Thr Met Gln Gly Tyr Asp Arg Asp Pro Arg Ser Ile Ala Lys Arg Ala
            100                 105                 110

Glu Glu Tyr Leu Arg Ser Thr Gly Leu Ala Asp Thr Val Leu Phe Gly
        115                 120                 125

Pro Glu Pro Glu Phe Phe Leu Phe Asp Asp Val Arg Phe Gly Ser Ser
        130                 135                 140

Ile Ser Gly Ser Ser Val Ala Ile Asp Asp Ile Glu Gly Ala Trp Asn
145                 150                 155                 160

Thr Ser Thr Lys Tyr Glu Gly Gly Asn Lys Gly His Arg Pro Ala Val
            165                 170                 175

Lys Gly Gly Tyr Phe Pro Val Pro Pro Val Asp Ser Ser Gln Asp Leu
            180                 185                 190

Arg Ser Thr Met Cys Leu Val Met Glu Glu Met Gly Leu Val Val Glu
        195                 200                 205

Ala His His His Glu Val Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
            245                 250                 255
```

-continued

```
Met Pro Lys Pro Met Phe Gly Asp Asn Gly Ser Gly Met His Cys His
        260             265             270

Met Ser Leu Ser Lys Asn Gly Thr Asn Leu Phe Ser Gly Asp Lys Tyr
        275             280             285

Ala Gly Leu Ser Glu Met Ala Leu Tyr Tyr Ile Gly Gly Val Ile Lys
        290             295             300

His Ala Lys Ala Ile Asn Ala Leu Ser Asn Pro Thr Thr Asn Ser Tyr
305             310             315             320

Lys Arg Leu Val Pro Gly Tyr Glu Ala Pro Val Met Leu Ala Tyr Ser
                325             330             335

Ala Arg Asn Arg Ser Ala Ser Ile Arg Ile Pro Val Val Ala Ser Pro
        340             345             350

Lys Ala Arg Arg Ile Glu Val Arg Phe Pro Asp Pro Ala Ala Asn Pro
        355             360             365

Tyr Leu Cys Phe Ala Ala Leu Leu Met Ala Gly Leu Asp Gly Ile Lys
    370             375             380

Asn Lys Ile His Pro Gly Glu Ala Met Asp Lys Asn Leu Tyr Asp Leu
385             390             395             400

Pro Ala Glu Glu Ala Lys Glu Ile Pro Gln Val Ala Gly Ser Leu Glu
                405             410             415

Glu Ala Leu Asn Ala Leu Asp Ala Asp Arg Glu Phe Leu Thr Ala Gly
            420             425             430

Gly Val Phe Thr Asp Asp Ala Ile Asp Ala Tyr Ile Ala Leu Arg Ile
            435             440             445

Glu Glu Asn Asp Arg Val Arg Met Thr Pro His Pro Val Glu Phe Glu
        450             455             460

Leu Tyr Tyr Ser Val
465
```

```
<210> SEQ ID NO 26
<211> LENGTH: 469
<212> TYPE: PRT
<213> ORGANISM: Metakosakonia intestini

<400> SEQUENCE: 26

Met Ser Ala Glu His Val Leu Thr Met Leu Asn Glu His Glu Val Lys
1               5               10              15

Phe Val Asp Leu Arg Phe Thr Asp Thr Lys Gly Lys Glu Gln His Val
            20              25              30

Thr Ile Pro Ala His Gln Val Asn Ala Asp Phe Phe Glu Glu Gly Lys
        35              40              45

Met Phe Asp Gly Ser Ser Ile Gly Gly Trp Lys Gly Ile Asn Glu Ser
        50              55              60

Asp Met Val Leu Met Pro Asp Ala Ser Thr Ala Val Ile Asp Pro Phe
65              70              75              80

Tyr Glu Glu Pro Thr Leu Ile Ile Arg Cys Asp Ile Leu Glu Pro Gly
                85              90              95

Thr Met Gln Gly Tyr Asp Arg Asp Pro Arg Ser Ile Ala Lys Arg Ala
            100             105             110

Glu Glu Tyr Leu Arg Ala Thr Gly Ile Ala Asp Thr Val Leu Phe Gly
        115             120             125

Pro Glu Pro Glu Phe Phe Leu Phe Asp Asp Val Arg Phe Gly Ser Ser
    130             135             140

Ile Ser Gly Ser His Val Ala Ile Asp Asp Ile Glu Gly Ala Trp Asn
```

-continued

```
145                 150                 155                 160

Ser Ser Thr Lys Tyr Glu Gly Gly Asn Lys Gly His Arg Pro Ala Val
                165                 170                 175

Lys Gly Gly Tyr Phe Pro Val Pro Pro Val Asp Ser Ala Gln Asp Leu
                180                 185                 190

Arg Ser Thr Met Cys Leu Val Met Glu Glu Met Gly Leu Val Val Glu
            195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Val Asn Leu Phe Ser Gly Asp Lys Tyr
            275                 280                 285

Ala Gly Leu Ser Glu Gln Ala Leu Tyr Tyr Ile Gly Gly Val Ile Lys
    290                 295                 300

His Ala Lys Ala Ile Asn Ala Leu Ser Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
                340                 345                 350

Lys Ala Arg Arg Ile Glu Val Arg Phe Pro Asp Pro Ala Ala Asn Pro
            355                 360                 365

Tyr Leu Cys Phe Ala Ala Leu Leu Met Ala Gly Leu Asp Gly Ile Lys
    370                 375                 380

Asn Lys Ile His Pro Gly Glu Ala Met Asp Lys Asn Leu Tyr Asp Leu
385                 390                 395                 400

Pro Ala Glu Glu Ala Lys Glu Ile Pro Gln Val Ala Gly Ser Leu Glu
                405                 410                 415

Glu Ala Leu Asn Cys Leu Asn Glu Asp Arg Glu Phe Leu Thr Ala Gly
                420                 425                 430

Gly Val Phe Thr Asp Asp Ala Ile Asp Ala Tyr Ile Ala Leu Arg Ile
            435                 440                 445

Glu Glu Asn Asp Arg Val Arg Met Thr Pro His Pro Val Glu Phe Glu
    450                 455                 460

Leu Tyr Tyr Ser Val
465
```

```
<210> SEQ ID NO 27
<211> LENGTH: 471
<212> TYPE: PRT
<213> ORGANISM: Paraburkholderia tropica

<400> SEQUENCE: 27

Met Ser Lys Ser Val Ala Asp Val Met Gln Leu Val Lys Asp Glu Asp
1               5                   10                  15

Val Lys Phe Val Asp Phe Arg Phe Thr Asp Thr Arg Gly Lys Glu Gln
                20                  25                  30

His Val Ser Val Pro Leu Ser His Phe Asp Glu Asp Lys Phe Glu Ser
        35                  40                  45
```

-continued

```
Gly His Ala Phe Asp Gly Ser Ser Ile Ala Gly Trp Lys Gly Ile Glu
    50              55                  60

Ala Ser Asp Met Leu Leu Val Pro Asp Ala Asn Thr Ala Phe Ile Asp
65              70                  75                  80

Pro Phe Tyr Glu Glu Ser Thr Leu Val Leu Thr Cys Asp Val Val Glu
            85                  90                  95

Pro Ala Asp Gly Lys Gly Tyr Glu Arg Asp Pro Arg Ser Leu Ala Lys
            100             105             110

Arg Ala Glu Ala Tyr Leu Lys Ser Thr Gly Leu Gly Asp Thr Ala Phe
        115             120             125

Phe Gly Pro Glu Pro Glu Phe Phe Ile Phe Asp Ser Val Gln Trp Asn
    130             135             140

Thr Asp Met Ser Gly Ser Phe Val Lys Ile Gly Ser Glu Glu Ala Pro
145             150             155             160

Trp Ser Ser Ser Lys Glu Phe Glu Gly Gly Asn Thr Gly His Arg Pro
            165             170             175

Gly Val Lys Gly Gly Tyr Phe Pro Val Ala Pro Val Asp Thr Phe Gln
            180             185             190

Asp Ile Arg Ser Glu Met Cys Leu Leu Leu Glu Gln Ile Gly Ile Pro
            195             200             205

Val Glu Val His His His Glu Val Ala Gly Gln Gly Gln Asn Glu Ile
    210             215             220

Gly Thr Lys Phe Ser Thr Leu Val Gln Arg Ala Asp Trp Thr Gln Gln
225             230             235             240

Met Lys Tyr Ile Ile His Asn Val Ala His Thr Tyr Gly Lys Thr Ala
            245             250             255

Thr Phe Met Pro Lys Pro Ile Val Gly Asp Asn Gly Ser Gly Met His
            260             265             270

Val His Gln Ser Ile Trp Lys Asp Gly Gln Asn Leu Phe Ala Gly Asn
            275             280             285

Gly Tyr Ala Gly Leu Ser Glu Phe Ala Leu Phe Tyr Ile Gly Gly Ile
    290             295             300

Ile Lys His Ala Arg Ala Leu Asn Ala Ile Thr Asn Pro Ser Thr Asn
305             310             315             320

Ser Tyr Lys Arg Leu Val Pro His Phe Glu Ala Pro Val Lys Leu Ala
            325             330             335

Tyr Ser Ala Arg Asn Arg Ser Ala Ser Ile Arg Ile Pro His Val Ser
            340             345             350

Asn Pro Lys Gly Arg Arg Ile Glu Thr Arg Phe Pro Asp Pro Met Ala
            355             360             365

Asn Pro Tyr Leu Cys Phe Ser Ala Leu Met Met Ala Gly Leu Asp Gly
    370             375             380

Val Gln Asn Lys Ile His Pro Gly Glu Ala Ala Asp Lys Asn Leu Tyr
385             390             395             400

Asp Leu Pro Pro Glu Glu Asp Ala Lys Ile Pro Thr Val Cys Ala Gly
            405             410             415

Leu Asp Gln Ala Leu Glu Ala Leu Asp Lys Asp Arg Glu Phe Leu Thr
            420             425             430

Arg Gly Gly Val Phe Thr Asp Ser Met Ile Asp Ala Tyr Leu Ala Leu
            435             440             445

Lys Glu Gly Glu Leu Gln Arg Val Arg Met Thr Thr His Pro Val Glu
    450             455             460

Phe Glu Leu Tyr Tyr Ser Leu
```

-continued

```
465                 470

<210> SEQ ID NO 28
<211> LENGTH: 945
<212> TYPE: PRT
<213> ORGANISM: Klebsiella variicola

<400> SEQUENCE: 28

Met Met Pro Leu Ser Pro Gln Leu Gln Gln His Trp Gln Thr Val Ala
1               5                   10                  15

Asp Arg Leu Pro Ala Asp Phe Pro Ile Ala Glu Leu Ser Pro Gln Ala
                20                  25                  30

Arg Ser Val Met Ala Phe Ser Asp Phe Val Glu Gln Ser Val Ile Ala
            35                  40                  45

Gln Pro Gly Trp Leu Asn Glu Leu Ala Asp Ser Ser Pro Glu Ala Glu
        50                  55                  60

Glu Trp Arg His Tyr Glu Ala Trp Leu Gln Asp Arg Leu Gln Ala Val
65                  70                  75                  80

Thr Asp Glu Ala Gly Leu Met Arg Glu Leu Arg Leu Phe Arg Arg Gln
                85                  90                  95

Met Met Val Arg Ile Ala Trp Ala Gln Ala Leu Ser Leu Val Ser Glu
            100                 105                 110

Glu Glu Thr Leu Gln Gln Leu Ser Val Leu Ala Glu Thr Leu Ile Val
            115                 120                 125

Ala Ala Arg Asp Trp Leu Tyr Ala Ala Cys Cys Lys Glu Trp Gly Thr
        130                 135                 140

Pro Cys Asn Ala Glu Gly Gln Pro Gln Pro Leu Leu Ile Leu Gly Met
145                 150                 155                 160

Gly Lys Leu Gly Gly Gly Glu Leu Asn Phe Ser Ser Asp Ile Asp Leu
                165                 170                 175

Ile Phe Ala Trp Pro Glu His Gly Ala Thr Arg Gly Gly Arg Arg Glu
            180                 185                 190

Leu Asp Asn Ala Gln Phe Phe Thr Arg Leu Gly Gln Arg Leu Ile Lys
        195                 200                 205

Ala Leu Asp Gln Pro Thr Gln Asp Gly Phe Val Tyr Arg Val Asp Met
        210                 215                 220

Arg Leu Arg Pro Phe Gly Asp Ser Gly Pro Leu Val Leu Ser Phe Ala
225                 230                 235                 240

Ala Leu Glu Asp Tyr Tyr Gln Glu Gln Gly Arg Asp Trp Glu Arg Tyr
                245                 250                 255

Ala Met Val Lys Ala Arg Ile Met Gly Asp Asn Asp Gly Val Tyr Ala
            260                 265                 270

Ser Glu Leu Arg Ala Met Leu Arg Pro Phe Val Phe Arg Arg Tyr Ile
            275                 280                 285

Asp Phe Ser Val Ile Gln Ser Leu Arg Asn Met Lys Gly Met Ile Ala
        290                 295                 300

Arg Glu Val Arg Arg Arg Gly Leu Lys Asp Asn Ile Lys Leu Gly Ala
305                 310                 315                 320

Gly Gly Ile Arg Glu Ile Glu Phe Ile Val Gln Val Phe Gln Leu Ile
                325                 330                 335

Arg Gly Gly Arg Glu Pro Ala Leu Gln Gln Arg Ala Leu Leu Pro Thr
            340                 345                 350

Leu Ala Ala Ile Asp Glu Leu His Leu Leu Pro Glu Gly Asp Ala Ala
            355                 360                 365
```

Leu Leu Arg Glu Ala Tyr Leu Phe Leu Arg Arg Leu Glu Asn Leu Leu
    370                 375                 380

Gln Ser Ile Asn Asp Glu Gln Thr Gln Thr Leu Pro Gln Asp Glu Leu
385                 390                 395                 400

Asn Arg Ala Arg Leu Ala Trp Gly Met His Thr Glu Asp Trp Glu Thr
                405                 410                 415

Leu Ser Ala Gln Leu Ala Ser Gln Met Ala Asn Val Arg Arg Val Phe
                420                 425                 430

Asn Glu Leu Ile Gly Asp Asp Glu Asp Gln Ser Pro Asp Glu Gln Leu
            435                 440                 445

Ala Glu Tyr Trp Arg Glu Leu Trp Gln Asp Ala Leu Glu Glu Asp Asp
    450                 455                 460

Ala Ser Pro Ala Leu Ala His Leu Asn Asp Thr Asp Arg Arg Ser Val
465                 470                 475                 480

Leu Ala Leu Ile Ala Asp Phe Arg Lys Glu Leu Asp Arg Arg Thr Ile
                485                 490                 495

Gly Pro Arg Gly Arg Gln Val Leu Asp Gln Leu Met Pro His Leu Leu
                500                 505                 510

Ser Glu Ile Cys Ser Arg Ala Asp Ala Pro Leu Pro Leu Ala Arg Ile
            515                 520                 525

Thr Pro Leu Leu Thr Gly Ile Val Thr Arg Thr Thr Tyr Leu Glu Leu
    530                 535                 540

Leu Ser Glu Phe Pro Gly Ala Leu Lys His Leu Ile Thr Leu Cys Ala
545                 550                 555                 560

Ala Ser Pro Met Val Ala Ser Gln Leu Ala Arg His Pro Leu Leu Leu
                565                 570                 575

Asp Glu Leu Leu Asp Pro Asn Thr Leu Tyr Gln Pro Thr Ala Thr Asp
            580                 585                 590

Ala Tyr Arg Asp Glu Leu Arg Gln Tyr Leu Leu Arg Val Pro Glu Glu
            595                 600                 605

Asp Glu Glu Gln Gln Leu Glu Ala Leu Arg Gln Phe Lys Gln Ala Gln
    610                 615                 620

Gln Leu His Ile Ala Ala Ala Asp Ile Ala Gly Thr Leu Pro Val Met
625                 630                 635                 640

Lys Val Ser Asp His Leu Thr Trp Leu Ala Glu Ala Ile Leu Asp Ala
                645                 650                 655

Val Val Gln Gln Ala Trp Gly Gln Met Val Ala Arg Tyr Gly Gln Pro
                660                 665                 670

Thr His Leu His Asp Arg Gln Gly Arg Gly Phe Ala Val Val Gly Tyr
            675                 680                 685

Gly Lys Leu Gly Gly Trp Glu Leu Gly Tyr Ser Ser Asp Leu Asp Leu
    690                 695                 700

Val Phe Leu His Asp Cys Pro Ala Glu Val Met Thr Asp Gly Glu Arg
705                 710                 715                 720

Glu Ile Asp Gly Arg Gln Phe Tyr Leu Arg Leu Ala Gln Arg Ile Met
                725                 730                 735

His Leu Phe Ser Thr Arg Thr Ser Ser Gly Ile Leu Tyr Glu Val Asp
                740                 745                 750

Ala Arg Leu Arg Pro Ser Gly Ala Ala Gly Met Leu Val Thr Thr Ala
            755                 760                 765

Asp Ala Phe Ala Asp Tyr Gln Gln Asn Glu Ala Trp Thr Trp Glu His
    770                 775                 780

Gln Ala Leu Val Arg Ala Arg Val Val Tyr Gly Asp Pro Ala Leu Gln

```
        785                   790                   795                   800

Ala Arg Phe Asp Ala Ile Arg Arg Asp Ile Leu Thr Thr Pro Arg Glu
                805                   810                   815

Gly Met Thr Leu Gln Thr Glu Val Arg Glu Met Arg Glu Lys Met Arg
                820                   825                   830

Ala His Leu Gly Asn Lys His Pro Asp Arg Phe Asp Ile Lys Ala Asp
                835                   840                   845

Ala Gly Gly Ile Thr Asp Ile Glu Phe Ile Thr Gln Tyr Leu Val Leu
                850                   855                   860

Arg Tyr Ala Ser Asp Lys Pro Lys Leu Thr Arg Trp Ser Asp Asn Val
865                   870                   875                   880

Arg Ile Leu Glu Leu Leu Ala Gln Asn Asp Ile Met Asp Glu Glu Glu
                885                   890                   895

Ala Arg Ala Leu Thr His Ala Tyr Thr Thr Leu Arg Asp Ala Leu His
                900                   905                   910

His Leu Ala Leu Gln Glu Gln Pro Gly His Val Ala Pro Glu Ala Phe
                915                   920                   925

Ser Arg Glu Arg Gln Gln Val Ser Ala Ser Trp Gln Lys Trp Leu Met
                930                   935                   940

Ala
945

<210> SEQ ID NO 29
<211> LENGTH: 469
<212> TYPE: PRT
<213> ORGANISM: Klebsiella variicola

<400> SEQUENCE: 29

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ser His Gln Val Asn Ala Glu Phe Phe Glu Glu Gly Lys
                35                  40                  45

Met Phe Asp Gly Ser Ser Ile Gly Gly Trp Lys Gly Ile Asn Glu Ser
                50                  55                  60

Asp Ile Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
                100                 105                 110

Glu Glu Tyr Leu Arg Ala Thr Gly Ile Ala Asp Thr Val Leu Phe Gly
                115                 120                 125

Pro Glu Pro Glu Phe Phe Leu Phe Asp Asp Ile Arg Phe Gly Ala Ser
                130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Pro Gly Val
                165                 170                 175

Lys Gly Gly Tyr Phe Pro Val Pro Val Asp Ser Ser Gln Asp Ile
                180                 185                 190

Arg Ser Thr Met Cys Met Ile Met Glu Glu Met Gly Leu Val Val Glu
                195                 200                 205
```

-continued

```
Ala His His His Glu Val Ala Thr Ala Gly Gln Asn Glu Val Ala Thr
    210             215             220

Arg Phe Asn Thr Met Thr Lys Lys Ala Asp Glu Ile Gln Ile Tyr Lys
225             230             235             240

Tyr Val Val His Asn Val Ala His Arg Phe Gly Lys Thr Ala Thr Phe
            245             250             255

Met Pro Lys Pro Met Phe Gly Asp Asn Gly Ser Gly Met His Cys His
            260             265             270

Met Ser Leu Ala Lys Asn Gly Thr Asn Leu Phe Ser Gly Asp Lys Tyr
        275             280             285

Ala Gly Leu Ser Glu Gln Ala Leu Phe Tyr Ile Gly Gly Val Ile Lys
    290             295             300

His Ala Lys Ala Ile Asn Ala Leu Ala Asn Pro Thr Thr Asn Ser Tyr
305             310             315             320

Lys Arg Leu Val Pro Gly Tyr Glu Ala Pro Val Met Leu Ala Tyr Ser
            325             330             335

Ala Arg Asn Arg Ser Ala Ser Ile Arg Ile Pro Val Val Thr Ser Pro
        340             345             350

Lys Ala Arg Arg Ile Glu Val Arg Phe Pro Asp Pro Ala Ala Asn Pro
        355             360             365

Tyr Leu Cys Phe Ala Ala Leu Leu Met Ala Gly Leu Asp Gly Ile Lys
    370             375             380

Asn Lys Ile His Pro Gly Glu Ala Met Asp Lys Asn Leu Tyr Asp Leu
385             390             395             400

Pro Pro Glu Glu Ala Lys Glu Ile Pro Gln Val Ala Gly Ser Leu Glu
            405             410             415

Glu Ala Leu Gln Ala Leu Asp Ala Asp Arg Glu Phe Leu Thr Ala Gly
        420             425             430

Gly Val Phe Thr Asn Asp Ala Ile Asp Ala Tyr Ile Ala Leu Arg Leu
        435             440             445

Glu Glu Asn Asp Arg Val Arg Met Thr Pro His Pro Val Glu Phe Glu
    450             455             460

Leu Tyr Tyr Ser Val
465

<210> SEQ ID NO 30
<211> LENGTH: 469
<212> TYPE: PRT
<213> ORGANISM: Klebsiella variicola

<400> SEQUENCE: 30

Met Ser Ala Glu His Val Leu Thr Met Leu Asn Glu His Glu Val Lys
1               5               10              15

Phe Val Asp Leu Arg Phe Thr Asp Thr Lys Gly Lys Glu Gln His Val
            20              25              30

Thr Ile Pro Ser His Gln Val Asn Ala Glu Phe Phe Glu Glu Gly Lys
        35              40              45

Met Phe Asp Gly Ser Ser Ile Gly Gly Trp Lys Gly Ile Asn Glu Ser
    50              55              60

Asp Val Val Leu Met Pro Asp Ala Ser Thr Ala Val Ile Asp Pro Phe
65              70              75              80

Tyr Glu Glu Pro Thr Leu Ile Ile Arg Cys Asp Ile Leu Glu Pro Gly
            85              90              95

Thr Leu Gln Gly Tyr Asp Arg Asp Pro Arg Ser Ile Ala Lys Arg Ala
            100             105             110
```

```
Glu Glu Tyr Leu Arg Ala Thr Gly Ile Ala Asp Thr Val Leu Phe Gly
        115                 120                 125

Pro Glu Pro Glu Phe Phe Leu Phe Asp Asp Ile Arg Phe Gly Ala Ser
        130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Pro Gly Val
                165                 170                 175

Lys Gly Gly Tyr Phe Pro Val Pro Pro Val Asp Ser Ser Gln Asp Ile
                180                 185                 190

Arg Ser Thr Met Cys Met Ile Met Glu Glu Met Gly Leu Val Val Glu
                195                 200                 205

Ala His His His Glu Val Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ala Lys Asn Gly Thr Asn Leu Phe Ser Gly Asp Lys Tyr
        275                 280                 285

Ala Gly Leu Ser Glu Gln Ala Leu Phe Tyr Ile Gly Gly Val Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Thr Ser Pro
                340                 345                 350

Lys Ala Arg Arg Ile Glu Val Arg Phe Pro Asp Pro Ala Ala Asn Pro
                355                 360                 365

Tyr Leu Cys Phe Ala Ala Leu Leu Met Ala Gly Leu Asp Gly Ile Lys
        370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                405                 410                 415

Glu Ala Leu Gln Ala Leu Asp Ala Asp Arg Glu Phe Leu Thr Ala Gly
                420                 425                 430

Gly Val Phe Thr Asn Asp Ala Ile Asp Ala Tyr Ile Ala Leu Arg Leu
                435                 440                 445

Glu Glu Asn Asp Arg Val Arg Met Thr Pro His Pro Val Glu Phe Glu
        450                 455                 460

Leu Tyr Tyr Ser Val
465
```

<210> SEQ ID NO 31
<211> LENGTH: 469
<212> TYPE: PRT
<213> ORGANISM: Klebsiella variicola

<400> SEQUENCE: 31

```
Met Ser Ala Glu His Val Leu Thr Met Leu Asn Glu His Glu Val Lys
```

-continued

```
1                 5                    10                   15

Phe Val Asp Leu Arg Phe Thr Asp Thr Lys Gly Lys Glu Gln His Val
                20               25                   30

Thr Ile Pro Ser His Gln Val Asn Ala Glu Phe Phe Glu Glu Gly Lys
                35               40                   45

Met Phe Asp Gly Ser Ser Ile Gly Gly Trp Lys Gly Ile Asn Glu Ser
        50               55                   60

Asp Met Val Leu Met Pro Asp Ala Ser Thr Ala Val Ile Asp Pro Phe
65               70                   75                   80

Tyr Glu Glu Pro Thr Leu Ile Ile Arg Cys Asp Ile Leu Glu Pro Gly
                85               90                   95

Thr Leu Gln Gly Tyr Asp Arg Asp Pro Arg Ser Ile Ala Lys Arg Ala
                100              105                  110

Glu Glu Tyr Leu Arg Ala Thr Gly Ile Ala Asp Thr Val Leu Phe Gly
                115              120                  125

Pro Glu Pro Glu Phe Phe Leu Phe Asp Asp Ile Arg Phe Gly Ala Ser
        130              135                  140

Ile Ser Gly Ser His Val Ala Ile Asp Asp Ile Glu Cys Ala Trp Asn
145              150                  155                  160

Ser Ser Thr Lys Tyr Glu Gly Gly Asn Lys Gly His Arg Pro Gly Val
                165              170                  175

Lys Gly Gly Tyr Phe Pro Val Pro Pro Val Asp Ser Ser Gln Asp Ile
                180              185                  190

Arg Ser Thr Met Cys Met Ile Met Glu Glu Met Gly Leu Val Val Glu
                195              200                  205

Ala His His His Glu Val Ala Thr Ala Gly Gln Asn Glu Val Ala Thr
        210              215                  220

Arg Phe Asn Thr Met Thr Lys Lys Ala Asp Glu Ile Gln Ile Tyr Lys
225              230                  235                  240

Tyr Val Val His Asn Val Ala His Arg Phe Gly Lys Thr Ala Thr Phe
                245              250                  255

Met Pro Lys Pro Met Phe Gly Asp Asn Gly Ser Gly Met His Cys His
                260              265                  270

Met Ser Leu Ala Lys Asn Gly Thr Asn Leu Phe Ser Gly Asp Lys Tyr
        275              280                  285

Ala Gly Leu Ser Glu Gln Ala Leu Phe Tyr Ile Gly Gly Val Ile Lys
        290              295                  300

His Ala Lys Ala Ile Asn Ala Leu Ala Asn Pro Thr Thr Asn Ser Tyr
305              310                  315                  320

Lys Arg Leu Val Pro Gly Tyr Glu Ala Pro Val Met Leu Ala Tyr Ser
                325              330                  335

Ala Arg Asn Arg Ser Ala Ser Ile Arg Ile Pro Val Val Thr Ser Pro
                340              345                  350

Lys Ala Arg Arg Ile Glu Val Arg Phe Pro Asp Pro Ala Ala Asn Pro
        355              360                  365

Tyr Leu Cys Phe Ala Ala Leu Leu Met Ala Gly Leu Asp Gly Ile Lys
        370              375                  380

Asn Lys Ile His Pro Gly Glu Ala Met Asp Lys Asn Leu Tyr Asp Leu
385              390                  395                  400

Pro Pro Glu Glu Ala Lys Glu Ile Pro Gln Val Ala Gly Ser Leu Glu
                405              410                  415

Glu Ala Leu Gln Ala Leu Asp Ala Asp Arg Glu Phe Leu Thr Ala Gly
        420              425                  430
```

-continued

```
Gly Val Phe Thr Asn Asp Ala Ile Asp Ala Tyr Ile Ala Leu Arg Leu
        435                 440                 445

Glu Glu Asn Asp Arg Val Arg Met Thr Pro His Pro Val Glu Phe Glu
        450                 455                 460

Leu Tyr Tyr Ser Val
465
```

```
<210> SEQ ID NO 32
<211> LENGTH: 469
<212> TYPE: PRT
<213> ORGANISM: Klebsiella variicola

<400> SEQUENCE: 32
```

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ser His Gln Val Asn Ala Glu Phe Phe Glu Glu Gly Lys
        35                  40                  45

Met Phe Asp Gly Ser Ser Ile Gly Gly Trp Lys Gly Ile Asn Glu Ser
        50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
            100                 105                 110

Glu Glu Tyr Leu Arg Ala Thr Gly Ile Ala Asp Thr Val Leu Phe Gly
            115                 120                 125

Pro Glu Pro Glu Phe Phe Leu Phe Asp Asp Ile Arg Phe Gly Ala Ser
        130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Leu Gly Val
                165                 170                 175

Lys Gly Gly Tyr Phe Pro Val Pro Pro Val Asp Ser Ser Gln Asp Ile
            180                 185                 190

Arg Ser Thr Met Cys Met Ile Met Glu Glu Met Gly Leu Val Val Glu
            195                 200                 205

Ala His His His Glu Val Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ala Lys Asn Gly Thr Asn Leu Phe Ser Gly Asp Lys Tyr
            275                 280                 285

Ala Gly Leu Ser Glu Gln Ala Leu Phe Tyr Ile Gly Gly Val Ile Lys
        290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
```

```
                    325              330              335
Ala Arg Asn Arg Ser Ala Ser Ile Arg Ile Pro Val Val Thr Ser Pro
            340              345              350

Lys Ala Arg Arg Ile Glu Val Arg Phe Pro Asp Pro Ala Ala Asn Pro
            355              360              365

Tyr Leu Cys Phe Ala Ala Leu Leu Met Ala Gly Leu Asp Gly Ile Lys
        370              375              380

Asn Lys Ile His Pro Gly Glu Ala Met Asp Lys Asn Leu Tyr Asp Leu
385              390              395              400

Pro Pro Glu Glu Ala Lys Glu Ile Pro Gln Val Ala Gly Ser Leu Glu
                405              410              415

Glu Ala Leu Gln Ala Leu Asp Ala Asp Arg Glu Phe Leu Thr Ala Gly
            420              425              430

Gly Val Phe Thr Asn Asp Ala Ile Asp Ala Tyr Ile Ala Leu Arg Leu
            435              440              445

Glu Glu Asn Asp Arg Val Arg Met Thr Pro His Pro Val Glu Phe Glu
        450              455              460

Leu Tyr Tyr Ser Val
465

<210> SEQ ID NO 33
<211> LENGTH: 469
<212> TYPE: PRT
<213> ORGANISM: Klebsiella variicola

<400> SEQUENCE: 33

Met Ser Ala Glu His Val Leu Thr Met Leu Asn Glu His Glu Val Lys
1               5               10              15

Phe Val Asp Leu Arg Phe Thr Asp Thr Lys Gly Lys Glu Gln His Val
            20              25              30

Thr Ile Pro Ser His Gln Val Asn Ala Glu Phe Phe Glu Glu Gly Lys
        35              40              45

Met Phe Asp Gly Ser Ser Ile Gly Gly Trp Lys Gly Ile Asn Glu Ser
        50              55              60

Asp Met Val Leu Met Pro Asp Ala Ser Thr Ala Val Ile Asp Pro Phe
65              70              75              80

Tyr Glu Glu Pro Thr Leu Ile Ile Arg Cys Asp Ile Leu Glu Pro Gly
                85              90              95

Thr Leu Gln Gly Tyr Asp Arg Asp Pro Arg Ser Ile Ala Lys Arg Ala
            100             105             110

Glu Glu Tyr Leu Arg Ala Thr Gly Ile Ala Asp Thr Val Leu Phe Gly
            115             120             125

Pro Glu Pro Glu Phe Phe Leu Phe Asp Asp Ile Arg Phe Gly Ala Ser
        130             135             140

Ile Ser Gly Ser His Val Ala Ile Asp Asp Ile Glu Gly Ala Trp Asn
145             150             155             160

Ser Ser Thr Lys Tyr Glu Gly Gly Asn Lys Gly His Arg Pro Gly Val
                165             170             175

Lys Gly Gly Tyr Phe Pro Val Pro Pro Val Asp Ser Phe Gln Asp Ile
            180             185             190

Arg Ser Thr Met Cys Met Ile Met Glu Glu Met Gly Leu Val Val Glu
            195             200             205

Ala His His His Glu Val Ala Thr Ala Gly Gln Asn Glu Val Ala Thr
        210             215             220
```

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ala Lys Asn Gly Thr Asn Leu Phe Ser Gly Asp Lys Tyr
                275                 280                 285

Ala Gly Leu Ser Glu Gln Ala Leu Phe Tyr Ile Gly Gly Val Ile Lys
                290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Thr Ser Pro
                340                 345                 350

Lys Ala Arg Arg Ile Glu Val Arg Phe Pro Asp Pro Ala Ala Asn Pro
                355                 360                 365

Tyr Leu Cys Phe Ala Ala Leu Leu Met Ala Gly Leu Asp Gly Ile Lys
                370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                405                 410                 415

Glu Ala Leu Gln Ala Leu Asp Ala Asp Arg Glu Phe Leu Thr Ala Gly
                420                 425                 430

Gly Val Phe Thr Asn Asp Ala Ile Asp Ala Tyr Ile Ala Leu Arg Leu
                435                 440                 445

Glu Glu Asn Asp Arg Val Arg Met Thr Pro His Pro Val Glu Phe Glu
                450                 455                 460

Leu Tyr Tyr Ser Val
465

<210> SEQ ID NO 34
<211> LENGTH: 469
<212> TYPE: PRT
<213> ORGANISM: Klebsiella variicola

<400> SEQUENCE: 34

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ser His Gln Val Asn Ala Glu Phe Phe Glu Glu Gly Lys
                35                  40                  45

Met Phe Asp Gly Ser Ser Ile Gly Gly Trp Lys Gly Ile Asn Glu Ser
                50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
                100                 105                 110

Glu Glu Tyr Leu Arg Ala Thr Gly Ile Ala Asp Thr Val Leu Phe Gly
                115                 120                 125

-continued

```
Pro Glu Pro Glu Phe Phe Leu Phe Asp Asp Ile Arg Phe Gly Ala Ser
    130             135             140

Ile Ser Gly Ser His Val Ala Ile Asp Asp Ile Glu Gly Ala Trp Asn
145             150             155             160

Ser Ser Thr Lys Tyr Glu Gly Gly Asn Lys Gly His Arg Pro Gly Val
                165             170             175

Lys Gly Gly Tyr Phe Pro Val Pro Pro Val Asp Ser Ser Gln Asp Ile
            180             185             190

Arg Ser Thr Met Cys Met Ile Met Glu Glu Met Gly Leu Val Val Lys
        195             200             205

Ala His His His Glu Val Ala Thr Ala Gly Gln Asn Glu Val Ala Thr
    210             215             220

Arg Phe Asn Thr Met Thr Lys Lys Ala Asp Glu Ile Gln Ile Tyr Lys
225             230             235             240

Tyr Val Val His Asn Val Ala His Arg Phe Gly Lys Thr Ala Thr Phe
            245             250             255

Met Pro Lys Pro Met Phe Gly Asp Asn Gly Ser Gly Met His Cys His
            260             265             270

Met Ser Leu Ala Lys Asn Gly Thr Asn Leu Phe Ser Gly Asp Lys Tyr
    275             280             285

Ala Gly Leu Ser Glu Gln Ala Leu Phe Tyr Ile Gly Gly Val Ile Lys
    290             295             300

His Ala Lys Ala Ile Asn Ala Leu Ala Asn Pro Thr Thr Asn Ser Tyr
305             310             315             320

Lys Arg Leu Val Pro Gly Tyr Glu Ala Pro Val Met Leu Ala Tyr Ser
            325             330             335

Ala Arg Asn Arg Ser Ala Ser Ile Arg Ile Pro Val Val Thr Ser Pro
            340             345             350

Lys Ala Arg Arg Ile Glu Val Arg Phe Pro Asp Pro Ala Ala Asn Pro
            355             360             365

Tyr Leu Cys Phe Ala Ala Leu Leu Met Ala Gly Leu Asp Gly Ile Lys
    370             375             380

Asn Lys Ile His Pro Gly Glu Ala Met Asp Lys Asn Leu Tyr Asp Leu
385             390             395             400

Pro Pro Glu Glu Ala Lys Glu Ile Pro Gln Val Ala Gly Ser Leu Glu
            405             410             415

Glu Ala Leu Gln Ala Leu Asp Ala Asp Arg Glu Phe Leu Thr Ala Gly
            420             425             430

Gly Val Phe Thr Asn Asp Ala Ile Asp Ala Tyr Ile Ala Leu Arg Leu
            435             440             445

Glu Glu Asn Asp Arg Val Arg Met Thr Pro His Pro Val Glu Phe Glu
    450             455             460

Leu Tyr Tyr Ser Val
465
```

<210> SEQ ID NO 35
<211> LENGTH: 469
<212> TYPE: PRT
<213> ORGANISM: Klebsiella variicola

<400> SEQUENCE: 35

```
Met Ser Ala Glu His Val Leu Thr Met Leu Asn Glu His Glu Val Lys
1               5               10              15

Phe Val Asp Leu Arg Phe Thr Asp Thr Lys Gly Lys Glu Gln His Val
```

```
                 20                    25                    30

Thr Ile Pro Ser His Gln Val Asn Ala Glu Phe Phe Glu Glu Gly Lys
             35                    40                    45

Met Phe Asp Gly Ser Ser Ile Gly Gly Trp Lys Gly Ile Asn Glu Ser
         50                    55                    60

Asp Met Val Leu Met Pro Asp Ala Ser Thr Ala Val Ile Asp Pro Phe
65                    70                    75                    80

Tyr Glu Glu Pro Thr Leu Ile Ile Arg Cys Asp Ile Leu Glu Pro Gly
                 85                    90                    95

Thr Leu Gln Gly Tyr Asp Arg Asp Pro Arg Ser Ile Ala Lys Arg Ala
             100                   105                   110

Glu Glu Tyr Leu Arg Ala Thr Gly Ile Ala Asp Thr Val Leu Phe Gly
         115                   120                   125

Pro Glu Pro Glu Phe Phe Leu Phe Asp Asp Ile Arg Phe Gly Ala Ser
     130                   135                   140

Ile Ser Gly Ser His Val Ala Ile Asp Asp Ile Glu Gly Ala Trp Asn
145                   150                   155                   160

Ser Ser Thr Lys Tyr Glu Gly Gly Asn Lys Gly His Arg Pro Gly Val
                 165                   170                   175

Lys Gly Gly Tyr Phe Pro Val Pro Pro Val Asp Ser Ser Gln Asp Ile
                 180                   185                   190

Arg Ser Thr Met Cys Met Ile Met Glu Glu Met Gly Leu Val Val Glu
             195                   200                   205

Ala His His His Glu Val Ala Thr Ala Gly Gln Asn Glu Val Ala Thr
         210                   215                   220

Arg Phe Asn Thr Met Thr Lys Lys Ala Asp Glu Ile Gln Ile Tyr Lys
225                   230                   235                   240

Tyr Val Val His Asn Val Ala His Arg Phe Gly Lys Thr Ala Thr Phe
                 245                   250                   255

Met Pro Lys Pro Met Phe Gly Asp Asn Gly Ser Ser Met His Cys His
                 260                   265                   270

Met Ser Leu Ala Lys Asn Gly Thr Asn Leu Phe Ser Gly Asp Lys Tyr
             275                   280                   285

Ala Gly Leu Ser Glu Gln Ala Leu Phe Tyr Ile Gly Gly Val Ile Lys
     290                   295                   300

His Ala Lys Ala Ile Asn Ala Leu Ala Asn Pro Thr Thr Asn Ser Tyr
305                   310                   315                   320

Lys Arg Leu Val Pro Gly Tyr Glu Ala Pro Val Met Leu Ala Tyr Ser
                 325                   330                   335

Ala Arg Asn Arg Ser Ala Ser Ile Arg Ile Pro Val Val Thr Ser Pro
             340                   345                   350

Lys Ala Arg Arg Ile Glu Val Arg Phe Pro Asp Pro Ala Ala Asn Pro
             355                   360                   365

Tyr Leu Cys Phe Ala Ala Leu Leu Met Ala Gly Leu Asp Gly Ile Lys
     370                   375                   380

Asn Lys Ile His Pro Gly Glu Ala Met Asp Lys Asn Leu Tyr Asp Leu
385                   390                   395                   400

Pro Pro Glu Glu Ala Lys Glu Ile Pro Gln Val Ala Gly Ser Leu Glu
                 405                   410                   415

Glu Ala Leu Gln Ala Leu Asp Ala Asp Arg Glu Phe Leu Thr Ala Gly
             420                   425                   430

Gly Val Phe Thr Asn Asp Ala Ile Asp Ala Tyr Ile Ala Leu Arg Leu
             435                   440                   445
```

```
Glu Glu Asn Asp Arg Val Arg Met Thr Pro His Pro Val Glu Phe Glu
    450                 455                 460

Leu Tyr Tyr Ser Val
465

<210> SEQ ID NO 36
<211> LENGTH: 469
<212> TYPE: PRT
<213> ORGANISM: Klebsiella variicola

<400> SEQUENCE: 36

Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ser His Gln Val Asn Ala Glu Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Leu Gln Gly Tyr Asp Arg Asp Pro Arg Ser Ile Ala Lys Arg Ala
            100                 105                 110

Glu Glu Tyr Leu Arg Ala Thr Gly Ile Ala Asp Thr Val Leu Phe Gly
            115                 120                 125

Pro Glu Pro Glu Phe Phe Leu Phe Asp Asp Ile Arg Phe Gly Ala Ser
    130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Pro Gly Val
                165                 170                 175

Lys Gly Gly Tyr Phe Pro Val Pro Pro Val Asp Ser Ser Gln Asp Ile
            180                 185                 190

Arg Ser Thr Met Cys Met Ile Met Glu Glu Met Gly Leu Val Val Glu
            195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ala Lys Asn Gly Thr Asn Leu Phe Ser Gly Asp Lys Tyr
            275                 280                 285

Ala Gly Leu Ser Glu Gln Ala Leu Phe Tyr Ile Gly Gly Val Ile Lys
    290                 295                 300

His Ala Lys Ala Ile Asn Ala Leu Ala Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asp Arg Ser Ala Ser Ile Arg Ile Pro Val Val Thr Ser Pro
```

-continued

```
                  340                 345                 350
Lys Ala Arg Arg Ile Glu Val Arg Phe Pro Asp Pro Ala Ala Asn Pro
            355                 360                 365

Tyr Leu Cys Phe Ala Ala Leu Leu Met Ala Gly Leu Asp Gly Ile Lys
            370                 375                 380

Asn Lys Ile His Pro Gly Glu Ala Met Asp Lys Asn Leu Tyr Asp Leu
385                 390                 395                 400

Pro Pro Glu Glu Ala Lys Glu Ile Pro Gln Val Ala Gly Ser Leu Glu
                  405                 410                 415

Glu Ala Leu Gln Ala Leu Asp Ala Asp Arg Glu Phe Leu Thr Ala Gly
                  420                 425                 430

Gly Val Phe Thr Asn Asp Ala Ile Asp Ala Tyr Ile Ala Leu Arg Leu
            435                 440                 445

Glu Glu Asn Asp Arg Val Arg Met Thr Pro His Pro Val Glu Phe Glu
            450                 455                 460

Leu Tyr Tyr Ser Val
465

<210> SEQ ID NO 37
<211> LENGTH: 945
<212> TYPE: PRT
<213> ORGANISM: Klebsiella variicola

<400> SEQUENCE: 37

Met Met Pro Leu Ser Pro Gln Leu Gln Gln His Trp Gln Thr Val Ala
1               5                   10                  15

Asp Arg Leu Pro Ala Asp Phe Pro Ile Ala Glu Leu Ser Pro Gln Ala
            20                  25                  30

Arg Ser Val Met Ala Phe Ser Asp Phe Val Glu Gln Ser Val Ile Ala
            35                  40                  45

Gln Pro Gly Trp Leu Asn Glu Leu Ala Asp Ser Ser Pro Glu Ala Glu
      50                  55                  60

Glu Trp Arg His Tyr Glu Ala Trp Leu Gln Asp Arg Leu Gln Ala Val
65                  70                  75                  80

Thr Asp Glu Ala Gly Leu Met Arg Glu Leu Arg Leu Phe Arg Arg Gln
                  85                  90                  95

Met Met Val Arg Ile Ala Trp Ala Gln Ala Leu Ser Leu Val Ser Glu
            100                 105                 110

Glu Glu Thr Leu Gln Gln Leu Ser Val Leu Ala Glu Thr Leu Ile Val
            115                 120                 125

Ala Ala Arg Asp Trp Leu Tyr Ala Ala Cys Cys Lys Glu Trp Gly Thr
      130                 135                 140

Pro Cys Asn Ala Glu Gly Gln Pro Gln Pro Leu Leu Ile Leu Gly Met
145                 150                 155                 160

Gly Lys Leu Gly Gly Gly Glu Leu Asn Phe Ser Ser Asp Ile Asp Leu
            165                 170                 175

Ile Phe Ala Trp Pro Glu His Gly Ala Thr Arg Gly Gly Arg Arg Glu
            180                 185                 190

Leu Asp Asn Ala Gln Phe Phe Thr Arg Leu Gly Gln Arg Leu Ile Lys
            195                 200                 205

Ala Leu Asp Gln Pro Thr Gln Asp Gly Phe Val Tyr Arg Val Asp Met
      210                 215                 220

Arg Leu Arg Pro Phe Gly Asp Ser Gly Pro Leu Val Leu Ser Phe Ala
225                 230                 235                 240
```

```
Ala Leu Glu Asp Tyr Tyr Gln Glu Gln Gly Arg Asp Trp Glu Arg Tyr
            245                 250                 255

Ala Met Val Lys Ala Arg Ile Met Gly Asp Asn Asp Gly Val Tyr Ala
            260                 265                 270

Ser Glu Leu Arg Ala Met Leu Arg Pro Phe Val Phe Arg Arg Tyr Ile
            275                 280                 285

Asp Phe Ser Val Ile Gln Ser Leu Arg Asn Met Lys Gly Met Ile Ala
        290                 295                 300

Arg Glu Val Arg Arg Arg Gly Leu Lys Asp Asn Ile Lys Leu Gly Ala
    305                 310                 315                 320

Gly Glu Ile Arg Glu Ile Glu Phe Ile Val Gln Val Phe Gln Leu Ile
                325                 330                 335

Arg Gly Gly Arg Glu Pro Ala Leu Gln Gln Arg Ala Leu Leu Pro Thr
            340                 345                 350

Leu Ala Ala Ile Asp Glu Leu His Leu Leu Pro Glu Gly Asp Ala Ala
            355                 360                 365

Leu Leu Arg Glu Ala Tyr Leu Phe Leu Arg Arg Leu Glu Asn Leu Leu
        370                 375                 380

Gln Ser Ile Asn Asp Glu Gln Thr Gln Thr Leu Pro Gln Asp Glu Leu
    385                 390                 395                 400

Asn Arg Ala Arg Leu Ala Trp Gly Met His Thr Glu Asp Trp Glu Thr
                405                 410                 415

Leu Ser Ala Gln Leu Ala Ser Gln Met Ala Asn Val Arg Arg Val Phe
            420                 425                 430

Asn Glu Leu Ile Gly Asp Asp Glu Asp Gln Ser Pro Asp Glu Gln Leu
            435                 440                 445

Ala Glu Tyr Trp Arg Glu Leu Trp Gln Asp Ala Leu Glu Glu Asp Asp
        450                 455                 460

Ala Ser Pro Ala Leu Ala His Leu Asn Asp Thr Asp Arg Arg Ser Val
    465                 470                 475                 480

Leu Ala Leu Ile Ala Asp Phe Arg Lys Glu Leu Asp Arg Arg Thr Ile
                485                 490                 495

Gly Pro Arg Gly Arg Gln Val Leu Asp Gln Leu Met Pro His Leu Leu
            500                 505                 510

Ser Glu Ile Cys Ser Arg Ala Asp Ala Pro Leu Pro Leu Ala Arg Ile
            515                 520                 525

Thr Pro Leu Leu Thr Gly Ile Val Thr Arg Thr Thr Tyr Leu Glu Leu
        530                 535                 540

Leu Ser Glu Phe Pro Gly Ala Leu Lys His Leu Ile Thr Leu Cys Ala
    545                 550                 555                 560

Ala Ser Pro Met Val Ala Ser Gln Leu Ala Arg His Pro Leu Leu Leu
                565                 570                 575

Asp Glu Leu Leu Asp Pro Asn Thr Leu Tyr Gln Pro Thr Ala Thr Asp
            580                 585                 590

Ala Tyr Arg Asp Glu Leu Arg Gln Tyr Leu Leu Arg Val Pro Glu Glu
            595                 600                 605

Asp Glu Glu Gln Gln Leu Glu Ala Leu Arg Gln Phe Lys Gln Ala Gln
        610                 615                 620

Gln Leu His Ile Ala Ala Ala Asp Ile Ala Gly Thr Leu Pro Val Met
    625                 630                 635                 640

Lys Val Ser Asp His Leu Thr Trp Leu Ala Glu Ala Ile Leu Asp Ala
                645                 650                 655

Val Val Gln Gln Ala Trp Gly Gln Met Val Ala Arg Tyr Gly Gln Pro
```

-continued

```
              660              665              670
Thr His Leu His Asp Arg Gln Gly Arg Gly Phe Ala Val Val Gly Tyr
              675              680              685

Gly Lys Leu Gly Gly Trp Glu Leu Gly Tyr Ser Ser Asp Leu Asp Leu
              690              695              700

Val Phe Leu His Asp Cys Pro Ala Glu Val Met Thr Asp Gly Glu Arg
705              710              715              720

Glu Ile Asp Gly Arg Gln Phe Tyr Leu Arg Leu Ala Gln Arg Ile Met
              725              730              735

His Leu Phe Ser Thr Arg Thr Ser Ser Asp Ile Leu Tyr Glu Val Asp
              740              745              750

Ala Arg Leu Arg Pro Ser Gly Ala Ala Gly Met Leu Val Thr Thr Ala
              755              760              765

Asp Ala Phe Ala Asp Tyr Gln Gln Asn Glu Ala Trp Thr Trp Glu His
              770              775              780

Gln Ala Leu Val Arg Ala Arg Val Val Tyr Gly Asp Pro Ala Leu Gln
785              790              795              800

Ala Arg Phe Asp Ala Ile Arg Arg Asp Ile Leu Thr Thr Pro Arg Glu
              805              810              815

Gly Met Thr Leu Gln Thr Glu Val Arg Glu Met Arg Glu Lys Met Arg
              820              825              830

Ala His Leu Gly Asn Lys His Pro Asp Arg Phe Asp Ile Lys Ala Asp
              835              840              845

Ala Gly Gly Ile Thr Asp Ile Glu Phe Ile Thr Gln Tyr Leu Val Leu
              850              855              860

Arg Tyr Ala Ser Asp Lys Pro Lys Leu Thr Arg Trp Ser Asp Asn Val
865              870              875              880

Arg Ile Leu Glu Leu Leu Ala Gln Asn Asp Ile Met Asp Glu Glu Glu
              885              890              895

Ala Arg Ala Leu Thr His Ala Tyr Thr Thr Leu Arg Asp Ala Leu His
              900              905              910

His Leu Ala Leu Gln Glu Gln Pro Gly His Val Ala Pro Glu Ala Phe
              915              920              925

Ser Arg Glu Arg Gln Gln Val Ser Ala Ser Trp Gln Lys Trp Leu Met
930              935              940

Ala
945

<210> SEQ ID NO 38
<211> LENGTH: 469
<212> TYPE: PRT
<213> ORGANISM: Kosakonia sacchari

<400> SEQUENCE: 38

Met Ser Ala Glu His Val Leu Thr Met Leu Asn Glu His Glu Val Lys
1               5               10              15

Phe Val Asp Leu Arg Phe Thr Asp Thr Lys Gly Lys Glu Gln His Val
              20              25              30

Thr Ile Pro Ala His Gln Val Asn Ala Asp Phe Phe Glu Glu Gly Lys
              35              40              45

Met Phe Asp Gly Ser Ser Ile Gly Gly Trp Lys Gly Ile Asn Glu Ser
              50              55              60

Asp Ile Val Leu Met Pro Asp Ala Thr Thr Ala Val Ile Asp Pro Phe
65              70              75              80
```

-continued

```
Tyr Glu Glu Ser Thr Leu Ile Ile Arg Cys Asp Ile Leu Glu Pro Gly
            85                  90                  95

Thr Met Gln Gly Tyr Asp Arg Asp Pro Arg Ser Ile Ala Lys Arg Ala
            100             105             110

Glu Glu Tyr Leu Arg Ser Thr Gly Leu Ala Asp Thr Val Leu Phe Gly
            115             120             125

Pro Glu Pro Glu Phe Phe Leu Phe Asp Asp Val Arg Phe Gly Ser Ser
    130             135             140

Ile Ser Gly Ser Ser Val Ala Ile Asp Asp Ile Glu Gly Ala Trp Asn
145             150             155             160

Thr Ser Thr Lys Tyr Glu Gly Gly Asn Lys Gly His Arg Pro Ala Val
            165             170             175

Lys Gly Gly Tyr Phe Pro Val Pro Pro Val Asp Ser Ser Gln Asp Leu
            180             185             190

Arg Ser Thr Met Cys Leu Val Met Glu Glu Met Gly Leu Val Val Glu
            195             200             205

Ala His His His Glu Val Ala Thr Ala Gly Gln Asn Glu Val Ala Thr
            210             215             220

Arg Phe Asn Thr Met Thr Lys Lys Ala Asp Glu Ile Gln Ile Tyr Lys
225             230             235             240

Tyr Val Val His Asn Val Ala His Arg Phe Gly Lys Thr Ala Thr Phe
            245             250             255

Met Pro Lys Pro Met Phe Gly Asp Asn Gly Ser Gly Met His Cys His
            260             265             270

Met Ser Leu Ser Lys Asn Gly Thr Asn Leu Phe Ser Gly Asp Lys Tyr
            275             280             285

Ala Gly Leu Ser Glu Met Ala Leu Tyr Tyr Ile Gly Gly Val Ile Lys
    290             295             300

His Ala Lys Ala Ile Asn Ala Leu Ser Asn Pro Thr Thr Asn Ser Tyr
305             310             315             320

Lys Arg Leu Val Pro Gly Tyr Glu Ala Pro Val Met Leu Ala Tyr Ser
            325             330             335

Ala Arg Asn Arg Ser Ala Ser Ile Arg Ile Pro Val Val Ala Ser Pro
            340             345             350

Lys Ala Arg Arg Ile Glu Val Arg Phe Pro Asp Pro Ala Ala Asn Pro
            355             360             365

Tyr Leu Cys Phe Ala Ala Leu Leu Met Ala Gly Leu Asp Gly Ile Lys
    370             375             380

Asn Lys Ile His Pro Gly Glu Ala Met Asp Lys Asn Leu Tyr Asp Leu
385             390             395             400

Pro Ala Glu Glu Ala Lys Glu Ile Pro Gln Val Ala Gly Ser Leu Glu
            405             410             415

Glu Ala Leu Asn Ala Leu Asp Ala Asp Arg Glu Phe Leu Thr Ala Gly
            420             425             430

Gly Val Phe Thr Asp Asp Ala Ile Asp Ala Tyr Ile Ala Leu Arg Ile
            435             440             445

Glu Glu Asn Asp Arg Val Arg Met Thr Pro His Pro Val Glu Phe Glu
    450             455             460

Leu Tyr Tyr Ser Val
465
```

```
<210> SEQ ID NO 39
<211> LENGTH: 469
<212> TYPE: PRT
```

<213> ORGANISM: Metakosakonia intestini

<400> SEQUENCE: 39

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ala Lys Arg Ala
            100                 105                 110

Glu Glu Tyr Leu Arg Ala Thr Gly Ile Ala Asp Thr Val Leu Phe Gly
        115                 120                 125

Pro Glu Pro Glu Phe Phe Leu Phe Asp Asp Val Arg Phe Gly Ser Ser
    130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly Leu Arg Pro Ala Val
                165                 170                 175

Lys Gly Gly Tyr Phe Pro Val Pro Pro Val Asp Ser Ala Gln Asp Leu
            180                 185                 190

Arg Ser Thr Met Cys Leu Val Met Glu Glu Met Gly Leu Val Val Glu
        195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Val Asn Leu Phe Ser Gly Asp Lys Tyr
        275                 280                 285

Ala Gly Leu Ser Glu Gln Ala Leu Tyr Tyr Ile Gly Gly Val Ile Lys
    290                 295                 300

His Ala Lys Ala Ile Asn Ala Leu Ser Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
            340                 345                 350

Lys Ala Arg Arg Ile Glu Val Arg Phe Pro Asp Pro Ala Ala Asn Pro
        355                 360                 365

Tyr Leu Cys Phe Ala Ala Leu Leu Met Ala Gly Leu Asp Gly Ile Lys
    370                 375                 380

Asn Lys Ile His Pro Gly Glu Ala Met Asp Lys Asn Leu Tyr Asp Leu
385                 390                 395                 400
```

```
Pro Ala Glu Glu Ala Lys Glu Ile Pro Gln Val Ala Gly Ser Leu Glu
                405                 410                 415

Glu Ala Leu Asn Cys Leu Asn Glu Asp Arg Glu Phe Leu Thr Ala Gly
            420                 425                 430

Gly Val Phe Thr Asp Asp Ala Ile Asp Ala Tyr Ile Ala Leu Arg Ile
            435                 440                 445

Glu Glu Asn Asp Arg Val Arg Met Thr Pro His Pro Val Glu Phe Glu
        450                 455                 460

Leu Tyr Tyr Ser Val
465

<210> SEQ ID NO 40
<211> LENGTH: 469
<212> TYPE: PRT
<213> ORGANISM: Metakosakonia intestini

<400> SEQUENCE: 40

Met Ser Ala Glu His Val Leu Thr Met Leu Asn Glu His Glu Val Lys
1               5                  10                  15

Phe Val Asp Leu Arg Phe Thr Asp Thr Lys Gly Lys Glu Gln His Val
            20                  25                  30

Thr Ile Pro Ala His Gln Val Asn Ala Asp Phe Phe Glu Glu Gly Lys
        35                  40                  45

Met Phe Asp Gly Ser Ser Ile Gly Gly Trp Lys Gly Ile Asn Glu Ser
        50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95

Thr Met Gln Gly Tyr Asp Arg Asp Pro Arg Ser Ile Ala Lys Arg Ala
            100                 105                 110

Glu Glu Tyr Leu Arg Ala Thr Gly Ile Ala Asp Thr Val Leu Phe Gly
            115                 120                 125

Pro Glu Pro Glu Phe Phe Leu Phe Asp Asp Val Arg Phe Gly Ser Ser
        130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Pro Ala Val
                165                 170                 175

Lys Gly Gly Tyr Phe Pro Val Pro Pro Val Asp Ser Ala Gln Asp Leu
            180                 185                 190

Arg Ser Thr Met Cys Leu Val Met Glu Glu Met Gly Leu Val Val Glu
            195                 200                 205

Ala His His Glu Val Ala Thr Ala Ser Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
            260                 265                 270

Met Ser Leu Ser Lys Asn Gly Val Asn Leu Phe Ser Gly Asp Lys Tyr
        275                 280                 285

Ala Gly Leu Ser Glu Gln Ala Leu Tyr Tyr Ile Gly Gly Val Ile Lys
        290                 295                 300
```

```
His Ala Lys Ala Ile Asn Ala Leu Ser Asn Pro Thr Thr Asn Ser Tyr
305                 310             315                 320

Lys Arg Leu Val Pro Gly Tyr Glu Ala Pro Val Met Leu Ala Tyr Ser
                325             330                 335

Ala Arg Asn Arg Ser Ala Ser Ile Arg Ile Pro Val Val Ala Ser Pro
            340             345             350

Lys Ala Arg Arg Ile Glu Val Arg Phe Pro Asp Pro Ala Ala Asn Pro
            355             360             365

Tyr Leu Cys Phe Ala Ala Leu Leu Met Ala Gly Leu Asp Gly Ile Lys
    370             375             380

Asn Lys Ile His Pro Gly Glu Ala Met Asp Lys Asn Leu Tyr Asp Leu
385             390             395                 400

Pro Ala Glu Glu Ala Lys Glu Ile Pro Gln Val Ala Gly Ser Leu Glu
            405             410             415

Glu Ala Leu Asn Cys Leu Asn Glu Asp Arg Glu Phe Leu Thr Ala Gly
            420             425             430

Gly Val Phe Thr Asp Asp Ala Ile Asp Ala Tyr Ile Ala Leu Arg Ile
            435             440             445

Glu Glu Asn Asp Arg Val Arg Met Thr Pro His Pro Val Glu Phe Glu
    450             455             460

Leu Tyr Tyr Ser Val
465
```

<210> SEQ ID NO 41
<211> LENGTH: 469
<212> TYPE: PRT
<213> ORGANISM: Metakosakonia intestini

<400> SEQUENCE: 41

```
Met Ser Ala Glu His Val Leu Thr Met Leu Asn Glu His Glu Val Lys
1               5               10                  15

Phe Val Asp Leu Arg Phe Thr Asp Thr Lys Gly Lys Glu Gln His Val
            20              25                  30

Thr Ile Pro Ala His Gln Val Asn Ala Asp Phe Phe Glu Glu Gly Lys
        35              40                  45

Met Phe Asp Gly Ser Ser Ile Gly Gly Trp Lys Gly Ile Asn Glu Ser
    50              55                  60

Asp Met Val Leu Met Pro Asp Ala Ser Thr Ala Val Ile Asp Pro Phe
65              70                  75                  80

Tyr Glu Glu Pro Thr Leu Ile Ile Arg Cys Asp Ile Leu Glu Pro Gly
                85              90                  95

Thr Met Gln Gly Tyr Asp Arg Asp Pro Arg Ser Ile Ala Lys Arg Ala
            100             105             110

Glu Glu Tyr Leu Arg Ala Thr Gly Ile Ala Asp Thr Val Leu Phe Gly
            115             120             125

Pro Glu Pro Glu Phe Phe Leu Phe Asp Asp Val Arg Phe Gly Ser Ser
    130             135             140

Ile Ser Gly Ser His Val Ala Ile Asp Asp Ile Glu Gly Ala Trp Asn
145             150             155             160

Ser Ser Thr Lys Tyr Glu Gly Gly Asn Lys Gly His Arg Pro Ala Val
                165             170             175

Lys Gly Gly Tyr Phe Pro Val Pro Pro Val Asp Ser Ala Gln Asp Leu
            180             185             190

Arg Ser Thr Met Cys Leu Val Met Glu Glu Met Gly Leu Val Val Glu
```

-continued

```
                195                 200                 205

Ala His His His Glu Val Ala Thr Ala Gly Gln Asn Glu Val Ala Thr
    210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Ile Phe
                245                 250                 255

Met Pro Lys Pro Met Phe Gly Asp Asn Gly Ser Gly Met His Cys His
                260                 265                 270

Met Ser Leu Ser Lys Asn Gly Val Asn Leu Phe Ser Gly Asp Lys Tyr
                275                 280                 285

Ala Gly Leu Ser Glu Gln Ala Leu Tyr Tyr Ile Gly Gly Val Ile Lys
    290                 295                 300

His Ala Lys Ala Ile Asn Ala Leu Ser Asn Pro Thr Thr Asn Ser Tyr
305                 310                 315                 320

Lys Arg Leu Val Pro Gly Tyr Glu Ala Pro Val Met Leu Ala Tyr Ser
                325                 330                 335

Ala Arg Asn Arg Ser Ala Ser Ile Arg Ile Pro Val Val Ala Ser Pro
                340                 345                 350

Lys Ala Arg Arg Ile Glu Val Arg Phe Pro Asp Pro Ala Ala Asn Pro
                355                 360                 365

Tyr Leu Cys Phe Ala Ala Leu Leu Met Ala Gly Leu Asp Gly Ile Lys
    370                 375                 380

Asn Lys Ile His Pro Gly Glu Ala Met Asp Lys Asn Leu Tyr Asp Leu
385                 390                 395                 400

Pro Ala Glu Glu Ala Lys Glu Ile Pro Gln Val Ala Gly Ser Leu Glu
                405                 410                 415

Glu Ala Leu Asn Cys Leu Asn Glu Asp Arg Glu Phe Leu Thr Ala Gly
                420                 425                 430

Gly Val Phe Thr Asp Asp Ala Ile Asp Ala Tyr Ile Ala Leu Arg Ile
                435                 440                 445

Glu Glu Asn Asp Arg Val Arg Met Thr Pro His Pro Val Glu Phe Glu
    450                 455                 460

Leu Tyr Tyr Ser Val
465
```

```
<210> SEQ ID NO 42
<211> LENGTH: 469
<212> TYPE: PRT
<213> ORGANISM: Metakosakonia intestini

<400> SEQUENCE: 42
```

```
Met Ser Ala Glu His Val Leu Thr Met Leu Asn Glu His Glu Val Lys
1               5                   10                  15

Phe Val Asp Leu Arg Phe Thr Asp Thr Lys Gly Lys Glu Gln His Val
                20                  25                  30

Thr Ile Pro Ala His Gln Val Asn Ala Asp Phe Phe Glu Glu Gly Lys
            35                  40                  45

Met Phe Asp Gly Ser Ser Ile Gly Gly Trp Lys Gly Ile Asn Glu Ser
    50                  55                  60

Asp Met Val Leu Met Pro Asp Ala Ser Thr Ala Val Ile Asp Pro Phe
65                  70                  75                  80

Tyr Glu Glu Pro Thr Leu Ile Ile Arg Cys Asp Ile Leu Glu Pro Gly
                85                  90                  95
```

-continued

```
Thr Met Gln Gly Tyr Asp Arg Asp Pro Arg Ser Ile Ala Lys Arg Ala
        100                 105                 110

Glu Glu Tyr Leu Arg Ala Thr Gly Ile Ala Asp Thr Val Leu Phe Gly
        115                 120                 125

Pro Glu Pro Glu Phe Phe Leu Phe Asp Asp Val Arg Phe Gly Ser Ser
    130                 135                 140

Ile Ser Gly Ser His Val Ala Ile Asp Asp Ile Glu Gly Ala Trp Asn
145                 150                 155                 160

Ser Ser Thr Lys Tyr Glu Gly Gly Asn Lys Gly His Arg Pro Ala Val
                165                 170                 175

Lys Gly Gly Tyr Phe Pro Val Pro Pro Val Asp Ser Ala Gln Asp Leu
                180                 185                 190

Arg Ser Thr Met Cys Leu Val Met Glu Glu Met Gly Leu Val Val Glu
        195                 200                 205

Ala His His His Glu Val Ala Thr Ala Gly Gln Asn Glu Val Ala Thr
        210                 215                 220

Arg Phe Asn Thr Met Thr Lys Lys Ala Asp Glu Ile Gln Ile Tyr Lys
225                 230                 235                 240

Tyr Val Val His Asn Val Ala His Arg Phe Gly Lys Thr Ala Thr Phe
                245                 250                 255

Met Pro Lys Pro Met Phe Gly Asp Asn Gly Ser Gly Met His Cys His
                260                 265                 270

Met Ser Leu Ser Lys Asn Gly Val Asn Leu Phe Ser Gly Asp Lys Tyr
        275                 280                 285

Ala Gly Leu Ser Glu Gln Ala Leu Tyr Tyr Ile Gly Gly Val Ile Lys
        290                 295                 300

His Ala Lys Ala Ile Asn Ala Leu Ser Asn Pro Thr Thr Asn Ser Tyr
305                 310                 315                 320

Lys Arg Leu Val Pro Gly Tyr Glu Val Pro Val Met Leu Ala Tyr Ser
                325                 330                 335

Ala Arg Asn Arg Ser Ala Ser Ile Arg Ile Pro Val Val Ala Ser Pro
                340                 345                 350

Lys Ala Arg Arg Ile Glu Val Arg Phe Pro Asp Pro Ala Ala Asn Pro
                355                 360                 365

Tyr Leu Cys Phe Ala Ala Leu Leu Met Ala Gly Leu Asp Gly Ile Lys
    370                 375                 380

Asn Lys Ile His Pro Gly Glu Ala Met Asp Lys Asn Leu Tyr Asp Leu
385                 390                 395                 400

Pro Ala Glu Glu Ala Lys Glu Ile Pro Gln Val Ala Gly Ser Leu Glu
                405                 410                 415

Glu Ala Leu Asn Cys Leu Asn Glu Asp Arg Glu Phe Leu Thr Ala Gly
        420                 425                 430

Gly Val Phe Thr Asp Asp Ala Ile Asp Ala Tyr Ile Ala Leu Arg Ile
        435                 440                 445

Glu Glu Asn Asp Arg Val Arg Met Thr Pro His Pro Val Glu Phe Glu
    450                 455                 460

Leu Tyr Tyr Ser Val
465

<210> SEQ ID NO 43
<211> LENGTH: 471
<212> TYPE: PRT
<213> ORGANISM: Paraburkholderia tropica

<400> SEQUENCE: 43
```

-continued

```
Met Ser Lys Ser Val Ala Asp Val Met Gln Leu Val Lys Asp Glu Asp
1               5                   10                  15

Val Lys Phe Val Asp Phe Arg Phe Thr Asp Thr Arg Gly Lys Glu Gln
                20                  25                  30

His Val Ser Val Pro Leu Ser His Phe Asp Glu Asp Lys Phe Glu Ser
        35                  40                  45

Gly His Ala Phe Asp Gly Ser Ser Ile Ala Gly Trp Lys Gly Ile Glu
        50                  55                  60

Ala Ser Asp Met Leu Leu Val Pro Asp Ala Asn Thr Ala Phe Ile Asp
65                  70                  75                  80

Pro Phe Tyr Glu Glu Ser Thr Leu Val Leu Thr Cys Asp Val Val Glu
                85                  90                  95

Pro Ala Asp Gly Lys Gly Cys Glu Arg Asp Pro Arg Ser Leu Ala Lys
                100                 105                 110

Arg Ala Glu Ala Tyr Leu Lys Ser Thr Gly Leu Gly Asp Thr Ala Phe
        115                 120                 125

Phe Gly Pro Glu Pro Glu Phe Phe Ile Phe Asp Ser Val Gln Trp Asn
        130                 135                 140

Thr Asp Met Ser Gly Ser Phe Val Lys Ile Gly Ser Glu Glu Ala Pro
145                 150                 155                 160

Trp Ser Ser Lys Glu Phe Glu Gly Gly Asn Thr Gly His Arg Pro
                165                 170                 175

Gly Val Lys Gly Gly Tyr Phe Pro Val Ala Pro Val Asp Thr Phe Gln
                180                 185                 190

Asp Ile Arg Ser Glu Met Cys Leu Leu Leu Glu Gln Ile Gly Ile Pro
                195                 200                 205

Val Glu Val His His His Glu Val Ala Gly Gln Gly Gln Asn Glu Ile
        210                 215                 220

Gly Thr Lys Phe Ser Thr Leu Val Gln Arg Ala Asp Trp Thr Gln Gln
225                 230                 235                 240

Met Lys Tyr Ile Ile His Asn Val Ala His Thr Tyr Gly Lys Thr Ala
                245                 250                 255

Thr Phe Met Pro Lys Pro Ile Val Gly Asp Asn Gly Ser Gly Met His
                260                 265                 270

Val His Gln Ser Ile Trp Lys Asp Gly Gln Asn Leu Phe Ala Gly Asn
        275                 280                 285

Gly Tyr Ala Gly Leu Ser Glu Phe Ala Leu Phe Tyr Ile Gly Gly Ile
        290                 295                 300

Ile Lys His Ala Arg Ala Leu Asn Ala Ile Thr Asn Pro Ser Thr Asn
305                 310                 315                 320

Ser Tyr Lys Arg Leu Val Pro His Phe Glu Ala Pro Val Lys Leu Ala
                325                 330                 335

Tyr Ser Ala Arg Asn Arg Ser Ala Ser Ile Arg Ile Pro His Val Ser
        340                 345                 350

Asn Pro Lys Gly Arg Arg Ile Glu Thr Arg Phe Pro Asp Pro Met Ala
        355                 360                 365

Asn Pro Tyr Leu Cys Phe Ser Ala Leu Met Met Ala Gly Leu Asp Gly
        370                 375                 380

Val Gln Asn Lys Ile His Pro Gly Glu Ala Ala Asp Lys Asn Leu Tyr
385                 390                 395                 400

Asp Leu Pro Pro Glu Glu Asp Ala Lys Ile Pro Thr Val Cys Ala Gly
                405                 410                 415
```

```
Leu Asp Gln Ala Leu Glu Ala Leu Asp Lys Asp Arg Glu Phe Leu Thr
        420                 425                 430

Arg Gly Gly Val Phe Thr Asp Ser Met Ile Asp Ala Tyr Leu Ala Leu
        435                 440                 445

Lys Glu Gly Glu Leu Gln Arg Val Arg Met Thr Thr His Pro Val Glu
    450                 455                 460

Phe Glu Leu Tyr Tyr Ser Leu
465                 470

<210> SEQ ID NO 44
<211> LENGTH: 471
<212> TYPE: PRT
<213> ORGANISM: Paraburkholderia tropica

<400> SEQUENCE: 44

Met Ser Lys Ser Val Ala Asp Val Met Gln Leu Val Lys Asp Glu Asp
1               5                   10                  15

Val Lys Phe Val Asp Phe Arg Phe Thr Asp Thr Arg Gly Lys Glu Gln
        20                  25                  30

His Val Ser Val Pro Leu Ser His Phe Asp Glu Asp Lys Phe Glu Ser
        35                  40                  45

Gly His Ala Phe Asp Gly Ser Ser Ile Ala Gly Trp Lys Gly Ile Glu
    50                  55                  60

Ala Ser Asp Met Leu Leu Val Pro Asp Ala Asn Thr Ala Phe Ile Asp
65                  70                  75                  80

Pro Phe Tyr Glu Glu Ser Thr Leu Val Leu Thr Cys Asp Val Val Glu
                85                  90                  95

Pro Ala Asp Gly Lys Gly Tyr Glu Arg Asp Pro Arg Ser Leu Ala Lys
        100                 105                 110

Arg Ala Glu Ala Tyr Leu Lys Ser Thr Gly Leu Gly Asp Thr Ala Phe
        115                 120                 125

Phe Gly Pro Glu Pro Glu Phe Phe Ile Phe Asp Ser Val Gln Trp Asn
    130                 135                 140

Thr Asp Met Ser Gly Ser Phe Val Lys Ile Gly Ser Glu Glu Ala Pro
145                 150                 155                 160

Trp Ser Pro Ser Lys Glu Phe Glu Gly Gly Asn Thr Gly His Arg Pro
                165                 170                 175

Gly Val Lys Gly Gly Tyr Phe Pro Val Ala Pro Val Asp Thr Phe Gln
        180                 185                 190

Asp Ile Arg Ser Glu Met Cys Leu Leu Leu Glu Gln Ile Gly Ile Pro
        195                 200                 205

Val Glu Val His His His Glu Val Ala Gly Gln Gly Gln Asn Glu Ile
    210                 215                 220

Gly Thr Lys Phe Ser Thr Leu Val Gln Arg Ala Asp Trp Thr Gln Gln
225                 230                 235                 240

Met Lys Tyr Ile Ile His Asn Val Ala His Thr Tyr Gly Lys Thr Ala
                245                 250                 255

Thr Phe Met Pro Lys Pro Ile Val Gly Asp Asn Gly Ser Gly Met His
                260                 265                 270

Val His Gln Ser Ile Trp Lys Asp Gly Gln Asn Leu Phe Ala Gly Asn
        275                 280                 285

Gly Tyr Ala Gly Leu Ser Glu Phe Ala Leu Phe Tyr Ile Gly Gly Ile
    290                 295                 300

Ile Lys His Ala Arg Ala Leu Asn Ala Ile Thr Asn Pro Ser Thr Asn
305                 310                 315                 320
```

-continued

```
Ser Tyr Lys Arg Leu Val Pro His Phe Glu Ala Pro Val Lys Leu Ala
            325             330             335

Tyr Ser Ala Arg Asn Arg Ser Ala Ser Ile Arg Ile Pro His Val Ser
            340             345             350

Asn Pro Lys Gly Arg Arg Ile Glu Thr Arg Phe Pro Asp Pro Met Ala
            355             360             365

Asn Pro Tyr Leu Cys Phe Ser Ala Leu Met Met Ala Gly Leu Asp Gly
        370             375             380

Val Gln Asn Lys Ile His Pro Gly Glu Ala Ala Asp Lys Asn Leu Tyr
385             390             395             400

Asp Leu Pro Pro Glu Glu Asp Ala Lys Ile Pro Thr Val Cys Ala Gly
                405             410             415

Leu Asp Gln Ala Leu Glu Ala Leu Asp Lys Asp Arg Glu Phe Leu Thr
            420             425             430

Arg Gly Gly Val Phe Thr Asp Ser Met Ile Asp Ala Tyr Leu Ala Leu
            435             440             445

Lys Glu Gly Glu Leu Gln Arg Val Arg Met Thr Thr His Pro Val Glu
        450             455             460

Phe Glu Leu Tyr Tyr Ser Leu
465             470

<210> SEQ ID NO 45
<211> LENGTH: 471
<212> TYPE: PRT
<213> ORGANISM: Paraburkholderia tropica

<400> SEQUENCE: 45

Met Ser Lys Ser Val Ala Asp Val Met Gln Leu Val Lys Asp Glu Asp
1               5               10              15

Val Lys Phe Val Asp Phe Arg Phe Thr Asp Thr Arg Gly Lys Glu Gln
            20              25              30

His Val Ser Val Pro Leu Ser His Phe Asp Glu Asp Lys Phe Glu Ser
        35              40              45

Gly His Ala Phe Asp Gly Ser Ser Ile Ala Gly Trp Lys Gly Ile Glu
    50              55              60

Ala Ser Asp Met Leu Leu Val Pro Asp Ala Asn Thr Ala Phe Ile Asp
65              70              75              80

Pro Phe Tyr Glu Glu Ser Thr Leu Val Leu Thr Cys Asp Val Val Glu
                85              90              95

Pro Ala Asp Gly Lys Gly Tyr Glu Arg Asp Pro Arg Ser Leu Ala Lys
            100             105             110

Arg Ala Glu Ala Tyr Leu Lys Ser Thr Gly Leu Gly Asp Thr Ala Phe
        115             120             125

Phe Gly Pro Glu Pro Glu Phe Phe Ile Phe Asp Ser Val Gln Trp Asn
        130             135             140

Thr Asp Met Ser Gly Ser Phe Val Lys Ile Gly Ser Glu Glu Ala Pro
145             150             155             160

Trp Ser Ser Ser Lys Glu Phe Glu Gly Gly Asp Thr Gly His Arg Pro
            165             170             175

Gly Val Lys Gly Gly Tyr Phe Pro Val Ala Pro Val Asp Thr Phe Gln
            180             185             190

Asp Ile Arg Ser Glu Met Cys Leu Leu Leu Glu Gln Ile Gly Ile Pro
        195             200             205

Val Glu Val His His His Glu Val Ala Gly Gln Gly Gln Asn Glu Ile
```

-continued

```
                 210                 215                 220

Gly Thr Lys Phe Ser Thr Leu Val Gln Arg Ala Asp Trp Thr Gln Gln
225                 230                 235                 240

Met Lys Tyr Ile Ile His Asn Val Ala His Thr Tyr Gly Lys Thr Ala
                245                 250                 255

Thr Phe Met Pro Lys Pro Ile Val Gly Asp Asn Gly Ser Gly Met His
                260                 265                 270

Val His Gln Ser Ile Trp Lys Asp Gly Gln Asn Leu Phe Ala Gly Asn
            275                 280                 285

Gly Tyr Ala Gly Leu Ser Glu Phe Ala Leu Phe Tyr Ile Gly Gly Ile
        290                 295                 300

Ile Lys His Ala Arg Ala Leu Asn Ala Ile Thr Asn Pro Ser Thr Asn
305                 310                 315                 320

Ser Tyr Lys Arg Leu Val Pro His Phe Glu Ala Pro Val Lys Leu Ala
                325                 330                 335

Tyr Ser Ala Arg Asn Arg Ser Ala Ser Ile Arg Ile Pro His Val Ser
            340                 345                 350

Asn Pro Lys Gly Arg Arg Ile Glu Thr Arg Phe Pro Asp Pro Met Ala
            355                 360                 365

Asn Pro Tyr Leu Cys Phe Ser Ala Leu Met Met Ala Gly Leu Asp Gly
        370                 375                 380

Val Gln Asn Lys Ile His Pro Gly Glu Ala Ala Asp Lys Asn Leu Tyr
385                 390                 395                 400

Asp Leu Pro Pro Glu Glu Asp Ala Lys Ile Pro Thr Val Cys Ala Gly
                405                 410                 415

Leu Asp Gln Ala Leu Glu Ala Leu Asp Lys Asp Arg Glu Phe Leu Thr
            420                 425                 430

Arg Gly Gly Val Phe Thr Asp Ser Met Ile Asp Ala Tyr Leu Ala Leu
            435                 440                 445

Lys Glu Gly Glu Leu Gln Arg Val Arg Met Thr Thr His Pro Val Glu
        450                 455                 460

Phe Glu Leu Tyr Tyr Ser Leu
465                 470

<210> SEQ ID NO 46
<211> LENGTH: 471
<212> TYPE: PRT
<213> ORGANISM: Paraburkholderia tropica

<400> SEQUENCE: 46

Met Ser Lys Ser Val Ala Asp Val Met Gln Leu Val Lys Asp Glu Asp
1               5                   10                  15

Val Lys Phe Val Asp Phe Arg Phe Thr Asp Thr Arg Gly Lys Glu Gln
                20                  25                  30

His Val Ser Val Pro Leu Ser His Phe Asp Glu Asp Lys Phe Glu Ser
            35                  40                  45

Gly His Ala Phe Asp Gly Ser Ser Ile Ala Gly Trp Lys Gly Ile Glu
        50                  55                  60

Ala Ser Asp Met Leu Leu Val Pro Asp Ala Asn Thr Ala Phe Ile Asp
65                  70                  75                  80

Pro Phe Tyr Glu Glu Ser Thr Leu Val Leu Thr Cys Asp Val Val Glu
                85                  90                  95

Pro Ala Asp Gly Lys Gly Tyr Glu Arg Asp Pro Arg Ser Leu Ala Lys
                100                 105                 110
```

```
Arg Ala Glu Ala Tyr Leu Lys Ser Thr Gly Leu Gly Asp Thr Ala Phe
        115                 120                 125

Phe Gly Pro Glu Pro Glu Phe Phe Ile Phe Asp Ser Val Gln Trp Asn
        130                 135                 140

Thr Asp Met Ser Gly Ser Phe Val Lys Ile Gly Ser Glu Glu Ala Pro
145                 150                 155                 160

Trp Ser Ser Ser Lys Glu Phe Glu Gly Gly Asn Thr Gly His Arg Pro
                165                 170                 175

Gly Val Lys Gly Gly Tyr Phe Pro Val Ala Pro Val Asp Thr Phe Gln
                180                 185                 190

Asp Ile Arg Ser Glu Met Cys Leu Leu Leu Glu Gln Ile Gly Ile Pro
                195                 200                 205

Val Glu Val His His His Glu Val Ala Gly His Gly Gln Asn Glu Ile
        210                 215                 220

Gly Thr Lys Phe Ser Thr Leu Val Gln Arg Ala Asp Trp Thr Gln Gln
225                 230                 235                 240

Met Lys Tyr Ile Ile His Asn Val Ala His Thr Tyr Gly Lys Thr Ala
                245                 250                 255

Thr Phe Met Pro Lys Pro Ile Val Gly Asp Asn Gly Ser Gly Met His
                260                 265                 270

Val His Gln Ser Ile Trp Lys Asp Gly Gln Asn Leu Phe Ala Gly Asn
                275                 280                 285

Gly Tyr Ala Gly Leu Ser Glu Phe Ala Leu Phe Tyr Ile Gly Gly Ile
        290                 295                 300

Ile Lys His Ala Arg Ala Leu Asn Ala Ile Thr Asn Pro Ser Thr Asn
305                 310                 315                 320

Ser Tyr Lys Arg Leu Val Pro His Phe Glu Ala Pro Val Lys Leu Ala
                325                 330                 335

Tyr Ser Ala Arg Asn Arg Ser Ala Ser Ile Arg Ile Pro His Val Ser
                340                 345                 350

Asn Pro Lys Gly Arg Arg Ile Glu Thr Arg Phe Pro Asp Pro Met Ala
                355                 360                 365

Asn Pro Tyr Leu Cys Phe Ser Ala Leu Met Met Ala Gly Leu Asp Gly
        370                 375                 380

Val Gln Asn Lys Ile His Pro Gly Glu Ala Ala Asp Lys Asn Leu Tyr
385                 390                 395                 400

Asp Leu Pro Pro Glu Glu Asp Ala Lys Ile Pro Thr Val Cys Ala Gly
                405                 410                 415

Leu Asp Gln Ala Leu Glu Ala Leu Asp Lys Asp Arg Glu Phe Leu Thr
                420                 425                 430

Arg Gly Gly Val Phe Thr Asp Ser Met Ile Asp Ala Tyr Leu Ala Leu
        435                 440                 445

Lys Glu Gly Glu Leu Gln Arg Val Arg Met Thr Thr His Pro Val Glu
        450                 455                 460

Phe Glu Leu Tyr Tyr Ser Leu
465                 470
```

HIGH-THROUGHPUT METHODS FOR ISOLATING AND CHARACTERIZING AMMONIUM-EXCRETING MUTANT LIBRARIES GENERATED BY CHEMICAL MUTAGENESIS

CROSS-REFERENCE TO RELATED APPLICATIONS

This application is a U.S. National Stage application under 35 U.S.C. § 371 of International PCT Application No. PCT/US2020/029831, filed Apr. 24, 2020, which claims the benefit of priority to U.S. Provisional Application No. 62/838,780, filed Apr. 25, 2019, each of which is herein incorporated by reference in its entirety for all purposes.

STATEMENT REGARDING SEQUENCE LISTING

The contents of the text file submitted electronically herewith are incorporated herein by reference in their entirety: A computer readable format copy of the Sequence Listing filename: PIVO_014_01WO_SeqList_ST25.txt, date created, Apr. 22, 2020, file size ~148 kilobytes.

BACKGROUND OF THE DISCLOSURE

Techniques used in the state of the art to randomly mutagenize microbes and evaluate and select for an increased ability to fix atmospheric nitrogen in the presence of exogenous nitrogen are slow and not capable of being scaled to mutagenize and select potential candidate microbes given that gauging nitrogenase activity and ammonium excretion are slow processes. There is a clear need for a rapid screen to determine whether a single microbe or a million microbes are capable of fixing nitrogen, and more importantly, doing so in the presence of exogenous nitrogen.

The compositions and methods of using the compositions of the present disclosure solve this bottleneck in the discovery process by combining large-scale microbial mutagenesis with a screening process that relies on a modified microbe to act as a biosensor for screening for the presence or absence of free ammonium and/or glutamine while co-culturing the biosensor with the mutagenized microbes. These methods are further paired with high-throughput assays that rapidly identify candidate microbes that fix atmospheric nitrogen.

SUMMARY OF THE DISCLOSURE

In one aspect, provided herein is a biosensor capable of detecting the presence of ammonium in a composition, the biosensor comprising: a bacterium comprising: (a) a nucleic acid sequence encoding a reporter molecule, (b) a promoter or fragment thereof selected from the Nif regulon operably linked to the nucleic acid sequence of (a), (c) a nucleic acid sequence encoding an inhibitory nitrogen fixation regulatory protein, and (d) a nucleic acid sequence encoding a positive nitrogen fixation regulatory protein; wherein the bacterium expresses the reporter molecule in the absence of ammonium. In some cases, the reporter molecule is a fluorescent protein, functional fragment, and/or fusions thereof. In some cases, the fluorescent protein is a GFP, RFP, YFP, CFP, or functional variant or fragment thereof. In some cases, the fluorescent protein is GFP. In some cases, the GFP is a superfolder GFP. In some cases, the promoter or fragment thereof is selected from the nifHDK operon. In some cases, the promoter is a nifH promoter. In some cases, the inhibitory nitrogen fixation regulatory protein is NifL. In some cases, the positive nitrogen fixation regulatory protein is NifA. In some cases, the bacterium in *Escherichia coli*.

In another aspect, provided herein is a method of detecting the presence of ammonium in a composition, the method comprising: (a) inoculating a composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein; wherein the bacterium expresses the reporter molecule in the absence of ammonium; (b) exposing the inoculated composition to a stimulus sufficient to activate the reporter molecule; and (c) detecting reporter molecule output of the inoculated composition following (b), as compared to a control composition. In some cases, the method further comprises quantifying the amount of ammonium in the composition based upon the detected reporter molecule output. In some cases, the stimulus is selected from the group consisting of a chemical stimulus, a physical stimulus, a genetic stimulus and an energy stimulus. In some cases, the stimulus is light. In some cases, the reporter molecule is a fluorescent protein, functional fragment, and/or fusions thereof. In some cases, the fluorescent protein is a GFP, RFP, YFP, CFP, or functional variant or fragment thereof. In some cases, the fluorescent protein is GFP. In some cases, the GFP is a superfolder GFP. In some cases, step (b) entails exposing the inoculated composition to light excitation sufficient to fluoresce the fluorescent protein, functional fragment, and/or fusions thereof. In some cases, step (c) entails detecting intensity of fluorescent output of the inoculated composition following (b), as compared to the control composition. In some cases, the fluorescence is detected with a flow cytometer, a plate reader, or fluorescence-activated droplet sorting. In some cases, the promoter or fragment thereof is selected from the nifHDK operon. In some cases, the promoter is a nifH promoter. In some cases, the inhibitory nitrogen fixation regulatory protein is NifL. In some cases, the positive nitrogen fixation regulatory protein is NifA.

In one aspect, provided herein is a method for identification of bacterial mutants capable of fixing atmospheric nitrogen, the method comprising: (a) exposing a population of bacteria to a mutagen in a microbial composition; (b) co-culturing the microbial composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein, wherein the bacterium expresses the reporter molecule in the absence of ammonium; (c) exposing the co-cultured composition to a stimulus sufficient to activate the reporter molecule; and (d) identifying bacterial mutants capable of fixing atmospheric nitrogen as those that result in decreased or no reporter molecule output as compared to a control. In some cases, the reporter molecule output of the co-cultured composition is detected following (c), as compared to a control composition. In some cases, the control composition comprises microbes that do not express the reporter molecule. In some cases, the control composition comprises microbes that express a functionally deleted variant of the reporter molecule. In some cases, the stimulus is selected from the group consisting of a chemical stimulus, a physical stimulus, a genetic stimulus and an energy stimulus. In some cases, the stimulus is light. In some cases, the reporter molecule is a fluorescent protein, functional fragment, and/or fusions thereof. In some cases, the fluorescent protein is a GFP, RFP, YFP, CFP, or functional variant or fragment thereof. In some cases, the fluorescent protein is GFP. In some cases, the GFP is a superfolder GFP. In some cases, step (c) entails exposing the inoculated composition to light excitation sufficient to fluoresce the fluorescent protein, functional fragment, and/or fusions thereof. In some cases, the fluorescence is detected with a flow cytometer, a plate reader, or fluorescence-activated droplet sorting. In some cases, the method further comprises isolating the bacterial mutants capable of fixing atmospheric nitrogen identified in (d). In some cases, the isolated bacterial mutants comprise a bacterium selected from a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof. In some cases, the isolated bacterial mutants comprise a bacterium comprising at least one genetic variation introduced into a member selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, a gene associated with biosynthesis of a nitrogenase enzyme, or combinations thereof. In some cases, the isolated bacterial mutants comprise a bacterium comprising at least one genetic variation in glnA. In some cases, the at least one genetic variation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the *Klebsiella* glnA gene comprises a nucleic acid sequence of SEQ ID NO: 1. In some cases, the homolog of the *Klebsiella* glnA gene is a *Kosakonia* glnA gene. In some cases, the homolog of the *Klebsiella* glnA gene comprises a nucleic acid sequence of SEQ ID NO: 2. In some cases, the homolog of the *Klebsiella* glnA gene is a *Metakosakonia* glnA gene. In some cases, the homolog of the *Klebsiella* glnA gene comprises a nucleic acid sequence of SEQ ID NO: 3. In some cases, the glnA gene comprising the at least one genetic variation comprises a nucleic acid sequence selected from the group consisting of SEQ ID NOs 6-13 and 15-19. In some cases, expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof. In some cases, expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a

*Klebsiella* GlnA protein and identical amino acid substitutions at homologous amino acid positions in a homolog thereof. In some cases, the *Klebsiella* GlnA protein comprises an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In some cases, the GlnA protein comprises an amino acid sequence selected from the group consisting of SEQ ID NOs 29-36 and 38-42. In some cases, the at least one genetic variation in glnA comprises at least one nucleotide substitution at nucleotide position 308, 487, 511 and/or 657 of a *Paraburkholderia* glnA gene or in a homologous nucleotide position in a homolog thereof. In some cases, the *Paraburkholderia* glnA gene comprises a nucleic acid sequence of SEQ ID NO: 4. In some cases, the glnA gene comprising the at least one genetic variation comprises a nucleic acid sequence selected from the group consisting of SEQ ID NOs 20-23. In some cases, expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof. In some cases, expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof. In some cases, the *Paraburkholderia* GlnA protein comprises an amino acid sequence of SEQ ID NO: 27. In some cases, the GlnA protein comprises an amino acid sequence selected from the group consisting of SEQ ID NOs 43-46. In some cases, the isolated bacterial mutants comprise a bacterium comprising at least one genetic variation in glnE. In some cases, the at least one genetic variation in glnE comprises at least one nucleotide substitution at nucleotide position 965 and/or 2838 of a *Klebsiella* glnE gene or at a homologous nucleotide position in a homolog thereof. In some cases, the at least one genetic variation in glnE comprises at least one nucleotide substitution at nucleotide position 965 and 2838 of a *Klebsiella* glnE gene or at a homologous nucleotide position in a homolog thereof. In some cases, the *Klebsiella* glnE gene comprises a nucleic acid sequence of SEQ ID NO: 5. In some cases, the glnE gene comprising the at least one genetic variation comprises a nucleic acid sequence of SEQ ID NO: 14. In some cases, expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof. In some cases, expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof. In some cases, the amino acid substitution at position 322 or the homologous amino acid position is a G to E substitution. In some cases, the amino acid substitution at position 746 or the homologous amino acid position is a G to D substitution. In some cases, the *Klebsiella* GlnE protein comprises an amino acid sequence of SEQ ID NO: 28. In some cases, the GlnE protein comprises an amino acid sequence of SEQ ID NO: 37.

In one aspect, provided herein is a method for high-throughput identification of one or more bacterial mutants capable of fixing atmospheric nitrogen, the method comprising: (a) exposing a population of bacteria to a mutagen; (b) transferring the population of bacteria in (a) into one or more samples comprising a medium; (c) co-culturing a biosensor within each of the one or more samples in (b), wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein; wherein the bacterium expresses the reporter molecule in the absence of ammonium; (d) exposing each of the one or more samples in (c) to a stimulus sufficient to activate the reporter molecule; and (e) identifying from the one or more samples in (d) one or more bacterial mutants capable of fixing atmospheric nitrogen as those that result in decreased output of the reporter molecule as compared to a control. In some cases, the output of the reporter molecule of the one or more samples in (d) is measured following (d), as compared to a control composition. In some cases, the control composition comprises microbes that do not express the reporter molecule. In some cases, the control composition comprises microbes that express a functionally deleted variant of the reporter molecule. In some cases, the stimulus is selected from the group consisting of a chemical stimulus, a physical stimulus, a genetic stimulus and an energy stimulus. In some cases, the stimulus is light. In some cases, the reporter molecule is a fluorescent protein, functional fragment, and/or fusions thereof. In some cases, the fluorescent protein is a GFP, RFP, YFP, CFP, or functional variant or fragment thereof. In some cases, the fluorescent protein is GFP. In some cases, the GFP is a superfolder GFP. In some cases, step (d) entails exposing the inoculated composition to light excitation sufficient to fluoresce the fluorescent protein, functional fragment, and/or fusions thereof. In some cases, the fluorescence is detected with a flow cytometer, a plate reader, or fluorescence-activated droplet sorting. In some cases, the method further comprises isolating the bacterial mutants capable of fixing atmospheric nitrogen. In some cases, the isolated bacterial mutants comprise a bacterium selected from a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof. In some cases, the isolated bacterial mutants comprise a bacterium comprising at least one genetic variation introduced into a member selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, a gene associated with biosynthesis of a nitrogenase enzyme, or combinations thereof. In some cases, the isolated bacterial mutants comprise a bacterium comprising at least one genetic variation in glnA. In some cases, the at least one genetic variation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the *Klebsiella* glnA gene comprises a nucleic acid sequence of SEQ ID NO: 1. In some cases, the homolog of the *Klebsiella* glnA gene is a *Kosakonia* glnA gene. In some cases, the homolog of the *Klebsiella* glnA gene comprises a nucleic acid sequence of SEQ ID NO: 2. In some cases, the homolog of the *Klebsiella* glnA gene is a *Metakosakonia* glnA gene. In some cases, the homolog of the *Klebsiella* glnA gene comprises a nucleic acid sequence of SEQ ID NO: 3. In some cases, the glnA gene comprising the at least one genetic variation comprises a nucleic acid sequence selected from the group consisting of SEQ ID NOs 6-13 and 15-19. In some cases, expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof. In some cases, expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof. In some cases, the *Klebsiella* GlnA protein comprises an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In some cases, the GlnA protein comprises an amino acid sequence selected from the group consisting of SEQ ID NOs 29-36 and 38-42. In some cases, the at least one genetic variation in glnA comprises at least one nucleotide substitution at nucleotide position 308, 487, 511 and/or 657 of a *Paraburkholderia* glnA gene or in a homologous nucleotide position in a homolog thereof. In some cases, the *Paraburkholderia* glnA gene comprises a nucleic acid sequence of SEQ ID NO: 4. In some cases, the glnA gene comprising the at least one genetic variation comprises a nucleic acid sequence selected from the group consisting of SEQ ID NOs 20-23. In some cases, expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof. In some cases, expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof. In some cases, the *Paraburkholderia* GlnA protein comprises an amino acid sequence of SEQ ID NO: 27. In some cases, the GlnA protein comprises an amino acid sequence selected from the group consisting of SEQ ID NOs 43-46. In some cases, the isolated bacterial mutants comprise at least one genetic variation in glnE. In some cases, the at least one genetic variation in glnE comprises at least one nucleotide substitution at nucleotide position 965 and/or 2838 of a *Klebsiella* glnE gene or at a homologous nucleotide position in a homolog thereof. In some cases, the at least one genetic variation in glnE comprises at least one nucleotide substitution at nucleotide position 965 and 2838 of a *Klebsiella* glnE gene or at a homologous nucleotide position in a homolog thereof. In some cases, the *Klebsiella* glnE gene comprises a nucleic acid sequence of SEQ ID NO: 5. In some cases, the glnE gene comprising the at least one genetic variation comprises a nucleic acid sequence of SEQ ID NO: 14. In some cases, expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof. In some cases, expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof. In some cases, the amino acid substitution at position 322 or the homologous amino acid position is a G to E substitution. In some cases, the amino acid substitution at position 746 or the homologous amino acid position is a G to D substitution. In some cases, the *Klebsiella* GlnE protein comprises an amino acid sequence of SEQ ID NO: 28. In some cases, the GlnE protein comprises an amino acid sequence of SEQ ID NO: 37. In some cases, the population of bacteria comprises at least 100,000 bacteria, and wherein the method for high-throughput identification is completed in less than four hours. In some cases, the promoter or fragment thereof is selected from the nifHDK operon. In some cases, the promoter is a nifH promoter. In some cases, the inhibitory nitrogen fixation regulatory protein is NifL. In some cases, the positive nitrogen fixation regulatory protein is NifA. In some cases, the mutagen is selected from mitomycin C (MMC), N-methyl-N-nitrosourea (MNU), nitrous acid (NA), diepoxybutane (DEB), 1, 2, 7, 8-diepoxyoctane (DEO), ethyl methane sulfonate (EMS), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamin)-acri-dinedihydrochloride (ICR-170), 2-amino purine (2AP), and hydroxylamine (HA). In some cases, the mutagen is EMS. In some cases, the population of bacteria is selected from wild-type bacteria, transgenic mutant bacteria, non-intergeneric mutant bacteria and intergeneric mutant bacteria.

In one aspect, provided herein is a method for identifying novel bacterial genes, pathways, and/or regulatory elements involved in fixing atmospheric nitrogen, the method comprising: (a) exposing a population of bacteria to a mutagen in a microbial composition; (b) inoculating the microbial composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein; wherein the bacterium expresses the reporter molecule in the absence of ammonium; (c) exposing the inoculated composition to a stimulus sufficient to activate the reporter molecule, (d) measuring the output of the reporter molecule of the inoculated composition following (c), as compared to a control composition; (e) isolating bacteria from inoculated compositions that exhibit a decreased output of the reporter molecule as compared to the control composition as bacteria capable of fixing atmospheric nitrogen; (f) sequencing the genome(s) of the bacteria capable of fixing atmospheric nitrogen from (e); and (g) identifying genes, pathways, and/or regulatory elements that contain mutations from the sequenced genomes. In some cases, the control composition comprises microbes that do not express the reporter molecule. In some cases, the control composition comprises microbes that express a functionally deleted variant of the reporter molecule. In some cases, the stimulus is selected from the group consisting of a chemical stimulus, a physical stimulus, a genetic stimulus and an energy stimulus. In some cases, the stimulus is light. In some cases, the reporter molecule is a fluorescent protein, functional fragment, and/or fusions thereof. In some cases, the fluorescent protein is a GFP, RFP, YFP, CFP, or functional variant or fragment thereof. In some cases, the fluorescent protein is GFP. In some cases, the GFP is a superfolder GFP. In some cases, step (c) entails exposing the inoculated composition to light excitation sufficient to fluoresce the fluorescent protein, functional fragment, and/or fusions thereof. In some cases, the fluorescence is detected with a flow cytometer, a plate reader, or fluorescence-activated droplet sorting. In some cases, the method further comprises determining whether the genes, pathways, and/or regulatory elements contain mutations known to be associated with the fixation of atmospheric nitrogen. In some cases, the identified mutations comprise at least one mutation in glnA or glnE. In some cases, the at least one mutation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the *Klebsiella* glnA gene comprises a nucleic acid sequence of SEQ ID NO: 1. In some cases, the homolog of the *Klebsiella* glnA gene is a *Kosakonia* glnA gene. In some cases, the homolog of the *Klebsiella* glnA gene comprises a nucleic acid sequence of SEQ ID NO: 2. In some cases, the homolog of the *Klebsiella* glnA gene is a *Metakosakonia* glnA gene. In some cases, the homolog of the *Klebsiella* glnA gene comprises a nucleic acid sequence of SEQ ID NO: 3. In some cases, the glnA gene comprising the at least one genetic variation comprises a nucleic acid sequence selected from the group consisting of SEQ ID NOs 6-13 and 15-19. In some cases, expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof. In some cases, expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof. In some cases, the *Klebsiella* GlnA protein comprises an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In some cases, the GlnA protein comprises an amino acid sequence selected from the group consisting of SEQ ID NOs 29-36 and 38-42. In some cases, the at least one genetic variation in glnA comprises at least one nucleotide substitution at nucleotide position 308, 487, 511 and/or 657 of a *Paraburkholderia* glnA gene or in a homologous nucleotide position in a homolog thereof. In some cases, the *Paraburkholderia* glnA gene comprises a nucleic acid sequence of SEQ ID NO: 4. In some cases, the glnA gene comprising the at least one genetic variation comprises a nucleic acid sequence selected from the group consisting of SEQ ID NOs 20-23. In some cases, expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof. In some cases, expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof. In some cases, the *Paraburkholderia* GlnA protein comprises an amino acid sequence of SEQ ID NO: 27. In some cases, the GlnA protein comprises an amino acid sequence selected from the group consisting of SEQ ID NOs 43-46. In some cases, the at least one genetic variation in glnE comprises at least one nucleotide substitution at nucleotide position 965 and/or 2838 of a *Klebsiella* glnE gene or at a homologous nucleotide position in a homolog thereof. In some cases, the at least one genetic variation in glnE comprises at least one nucleotide substitution at nucleotide position 965 and 2838 of a *Klebsiella* glnE gene or at a homologous nucleotide position in a homolog thereof. In some cases, the *Klebsiella* glnE gene comprises a nucleic acid sequence of SEQ ID NO: 5. In some cases, the glnE gene comprising the at least one genetic variation comprises a nucleic acid sequence of SEQ ID NO: 14. In some cases, expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof. In some cases, expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof. In some cases, the amino acid substitution at position 322 or the homologous amino acid position is a G to E substitution. In some cases, the amino acid substitution at position 746 or the homologous amino acid position is a G to D substitution. In some cases, the *Klebsiella* GlnE protein comprises an amino acid sequence of SEQ ID NO: 28. In some cases, the GlnE protein comprises an amino acid sequence of SEQ ID NO: 37. In some cases, the promoter or fragment thereof is selected from the nifHDK operon. In some cases, the promoter is a nifH promoter. In some cases, the inhibitory nitrogen fixation regulatory protein is NifL. In some cases, the positive nitrogen fixation regulatory protein is NifA. In some cases, the mutagen is selected from mitomycin C (MMC), N-methyl-N-nitrosourea (MNU), nitrous acid (NA), diepoxybutane (DEB), 1, 2, 7, 8-diepoxyoctane (DEO), ethyl methane sulfonate (EMS), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamin)-acridinedihydrochloride (ICR-170), 2-amino purine (2AP), and hydroxylamine (HA). In some cases, the mutagen is EMS. In some cases, the population of bacteria is selected from wild-type bacteria, transgenic mutant bacteria, non-intergeneric mutant bacteria and intergeneric mutant bacteria.

In another aspect, provided herein is a method for identification of bacterial mutants capable of fixing atmospheric nitrogen, the method comprising: (a) exposing a population of bacteria to a mutagen; (b) exposing the population of bacteria exposed to the mutagen in (a) to a diazotrophic growth inhibitor in a microbial composition: (c) co-culturing the microbial composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein, wherein the bacterium expresses the reporter molecule in the absence of ammonium; (d) exposing the co-cultured composition to a stimulus sufficient to activate the reporter molecule; and (e) identifying bacterial mutants capable of fixing atmospheric nitrogen as those that result in decreased or no output of the reporter molecule, as compared to a control. In some cases, the diazotrophic growth inhibitor is ethylenediamine (EDA) or methylammonium. In some cases, the output of the reporter molecule of the one or more samples in (d) is measured following (d), as compared to a control composition. In some cases, the control composition comprises microbes that do not express the reporter molecule. In some cases, the control composition comprises microbes that express a functionally deleted variant of the reporter molecule. In some cases, the stimulus is selected from the group consisting of a chemical stimulus, a physical stimulus, a genetic stimulus and an energy stimulus. In some cases, the stimulus is light. In some cases, the reporter molecule is a fluorescent protein, functional fragment, and/or fusions thereof. In some cases, the fluorescent protein is a GFP, RFP, YFP, CFP, or functional variant or fragment thereof. In some cases, the fluorescent protein is GFP. In some cases, the GFP is a superfolder GFP. In some cases, step (d) entails exposing the inoculated composition to light excitation sufficient to fluoresce the fluorescent protein, functional fragment, and/or fusions thereof. In some cases, the fluorescence is detected with a flow cytometer, a plate reader, or fluorescence-activated droplet sorting. In some cases, the method further comprises isolating the bacterial mutants identified as capable of fixing atmospheric nitrogen. In some cases, the isolated bacterial mutants comprise a bacterium selected from a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof. In some cases, the isolated bacterial mutants comprise bacteria which comprise at least one genetic variation introduced into a member selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifQ, a gene associated with biosynthesis of a nitrogenase enzyme, or combinations thereof. In some cases, the isolated bacterial mutants comprise a bacterium comprising a genetic variation in glnA. In some cases, the at least one genetic variation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the *Klebsiella* glnA gene comprises a nucleic acid sequence of SEQ ID NO: 1. In some cases, the homolog of the *Klebsiella* glnA gene is a *Kosakonia* glnA gene. In some cases, the homolog of the *Klebsiella* glnA gene comprises a nucleic acid sequence of SEQ ID NO: 2. In some cases, the homolog of the *Klebsiella* glnA gene is a *Metakosakonia* glnA gene. In some cases, the homolog of the *Klebsiella* glnA gene comprises a nucleic acid sequence of SEQ ID NO: 3. In some cases, the glnA gene comprising the at least one genetic variation comprises a nucleic acid sequence selected from the group consisting of SEQ ID NOs 6-13 and 15-19. In some cases, expression of the glnA gene comprising the at least one genetic variation produces a GlnA protein comprising at least one amino acid substitution at amino acid position 66, 157, 172, 174, 189, 208, 218, 255, 268,329 and/or 339 of a *Klebsiella* GlnA protein or at a homologous amino acid position in a homolog thereof. In some cases, expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof. In some cases, the *Klebsiella* GlnA protein comprises an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In some cases, the GlnA protein comprises an amino acid sequence selected from the group consisting of SEQ ID NOs 29-36 and 38-42. In some cases, the at least one genetic variation in glnA comprises at least one nucleotide substitution at nucleotide position 308, 487, 511 and/or 657 of a *Paraburkholderia* glnA gene or in a homologous nucleotide position in a homolog thereof. In some cases, the *Paraburkholderia* glnA gene comprises a nucleic acid sequence of SEQ ID NO: 4. In some cases, the glnA gene comprising the at least one genetic variation comprises a nucleic acid sequence selected from the group consisting of SEQ ID NOs 20-23. In some cases, expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof. In some cases, expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof. In some cases, the *Paraburkholderia* GlnA protein comprises an amino acid sequence of SEQ ID NO: 27. In some cases, the GlnA protein comprises an amino acid sequence selected from the group consisting of SEQ ID NOs 43-46. In some cases, the isolated bacterial mutants comprise at least one genetic variation in glnE. In some cases, the at least one genetic variation in glnE comprises at least one nucleotide substitution at nucleotide position 965 and/or 2838 of a *Klebsiella* glnE gene or at a homologous nucleotide position in a homolog thereof. In some cases, the at least one genetic variation in glnE comprises at least one nucleotide substitution at nucleotide position 965 and 2838 of a *Klebsiella* glnE gene or at a homologous nucleotide position in a homolog thereof. In some cases, the *Klebsiella* glnE gene comprises a nucleic acid sequence of SEQ ID NO: 5. In some cases, the glnE gene comprising the at least one genetic variation comprises a nucleic acid sequence of SEQ ID NO: 14. In some cases, expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof. In some cases, expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof. In some cases, the amino acid substitution at position 322 or the homologous amino acid position is a G to E substitution. In some cases, the amino acid substitution at position 746 or the homologous amino acid position is a G to D substitution. In some cases, the *Klebsiella* GlnE protein comprises an amino acid sequence of SEQ ID NO: 28. In some cases, the GlnE protein comprises an amino acid sequence of SEQ ID NO: 37. In some cases, the promoter or fragment thereof is selected from the nifHDK operon. In some cases, the promoter is a nifH promoter. In some cases, the inhibitory nitrogen fixation regulatory protein is NifL. In some cases, the positive nitrogen fixation regulatory protein is NifA. In some cases, the mutagen is selected from mitomycin C (MMC), N-methyl-N-nitrosourea (MNU), nitrous acid (NA), diepoxybutane (DEB), 1, 2, 7, 8-diepoxyoctane (DEO), ethyl methane sulfonate (EMS), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamin)-acridinedihydrochloride (ICR-170), 2-amino purine (2AP), and hydroxylamine (HA). In some cases, the mutagen is EMS. In some cases, the population of bacteria is selected from wild-type bacteria, transgenic mutant bacteria, non-intergeneric mutant bacteria and intergeneric mutant bacteria.

In still another aspect, provided herein is a microbial composition, comprising: one or more isolated bacteria selected from the group consisting of a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725 and a bacterium deposited as PTA-126726. In some cases, the composition further comprises an agriculturally acceptable carrier. In some cases, the one or more isolated bacteria fix atmospheric nitrogen at a rate higher than a wild type parental lineage bacteria.

In one aspect, provided herein is a nitrogen fixing bacterium comprising a mutant glnE gene comprising at least one nucleotide substitution at nucleotide position 965 and/or 2838 of a *Klebsiella* glnE gene or at a homologous nucleotide position in a homolog thereof. In some cases, the mutant glnE gene comprises a nucleotide substitution at nucleotide position 965 and 2838 of the *Klebsiella* glnE gene or in homologous nucleotide positions in the homolog thereof. In some cases, the mutant glnE gene shares at least 85%, 86%, 87%, 88%, 89%, 90%, 91%, 92%, 93%, 94%, 95%, 96%, 97%, 98%, or 99% identity with the *Klebsiella* glnE gene or the homolog thereof. In some cases, expression of the mutant glnE gene produces a mutant GlnE protein with at least one amino acid substitution at amino acid position 322 and/or 746 of a *Klebsiella* GlnE protein or at a homologous amino acid position in a homolog thereof. In some cases, expression of the mutant glnE gene produces a mutant GlnE protein with amino acid substitutions at amino acid positions 322 and 746 of the *Klebsiella* GlnE protein or at homologous amino acid positions in the homolog thereof. In some cases, the amino acid substitution at position 322 or the homologous amino acid position is a G to E substitution. In some cases, the amino acid substitution at position 746 or the homologous amino acid position is a G to D substitution. In some cases, the mutant GlnE protein shares at least 90%, 91%, 92%, 93%, 94%, 95%, 96%, 97%, 98%, or 99% identity with the *Klebsiella* GlnE protein or the homolog thereof. In some cases, the *Klebsiella* glnE gene comprises a nucleic acid sequence of SEQ ID NO: 5. In some cases, the mutant glnE gene comprises a nucleic acid sequence of SEQ ID NO: 14. In some cases, the *Klebsiella* GlnE protein comprises an amino acid sequence of SEQ ID NO: 28. In some cases, the mutant GlnE protein comprises an amino acid sequence of SEQ ID NO: 37. In some cases, the bacterium is genetically engineered.

In one aspect, provided herein is a nitrogen fixing bacterium comprising a mutant glnE gene encoding a GlnE protein comprising an amino acid sequence with at least one amino acid substitution at amino acid positions 322 and/or 746 of a *Klebsiella* GlnE protein or at a homologous amino acid position in a homolog thereof. In some cases, the GlnE protein comprises amino acid substitutions at amino acid positions 322 and 746 of the *Klebsiella* GlnE protein or at homologous amino acid positions in the homolog thereof. In some cases, the amino acid substitution at position 322 or the homologous amino acid position is a G to E substitution. In some cases, the amino acid substitution at position 746 or the homologous amino acid position is a G746D substitution. In some cases, the GlnE protein shares at least 90%, 91%, 92%, 93%, 94%, 95%, 96%, 97%, 98%, or 99% identity with the *Klebsiella* GlnE protein or the homolog thereof. In some cases, the *Klebsiella* GlnE protein comprises an amino acid sequence of SEQ ID NO: 20. In some cases, the mutant GlnE protein comprises an amino acid sequence of SEQ ID NO: 37. In some cases, the bacterium is genetically engineered.

In another aspect, provided herein is a nitrogen fixing bacterium comprising a mutant GlnE protein comprising an amino acid sequence with at least one amino acid substitution at amino acid positions 322 and/or 746 of a *Klebsiella* GlnE protein or at a homologous amino acid position in a homolog thereof. In some cases, the GlnE protein comprises amino acid substitutions at amino acid positions 322 and 746 of the *Klebsiella* GlnE protein or at homologous amino acid positions in the homolog thereof. In some cases, the amino acid substitution at position 322 or the homologous amino acid position is a G to E substitution. In some cases, the amino acid substitution at position 746 or the homologous amino acid position is a G to D substitution. In some cases, the GlnE protein shares at least 90%, 91%, 92%, 93%, 94%, 95%, 96%, 97%, 98%, or 99% identity with the *Klebsiella* GlnE protein or the homolog thereof. In some cases, the *Klebsiella* GlnE protein comprises an amino acid sequence of SEQ ID NO: 20. In some cases, the mutant GlnE protein comprises an amino acid sequence of SEQ ID NO: 37. In some cases, the nitrogen fixing bacterium is *Klebsiella variicola* CI4874. In some cases, the bacterium is genetically engineered.

In one aspect, provided herein is a nitrogen fixing bacterium comprising a mutant glnA gene comprising at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the mutant glnA gene shares at least 85%, 86%, 87%, 88%, 89%, 90%, 91%, 92%, 93%, 94%, 95%, 96%, 97%, 98%, or 99% identity with the *Klebsiella* glnA gene or the homolog thereof. In some cases, expression of the mutant glnA gene produces a mutant GlnA protein with at least one amino acid substitution at amino acid position 66, 157, 172, 174, 189, 208, 218, 255, 268, 329 and/or 339 of a *Klebsiella* GlnA protein or at a homologous amino acid position in a homolog thereof. In some cases, expression of the mutant glnA gene produces a mutant GlnA protein with at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof. In some cases, the mutant GlnA protein shares at least 90%, 91%, 92%, 93%, 94%, 95%, 96%, 97%, 98%, or 99% identity with the *Klebsiella* GlnA protein or the homolog thereof. In some cases, the *Klebsiella* glnA gene comprises a nucleic acid sequence of SEQ ID NO: 1. In some cases, the homolog of the *Klebsiella* glnA gene is a *Kosakonia* glnA gene. In some cases, the homolog of the *Klebsiella* glnA gene comprises a nucleic acid sequence of SEQ ID NO: 2. In some cases, the homolog of the *Klebsiella* glnA gene is a *Metakosakonia* glnA gene. In some cases, the homolog of the *Klebsiella* glnA gene comprises a nucleic acid sequence of SEQ ID NO: 3. In some cases, the mutant glnA gene comprises a nucleic acid sequence selected from the group consisting of SEQ ID NOs 6-13 and 15-19. In some cases, the *Klebsiella* GlnA protein comprises an amino acid sequence of SEQ ID NO: 24. In some cases, the homolog of the *Klebsiella* GlnA protein comprises an amino acid sequence of SEQ ID NO: 25. In some cases, the homolog of the *Klebsiella* GlnA protein comprises an amino acid sequence of SEQ ID NO: 26. In some cases, the mutant GlnA protein comprises an amino acid sequence selected from the group consisting of SEQ ID NOs 29-36 and 38-42. In some cases, the bacterium is genetically engineered.

In one aspect, provided herein is a nitrogen fixing bacterium comprising a mutant glnA gene encoding a GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some cases, the least one amino acid substitution is selected from the group consisting of M66I, M66V, G157C, H172L, P174L, S189F, E208K, G218S, T255I, G268S, A329V and N339D of the *Klebsiella* GlnA protein and identical amino acid substitutions at homologous positions in the homolog thereof. In some cases, the mutant GlnA protein shares at least 90%, 91%, 92%, 93%, 94%, 95%, 96%, 97%, 98%, or 99% identity with the *Klebsiella* GlnA protein or the homolog thereof. In some cases, the *Klebsiella* GlnA protein comprises an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In some cases, the GlnA protein comprises an amino acid sequence selected from the group consisting of SEQ ID NOs 29-36 and 38-42. In some cases, the bacterium is genetically engineered.

In another aspect, provided herein is a nitrogen fixing bacterium comprising a mutant GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some cases, the least one amino acid substitution is selected from the group consisting of M66I, M66V, G157C, H172L, P174L, S189F, E208K, G218S, T255I, G268S, A329V and N339D of the *Klebsiella* GlnA protein and identical amino acid substitutions in homologous amino acid positions in the homolog thereof. In some cases, the mutant GlnA protein shares at least 90%, 91%, 92%, 93%, 94%, 95%, 96%, 97%, 98%, or 99% identity with the *Klebsiella* GlnA protein or the homolog thereof. In some cases, the *Klebsiella* GlnA protein comprises an amino acid sequence of SEQ ID NO. 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO. 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In some cases, the GlnA protein comprises an amino acid sequence selected from the group consisting of SEQ ID NOs 29-36 and 38-42. In some cases, the nitrogen fixing bacterium is selected from the group consisting of *Klebsiella variicola* CI3296, *Klebsiella variicola* CI3936, *Klebsiella variicola* CI3933, *Klebsiella variicola* CI3927, *Klebsiella variicola* CI3925, *Klebsiella* variicola CI3943, *Klebsiella variicola* CI3940, *Klebsiella variicola* CI3938, *Kosakonia sacchari* CI4065, *Metakosakonia intestini* CI4875, *Metakosakonia intestini* CI4876, *Metakosakonia intestini* CI4877 and *Metakosakonia intestini* CI4878. In some cases, the bacterium is genetically engineered.

In one aspect, provided herein is a nitrogen fixing bacterium comprising a mutant glnA gene comprising at least one nucleotide substitution at nucleotide position 308, 487, 511 and/or 657 of a *Paraburkholderia* glnA gene or in a homologous nucleotide position in a homolog thereof. In some cases, the mutant glnA gene shares at least 85%, 86%, 87%, 88%, 89%, 90%, 91%, 92%, 93%, 94%, 95%, 96%, 97%, 98%, or 99% identity with the *Paraburkholderia* glnA gene or the homolog thereof. In some cases, expression of the mutant glnA gene produces a mutant GlnA protein with at least one amino acid substitution at amino acid position 103, 163, 171 and/or 219 of a *Paraburkholderia* GlnA protein or in a homologous position in a homolog thereof. In some cases, expression of the mutant glnA gene produces a mutant GlnA protein with at least one amino acid substitution selected from the group consisting of Y103C, S163P, N171D and/or Q219H of a *Paraburkholderia* GlnA protein and identical amino acid substitutions in homologous amino acid positions in a homolog thereof. In some cases, the mutant GlnA protein shares at least 90%, 91%, 92%, 93%, 94%, 95%, 96%, 97%, 98%, or 99% identity with the *Paraburkholderia* GlnA protein or the homolog thereof. In some cases, the *Paraburkholderia* glnA gene comprises a nucleic acid sequence of SEQ ID NO: 4. In some cases, the mutant glnA gene comprises a nucleic acid sequence selected from the group consisting of SEQ ID NOs 20-23. In some cases, the *Paraburkholderia* GlnA protein comprises an amino acid sequence of SEQ ID NO: 27. In some cases, the mutant GlnA protein comprises an amino acid sequence selected from the group consisting of SEQ ID NOs 43-46. In some cases, the bacterium is genetically engineered.

In one aspect, provided herein is a nitrogen fixing bacterium comprising a mutant glnA gene encoding a GlnA protein comprising an amino acid sequence with at least one amino acid substitution at amino acid positions 103, 163, 171 and/or 219 of a *Paraburkholderia* GlnA protein or in a homologous amino acid position in a homolog thereof. In some cases, the least one amino acid substitution is selected from the group consisting of Y103C, S163P, N171D and Q219H of the *Paraburkholderia* GlnA protein and identical amino acid substitutions in homologous amino acid positions in the homolog thereof. In some cases, the mutant GlnA protein shares at least 90%, 91%, 92%, 93%, 94%, 95%, 96%, 97%, 98%, or 99% identity with the *Paraburkholderia* GlnA protein or the homolog thereof. In some cases, the *Paraburkholderia* GlnA protein comprises an amino acid sequence of SEQ ID NO: 27. In some cases, the GlnA protein comprises an amino acid sequence selected from the group consisting of SEQ ID NOs 43-46. In some cases, the bacterium is genetically engineered.

In one aspect, provided herein is a nitrogen fixing bacterium comprising a mutant GlnA protein comprising an amino acid sequence with at least one amino acid substitution at amino acid positions 103, 163, 171 and/or 219 of a *Paraburkholderia* GlnA protein or in homologous amino acid positions in a homolog thereof. In some cases, the least one amino acid substitution is selected from the group consisting of Y103C, S163P, N171D and Q219H of the *Paraburkholderia* GlnA protein and identical amino acid substitutions in homologous amino acid positions in the homolog thereof. In some cases, the mutant GlnA protein shares at least 90%, 91%, 92%, 93%, 94%, 95%, 96%, 97%, 98%, or 99% identity with the *Paraburkholderia* GlnA protein or the homolog thereof. In some cases, the *Paraburkholderia* GlnA protein comprises an amino acid sequence of SEQ ID NO: 27. In some cases, the GlnA protein comprises an amino acid sequence selected from the group consisting of SEQ ID NOs 43-46. In some cases, the nitrogen fixing bacterium is selected from the group consisting of *Paraburkholderia tropica* CI4751, *Paraburkholderia tropica* CI4753, *Paraburkholderia tropica* CI4879 and *Paraburkholderia tropica* CI4752. In some cases, the bacterium is genetically engineered.

In one aspect provided herein is a microbial composition comprising the nitrogen fixing bacterium and a carrier. In some cases, the carrier is an agriculturally acceptable carrier. In some cases, the bacterium is genetically engineered. In some cases, the at least one nitrogen fixing bacterium is a nitrogen fixing bacterium comprising a mutant glnE gene comprising at least one nucleotide substitution at nucleotide position 965 and/or 2838 of a *Klebsiella* glnE gene or at a homologous nucleotide position in a homolog thereof. In some cases, the at least one nitrogen fixing bacterium is a nitrogen fixing bacterium comprising a mutant glnE gene encoding a GlnE protein comprising an amino acid sequence with at least one amino acid substitution at amino acid positions 322 and/or 746 of a *Klebsiella* GlnE protein or at a homologous amino acid position in a homolog thereof. In some cases, the at least one nitrogen fixing bacterium is a nitrogen fixing bacterium comprising a mutant GlnE protein comprising an amino acid sequence with at least one amino acid substitution at amino acid positions 322 and/or 746 of a *Klebsiella* GlnE protein or at a homologous amino acid position in a homolog thereof. In some cases, the at least one nitrogen fixing bacterium is a nitrogen fixing bacterium comprising a mutant glnA gene comprising at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the at least one nitrogen fixing bacterium is a nitrogen fixing bacterium comprising a mutant glnA gene encoding a GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some cases, the at least one nitrogen fixing bacterium is a nitrogen fixing bacterium comprising a mutant GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some cases, the at least one nitrogen fixing bacterium is a nitrogen fixing bacterium comprising a mutant glnA gene comprising at least one nucleotide substitution at nucleotide position 308, 487, 511 and/or 657 of a *Paraburkholderia* glnA gene or in a homologous nucleotide position in a homolog thereof. In some cases, the at least one nitrogen fixing bacterium is a nitrogen fixing bacterium comprising a mutant glnA gene encoding a GlnA protein comprising an amino acid sequence with at least one amino acid substitution at amino acid positions 103, 163, 171 and/or 219 of a *Paraburkholderia* GlnA protein or in a homologous amino acid position in a homolog thereof. In some cases, the at least one nitrogen fixing bacterium is a nitrogen fixing bacterium comprising a mutant GlnA protein comprising an amino acid sequence with at least one amino acid substitution at amino acid positions 103, 163, 171 and/or 219 of a *Paraburkholderia* GlnA protein or in homologous amino acid positions in a homolog thereof. In some cases, the at least one nitrogen fixing bacterium is a selected from the group consisting of a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725 and a bacterium deposited as PTA-126726. In some cases, the at least one nitrogen fixing bacterium is a selected from the group consisting of *Klebsiella variicola* CI3296, *Klebsiella variicola* CI3936, *Klebsiella variicola* CI3933, *Klebsiella*

*variicola* CI3927, *Klebsiella variicola* CI3925, *Klebsiella variicola* CI3943, *Klebsiella variicola* CI3940, *Klebsiella variicola* CI3938, *Klebsiella variicola* CI4874, *Kosakonia sacchari* CI4065, *Metakosakonia intestini* CI4875, *Metakosakonia intestini* CI4876, *Metakosakonia intestini* CI4877, *Metakosakonia intestini* CI4878, *Paraburkholderia tropica* CI4751, *Paraburkholderia tropica* CI4753, *Paraburkholderia tropica* CI4879 and *Paraburkholderia tropica* CI4752.

In another aspect, provided herein is a method of providing fixed nitrogen to a plant comprising applying a microbial composition to a plant, a plant part, or a locus in which the plant is located, or a locus in which the plant will be grown, wherein the microbial composition comprising at least one of the nitrogen fixing bacterium provided herein. In some cases, the at least one nitrogen fixing bacterium is selected from the microbial strains found in Table 6. In some cases, the at least one nitrogen fixing bacterium is a nitrogen fixing bacterium comprising a mutant glnE gene comprising at least one nucleotide substitution at nucleotide position 965 and/or 2838 of a *Klebsiella* glnE gene or at a homologous nucleotide position in a homolog thereof. In some cases, the at least one nitrogen fixing bacterium is a nitrogen fixing bacterium comprising a mutant glnE gene encoding a GlnE protein comprising an amino acid sequence with at least one amino acid substitution at amino acid positions 322 and/or 746 of a *Klebsiella* GlnE protein or at a homologous amino acid position in a homolog thereof. In some cases, the at least one nitrogen fixing bacterium is a nitrogen fixing bacterium comprising a mutant GlnE protein comprising an amino acid sequence with at least one amino acid substitution at amino acid positions 322 and/or 746 of a *Klebsiella* GlnE protein or at a homologous amino acid position in a homolog thereof. In some cases, the at least one nitrogen fixing bacterium is a nitrogen fixing bacterium comprising a mutant glnA gene comprising at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the at least one nitrogen fixing bacterium is a nitrogen fixing bacterium comprising a mutant glnA gene encoding a GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some cases, the at least one nitrogen fixing bacterium is a nitrogen fixing bacterium comprising a mutant GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some cases, the at least one nitrogen fixing bacterium is a nitrogen fixing bacterium comprising a mutant glnA gene comprising at least one nucleotide substitution at nucleotide position 308, 487, 511 and/or 657 of a *Paraburkholderia* glnA gene or in a homologous nucleotide position in a homolog thereof. In some cases, the at least one nitrogen fixing bacterium is a nitrogen fixing bacterium comprising a mutant glnA gene encoding a GlnA protein comprising an amino acid sequence with at least one amino acid substitution at amino acid positions 103, 163, 171 and/or 219 of a *Paraburkholderia* GlnA protein or in a homologous amino acid position in a homolog thereof. In some cases, the at least one nitrogen fixing bacterium is a nitrogen fixing bacterium comprising a mutant GlnA protein comprising an amino acid sequence with at least one amino acid substitution at amino acid positions 103, 163, 171 and/or 219 of a

*Paraburkholderia* GlnA protein or in homologous amino acid positions in a homolog thereof. In some cases, the at least one nitrogen fixing bacterium is a selected from the group consisting of a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725 and a bacterium deposited as PTA-126726. In some cases, the at least one nitrogen fixing bacterium is a selected from the group consisting of *Klebsiella variicola* CI3296, *Klebsiella variicola* CI3936, *Klebsiella variicola* CI3933, *Klebsiella variicola* CI3927. *Klebsiella variicola* CI3925, *Klebsiella variicola* CI3943, *Klebsiella variicola* CI3940, *Klebsiella variicola* CI3938, *Klebsiella variicola* CI4874, *Kosakonia sacchari* CI4065, *Metakosakonia intestini* CI4875, *Metakosakonia intestini* CI4876, *Metakosakonia intestini* CI4877, *Metakosakonia intestini* CI4878, *Paraburkholderia tropica* CI4751, *Paraburkholderia tropica* CI4753, *Paraburkholderia tropica* CI4879 and *Paraburkholderia tropica* CI4752. In some cases, the microbial composition produces 1% or more of fixed nitrogen in the plant. In some cases, the composition is a solid. In some cases, the composition is a liquid. In some cases, the applying comprises coating a seed or other plant propagation member with the microbial composition. In some cases, the at least one nitrogen fixing bacterium in the microbial composition has an average colonization ability per unit of plant root tissue of at least about $1.0 \times 10^4$ cfu per gram of fresh weight of plant root tissue and produce fixed N of at least about $1 \times 10^{-15}$ mmol N per bacterial cell per hour. In some cases, the applying comprises performing in-furrow treatment of the microbial composition. In some cases, the in-furrow treatment comprises applying the microbial composition at a concentration per acre of between about $1 \times 10^6$ to about $3 \times 10^{12}$ cfu per acre. In some cases, the microbial composition is a liquid formulation comprising about $1 \times 10^6$ to about $1 \times 10^{11}$ cfu of bacterial cells per milliliter.

BRIEF DESCRIPTION OF THE FIGURES

(FIG. 10B), the amounts of ammonium excreted from *Paraburkholderia tropica, Metakosakonia intestini*, and *Kosakonia sacchari* are provided.

FIG. 11 illustrates the experiment described in Example 6 in which differential colonization of 137 mutant barcoded strains were determined across nine plants in terms of percent relative abundance.

DETAILED DESCRIPTION OF THE DISCLOSURE

Figure 1A:
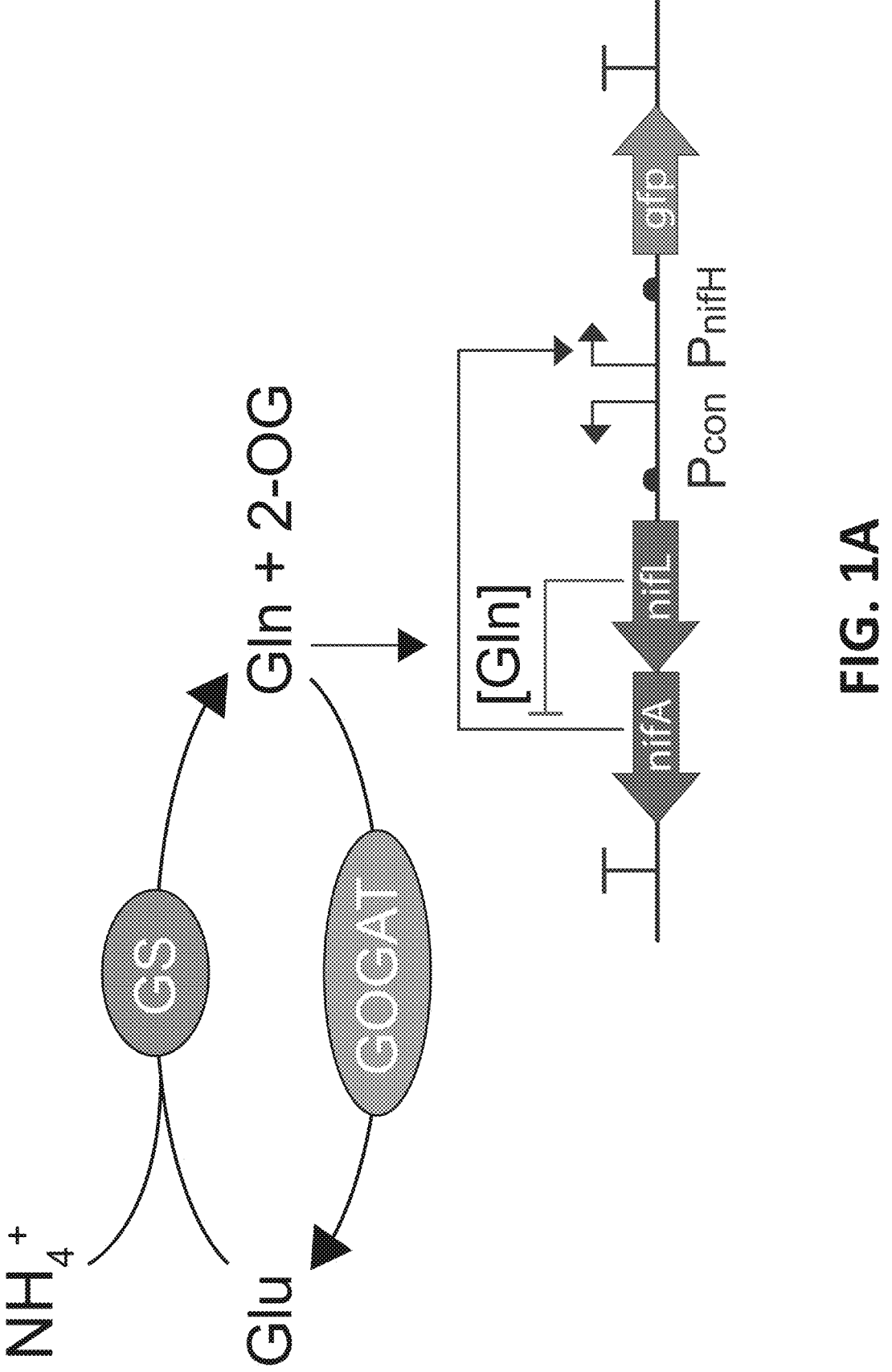
FIGS. 1A-B depict an illustration of a molecular circuit for detecting the presence or absence of free ammonium. T=terminator, Pcon=constitutive promoter controlling the transcription of nifA and nifL, PnifH=promoter controlling the transcription of gfp (FIG. 1A), In the absence of free ammonium or below a given concentration threshold of free ammonium, the NifL disassociates with the NifA, which in turn acts upon the nifH promoter operably linked to the gfp, thus resulting in the expression of GFP. The figure further depicts molecular nitrogen (atmospheric nitrogen, $N_2$) entering a nitrogen fixing bacterium and excreting free nitrogen that is sensed by a biosensor strain comprising the molecular circuit (FIG. 1B). Gln, glutamine; Glu, glutamate; 2-OG, 2-oxoglutarate; GS, glutamine synthetase; GOGAT, glutamate synthase.

Development pipelines for constructing microbial products that are resistant to fixed nitrogen present in fertilizers, while also exhibiting improved ammonium excretion while balancing ammonium assimilation, have relied on rational approaches based on the previously identified candidate genes and pathways. Traditional genetic modifications that utilize heterologous constructs, genes, and vectors are considered genetically modified organisms in some jurisdictions. The nature of the random process of generating microbes that excrete ammonium in the presence of fertilizers poses the need to analyze large mutant libraries. However, the predominant technique utilizing the acetylene reduction assay to gauge nitrogenase activity and ammonium excretion is slow and unscalable. The biosensor strain of the present disclosure allows a large mutant library to be analyzed in a high-throughput manner.

Other co-culture methods rely on the growth of a co-culturing strain to address the nitrogen level. Increases in biomass under nitrogen fixing conditions often show little change and requires a long incubation time before any growth occurs due to the anaerobic nature of the assay conditions. This qualitative output necessarily precludes a high-throughput selection process.

While the following terms are believed to be well understood by one or ordinary skill in the art, the following definitions are set forth to facilitate explanation of the presently disclosed subject matter. Numerous variations, changes, and substitutions may occur to those skilled in the art without departing from the disclosure. It should be understood that various alternatives to the embodiments of the disclosure described herein may be employed.

Definitions

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

As used herein, the term "about" is used synonymously with the term "approximately." Illustratively, the use of the term "about" with regard to an amount indicates that values slightly outside the cited values, e.g., plus or minus 0.1% to 10%.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

As used herein, "non-nitrogen limiting conditions" refers to non-atmospheric nitrogen available in the soil, field and media at concentrations greater than about 4 mM nitrogen, as disclosed by Kant el al. (2010. J. Exp. Biol. 62(4):1499-1509), which is incorporated herein by reference.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, a "control sequence" refers to an operator, promoter, silencer, or terminator.

As used herein, "introduced" refers to the introduction by means of modern biotechnology, and not a naturally occurring introduction.

As used herein, "introduced genetic material" means genetic material that is added to, and remains as a component of, the genome of the recipient.

In some embodiments, native or endogenous control sequences of genes of the present disclosure are replaced with one or more intrageneric control sequences.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

As used herein, "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein the terms "microorganism" or "microbe" should be taken broadly. These terms, used interchangeably, include but are not limited to, the two prokaryotic domains, Bacteria and Archaea. The term may also encompass eukaryotic fungi and protists.

As used herein, "isolate," "isolated," "isolated microbe," and like terms, are intended to mean that the one or more microorganisms has been separated from at least one of the materials with which it is associated in a particular environment (for example soil, water, plant tissue, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be an agriculturally acceptable carrier.

In certain aspects of the disclosure, the isolated microbes exist as "isolated and biologically pure cultures." It will be appreciated by one of skill in the art that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970) discussing purified prostaglandins), see also, In re Bergy, 596 F.2d 952 (CCPA 1979)(discussing purified microbes), see also, Parke-Davis & Co. v. H. K. Mulford & Co., 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture.

The presence of these purity values, in certain embodiments, is a further attribute that distinguishes the presently disclosed microbes from those microbes existing in a natural state. See, e.g., Merck & Co. v. Olin Mathieson Chemical Corp., 253 F.2d 156 (4th Cir. 1958) (discussing purity limitations for vitamin B12 produced by microbes), incorporated herein by reference.

The term "biologically pure culture" or "substantially pure culture" refers to a culture of a bacterial species described herein containing no other bacterial species in quantities sufficient to interfere with the replication of the culture or be detected by normal bacteriological techniques.

In some embodiments, the microbes of the present disclosure have been modified such that they are not naturally occurring bacteria.

As used herein, an "intergeneric microorganism" is a microorganism that is formed by the deliberate combination of genetic material originally isolated from organisms of different taxonomic genera. An "intergeneric mutant" can be used interchangeably with "intergeneric microorganism". An exemplary "intergeneric microorganism" includes a microorganism containing a mobile genetic element which was first identified in a microorganism in a genus different from the recipient microorganism. Further explanation can be found, inter alia, in 40 C.F.R. § 725.3.

In some aspects, microbes taught herein are "non-intergeneric," which means that the microbes are not intergeneric.

A "non-intergeneric remodeled microorganism" has a synonymous meaning to "non-intergeneric engineered microorganism," and will be utilized interchangeably.

Microbes of the present disclosure may include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconductive to the survival or growth of vegetative cells.

As used herein, "microbial composition" refers to a composition comprising one or more microbes of the present disclosure. In some embodiments, a microbial composition is administered to plants (including various plant parts) and/or in agricultural fields.

As used herein, "carrier," "acceptable carrier," or "agriculturally acceptable carrier" refers to a diluent, adjuvant, excipient, or vehicle with which the microbe can be administered, which does not detrimentally effect the microbe.

As used herein, "plant part" refers to any part of a plant such as a seed, root, stem, tissue, etc.

In some embodiments, the nitrogen fixation and assimilation genetic regulatory network comprises polynucleotides encoding genes and non-coding sequences that direct, modulate, and/or regulate microbial nitrogen fixation and/or assimilation and can comprise polynucleotide sequences of the nif cluster (e.g., nifA, nifB, nifC, . . . nifZ), polynucleotides encoding nitrogen regulatory protein C, polynucleotides encoding nitrogen regulatory protein B, polynucleotide sequences of the gln cluster (e.g. glnA and glnD), draT, and ammonia transporters/permeases. In some cases, the Nif cluster may comprise NifB, NifH, NifD, NifK, NifE, NifN, NifX, hesa, and NifV. In some cases, the Nif cluster may comprise a subset of NifB, NifH, NifD, NifK, NifE, NifN, NifX, hesa, and NifV.

In some embodiments, the increase of nitrogen fixation in microbes and/or the production of 1% or more of the nitrogen in the microbes or media containing the microbes is measured relative to control microbes, which have not been exposed to the microbes of the present disclosure. All increases or decreases in microbes are measured relative to control microbes.

In some embodiments, the increase or decrease in the output of a reporter gene, such as a gfp, in the microbes or media containing the microbes is measured relative to control microbes, which either do not express the reporter gene or express a functionally deleted variant thereof. All increases or decreases in reporter genes in the microbes are measured relative to control microbes.

Regulation of Nitrogen Fixation

In order to utilize elemental nitrogen (N) for chemical synthesis, life forms convert nitrogen gas ($N_2$) available in the atmosphere into ammonia in a process known as nitrogen fixation. Because of the energy-intensive nature of biological nitrogen fixation, diazotrophs (bacteria and archaea that fix atmospheric nitrogen gas) have evolved sophisticated and tight regulation of the n gene cluster in response to environmental oxygen and available nitrogen. Nif genes encode enzymes involved in nitrogen fixation (such as the nitrogenase complex) and proteins that regulate nitrogen fixation. Shamseldin (2013. Global J. Biotechnol. Biochem. 8(4):84-94) discloses detailed descriptions of nif genes and their products, and is incorporated herein by reference.

In Proteobacteria, regulation of nitrogen fixation centers around the $\sigma_{54}$-dependent enhancer-binding protein NifA, the positive transcriptional regulator of the nif cluster.

Intracellular levels of active NifA are controlled by two key factors: transcription of the nifLA operon and inhibition of NifA activity by protein-protein interaction with NifL. Both of these processes are responsive to intracellular glutamine levels via the PII protein signaling cascade. This cascade is mediated by GlnD, which directly senses glutamine and catalyzes the uridylylation or deuridylylation of two PII regulatory proteins—GlnB and GlnK—in response the absence or presence, respectively, of bound glutamine. Under conditions of nitrogen excess, unmodified GlnB signals the deactivation of the nifLA promoter. However, under conditions of nitrogen limitation, GlnB is post-translationally modified, which inhibits its activity and leads to transcription of the nifLA operon. In this way, nifLA transcription is tightly controlled in response to environmental nitrogen via the PII protein signaling cascade. On the post-translational level of NifA regulation, GlnK inhibits the NifL/NifA interaction in a matter dependent on the overall level of free GlnK within the cell.

NifA is transcribed from the nifLA operon, whose promoter is activated by phosphorylated NtrC, another $\sigma_{54}$-dependent regulator. The phosphorylation state of NtrC is mediated by the histidine kinase NtrB, which interacts with deuridylylated GlnB but not uridylylated GlnB. Under conditions of nitrogen excess, a high intracellular level of glutamine leads to deuridylylation of GlnB, which then interacts with NtrB to deactivate its phosphorylation activity and activate its phosphatase activity, resulting in dephosphorylation of NtrC and the deactivation of the nifLA promoter. However, under conditions of nitrogen limitation, a low level of intracellular glutamine results in uridylylation of GlnB, which inhibits its interaction with NtrB and allows the phosphorylation of NtrC and transcription of the nifLA operon. In this way, nifLA expression is tightly controlled in response to environmental nitrogen via the PII protein signaling cascade. nifA, ntrB, ntrC, and glnB, are all genes that can be mutated in the methods described herein. These processes may also be responsive to intracellular or extracellular levels of ammonia, urea or nitrates.

Although some endophytes have the ability to fix nitrogen in vitro, often the genetics are silenced in the field by high levels of exogenous chemical fertilizers. One can decouple the sensing of exogenous nitrogen from expression of the nitrogenase enzyme to facilitate field-based nitrogen fixation. Improving the integral of nitrogenase activity across time further serves to augment the production of nitrogen for utilization by the crop. Specific targets for genetic variation to facilitate field-based nitrogen fixation using the methods described herein include one or more genes selected from the group consisting of nifA, nifL, ntrB, ntrC, glnA, glnB, glnK, draT, amtB, glnD, glnE, nifJ, nifH, nifD, nifK, nifY, nifE, nifN, nifU, nifS, nifV, nifW, nifZ, nifM, nifF, nifB, and nifQ.

An additional target for genetic variation to facilitate field-based nitrogen fixation using the methods described herein is the NifA protein. The NifA protein is typically the activator for expression of nitrogen fixation genes. Increasing the production of NifA (either constitutively or during high ammonia condition) circumvents the native ammonia-sensing pathway. In addition, reducing the production of NifL proteins, a known inhibitor of NifA, also leads to an increased level of freely active NifA. In addition, increasing the transcription level of the nifLA operon (either constitutively or during high ammonia condition) also leads to an overall higher level of NifA proteins. Elevated level of nifLA expression is achieved by altering the promoter itself or by reducing the expression of NtrB (part of ntrB and ntrC signaling cascade that originally would result in the shutoff of nifLA operon during high nitrogen condition). High level of NifA achieved by these or any other methods described herein increases the nitrogen fixation activity of the endophytes.

Biosensor

The biosensor microbe of the present disclosure enables the screening of ammonium-excreting microbes based on a co-culture system. The use of the biosensor has clear advantages, including: (i) excretion of ammonium from a mutant library can be visualized by fluorescence detection of the biosensor in liquid culture as well as on solid media; (ii) intracellular nitrogen level of the mutants that fixed atmospheric nitrogen into ammonium can be analyzed with a biosensor strain; (iii) as a biosensor utilizes ammonium fixed by the co-culture library, this system is more pertinent to the field environments in which microbes reside without artificial ammonium accumulation.

Figure 1B:
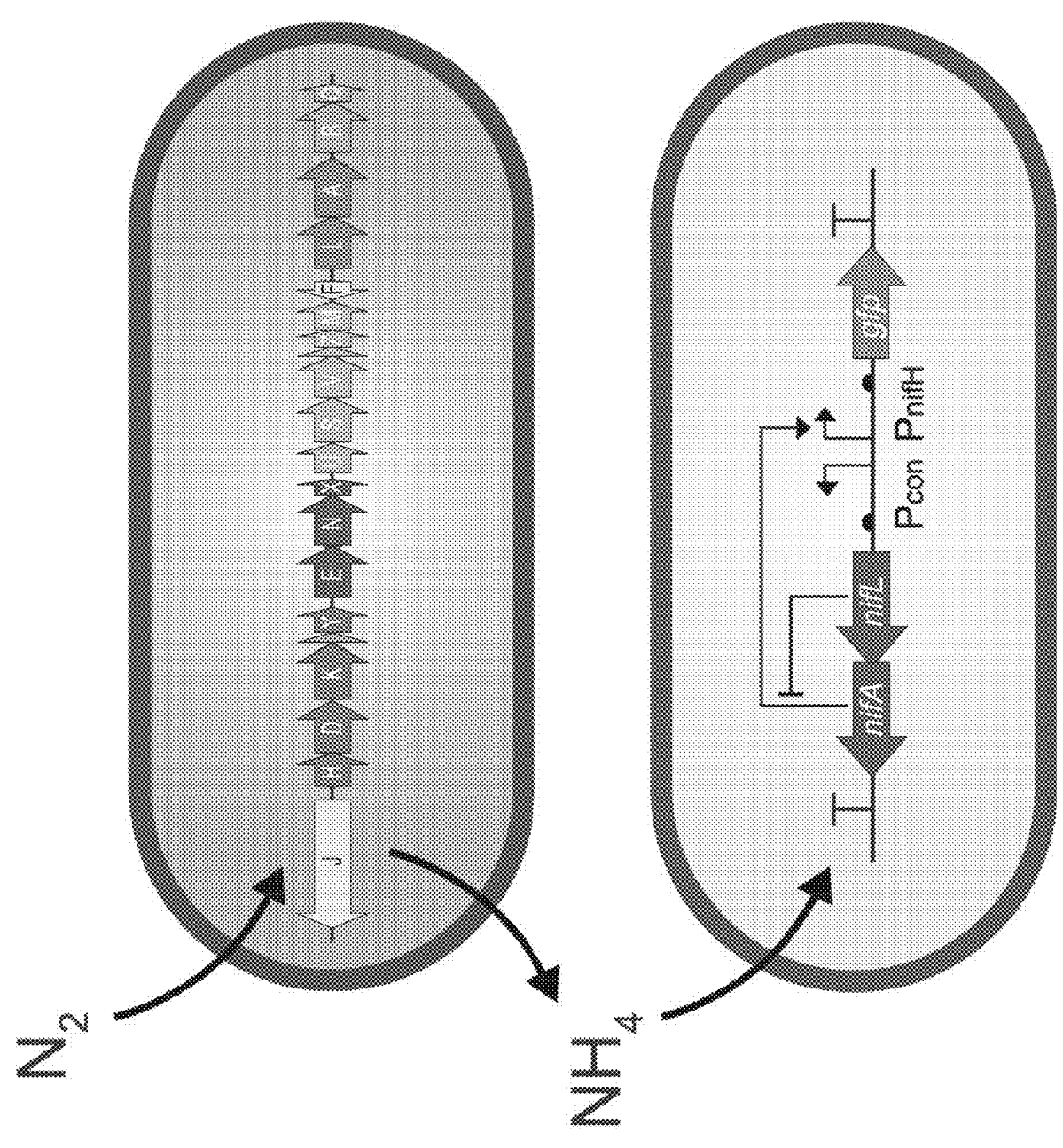
Figure 2:
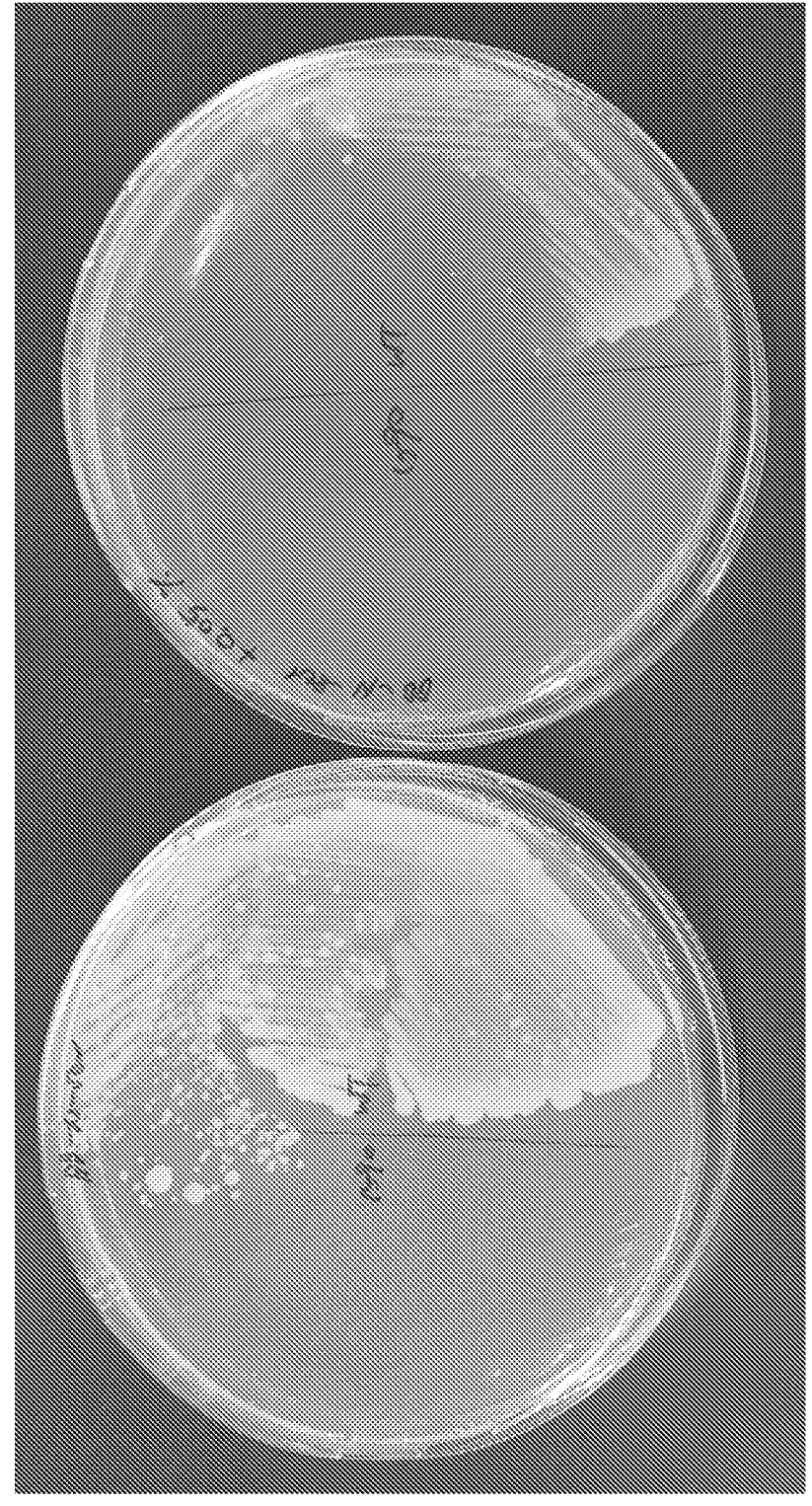
FIG. 2 depicts a wild type *Klebsiella variicola* strain (right side of each plate) that exhibits diazotrophic growth versus a strain that cannot fix nitrogen (left side of each plate) under anaerobic conditions. The right plate differs from the left plate in that it contains EDA, which inhibits diazotrophic growth of the *Klebsiella variicola* 137 wild-type.

In some aspects, the biosensor comprises a heterologous sequence that acts as a circuit. See FIG. 1A-B. In some aspects, the circuit comprises both a nucleic acid sequence encoding an inhibitory nitrogen fixation regulatory protein under the control of a promoter and a nucleic acid sequence encoding a positive nitrogen fixation regulatory protein under the control of a promoter. In some aspects, the nucleic acid sequence encoding an inhibitory nitrogen fixation regulatory protein and the nucleic acid sequence encoding a positive nitrogen fixation regulatory protein are each under the control of a constitutive promoter. In some aspects, the nucleic acid sequence encoding an inhibitory nitrogen fixation regulatory protein and the nucleic acid sequence encoding a positive nitrogen fixation regulatory protein are present as an operon under the control of a constitutive promoter. In some aspects, the directionality of transcription of the nucleic acid sequence encoding an inhibitory nitrogen fixation regulatory protein and the nucleic acid sequence encoding a positive nitrogen fixation regulatory protein are each in the opposite direction of transcription from one or more other elements of the circuit. In some aspects, the directionality of transcription of the operon comprising the nucleic acid sequence encoding an inhibitory nitrogen fixation regulatory protein and the nucleic acid sequence encoding a positive nitrogen fixation regulatory protein is in the opposite direction of transcription from one or more other elements of the circuit. In some aspects, the circuit comprises a nifLA operon under the control of a promoter. In some aspects, the nifLA operon is under the control of a constitutive promoter. In some aspects, the directionality of transcription of the nifLA operon is in the opposite direction of transcription from one or more other elements of the circuit. In some aspects, the circuit comprises a nucleotide sequence encoding a fluorescent protein or a functional fragment and/or fusion thereof, or another reporter protein or molecule. In some aspects, the nucleotide sequence encoding a reporter protein is under the control of a promoter and a terminator. In some aspects, the nucleotide sequence encoding a fluorescent protein is under the control of a promoter and a terminator. In some aspects, the reporter protein is operably linked to or under the control of a promoter or fragment thereof selected from the Nif regulon. In some aspects, the fluorescent protein is operably linked to or under the control of a promoter or fragment thereof selected from the Nif regulon. In some aspects, the reporter protein is operably linked to or under the control of a promoter or fragment thereof selected from the nifHDK operon. In some aspects, the fluorescent protein is operably linked to or under the control of a promoter or fragment thereof selected from the nifHDK operon. In some aspects, the reporter protein is operably linked to or under the control of a nifH promoter. In some aspects, the fluorescent protein is operably linked to or under the control of a nifH promoter. In some aspects, the directionality of transcription of the reporter protein is in the opposite direction of transcription from one or more other elements of the circuit. In some aspects, the directionality of transcription of the fluorescent protein is in the opposite direction of transcription from one or more other elements of the circuit. In some aspects, the circuit comprises one or more constitutive promoters. In some aspects, the circuit comprises one or more terminators.

In some aspects, the nucleic acid sequence encoding an inhibitory nitrogen fixation regulatory protein is a nifL gene that encodes NifL. In some aspects, the nucleic acid sequence encoding a positive nitrogen fixation regulatory protein is a nifA gene that encodes NifA. In some aspects, NifL is bound to NifA in the presence of free ammonium or glutamine. In some aspects, in the absence of free ammonium or glutamine, the NifL is not bound to NifA. In some aspects, unbound NifA acts on the nifH promoter to initiate transcription and expression of the reporter protein (e.g., GFP). In some aspects, a microbe comprising the circuit does not express detectable amounts of reporter protein (e.g., GFP) in the presence of free ammonium or glutamine. In some aspects, a microbe comprising the circuit expresses detectable amounts of reporter protein (e.g., GFP) in the absence of free ammonium or glutamine.

In some aspects, a reporter element, such as a reporter protein, molecule or enzyme is produced or expressed by the biosensor. The reporter protein emits a detectable signal in response to certain predetermined changes in the cytosol of the living, engineered biosensor. In some aspects, the reporter protein is a bioluminescent photoprotein such as aequorin, which is derived from the hydrozoan *Aequorea victoria*. In some aspects, production of the reporter protein within the biosensor cell will then be controlled by expression of the introduced genetic material. In some aspects, other photoproteins or other types of reporter proteins, enzymes, and molecules may be incorporated into and utilized with various alternate embodiments of the present disclosure.

In some aspects, the reporter can be a protein that has fluorescent properties that undergo a detectable change in response to activation of the biosensor circuit. In some aspects, the reporter or reporter protein can be calcium-sensitive luminescent or fluorescent molecules, such as obelin, thalassicolin, mitrocomin (halistaurin), clytin (phialidin), mnemopsin, berovin, Indo-1, Fura-2, Quin-2, Fluo-3, Rhod-2, calcium green, BAPTA, cameleons, or similar molecules. In some aspects, the reporter protein can be a chimeric protein that includes a Ca' binding domain and an associated fluorescent protein. In some aspects, the reporter can be an enzyme that is adapted to produce a luminescent or fluorescent signal. In some aspects, the reporter protein can be an enzyme such as luciferase or alkaline phosphatase that yields a luminescent or fluorescent signal respectively. In some aspects, the reporter can also be a fluorescent protein or can include fluorescent, charged, or magnetic nanoparticles, nanodots, or quantum dots. In some aspects, the reporter can be a dye that has fluorescent, ultraviolet, or visible properties, wherein the fluorescent, ultraviolet, or visible properties undergo a detectable change in response to the activation of the biosensor circuit.

In some aspects, the reporter gene is a fluorescent reporter gene. In some aspects, the fluorescent reporter gene encodes a fluorescent protein. In some aspects, the fluorescent reporter gene encodes an aequorin. In some aspects, the fluorescent protein is selected from the far-red class of fluorescent proteins. In some aspects, the far-red fluorescent protein is mPlum or a variant thereof.

In some aspects, the fluorescent protein is selected from the red class of fluorescent proteins. In some aspects the red fluorescent protein is selected from RFP, mCherry, tdTomato, mStrawberry, J-Red, DsRed-monomer, or a variant thereof. In some aspects, the fluorescent protein is selected from the orange class of fluorescent proteins. In some aspects, the orange fluorescent protein is selected from OFP, mOrange, mKO, or a variant thereof.

In some aspects, the fluorescent protein is selected from the yellow-green class of fluorescent proteins. In some aspects, the yellow-green fluorescent protein is selected from YFP, mCitrine, Venus, YPet, EYFP, or a variant thereof.

In some aspects, the fluorescent protein is selected from the green class of fluorescent proteins. In some aspects, the green fluorescent protein is selected from GFP, EGFP, Emerald, or a variant thereof. In some aspects, the fluorescent protein is selected from the cyan class of fluorescent proteins. In some aspects, the cyan fluorescent protein is selected from Cypet, mCFPm, Cerulean, CFP, or a variant thereof. In some aspects, the fluorescent protein is selected from the UV-excitable green class of fluorescent proteins. In some aspects the UV-excitable green fluorescent protein is selected from T-sapphire. In one embodiment, the GFP is a superfolder GFP.

In some aspects, the reporter gene is operably linked to promoter or a fragment thereof from the Nif regulon. The promoter is selected from the nifRLA operon, nifHDK operon, nifEN operon, nifBQ operon, nifJ operon, nifUSVM operon, or the nifWF operon. In some aspects, the promoter is selected from the nifHDK operon. In some aspects, the promoter is selected from nifH.

In some aspects, the oxygen sensor of nifL is modified such that the presence of oxygen cannot change the conformational shape of NifL between its oxidized or reduced form. In some aspects, the nifA and/or nifL genes are modified such that the concentration of oxygen has no effect on the ability of NifA to activate a promoter controlling the transcription of the reporter gene in the biosensor circuit. In some aspects, the nifA and/or nifL genes are modified such that the concentration of oxygen has no effect on the ability of NifA to activate the nifH promoter.

In some aspects, the nifA and the nifL genes utilized in the biosensor circuit are isolated from species of the following genera: *Klebsiella, Kosakonia, Serratia, Rahnella, Pectobacterium, Dickeya, Vibrio, Pseudomonas, Azotobacter, Teredinibacter, Methylomonas, Methylovulum, Thiocystis, Thiodictyon, Thioflavicoccus, Aquaspirillum, Dechioromonas, Azoarcus,* and *Wolinella*. In some aspects, the nifA and the nifL genes utilized in the biosensor circuit are isolated from any species within Enterobacteriaceae, Rhodocyclaceae, or Zoogloeaceae. In some aspects, the nifA is selected from one species of the listed genera and the nifL is selected from a different species of the listed genera. In some aspects, the nifA is selected from a species of the listed genera and the nifL is selected from a species of a different genus than the nifA.

In some aspects, the nifH promoter utilized in the biosensor circuit is isolated from species of the following genera: *Klebsiella, Kosakonia, Serratia, Rahnella, Pectobacterium, Dickeya, Vibrio, Pseudomonas, Azotobacter, Teredinibacter, Methylomonas, Methylovulum, Thiocystis, Thiodictyon, Thioflavicoccus, Aquaspirillum, Dechloromonas, Azoarcus,* and *Wolinella*. In some aspects, the nifH promoter utilized in the biosensor circuit is isolated from any species within Enterobacteriaceae, Rhodocyclaceae, or Zoogloeaceae.

In some aspects, the nifH promoter and the nifL and nifA genes are each isolated from a different species within the same genus. In some aspects, the nifH promoter and the nifL and nifA genes are each isolated from a different genera of bacteria. In some aspects, the nifH promoter and the nifL and nifA genes are each isolated from the same species.

In some aspects, the nifH promoter, the nifL gene, and the nifA gene are each isolated from a species of *Klebsiella*. In some aspects, at least one of the nifH promoter, the nifL gene, and the nifA gene are isolated from a species of *Klebsiella*.

In some aspects, the nifH promoter, the nifL gene, and the nifA gene are each isolated from a species of *Kosakonia*. In some aspects, at least one of the nifH promoter, the nifL gene, and the if gene are isolated from a species of *Kosakonia*.

In some aspects, the nifH promoter, the nifL gene, and the nifA gene are each isolated from a species of *Azotobacter*. In some aspects, at least one of the nifH promoter, the nifL gene, and the nifA gene are isolated from a species of *Azotobacter*.

In some aspects, the constitutive promoter controlling the nucleic acid sequence encoding the inhibitory nitrogen fixation regulatory protein and/or the nucleic acid sequence encoding the positive nitrogen fixation regulatory protein is selected from *E. coli* or *Bacillus subtilis*. In some aspects, the constitutive promoter controlling the nifLA is selected from *E. coli* or *Bacillus subtilis*. *In some aspects, the constitutive promoter is selected from an E coli constitutive* promoter. In some aspects, the constitutive promoter is a constitutive $\sigma^{70}$ promoter. In some aspects, the constitutive promoter is a constitutive $\sigma^s$ promoter. In some aspects, the constitutive promoter is a constitutive $\sigma^{32}$ promoter. In some aspects, the constitutive promoter is a constitutive $\sigma^{54}$ promoter. In some aspects, the constitutive promoter is selected from a *B. subtilis* constitutive promoter. In some aspects, the constitutive promoter is a constitutive $\sigma^A$ promoter. In some aspects, the constitutive promoter is a constitutive $\sigma^B$ promoter.

In some aspects, the one or more transcriptional terminators are selected from rho-independent terminators and rho-dependent terminators. In some aspects, the one of more transcriptional terminators are selected from any one or more bacterial terminator. In some aspects, the biosensor circuit comprises two or more transcriptional terminators. In some aspects, the two or more transcriptional terminators are from different species. In some aspects, the two or more transcriptional terminators are from the same genus. In some aspects, the two or more transcriptional terminators are from different genera.

In some aspects, the biosensor is a prokaryotic cell or a eukaryotic cell. In some aspects, the biosensor is a yeast or fungal cell. In some aspects, the biosensor is an insect cell, mammalian cell, animal cell, plant cell, or a bacterial cell. In some aspects, the biosensor is a fixed cell. In some aspects, the biosensor is an artificial cell. In some aspects, the biosensor is a synthetic cell. In some aspects, the insect cell is a sf9 cell or a *Drosophila* Schneider 2 cell. In some aspects, the mammalian cell is a HEK cell, a CHO cell, a COS cell, a 3t3 cell, or other cultured, immortalized, or passaged mammalian cell. In some aspects, the yeast or fungal cell is a *Saccharomyces, Cryptococcus*, or *Candida* cell.

In some aspects, the bacterial cell is a species of one or more of the following taxa: *Achromobacter, Acidithiobacillus, Acidovorax, Acidovorax, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium. Brevibacillus, Brevundimonas, Burkholderia, Candidatus Haloredivivus, Caulobacter, Cellulomonas, Cellvibrio, Chryseobacterium, Citrobacter, Clostridium, Coralionargarita, Corynebacterium, Cupriavidus, Curtobacterium, Curvibacter, Deinococcus, Delfiia, Desemzia, Devosia, Dokdonella, Dyella, Enhydrobacter. Enterobacter. Enterococcus. Erwinia, Escherichia. Escherichia/Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Metakosakonia, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Paraburkholderia Pelomonas, Perlucidibaca, Plantibacter, Polymucleobacter, Propionibacterium, Propioniciclava, Pseudo-*

*clavibacter, Pseudomonas, Pseudonocardia, Pseudoxanthomonas, Psychrobacter, Rahnella, Raistonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus, Stenotrophomonas, Strenotrophomonas, Streptococcus, Streptomyces, Stygiolobus, Sufurisphaera, Tatumella, Tepidimonas, Thermomonas, Thiobacillus, Variovorax*, WPS-2 genera incertae sedis, *Xanthomonas*, and *Zimmermannella*.

In some aspects, the bacterial cell is a species of one or more of the following taxa: *Agrobacterium radiobacter, Bacillus acidocaldarius, Bacillus acidoterrestris, Bacillus agri, Bacillus aizawai, Bacillus albolactis, Bacillus alcalophilus, Bacillus alvei, Bacillus aninoglucosidicus, Bacillus aminovorans, Bacillus amylolyticus* (also known as *Paenibacillus amylolyticus*), *Bacillus amyloliquefaciens, Bacillus aneurinolyticus, Bacillus atrophaeus, Bacillus azotoformans, Bacillus badius, Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus lactis, Bacillus laterosxrus* (also known as *Brevibacillus laterosporus*), *Bacillus lautus, Bacillus lentimorbus. Bacillus lentus, Bacillus lichenformis, Bacillus maroccanus, Bacillus megaterium, Bacillus metiens, Bacillus mycoides, Bacillus natto, Bacillus nematocida, Bacillus nigrificans, Bacillus nigrum, Bacillus pantothenticus, Bacillus popillae, Bacillus psychrosaccharolyticus, Bacillus immilus, Bacillus siamensis, Bacillus smithii, Bacillus sphaericus, Bacillus subtilis, Bacillus thuringiensis, Bacillus uiflagellatus, Bradyrhizobium japonicum, Brevibacillus brevis Brevibacillus laterosporus* (formerly *Bacillus laterosporus*), *Chromobacterium subtsugae, Detftia acidovorans. Escherichia coli, Klebsiella variicola, Lactobacillus acidophilus, Lysobacter anlibioticus, Lysobacter enzymogenes, Paenibacillus alvei, Paenibacillus polynyxa, Paenibacillus popilliae* (formerly *Bacillus popilliae*), *Pantoea agglomerans, Pasteuria peneirans* (formerly *Bacillus penetrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae. Serratia entomophila, Serratia marcescens, Streptomyces colombiensis, Streptomyces galbus, Streptomyces goshikiensis, Streptomyces griseoviridis, Streptomyces lavendulae, Streptomyces prasins, Streptomyces saraceticus, Streptomyces venezuelae, Xanthomonas campestris, Xenorhabdus luminescens*, and *Xenorhabdus nematophila*, In some cases the bacterium may be *Azotobacter chroococcum, Methanosarcina barkeri, Klebsiella pneumoniae, Azotobacter vinelandii, Rhodobacter spharoides, Rhodobacter capsulatus, Rhodobacter palustris, Rhodospirillum rubrum, Rhizobium leguminosarum*, or *Rhizobium etli*.

In some aspects, genetic manipulation of a cell to create the biosensor is desired. Genetic manipulation and modification of cells to create a biosensor typically involve the use of appropriately selected genetic delivery vehicles that function efficiently in the cell type of choice. In some aspects, a gene delivery vehicle such as, for example, bacterial plasmid vectors or viral vectors, for introducing the appropriate genetic material into the biosensor cells may be utilized.

In some aspects, it is useful to utilize a promoter element that directs high level expression of introduced genetic elements in the biosensor cell of choice. In some aspects, the promoter element is derived directly from the biosensor cell itself and then used to express one or more genes of interest from the biosensor circuit. In some aspects, the biosensor circuit may be introduced into the biosensor cell using standard techniques such as electroporation, transfection, etc. Other genetic engineering methods known to those or ordinary skill in the art are also compatible with the present disclosure.

In some aspects, the biosensor exhibits a high cooperativity, meaning that the biosensor has a narrow range of response to ammonium. In some instances, if the concentration or amount of ammonium is out of the narrow response range of the biosensor, it exhibits an on signal (high reporter protein, e.g., GFP) or an off signal (no reporter protein, e.g., GFP). In some aspects, the ammonium levels of the positive control can be quantified by the following: ~1.4 mM (0.7 mM*2 from 2 times dilution (×0.5)) from the response curve. In some aspects, when the medium is diluted four (4) times (×0.25), the ammonium level is ~0.35 mM for the biosensor which yields high reporter protein (e.g., GFP) signal. In embodiments wherein the reporter protein is a fluorescent protein, the reporter protein can be detected by applying light excitation sufficient to fluoresce the fluorescent protein, functional fragment, and/or fusions thereof. In embodiments wherein the reporter protein is a fluorescent protein, the fluorescence can be detected with a flow cytometer, plate reader or fluorescence-activated droplet sorting.

In some aspects, the non-biosensor microbes are grown in a medium and the non-biosensor microbes are then removed from the media. In some aspects, the resulting media are essentially free of the non-biosensor microbes. In some aspects, one or more biosensors are added to the media that are essentially free of the non-biosensor microbes.

In some aspects, the non-biosensor microbes are grown in a medium and the medium is diluted with a buffered solution or media. In some aspects, the medium is diluted at least 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:60, 1:70, 1:80, 1:90, 1:100, 1:200, 1:300, 1:400, 1:500, 1:600, 1:700, 1:800, 1:900, 1:1000, 1:1500, 1:2000, 1:2500, 1:3000, 1:3500, 1:4000, 1:4500, 1:5000, 1:5500, 1:6000, 1:6500, 1:7000, 1:7500, 1:8000, 1:8500, 1:9000, 1:9500, or 1:10000. In some aspects, the non-biosensor microbes are removed from the medium prior to the dilution such that the medium is essentially free of the non-biosensor microbes. In some aspects, one or more biosensors are added to the diluted medium. In some aspects, one or more biosensors are added to the medium that is essentially free of non-biosensor microbes. In some aspects, one or more biosensors are added to the diluted medium that is essentially free of non-biosensor microbes.

In some aspects, the medium is diluted prior to adding one or more biosensors due to the response curve the one or more biosensors operate within.

In some aspects, an ammonium transporter of the biosensor strain is modified. In some aspects, a regulatory sequence of an ammonium transporter of the biosensor strain is modified. In some aspects, the modification results in a modulation of the expression of the ammonium transporter. In some aspects, the modulation is an increase in the expression of the ammonium transporter. In some aspects, the modulation is a decrease in the expression of the ammonium transporter. In some aspects, the modulation results in a change in the ammonium and/or glutamine response curve in the biosensor strain. In some aspects, this change in the ammonium and/or glutamine response curve results in the biosensor strain being capable of effectively indicating the presence or absence of ammonium and/or glutamine in the medium in which the biosensor strain is placed. In some aspects, the ammonia transporter is AmtB.

In some aspects, the non-biosensor microbes grown in the medium are diluted such that the diluted medium comprises at least 1, at least 5, at least 10, at least 20, at least 30, at least 40, at least 50, at least 60, at least 70, at least 80, at least 90, at least 100, at least 150, at least 200, at least 300, at least 400, at least 500, at least 600, at least 700, at least 800, at least 900, at least $10^4$, at least $10^1$, $10^6$, $10^7$, $10^8$, $10^9$, $10^{10}$, $10^{11}$, $10^{11}$, $10^{11}$, $10^{14}$, $10^{15}$, $10^{16}$, $10^{17}$, $10^{18}$ biosensor microbes.

Bacteria

Microbes useful in the methods and compositions disclosed herein may be obtained from any source. In some aspects, microbes may be bacteria, archaea, protozoa or fungi. The microbes of this disclosure may be nitrogen fixing microbes, for example a nitrogen fixing bacteria, nitrogen fixing archaea, nitrogen fixing fungi, nitrogen fixing yeast, or nitrogen fixing protozoa. Microbes useful in the methods and compositions disclosed herein may be sporeforming microbes, for example spore forming bacteria. In some aspects, bacteria useful in the methods and compositions disclosed herein may be Gram-positive bacteria or Gram-negative bacteria. In some aspects, the bacteria may be an endospore forming bacteria of the Firmicute phylum. In some aspects, the bacteria may be a diazatroph. In some aspects, the bacteria may not be a diazotroph.

The methods and compositions of this disclosure may be used with an archaea, such as, for example, Methantothermobacter thernoautotrophicus.

In some aspects, bacteria useful in the methods and compositions disclosed herein can be a species of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulonionas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Fahydrobacter, Enterobacter, Enterococcus, Erwinia, Escherichia, Escherichia-Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Metakosakonia, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Paraburkholderia, Pelomonas, Perlucidibaca, Plantibacter, Polynucleobacter, Propionibacterium, Propioniciclava, Pseudoclavibacter, Pseudomonas, Pseudonocardia, Pseudoxanthomonas, Psychrobacter, Rahnella, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus, Stenotrophomonas, Strenotrophomonas, Streptococcus,*

*Streptomyces, Stygiolobus, Sulfurisphaera, Tatumella, Tepidimonas, Thermonionas, Thiobacillus, Variovorax,* WPS-2 genera incertae sedis, *Xanthomonas,* and *Zimmermannella.*

In some aspects, bacteria which may be useful include, but are not limited to, *Agrobacterium radiobacter, Bacillus acidocaldarius, Bacillus acidoterrestris, Bacillus agri, Bacillus aizawai, Bacillus albolactis, Bacillus alcalophilus. Bacillus alvei, Bacillus aminoglucosidicus, Bacillus aminovorans, Bacillus amylolyticus* (also known as *Paenibacillus amylolyticus*), *Bacillus amyloliquefaciens, Bacillus aneurinolyticus, Bacillus atrophaeus, Bacillus azotoformans. Bacillus badius. Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporus*), *Bacillus lautus, Bacillus lentimorbus, Bacillus lentus, Bacillus licheniformis. Bacillus maroccanus, Bacillus megaterium, Bacillus metiens, Bacillus mycoides, Bacillus natto, Bacillus nematocida, Bacillus nigrificans, Bacillus nigrum, Bacillus pantothenticus, Bacillus popillae, Bacillus psychrosaccharolyticus, Bacillus pumilus, Bacillus siamensis, Bacillus smithii, Bacillus sphaericus, Bacillus subtillis, Bacillus thuringiensis, Bacillus uniflagellatus, Bradyrhizobium japonicum, Brevibacillus brevis Brevibacillus laterosporus* (formerly *Bacillus laterosporus*), *Chromobacterium subtsugae, Delftia acidovorans, Escherichia coli, Klebsiella variicola, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penelrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae, Serratia entomophila, Serratia marcescens, Streptomyces colombiensis, Streptomyces galbus, Streptomyces goshikiensis, Streptomyces griseoviridis, Streptomyces lavendulae. Streptomyces prasinus, Streptomyces saraceticus, Streptomyces venezuelae, Xanthomonas campestris, Xenorhabdus luminescens, Kosakonia sacchari, Metakosakonia intestini, Paraburkholderia tropica* and *Xenorhabdus nematophila.* In some cases the bacterium may be *Azolobacter chroocccum, Methanosarcina barkeri, Klebsiella pneumoniae, Azotobacter vinelandii, Rhodobacter spharoides, Rhodobacter capsulatus, Rhodobacter palustris, Rhodosporillum rubrum, Rhizobium leguminosarum,* or *Rhizobium etli.*

Budapest Treaty on the International Recognition of the Deposit of Microorganisms for the Purpose of Patent Procedures The microbial deposits of the present disclosure were made under the provisions of the Budapest Treaty on the International Recognition of the Deposit of Microorganisms for the Purpose of Patent Procedure (Budapest Treaty). See Table 7. The disclosure contemplates embodiments comprising any one of the microbes listed in Table 7, as well as derivatives, variants, and/or mutants thereof. Further, the disclosure contemplates agricultural compositions comprising any one of the microbes listed in Table 7, as well as derivatives, variants, and/or mutants thereof. Further, the disclosure contemplates methods of utilizing any one of the microbes listed in Table 7, as well as derivatives, variants, and/or mutants thereof. Methods of the disclosure may comprise applying said microbe to a plant or plant part (such as a seed), or to an area in which said plant or plant part is to be grown, in order to supply fixed atmospheric nitrogen to said plant.

Applicants state that pursuant to 37 C.F.R. § 1.808(a)(2) "all restrictions imposed by the depositor on the availability to the public of the deposited material will be irrevocably removed upon the granting of the patent." This statement is subject to paragraph (b) of this section (i.e. 37 C.F.R. § 1.808(b)).

In some aspects, the bacteria is selected from Table 7. In some aspects, the bacteria is selected from Table 7 and was deposited with the Bigelow National Center for Marine Algae and Microbiota (NCMA), located at 60 Bigelow Drive, East Boothbay, Maine 04544, USA with the name designation, taxonomy, accession number and date of deposit as found in Table 7. In some aspects, the bacteria is selected from Table 7 and was deposited with the American Type Culture Collection (ATCC), located at 10801 University Boulevard, Manassas, Virginia 20110-2209, USA with the name designation, taxonomy, accession number and date of deposit as found in Table 7.

TABLE 7

| Depository | Name Designation | Taxonomy | Accession Number | Date of Deposit |
|---|---|---|---|---|
| | [Microorganisms Deposited under the Budapest Treaty | | | |
| ATCC | 137-3296, CI3296 | *Klebsiella variicola* | PTA-126709 | Mar. 25, 2020 |
| ATCC | 137-3936, CI3936 | *Klebsiella variicola* | PTA-126710 | Mar. 25, 2020 |
| ATCC | 137-3933, CI3933 | *Klebsiella variicola* | PTA-126711 | Mar. 25, 2020 |
| ATCC | 137-3927, CI3927 | *Klebsiella variicola* | PTA-126712 | Mar. 25, 2020 |
| ATCC | 137-3925, CI3925 | *Klebsiella variicola* | PTA-126713 | Mar. 25, 2020 |
| ATCC | 137-3943, CI3943 | *Klebsiella variicola* | PTA-126714 | Mar. 25, 2020 |
| ATCC | 137-3940, CI3940 | *Klebsiella variicola* | PTA-126715 | Mar. 25, 2020 |
| ATCC | 137-3938, CI3938 | *Klebsiella variicola* | PTA-126716 | Mar. 25, 2020 |
| ATCC | 137-4874, CI4874 | *Klebsiella variicola* | PTA-126717 | Mar. 25, 2020 |
| ATCC | 6-4065, CI4065 | *Kosakonia sacchari* | PTA-126718 | Mar. 25, 2020 |
| ATCC | 910-4875, CI4875 | *Metakosakonia intestini* | PTA-126719 | Mar. 25, 2020 |
| ATCC | 910-4876, CI4876 | *Metakosakonia intestini* | PTA-126720 | Mar. 25, 2020 |
| ATCC | 910-4877, CI4877 | *Metakosakonia intestini* | PTA-126721 | Mar. 25, 2020 |
| ATCC | 910-4878, CI4878 | *Metakosakonia intestini* | PTA-126722 | Mar. 25, 2020 |
| ATCC | 8-4751, CI4751 | *Paraburkholderia tropica* | PTA-126723 | Mar. 25, 2020 |
| ATCC | 8-4753, CI4753 | *Paraburkholderia tropica* | PTA-126724 | Mar. 25, 2020 |
| ATCC | 8-4879, CI4879 | *Paraburkholderia tropica* | PTA-126725 | Mar. 25, 2020 |
| ATCC | 8-4752, CI4752 | *Paraburkholderia tropica* | PTA-126726 | Mar. 25, 2020 |
| NCMA | CI137, 137, PB137 | *Klebsiella variicola* (WT) | 201708001 | Aug. 11, 2017 |

Random Mutagenesis

The present disclosure relates to methods of exposing a microbe or a population of microbes to a mutagen in order to randomly mutagenize the genomic and extragenomic DNA such that the DNA of the microbes accumulate one or more mutations. The goal is to expose the microbes to the mutagen at a dose high enough to cause genetic mutations, but also at a dose low enough not to cause too many genetic mutations that are deleterious. In some aspects, the one or more mutations result in a stop codon.

In some aspects, a population of microbes comprises microbes of the same genus or species. In some aspects, a population of bacteria comprises one or more different genera or species of microbes. In some aspects, a population of microbes comprises at least $10^{18}$, $10^{17}$, $10^{16}$, $10^{15}$, $10^{14}$, $10^{13}$, $10^{12}$, $10^{11}$, $10^{10}$, $10^{9}$, $10^{8}$, $10^{7}$, $10^{6}$, $10^{5}$, $10^{4}$, $10^{3}$, or $10^{2}$ microbial cells.

In some aspects, the population of microbes occurs on solid media. In some aspects, the population of microbes occurs in liquid media. In some aspects, the population of microbes occurs in semi-solid media.

In some aspects, the population of microbes are exposed to one or more mutagens. In some aspects, the population of microbes are exposed to one or more mutagens for a period of time sufficient to cause at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33 at least 34, or at least 35 mutations relative to the parent microbe.

In some aspects, a nucleotide sequence in the one or more microbes is inactivated. In some aspects, the nucleotide sequence is a coding region for a protein. In some aspects, the nucleotide sequence is a leader sequence, a signal peptide sequence. In some aspects, the nucleotide sequence is a regulatory or control sequence. In some aspects, the regulatory or control sequence is selected from a promoter, a terminator, an operator, a repressor, an activator, a trans-acting element, or a cis-acting element.

In some embodiments, the random mutagenesis is selected from chemical mutagenesis, and ultraviolet mutagenesis. In some aspects, chemical mutagens are selected from mitomycin C (MMC), N-methyl-N-nitrosourea (MNU), nitrous acid (NA), diepoxybutane (DEB), 1, 2, 7, 8-diepoxyoctane (DEO), ethyl methane sulfonate (EMS), methyl methane sulfonate (MMS), N-methyl-N'-nitro-N-nitrosoguanidine (MNNG), 4-nitroquinoline 1-oxide (4-NQO), 2-methyloxy-6-chloro-9(3-[ethyl-2-chloroethyl]-aminopropylamin)-acridinedihydrochloride (ICR-170), 2-amino purine (2AP), and hydroxylamine (HA). In some aspects, EMS is selected. In some aspects, one or more chemical mutagen is selected.

In some aspects, the mutagen is applied to a population of microbes. In some aspects, the mutagen is applied to the media and the microbes are incubated under suitable conditions for growth. In some aspects, the microbes are washed one or more times to remove remaining traces of the mutagen. In some aspects, the resulting mutagenized cells are a mutant library that are capable of being screened for any number of phenotypic changes.

In some aspects, the concentration of the chemical mutagen applied to the population of microbes is 0.05%, 0.1%, 0.15%, 0.2%, 0.25%, 0.3%, 0.35%, 0.4%, 0.45%, 0.5%, 0.55%, 0.6%, 0.65%, 0.7%, 0.8%, 0.85%, 0.9%, 0.95%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.5%, 16%, 16.5%, 17%, 17.5%, 18%, 18.5%, 19%, 19.5%, or 20%.

In some aspects, the concentration of the chemical mutagen applied to the population of microbes is about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.8%, about 0.85%, about 0.9%, about 0.95%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, about 5%, about 5.25%, about 5.5%, about 5.75%, about 6%, about 6.25%, about 6.5%, about 6.75%, about 7%, about 7.25%, about 7.5%, about 7.75%, about 8%, about 8.25%, about 8.5%, about 8.75%, about 9%, about 9.25%, about 9.5%, about 9.75%, about 10%, about 10.25%, about 10.5%, about 10.75%, about 11%, about 11.25%, about 11.5%, about 11.75%, about 12%, about 12.25%, about 12.5%, about 12.75%, about 13%, about 13.25%, about 13.5%, about 13.75%, about 14%, about 14.25%, about 14.5%, about 14.75%, about 15%, about 15.5%, about 16%, about 16.5%, about 17%, about 17.5%, about 18%, about 18.5%, about 19%, about 19.5%, or about 20%.

In some aspects, mutagenesis libraries can be optimized by selecting for the ability to grow on an ammonium analog such as ethylenediamine (EDA) and methylammonium, which would inhibit growth in microbes that are otherwise not capable of fixing nitrogen while in the presence of an exogenous nitrogen source. Given that nitrogen fixation of diazotrophs is repressed in the presence of fixed nitrogen, ammonium assimilation by glutamine synthetase (GlnA) can be inhibited by the binding of an ammonium analog such as ethylenediamine (EDA) and methylammonium to the ammonium-binding site of GlnA. Thus, diazotrophy of microbes that possess a nitrogen fixing gene cluster can be selectively evolved while ammonium assimilation of the microbes is inhibited by EDA or methylammonium. In some embodiments, the use of EDA or methylammonium as a negative selection pressure provides for the ability to identify mutants capable of growing and thriving under what would otherwise be an inhibition in the presence of EDA, overcoming nitrogenase repression by fixed nitrogen in fertilizers and the like.

In some aspects, the selection pressure by EDA or methylammonium comprises culturing the microbes in the presence of a first EDA or methylammonium concentration, followed by culturing the microbes in the presence of a second EDA or methylammonium concentration. In some aspects, the selection pressure by EDA or methylammonium further comprises culturing the microbes in the presence of a third EDA or methylammonium concentration. In some aspects, the selection pressure by EDA or methylammonium further comprises culturing the microbes in the presence of a fourth EDA or methylammonium concentration.

In some aspects, the first EDA or methylammonium concentration is the lowest concentration. In some aspects, the second EDA or methylammonium concentration is higher than the first EDA or methylammonium concentration. In some aspects, the third EDA or methylammonium concentration is higher than the first and second EDA or methylammonium concentrations. In some aspects, the fourth EDA or methylammonium concentration is higher than the first, second, and third EDA or methylammonium concentrations.

In some aspects, the EDA concentration is 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.55%, 0.6%, 0.65%, 0.7%, 0.75%, 0.8%, 0.85%, 0.9%, 0.95%, 1%, 1.1%, 1.2%, 1.3%, 1.4%, 1.5%, 1.6%, 1.7%, 1.8%, or 1.9%.

In some aspects, the EDA concentration is about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.4%, about 0.41%, about 0.42%, about 0.43%, about 0.44%, about 0.45%, about 0.46%, about 0.47%, about 0.48%, about 0.49%, about 0.5%, about 0.55%, about 0.6%, about 0.65%, about 0.7%, about 0.75%, about 0.8%, about 0.85%, about 0.9%, about 0.95%, about 1%, about 1.1%, about 1.2%, about 1.3%, about 1.4%, about 1.5%, about 1.6%, about 1.7%, about 1.8%, or about 1.9%.

In some embodiments, the methylammonium concentration is 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, or 200 mM.

In some embodiments, the methylammonium concentration is about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, 80 about mM, 85 about mM, 90 about mM, 95 about mM, 100 about mM, 110 about mM, 120 about mM, 130 about mM, 140 about mM, 150 about mM, 160 about mM, 170 about mM, 180 about mM, 190 about mM, or 200 about mM.

In some embodiments, the mutagenesis methods are combined with EDA or methylammonium selection to further weed out a mutant library for false positives.

In one aspect, provided herein is a composition comprising one or more bacteria comprising at least one genetic variation in at least one gene, or non-coding polynucleotide, of the nitrogen fixation or assimilation genetic regulatory network. It should be recognized that the mutations can be made using the methods (e.g., random mutagenesis) provided herein or can be introduced, through the use of genetic engineering methods, or other methods known in the art.

The composition can further comprise an agriculturally acceptable carrier. The agriculturally acceptable carrier can be any carrier known in the art.

In some aspects, one or more of the bacteria herein comprises at least one genetic variation in a member selected from the group consisting of: nifA, nifL, ntrB, ntrC, polynucleotide encoding glutamine synthetase, GlnA, GlnB, GlnK, Drat, AmtB, polynucleotide encoding glutaminase, GlnD, FlnE, NifJ, NifH, NifD, NifK, NifY, NifE, NifN, NifU, NifS, NifV, NifW, NifZ, NifM, NifF, NifB, NifQ, a gene associated with biosynthesis of a nitrogenase enzyme, or combinations thereof.

In some aspects, one or more of the bacteria comprises at least one genetic variation in at least one gene, or non-coding polynucleotide, of the nitrogen fixation or assimilation genetic regulatory network that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased uridylyl-removing activity of GlnD.

In some aspects, one or more of the bacteria are selected from the bacterial strains listed in Table 6.

In some aspects, one or more of the bacteria fix atmospheric nitrogen at a rate higher than a wild-type parental lineage bacteria.

In some aspects, one or more of the bacteria are selected from: *Klebsiella variicola* CI3296, *Klebsiella variicola* CI3936, *Klebsiella variicola* CI3933, *Klebsiella variicola* CI3927, *Klebsiella variicola* CI3925, *Klebsiella variicola* CI3943, *Klebsiella variicola* CI3940, *Klebsiella variicola* CI3938. *Klebsiella variicola* CI4874. *Kosakonia sacchari* CI4065, *Metakosakonia intestini* CI4875, *Metakosakonia intestini* CI4876, *Metakosakonia intestini* CI4877, *Metakosakonia intestini* CI4878, *Paraburkholderia tropica* CI4751, *Paraburkholderia tropica* CI4753, *Paraburkholderia tropica* CI4879 and *Paraburkholderia tropica* CI4752. The one or more bacteria can be genetically engineered. The one or more bacteria can be part of a composition as provided herein. The composition can comprise an agriculturally acceptable carrier as provided herein.

In some aspects, one or more of the bacteria are selected from: a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof. The one or more bacteria can be genetically engineered. The one or more bacteria can be part of a composition as provided herein. The composition can comprise an agriculturally acceptable carrier as provided herein.

In some aspects, one or more of the bacteria comprise at least one genetic variation in glnA. The one or more bacteria can be genetically engineered. The at least one genetic variation can be introduced via random mutagenesis as described herein. The one or more bacteria can be part of a composition as provided herein. The composition can comprise an agriculturally acceptable carrier as provided herein.

In some cases, the one or more bacteria can comprise a mutant glnA gene comprising at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof. In some cases, the mutant glnA gene can share at least 85%, 86%, 87%, 88%, 89%, 90%, 91%, 92%, 93%, 94%, 95%, 96%, 97%, 98%, or 99% identity with the *Klebsiella* glnA gene or the homolog thereof. In some cases, outside of the at least nucleotide substitution, the remainder of the mutant glnA gene can share at least 85%, 86%, 87%, 88%, 89%, 90%, 91%, 92%, 93%, 94%, 95%, 96%, 97%, 98%, 99% or 100% identity with the *Klebsiella* glnA gene or the homolog thereof. In one embodiment, the *Klebsiella* glnA gene comprises a nucleic acid sequence of SEQ ID NO: 1. In some cases, the homolog of the *Klebsiella* glnA gene is a *Kosakonia* glnA gene. In some cases, the homolog of the *Klebsiella* glnA gene comprises a nucleic acid sequence of SEQ ID NO: 2. In some cases, the homolog of the *Klebsiella* glnA gene is a *Metakosakonia* glnA gene. In some cases, the homolog of the *Klebsiella* glnA gene comprises a nucleic acid sequence of SEQ ID NO: 3. In one embodiment, the mutant glnA gene comprising at least one genetic variation or mutation comprises a nucleic acid sequence selected from the group consisting of SEQ ID NOs 6-13 and 15-19.

In some cases, the one or more bacteria can comprise a mutant glnA gene comprising at least one nucleotide substitution at nucleotide position 308, 487, 511 and/or 657 of a *Paraburkholderia* glnA gene or in a homologous nucleotide position in a homolog thereof. In some cases, the mutant glnA gene can share at least 85%, 86%, 87%, 88%, 89%, 90%, 91%, 92%, 93%, 94%, 95%, 96%, 97%, 98%, or 99% identity with the *Paraburkholderia* glnA gene or the homolog thereof. In some cases, outside of the at least nucleotide substitution, the remainder of the mutant glnA gene can share at least 85%, 86%, 87%, 88%, 89%, 90%, 91%, 92%, 93%, 94%, 95%, 96%, 97%, 98%, 99% or 100% identity with the *Paraburkholderia* glnA gene or the homolog thereof. In one embodiment, the *Paraburkholderia* glnA gene comprises a nucleic acid sequence of SEQ ID NO: 4. In one embodiment, the mutant glnA gene comprising at least one genetic variation or mutation comprises a nucleic acid sequence selected from the group consisting of SEQ ID NOs 20-23.

In one embodiment, expression of a glnA gene comprising at least one genetic variation or mutation provided herein encodes a GlnA protein with at least one amino acid substitution at amino acid position 66, 157, 172, 174, 189, 208, 218, 255, 268, 329 and/or 339 of a *Klebsiella* GlnA protein or at a homologous amino acid position in a homolog thereof. In one embodiment, expression of a glnA gene comprising at least one genetic variation or mutation provided herein produces a GlnA protein with at least one amino acid substitution selected from the group consisting of M66I, M66V, G157C, H172L, P174L, S189F, E208K, G218S, T255I, G268S, A329V and N339D of a *Klebsiella* GlnA protein and identical amino acid substitutions at homologous amino acid positions in a homolog thereof. In some cases, the GlnA protein encoded by a glnA gene comprising at least one genetic variation or mutation herein shares at least 90%, 91%, 92%, 93%, 94%, 95%, 96%, 97%, 98%, or 99% identity with the *Klebsiella* GlnA protein or the homolog thereof. In some cases, the remainder of the GlnA protein not including the at least one amino acid substitution that is encoded by a glnA gene comprising at least one genetic variation or mutation provided herein shares at least 90%, 91%, 92%, 93%, 94%, 95%, 96%, 97%, 98%, 99 0/or 100% identity with the *Klebsiella* GlnA protein or the homolog thereof. The *Klebsiella* GlnA protein can comprise an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In one embodiment, a GlnA protein encoded by a glnA gene comprising at least one genetic variation or mutation provided herein comprises an amino acid sequence selected from the group consisting of SEQ ID NOs 29-36 and 38-42.

In one embodiment, expression of a glnA gene comprising at least one genetic variation or provided herein encodes a GlnA protein with at least one amino acid substitution at amino acid position 103, 163, 171 and/or 219 of a *Parabur-*

*kholderia* GlnA protein or at a homologous amino acid position in a homolog thereof. In one embodiment, expression of a glnA gene comprising at least one genetic variation or mutation provided herein produces a GlnA protein with at least one amino acid substitution selected from the group consisting of Y103C, S163P, N171D and Q219H of a *Paraburkholderia* GlnA protein and identical amino acid substitutions in homologous amino acid positions in a homolog thereof. In some cases, the GlnA protein encoded by a glnA gene comprising at least one genetic variation or mutation shares at least 90%, 91%, 92%, 93%, 94%, 95%, 96%, 97%, 98%, or 99% identity with the *Paraburkholderia* GlnA protein or the homolog thereof. In some cases, the remainder of the GlnA protein not including the at least one amino acid substitution that is encoded by a glnA gene comprising at least one genetic variation or mutation shares at least 90%, 91%, 92%, 93%, 94%, 95%, 96%, 97%, 98%, 99% or 100% identity with the *Paraburkholderia* GlnA protein or the homolog thereof. The *Paraburkholderia* GlnA protein can comprise an amino acid sequence of SEQ ID NO: 27. In one embodiment, a GlnA protein encoded by a glnA gene comprising at least one genetic variation or mutation provided herein comprises an amino acid sequence selected from the group consisting of SEQ ID NOs 43-46.

In some aspects, the one or more bacteria comprise a mutant GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof. In some aspects, the one or more bacteria comprise a mutant GlnA protein comprising an amino acid sequence with at least one amino acid substitution selected from the group consisting of M66I, M66V, G157C, H172L, P174L, S189F, E208K, G218S, T255I, G268S, A329V and N339D of a *Klebsiella* GlnA protein and identical amino acid substitution at homologous amino acid positions in a homolog thereof. In some cases, the mutant GlnA protein shares at least 90%, 91%, 92%, 93%, 94%, 95%, 96%, 97%, 98%, or 99% identity with the *Klebsiella* GlnA protein or the homolog thereof. In some cases, the mutant GlnA protein shares at least 90%, 91%, 92%, 93%, 94%, 95%, 96%, 97%, 98%, 99% or 100% identity with the *Klebsiella* GlnA protein or the homolog thereof outside of the at least one amino acid substitution. The *Klebsiella* GlnA protein can comprise an amino acid sequence of SEQ ID NO: 24. In some cases, the homolog of the *Klebsiella* GlnA protein is a *Kosakonia* GlnA protein. In some cases, the homolog of the *Klebsiella* GlnA protein comprises an amino acid sequence of SEQ ID NO: 25. In some cases, the homolog of the *Klebsiella* GlnA protein is a *Metakosakonia* GlnA protein. In some cases, the homolog of the *Klebsiella* GlnA protein comprises an amino acid sequence of SEQ ID NO: 26. In one embodiment, the mutant GlnA protein comprises an amino acid sequence selected from the group consisting of SEQ ID NOs 29-36 and 38-42.

In some aspects, the one or more bacteria comprise a mutant GlnA protein comprising an amino acid sequence with at least one amino acid substitution at amino acid positions 103, 163, 171 and/or 219 of a *Paraburkholderia* GlnA protein or at a homologous amino acid position in a homolog thereof. In some aspects, the one or more bacteria comprise a mutant GlnA protein comprising an amino acid sequence with at least one amino acid substitution selected from the group consisting of Y103C, S163P, N171D and Q219H of a *Paraburkholderia* GlnA protein or at a homologous amino acid position in a homolog thereof. In some cases, the mutant GlnA protein shares at least 90%, 91%, 92%, 93%, 94%, 95%, 96%, 97%, 98%, or 990% identity with the *Paraburkholderia* GlnA protein or the homolog thereof. In some cases, the mutant GlnA protein shares at least 90%, 91%, 92%, 93%, 94%, 95%, 96%, 97%, 98%, 99% or 100% identity with the *Paraburkholderia* GlnA protein or the homolog thereof outside of the at least one amino acid substitution. The *Paraburkholderia* GlnA protein can comprise an amino acid sequence of SEQ ID NO: 27. In one embodiment, the mutant GlnA protein comprises an amino acid sequence selected from the group consisting of SEQ ID NOs 43-46.

In some aspects, the one or more bacteria comprise at least one genetic variation in glnE. The one or more bacteria can comprise a mutant glnE gene comprising at least one nucleotide substitution at nucleotide position 965 and/or 2838 of a *Klebsiella* glnE gene or at a homologous nucleotide position in a homolog thereof. The one or more bacteria can comprise a mutant glnE gene that comprises a nucleotide substitution at nucleotide position 965 and 2838 of a *Klebsiella* glnE gene or in homologous nucleotide positions in the homolog thereof. In some cases, the mutant glnE gene can share at least 85%, 86%, 87%, 88%, 89%, 90%, 91%, 92%, 93%, 94%, 95%, 96%, 97%, 98%, or 99% identity with the *Klebsiella* glnE gene or the homolog thereof. In some cases, outside of the at least nucleotide substitution, the remainder of the mutant glnE gene can share at least 85%, 86%, 87%, 88%, 89%, 90%, 91%, 92%, 93%, 94%, 95%, 96%, 97%, 98%, 99% or 100% identity with the *Klebsiella* glnE gene or the homolog thereof. In one embodiment, the *Klebsiella* glnE gene comprises a nucleic acid sequence of SEQ ID NO: 5. In one embodiment, the mutant glnE gene comprising at least one genetic variation or mutation comprises a nucleic acid sequence of SEQ ID NO: 14.

In one embodiment, expression of a glnE gene comprising at least one genetic variation or mutation encodes a GlnE protein with at least one amino acid substitution at amino acid position 322 and/or 746 of a *Klebsiella* GlnE protein or at a homologous amino acid position in a homolog thereof. In another embodiment, expression of a glnE gene comprising at least one genetic variation or mutation produces a mutant GlnE protein with amino acid substitutions at amino acid positions 322 and 746 of the *Klebsiella* GlnE protein or at homologous amino acid positions in the homolog thereof. The amino acid substitution at position 322 or the homologous amino acid position can be a G to E substitution. The amino acid substitution at position 746 or the homologous amino acid position can be a G to D substitution. In some cases, the GlnE protein encoded by a glnE gene comprising at least one genetic variation or mutation shares at least 90%, 91%, 92%, 93%, 94%, 95%, 96%, 97%, 98%, or 99% identity with the *Klebsiella* GlnE protein or the homolog thereof. In some cases, the remainder of the GlnE protein not including the at least one amino acid substitution that is encoded by a glnE gene comprising at least one genetic variation or mutation shares at least 90%, 91%, 92%, 93%, 94%, 95%, 96%, 97%, 98%, 99% or 100% identity with the *Klebsiella* GlnE protein or the homolog thereof. The *Klebsiella* GlnE protein can comprise an amino acid sequence of SEQ ID NO: 28. In one embodiment, a mutant GlnE protein encoded by a glnE gene comprising at least one genetic variation or mutation comprises an amino acid sequence of SEQ ID NO: 37.

In some aspects, the one or more bacteria comprise a mutant GlnE protein comprising an amino acid sequence with at least one amino acid substitution at amino acid positions 322 and/or 746 of a *Klebsiella* GlnE protein or at a homologous amino acid position in a homolog thereof. In other aspects, the one or more bacteria comprise a mutant GlnE protein comprising amino acid substitutions at amino acid positions 322 and 746 of a *Klebsiella* GlnE protein or at homologous amino acid positions in the homolog thereof. In some cases, the amino acid substitution at position 322 or the homologous amino acid position is a G to E substitution. In some cases, the amino acid substitution at position 746 or the homologous amino acid position is a G to D substitution. In some cases, the mutant GlnE protein shares at least 90%, 91%, 92%, 93%, 94%, 95%, 96%, 97%, 98%, or 99% identity with the *Klebsiella* GlnE protein or the homolog thereof. In some cases, the mutant GlnE protein shares at least 90%, 91%, 92%, 93%, 94%, 95%, 96%, 97%, 98%, 99% or 100%6 identity with the *Klebsiella* GlnE protein or the homolog thereof outside of the at least one amino acid substitution. The *Klebsiella* GlnE protein can comprise an amino acid sequence of SEQ ID NO: 28. In one embodiment, the mutant GlnE protein comprises an amino acid sequence of SEQ ID NO: 37.

It would be recognized by those of skill in the art, that nucleotide and protein sequence homologs may be of the same length or may contain insertions and/or deletions. In some cases, the homologous nucleotide and/or amino acid position in a homolog is identical to the nucleotide or amino acid position in a base sequence. In other cases, the homologous nucleotide and/or amino acid position in a homolog is a different nucleotide or amino acid position than in the base sequence. The homologous nucleotide or amino acid position in the homolog (the position in the homolog at which a substitution would occur based upon a substitution position disclosed herein) can be identified by aligning the homolog to a base sequence with a substitution disclosed herein and identifying the position of the nucleotide or the amino acid in the homolog that aligns with the position of the nucleotide or the amino acid in the base sequence that contains a substitution as disclosed herein. Such sequence alignment can be carried out by methods known to those of skill in the art.

Applications

Methods of the present disclosure utilizing strains identified herein may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions.

A preferred trait to be introduced or improved is nitrogen fixation, as described herein. In some cases, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil.

In additional examples, a plant resulting from the methods described herein exhibits a difference in the trait that is at least about 5% greater, for example at least about 5%, at least about 8%, at least about 10%, at least about 15%, at least about 20%, at least about 25%, at least about 300, at least about 40%, at least about 50%, at least about 60%, at least about 75%, at least about 80%, at least about 80%, at least about 900, or at least 100%, at least about 200%, at least about 300%, at least about 400% or greater than a reference agricultural plant grown under similar conditions in the soil.

The trait to be improved utilizing microbial strains identified herein may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and compositions utilizing microbial strains identified herein may be nitrogen fixation, including in a plant not previously capable of nitrogen fixation. In some cases, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from a plant before introducing any genetic variation. In some cases, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some cases, enhanced levels of nitrogen fixation are achieved in the presence of fertilizer supplemented with glutamine, ammonia, or other chemical source of nitrogen. Methods for assessing degree of nitrogen fixation are known, examples of which are described herein.

Measuring Nitrogen Delivered in an Agriculturally Relevant Field Context

In the field, the amount of nitrogen delivered can be determined by the function of colonization multiplied by the activity.

$$\text{Nitrogen delivered} = \int_{Time\ \&\ Space} \text{Colonization} \times \text{Activity}$$

The above equation requires (1) the average colonization per unit of plant tissue, and (2) the activity as either the amount of nitrogen fixed or the amount of ammonia excreted by each microbial cell. To convert to pounds of nitrogen per acre, corn growth physiology is tracked over time, e.g., size of the plant and associated root system throughout the maturity stages.

The pounds of nitrogen delivered to a crop per acre-season can be calculated by the following equation:

$$\text{Nitrogen delivered} = \int [\text{Plant Tissue}(t) \times \text{Colonization}(t) \times \text{Activity}(t)] dt$$

The Plant Tissue(t) is the fresh weight of corn plant tissue over the growing time (t). Values for reasonably making the calculation are described in detail in the publication entitled Roots, Growth and Nutrient Uptake (Mengel. Dept. of Agronomy Pub. #AGRY-95-08 (Rev. May-95. p. 1-8).

The Colonization (t) is the amount of the microbes of interest found within the plant tissue, per gram fresh weight of plant tissue, at any particular time, t, during the growing season. In the instance of only a single timepoint available, the single timepoint is normalized as the peak colonization rate over the season, and the colonization rate of the remaining timepoints are adjusted accordingly.

Activity(t) is the rate of which N is fixed by the microbes of interest per unit time, at any particular time, t, during the growing season. In the embodiments disclosed herein, this activity rate is approximated by in vitro acetylene reduction assay (ARA) in ARA media in the presence of 5 mM glutamine or Ammonium excretion assay in ARA media in the presence of 5 mM ammonium ions.

The Nitrogen delivered amount is then calculated by numerically integrating the above function. In cases where the values of the variables described above are discretely measured at set timepoints, the values in between those timepoints are approximated by performing linear interpolation.

Nitrogen Fixation

Described herein are methods of increasing nitrogen fixation in a plant, comprising exposing the plant to one or more bacteria described herein, including through the application of compositions comprising the bacteria, as described herein. It should be understood that the bacteria may be generated and/or identified using the methods and compositions provided herein (e.g., through the use of a biosensor as provided herein) or through other methods known in the art. These bacteria comprise one or more genetic variations in one or more genes regulating nitrogen fixation, wherein the bacteria produce 1% or more (e.g. 2%, 3%, 4%, 5%, 6%, 7%, 8%, 9%, 10%, 15%, 20%, or more) of nitrogen in the plant, which may represent a nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to the plant in the absence of the bacteria. The bacteria may produce the nitrogen in the presence of fertilizer supplemented with glutamine, urea, nitrates or ammonia. Genetic variations can be any genetic variation described herein, including examples provided herein, in any number and any combination.

The amount of nitrogen fixation that occurs in the plants described herein may be measured in several ways, for example by an acetylene-reduction (AR) assay. An acetylene-reduction assay can be performed in vitro or in vivo. Evidence that a particular bacterium is providing fixed nitrogen to a plant can include: 1) total plant N significantly increases upon inoculation, preferably with a concomitant increase in N concentration in the plant; 2) nitrogen deficiency symptoms are relieved under N-limiting conditions upon inoculation (which should include an increase in dry matter); 3) $N_2$ fixation is documented through the use of an $^{15}N$ approach (which can be isotope dilution experiments, $^{15}N_2$ reduction assays, or $^{15}N$ natural abundance assays); 4) fixed N is incorporated into a plant protein or metabolite; and 5) all of these effects are not be seen in non-inoculated plants or in plants inoculated with a mutant of the inoculum strain.

Agricultural Compositions

Compositions comprising bacteria or bacterial populations described herein can be in the form of a liquid, a foam, or a dry product. Compositions comprising bacteria or bacterial populations described herein may also be used to improve plant traits. Compositions comprising bacteria or bacterial populations can comprise engineered or randomly mutagenized microbes that comprise one or any combination of genetic variations in a glnA gene and/or glnE gene as provided herein. Any composition provided herein comprising one or more strains of microbes as provided herein can further comprise one or more strains from Table 6 as provided herein.

In some examples, a composition comprising bacterial populations may be in the form of a dry powder, a slurry of powder and water, or a flowable seed treatment. The compositions comprising bacterial populations may be coated on a surface of a seed, and may be in liquid form.

The composition can be fabricated in bioreactors such as continuous stirred tank reactors, batch reactors, and on the farm. In some examples, compositions can be stored in a container, such as a jug or in mini bulk. In some examples, compositions may be stored within an object selected from the group consisting of a bottle, jar, ampule, package, vessel, bag, box, bin, envelope, carton, container, silo, shipping container, truck bed, and/or case.

Compositions may also be used to improve plant traits. In some examples, one or more compositions may be coated onto a seed. In some examples, one or more compositions may be coated onto a seedling. In some examples, one or more compositions may be coated onto a surface of a seed. In some examples, one or more compositions may be coated as a layer above a surface of a seed. In some examples, a composition that is coated onto a seed may be in liquid form, in dry product form, in foam form, in a form of a slurry of powder and water, or in a flowable seed treatment. In some examples, one or more compositions may be applied to a seed and/or seedling by spraying, immersing, coating, encapsulating, and/or dusting the seed and/or seedling with the one or more compositions. In some examples, multiple bacteria or bacterial populations can be coated onto a seed and/or a seedling of the plant. In some examples, at least two, at least three, at least four, at least five, at least six, at least seven, at least eight, at least nine, at least ten, or more than ten bacteria of a bacterial combination can be selected from the strains of bacteria found in Table 6.

Examples of compositions may include seed coatings for commercially important agricultural crops, for example, *sorghum*, canola, tomato, strawberry, barley, rice, maize, and wheat. Examples of compositions can also include seed coatings for corn, soybean, canola, *sorghum*, potato, rice, vegetables, cereals, and oilseeds. Seeds as provided herein can be genetically modified organisms (GMO), non-GMO, organic, or conventional. In some examples, compositions may be sprayed on the plant aerial parts, or applied to the roots by inserting into furrows in which the plant seeds are planted, watering to the soil, or dipping the roots in a suspension of the composition. In some examples, compositions may be dehydrated in a suitable manner that maintains cell viability and the ability to artificially inoculate and colonize host plants. The bacterial species may be present in compositions at a concentration of between $10^8$ to $10^{10}$ CFU/ml. In some examples, compositions may be supplemented with trace metal ions, such as molybdenum ions, iron ions, manganese ions, or combinations of these ions. The concentration of ions in examples of compositions as described herein may between about 0.1 mM and about 50 mM. Some examples of compositions may also be formulated with a carrier, such as beta-glucan, carboxylmethyl cellulose (CMC), bacterial extracellular polymeric substance (EPS), sugar, animal milk, or other suitable carriers. In some examples, peat or planting materials can be used as a carrier, or biopolymers in which a composition is entrapped in the biopolymer can be used as a carrier. The compositions comprising the bacterial populations described herein can improve plant traits, such as promoting plant growth, maintaining high chlorophyll content in leaves, increasing fruit or seed numbers, and increasing fruit or seed unit weight.

The compositions comprising the bacterial populations described herein may be coated onto the surface of a seed. As such, compositions comprising a seed coated with one or more bacteria described herein are also contemplated. The seed coating can be formed by mixing the bacterial population with a porous, chemically inert granular carrier. Alternatively, the compositions may be inserted directly into the furrows into which the seed is planted or sprayed onto the plant leaves or applied by dipping the roots into a suspension of the composition. An effective amount of the composition can be used to populate the sub-soil region adjacent to the roots of the plant with viable bacterial growth, or populate the leaves of the plant with viable bacterial growth. In general, an effective amount is an amount sufficient to result in plants with improved traits (e.g. a desired level of nitrogen fixation).

Bacterial compositions described herein can be formulated using an agriculturally acceptable carrier. The formulation useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a dessicant, a bactericide, a nutrient, a hormone, or any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, bacteria are mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, and the like, micro-encapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, NH4H2PO4, (NH4) 2SO4, glycerol, valine, L-leucine, lactic acid, propionic acid, succinic acid, malic acid, citric acid, KH tartrate, xylose, lyxose, and lecithin. In one embodiment, the formulation can include a tackifier or adherent (referred to as an adhesive agent) to help bind other active agents to a substance (e.g., a surface of a seed). Such agents are useful for combining bacteria with carriers that can contain other compounds (e.g., control agents that are not biologic), to yield a coating composition. Such compositions help create coatings around the plant or seed to maintain contact between the microbe and other agents with the plant or plant part. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some examples, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The formulation can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II™ (adjuvant; AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic® (nonionic organosilicone spray adjuvant; Helena), Sylgard® 309 (nonionic silicone polyether surfactant; Wilbur-Ellis) and Century (Precision). In one embodiment, the surfactant is present at a concentration of between 0.01% v/v to 10%/o v/v. In another embodiment, the surfactant is present at a concentration of between 0.1% v/v to 1% v/v.

In certain cases, the formulation includes a microbial stabilizer. Such an agent can include a desiccant, which can include any compound or mixture of compounds that can be classified as a desiccant regardless of whether the compound or compounds are used in such concentrations that they in fact have a desiccating effect on a liquid inoculant. Such desiccants are ideally compatible with the bacterial population used, and should promote the ability of the microbial population to survive application on the seeds and to survive desiccation. Examples of suitable desiccants include one or more of trehalose, sucrose, glycerol, and Methylene glycol. Other suitable desiccants include, but are not limited to, non reducing sugars and sugar alcohols (e.g., mannitol or sorbitol). The amount of desiccant introduced into the formulation can range from about 5% to about 50% by weight/ volume, for example, between about 10% to about 40%, between about 15% to about 35%, or between about 20% to about 30%. In some cases, it is advantageous for the formulation to contain agents such as a fungicide, an antibacterial agent, an herbicide, a nematicide, an insecticide, a plant growth regulator, a rodenticide, bactericide, or a nutrient. In some examples, agents may include protectants that provide protection against seed surface-borne pathogens. In some examples, protectants may provide some level of control of soil-borne pathogens. In some examples, protectants may be effective predominantly on a seed surface.

In some examples, a fungicide may include a compound or agent, whether chemical or biological, that can inhibit the growth of a fungus or kill a fungus. In some examples, a fungicide may include compounds that may be fungistatic or fungicidal. In some examples, fungicide can be a protectant, or agents that are effective predominantly on the seed surface, providing protection against seed surface-borne pathogens and providing some level of control of soil-borne pathogens. Non-limiting examples of protectant fungicides include captan, maneb, thiram, or fludioxonil.

In some examples, fungicide can be a systemic fungicide, which can be absorbed into the emerging seedling and inhibit or kill the fungus inside host plant tissues. Systemic fungicides used for seed treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some examples, fungicide can be a biological control agent, such as a bacterium or fungus. Such organisms may be parasitic to the pathogenic fungi, or secrete toxins or other substances that can kill or otherwise prevent the growth of fungi. Any type of fungicide, particularly ones that are commonly used on plants, can be used as a control agent in a seed composition.

In some examples, the seed coating composition comprises a control agent that has antibacterial properties. In one embodiment, the control agent with antibacterial properties is selected from the compounds described herein elsewhere. In another embodiment, the compound is Streptomycin, oxytetracycline, oxolinic acid, or gentamicin. Other examples of antibacterial compounds which can be used as part of a seed coating composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some examples, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-tri-iodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural seed or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.: *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and *Rhizobacteria*. Particularly preferred nematode-antagonistic biocontrol agents include ARF18, *Arthrobotrys oligospora*,

*Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli,* vesicular-arbuscular mycorrhizal fungi, *Burkholderia cepacia, Pasteuria penetrans, Pasteuria thornei, Pasteuria nishizawae, Pasteuria ramosa, Pasteuria usage, Brevibacillus laterosporus* strain G4, *Pseudomonas fluorescens* and *Rhizobacteria*.

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the seed coat composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino)benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In the liquid form, for example, solutions or suspensions, bacterial populations can be mixed or suspended in water or in aqueous solutions. Suitable liquid diluents or carriers include water, aqueous solutions, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

Application of Bacterial Populations on Crops

The composition of the bacteria or bacterial population described herein can be applied in furrow, in talc, or as seed treatment. The composition can be applied to a seed package in bulk, mini bulk, in a bag, or in talc.

The planter can plant the treated seed and grows the crop according to conventional ways, twin row, or ways that do not require tilling. The seeds can be distributed using a control hopper or an individual hopper. Seeds can also be distributed using pressurized air or manually. Seed placement can be performed using variable rate technologies. Additionally, application of the bacteria or bacterial population described herein may be applied using variable rate technologies. In some examples, the bacteria can be applied to seeds of corn, soybean, canola, *sorghum*, potato, rice, vegetables, cereals, pseudocereals, and oilseeds. Examples of cereals may include barley, fonio, oats, palmer's grass, rye, pearl millet, *sorghum*, spelt, teff, triticale, and wheat. Examples of pseudocereals may include breadnut, buckwheat, cattail, chia, flax, grain amaranth, hanza, *quinoa*, and sesame. In some examples, seeds can be genetically modified organisms (GMO), non-GMO, organic or conventional.

Additives such as micro-fertilizer, PGR, herbicide, insecticide, and fungicide can be used additionally to treat the crops. Examples of additives include crop protectants such as insecticides, nematicides, fungicide, enhancement agents such as colorants, polymers, pelleting, priming, and disinfectants, and other agents such as inoculant, PGR, softener, and micronutrients. PGRs can be natural or synthetic plant hormones that affect root growth, flowering, or stem elongation. PGRs can include auxins, gibberellins, cytokinins, ethylene, and abscisic acid (ABA).

The composition can be applied in furrow in combination with liquid fertilizer. In some examples, the liquid fertilizer may be held in tanks. NPK fertilizers contain macronutrients of sodium, phosphorous, and potassium.

The composition, by providing fixed nitrogen, may improve plant traits, such as promoting plant growth, maintaining high chlorophyll content in leaves, increasing fruit or seed numbers, and increasing fruit or seed unit weight. Methods of the present disclosure may be employed to introduce or improve one or more of a variety of desirable traits. Examples of traits that may introduced or improved include: root biomass, root length, height, shoot length, leaf number, water use efficiency, overall biomass, yield, fruit size, grain size, photosynthesis rate, tolerance to drought, heat tolerance, salt tolerance, tolerance to low nitrogen stress, nitrogen use efficiency, resistance to nematode stress, resistance to a fungal pathogen, resistance to a bacterial pathogen, resistance to a viral pathogen, level of a metabolite, modulation in level of a metabolite, proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under identical conditions. In some examples, the desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the introduced and/or improved traits) grown under similar conditions.

An agronomic trait to a host plant may include, but is not limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health e4nhancement, heat tolerance, herbicide tolerance, herbivore resistance improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation.

In some cases, plants are inoculated with bacteria or bacterial populations that are isolated from the same species of plant as the plant element of the inoculated plant. For example, a bacteria or bacterial population that is normally found in one variety of *Zea mays* (corn) is associated with a plant element of a plant of another variety of *Zea mays* that in its natural state lacks said bacteria and bacterial populations. In one embodiment, the bacteria and bacterial populations is derived from a plant of a related species of plant as the plant element of the inoculated plant. For example, an bacteria and bacterial populations that is normally found in *Zea diploperennis* Iltis et al., (diploperennial teosinte) is applied to a *Zea mays* (corn), or vice versa. In some cases, plants are inoculated with bacteria and bacterial populations that are heterologous to the plant element of the inoculated plant. In one embodiment, the bacteria and bacterial populations is derived from a plant of another species. For example, a bacteria and bacterial populations that is normally found in dicots is applied to a monocot plant (e.g., inoculating corn with a soybean-derived bacteria and bacterial populations), or vice versa. In other cases, the bacteria and bacterial populations to be inoculated onto a plant is derived from a related species of the plant that is being inoculated. In one embodiment, the bacteria and bacterial populations is derived from a related taxon, for example, from a related species. The plant of another species can be an agricultural plant. In another embodiment, the bacteria and bacterial populations is part of a designed composition inoculated into any host plant element.

In some examples, the bacteria or bacterial population is exogenous wherein the bacteria and bacterial population is isolated from a different plant than the inoculated plant. For example, in one embodiment, the bacteria or bacterial population can be isolated from a different plant of the same species as the inoculated plant. In some cases, the bacteria or bacterial population can be isolated from a species related to the inoculated plant.

In some examples, the bacteria and bacterial populations described herein are capable of moving from one tissue type to another. For example, the present disclosure's detection and isolation of bacteria and bacterial populations within the mature tissues of plants after coating on the exterior of a seed demonstrates their ability to move from seed exterior into the vegetative tissues of a maturing plant. Therefore, in one embodiment, the population of bacteria and bacterial populations is capable of moving from the seed exterior into the vegetative tissues of a plant. In one embodiment, the bacteria and bacterial populations that is coated onto the seed of a plant is capable, upon germination of the seed into a vegetative state, of localizing to a different tissue of the plant. For example, bacteria and bacterial populations can be capable of localizing to any one of the tissues in the plant, including: the root, adventitious root, seminal 5 root, root hair, shoot, leaf, flower, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In one embodiment, the bacteria and bacterial populations is capable of localizing to the root and/or the root hair of the plant. In another embodiment, the bacteria and bacterial populations is capable of localizing to the photosynthetic tissues, for example, leaves and shoots of the plant. In other cases, the bacteria and bacterial populations is localized to the vascular tissues of the plant, for example, in the xylem and phloem. In still another embodiment, the bacteria and bacterial populations is capable of localizing to the reproductive tissues (flower, pollen, pistil, ovaries, stamen, fruit) of the plant. In another embodiment, the bacteria and bacterial populations is capable of localizing to the root, shoots, leaves and reproductive tissues of the plant. In still another embodiment, the bacteria and bacterial populations colonizes a fruit or seed tissue of the plant. In still another embodiment, the bacteria and bacterial populations is able to colonize the plant such that it is present in the surface of the plant (i.e., its presence is detectably present on the plant exterior, or the episphere of the plant). In still other embodiments, the bacteria and bacterial populations is capable of localizing to substantially all, or all, tissues of the plant. In certain embodiments, the bacteria and bacterial populations is not localized to the root of a plant. In other cases, the bacteria and bacterial populations is not localized to the photosynthetic tissues of the plant.

The effectiveness of the compositions can also be assessed by measuring the relative maturity of the crop or the crop heating unit (CHU). For example, the bacterial population can be applied to corn, and corn growth can be assessed according to the relative maturity of the corn kernel or the time at which the corn kernel is at maximum weight. The crop heating unit (CHU) can also be used to predict the maturation of the corn crop. The CHU determines the amount of heat accumulation by measuring the daily maximum temperatures on crop growth.

In examples, bacterial may localize to any one of the tissues in the plant, including: the root, adventitious root, seminal root, root hair, shoot, leaf, flower, bud tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In another embodiment, the bacteria or bacterial population is capable of localizing to the photosynthetic tissues, for example, leaves and shoots of the plant. In other cases, the bacteria and bacterial populations is localized to the vascular tissues of the plant, for example, in the xylem and phloem. In another embodiment, the bacteria or bacterial population is capable of localizing to reproductive tissues (flower, pollen, pistil, ovaries, stamen, or fruit) of the plant. In another embodiment, the bacteria and bacterial populations is capable of localizing to the root, shoots, leaves and reproductive tissues of the plant.

In another embodiment, the bacteria or bacterial population colonizes a fruit or seed tissue of the plant. In still another embodiment, the bacteria or bacterial population is able to colonize the plant such that it is present in the surface of the plant. In another embodiment, the bacteria or bacterial population is capable of localizing to substantially all, or all, tissues of the plant. In certain embodiments, the bacteria or bacterial population is not localized to the root of a plant. In other cases, the bacteria and bacterial populations is not localized to the photosynthetic tissues of the plant.

The effectiveness of the bacterial compositions applied to crops can be assessed by measuring various features of crop growth including, but not limited to, planting rate, seeding vigor, root strength, drought tolerance, plant height, dry down, and test weight.

Plant Species

The methods and bacteria described herein are suitable for any of a variety of plants, such as plants in the genera *Hordeum*, *Oryza*, *Zea*, and Triticeae. Other non-limiting examples of suitable plants include mosses, lichens, and algae. In some cases, the plants have economic, social and/or environmental value, such as food crops, fiber crops, oil crops, plants in the forestry or pulp and paper industries, feedstock for biofuel production and/or ornamental plants. In some examples, plants may be used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human-food product, a sugar, an alcohol, and/or a protein. Non-limiting examples of crop plants include maize, rice, wheat, barley, *sorghum*, millet, oats, rye triticale, buckwheat, sweet corn, sugar cane, onions, tomatoes, strawberries, and asparagus. In some embodiments, the methods and bacteria described herein are suitable for any of a variety of transgenic plants, non-transgenic plants, and hybrid plants thereof.

In some examples, plants that may be obtained or improved using the methods and composition disclosed herein may include plants that are important or interesting for agriculture, horticulture, biomass for the production of biofuel molecules and other chemicals, and/or forestry. Some examples of these plants may include pineapple, banana, coconut, lily, grasspeas and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum bicolor* (*sorghum*, sudan), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp. *Sorghum* spp., *Miscanthus* spp., *Saccharum* spp., Erianthus spp., *Populus* spp., *Secale cereale* (rye), Salix spp. (willow), *Eucalyptus* spp. (*eucalyptus*), Triticosecale spp. (*triticum*-25 wheat X rye), Bamboo, Carthamus tinctorius (safflower), Jatropha curcas (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassaya), *Lycopersicon esculentum* (tomato), *Lactuca* saliva (lettuce), Musa paradisiaca (banana), *Solanum tuberosum* (potato), *Brassica oleracea* (broccoli, cauliflower, brussel sprouts), *Camellia sinensis* (tea), Fragaria *ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis* saliva, Camptotheca acuminate, Catharanthus *roseus, Vinca rosea, Cinchona officinalis, Coichicum autumnale, Veratrum californica, Digitalis lanata, Digitalis purpurea, Dioscorea* 5 spp., Andrographis *paniculata, Atropa belladonna, Datura stomonium, Berberis* spp., *Cephalotaxus* spp., Ephedra *sinica,* Ephedra spp., *Erythroxylum coca, Galanthus wornorii, Scopolia* spp., Lycopodium *serratum* (Huperzia *serrata*), Lycopodium spp., Rauwolfia *serpentina,* Rauwolfia spp., *Sanguinaria canadensis, Hyoscyamus* spp., *Calendula officinalis, Chrysanthemum parthenium, Coleus forskohlii, Tanacetum parthenium, Parthenium* argentatum (guayule), Hevea spp. (rubber), *Mentha spicata* (mint), *Mentha piperita* (mint), *Bixa orellana,* Alstroemeria spp., Rosa spp. (rose), *Dianthus* caryophyllus (carnation), *Petunia* spp. (*petunia*), Poinsettia *pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some examples, a monocotyledonous plant may be used. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales. In some examples, the monocotyledonous plant can be selected from the group consisting of a maize, rice, wheat, barley, and sugarcane.

In some examples, a dicotyledonous plant may be used, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. In some examples, the dicotyledonous plant can be selected from the group consisting of cotton, soybean, pepper, and tomato.

In some cases, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria,* Brachypodium, and *Arabidopsis.* Ability of bacteria isolated according to a method of the disclosure using a model plant may then be applied to a plant of another type (e.g. a crop plant) to confirm conferral of the improved trait.

Traits that may be improved by the methods disclosed herein include any observable characteristic of the plant, including, for example, growth rate, height, weight, color, taste, smell, changes in the production of one or more compounds by the plant (including for example, metabolites, proteins, drugs, carbohydrates, oils, and any other compounds). Selecting plants based on genotypic information is also envisaged (for example, including the pattern of plant gene expression in response to the bacteria, or identifying the presence of genetic markers, such as those associated with increased nitrogen fixation). Plants may also be selected based on the absence, suppression or inhibition of a certain feature or trait (such as an undesirable feature or trait) as opposed to the presence of a certain feature or trait (such as a desirable feature or trait).

Concentrations and Rates of Application of Agricultural Compositions

As aforementioned, the agricultural compositions of the present disclosure, which comprise a generated and/or identified microbe, can be applied to plants in a multitude of ways. In two particular aspects, the disclosure contemplates an in-furrow treatment or a seed treatment For seed treatment embodiments, the microbes of the disclosure can be present on the seed in a variety of concentrations. For example, the microbes can be found in a seed treatment at a cfu concentration, per seed of: $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, or more. In particular aspects, the seed treatment compositions comprise about $1\times10^4$ to about $1\times10^8$ cfu per seed. In other particular aspects, the seed treatment compositions comprise about $1\times10^5$ to about $1\times10^7$ cfu per seed. In other aspects, the seed treatment compositions comprise about $1\times10^6$ cfu per seed. In general, the one or more bacteria present in an agricultural or microbial composition provided herein can have an average colonization ability per unit of plant root tissue of at least about $1.0\times10^4$ bacterial cells per gram of fresh weight of plant root tissue and can produce fixed N of at least about $1\times10^{-17}$ mmol N per bacterial cell per hour.

In the United States, about 10% of corn acreage is planted at a seed density of above about 36,000 seeds per acre: ⅓ of the corn acreage is planted at a seed density of between about 33,000 to 36,000 seeds per acre; ⅓ of the corn acreage is planted at a seed density of between about 30,000 to 33,000 seeds per acre, and the remainder of the acreage is variable. See, "Corn Seeding Rate Considerations," written by Steve Butzen, available at: www.pioneer.com/home/site/us/agronomy/library/corn-seeding-rate-considerations/

Table 8 below utilizes various cfu concentrations per seed in a contemplated seed treatment embodiment (rows across) and various seed acreage planting densities (1$^{st}$ column: 15K-41K) to calculate the total amount of cfu per acre, which would be utilized in various agricultural scenarios (i.e. seed treatment concentration per seed×seed density planted per acre). Thus, if one were to utilize a seed treatment with $1\times10^6$ cfu per seed and plant 30,000 seeds per acre, then the total cfu content per acre would be $3\times10^{10}$ (i.e. 30K*$1\times10^6$).

TABLE 8

Total CFU Per Acre Calculation for Seed Treatment Embodiments

| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
|---|---|---|---|---|---|---|---|---|
| 15,000 | 1.50E+06 | 1.50E+07 | 1.50E+08 | 1.50E+09 | 1.50E+10 | 1.50E+11 | 1.50E+12 | 1.50E+13 |
| 16,000 | 1.60E+06 | 1.60E+07 | 1.60E+08 | 1.60E+09 | 1.60E+10 | 1.60E+11 | 1.60E+12 | 1.60E+13 |
| 17,000 | 1.70E+06 | 1.70E+07 | 1.70E+08 | 1.70E+09 | 1.70E+10 | 1.70E+11 | 1.70E+12 | 1.70E+13 |
| 18,000 | 1.80E+06 | 1.80E+07 | 1.80E+08 | 1.80E+09 | 1.80E+10 | 1.80E+11 | 1.80E+12 | 1.80E+13 |
| 19,000 | 1.90E+06 | 1.90E+07 | 1.90E+08 | 1.90E+09 | 1.90E+10 | 1.90E+11 | 1.90E+12 | 1.90E+13 |
| 20,000 | 2.00E+06 | 2.00E+07 | 2.00E+08 | 2.00E+09 | 2.00E+10 | 2.00E+11 | 2.00E+12 | 2.00E+13 |
| 21,000 | 2.10E+06 | 2.10E+07 | 2.10E+08 | 2.10E+09 | 2.10E+10 | 2.10E+11 | 2.10E+12 | 2.10E+13 |
| 22,000 | 2.20E+06 | 2.20E+07 | 2.20E+08 | 2.20E+09 | 2.20E+10 | 2.20E+11 | 2.20E+12 | 2.20E+13 |
| 23,000 | 2.30E+06 | 2.30E+07 | 2.30E+08 | 2.30E+09 | 2.30E+10 | 2.30E+11 | 2.30E+12 | 2.30E+13 |
| 24,000 | 2.40E+06 | 2.40E+07 | 2.40E+08 | 2.40E+09 | 2.40E+10 | 2.40E+11 | 2.40E+12 | 2.40E+13 |
| 25,000 | 2.50E+06 | 2.50E+07 | 2.50E+08 | 2.50E+09 | 2.50E+10 | 2.50E+11 | 2.50E+12 | 2.50E+13 |
| 26,000 | 2.60E+06 | 2.60E+07 | 2.60E+08 | 2.60E+09 | 2.60E+10 | 2.60E+11 | 2.60E+12 | 2.60E+13 |
| 27,000 | 2.70E+06 | 2.70E+07 | 2.70E+08 | 2.70E+09 | 2.70E+10 | 2.70E+11 | 2.70E+12 | 2.70E+13 |
| 28,000 | 2.80E+06 | 2.80E+07 | 2.80E+08 | 2.80E+09 | 2.80E+10 | 2.80E+11 | 2.80E+12 | 2.80E+13 |
| 29,000 | 2.90E+06 | 2.90E+07 | 2.90E+08 | 2.90E+09 | 2.90E+10 | 2.90E+11 | 2.90E+12 | 2.90E+13 |
| 30,000 | 3.00E+06 | 3.00E+07 | 3.00E+08 | 3.00E+09 | 3.00E+10 | 3.00E+11 | 3.00E+12 | 3.00E+13 |
| 31,000 | 3.10E+06 | 3.10E+07 | 3.10E+08 | 3.10E+09 | 3.10E+10 | 3.10E+11 | 3.10E+12 | 3.10E+13 |
| 32,000 | 3.20E+06 | 3.20E+07 | 3.20E+08 | 3.20E+09 | 3.20E+10 | 3.20E+11 | 3.20E+12 | 3.20E+13 |
| 33,000 | 3.30E+06 | 3.30E+07 | 3.30E+08 | 3.30E+09 | 3.30E+10 | 3.30E+11 | 3.30E+12 | 3.30E+13 |
| 34,000 | 3.40E+06 | 3.40E+07 | 3.40E+08 | 3.40E+09 | 3.40E+10 | 3.40E+11 | 3.40E+12 | 3.40E+13 |
| 35,000 | 3.50E+06 | 3.50E+07 | 3.50E+08 | 3.50E+09 | 3.50E+10 | 3.50E+11 | 3.50E+12 | 3.50E+13 |
| 36,000 | 3.60E+06 | 3.60E+07 | 3.60E+08 | 3.60E+09 | 3.60E+10 | 3.60E+11 | 3.60E+12 | 3.60E+13 |
| 37,000 | 3.70E+06 | 3.70E+07 | 3.70E+08 | 3.70E+09 | 3.70E+10 | 3.70E+11 | 3.70E+12 | 3.70E+13 |
| 38,000 | 3.80E+06 | 3.80E+07 | 3.80E+08 | 3.80E+09 | 3.80E+10 | 3.80E+11 | 3.80E+12 | 3.80E+13 |
| 39,000 | 3.90E+06 | 3.90E+07 | 3.90E+08 | 3.90E+09 | 3.90E+10 | 3.90E+11 | 3.90E+12 | 3.90E+13 |
| 40,000 | 4.00E+06 | 4.00E+07 | 4.00E+08 | 4.00E+09 | 4.00E+10 | 4.00E+11 | 4.00E+12 | 4.00E+13 |
| 41,000 | 4.10E+06 | 4.10E+07 | 4.10E+08 | 4.10E+09 | 4.10E+10 | 4.10E+11 | 4.10E+12 | 4.10E+13 |

For in-furrow embodiments, the microbes of the disclosure can be applied at a cfu concentration per acre of: $1 \times 10^6$, $3.20 \times 10^{10}$, $1.60 \times 10^{11}$, $3.20 \times 10^{11}$, $8.0 \times 10^{11}$, $1.6 \times 10^{12}$, $3.20 \times 10^{12}$, or more. Therefore, in aspects, the liquid in-furrow compositions can be applied at a concentration of between about $1 \times 10^6$ to about $3 \times 10^{12}$ cfu per acre.

In some aspects, the in-furrow compositions are contained in a liquid formulation. In the liquid in-furrow embodiments, the microbes can be present at a cfu concentration per milliliter of: $1 \times 10^1$, $1 \times 10^2$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, or more. In certain aspects, the liquid in-furrow compositions comprise microbes at a concentration of about $1 \times 10^6$ to about $1 \times 10^{11}$ cfu per milliliter. In other aspects, the liquid in-furrow compositions comprise microbes at a concentration of about $1 \times 10^7$ to about $1 \times 10^{10}$ cfu per milliliter. In other aspects, the liquid in-furrow compositions comprise microbes at a concentration of about $1 \times 10^8$ to about $1 \times 10^9$ cfu per milliliter. In other aspects, the liquid in-furrow compositions comprise microbes at a concentration of up to about $1 \times 10^{13}$ cfu per milliliter.

Biosensor Applications

In some aspects, provided herein are methods of utilizing a biosensor as provided herein to detect the presence of ammonium in a composition or medium. The method can comprise: (a) inoculating a composition with a biosensor, wherein the biosensor comprises a bacterium expressing a reporter protein, wherein the bacterium expresses the reporter molecule in the absence of ammonium; (b) exposing the inoculated composition to a stimulus sufficient to activate the reporter molecule; and (c) detecting reporter molecule output of the inoculated composition following (b), as compared to a control composition. In some cases, the method further comprises quantifying the amount of ammonium in the composition based upon the detected reporter molecule output.

In some aspects, provided herein are methods of utilizing a biosensor as provided herein to identify bacteria comprising at least one genetic variation introduced into at least one gene, or non-coding polynucleotide, of the nitrogen fixation or assimilation genetic regulatory network. The at least one genetic variation can be introduced via the random mutagenesis methods described herein.

In one embodiment, provided herein are methods for identification of bacterial mutants capable of fixing atmospheric nitrogen. The method for the identification of bacterial mutants capable of fixing atmospheric nitrogen can comprise: (a) exposing a population of bacteria to a mutagen in a microbial composition; (b) co-culturing the microbial composition with a biosensor, wherein the biosensor comprises a bacterium expressing a reporter protein, wherein the bacterium expresses the reporter molecule in the absence of ammonium; (c) exposing the co-cultured composition to a stimulus sufficient to activate the reporter molecule; and (d) identifying bacterial mutants capable of fixing atmospheric nitrogen as those that result in decreased or no reporter molecule output as compared to a control. The control can be a co-culture comprising the biosensor comprising bacterium and a bacterial strain known to be capable of fixing atmospheric nitrogen. The control can be a co-culture comprising the biosensor comprising bacterium and a bacterial strain known to be incapable of fixing atmospheric nitrogen. In some cases, the method further comprises isolating the bacterial mutants capable of fixing atmospheric nitrogen identified in (d).

The method for identification of bacterial mutants capable of fixing atmospheric nitrogen can comprise: (a) exposing a population of bacteria to a mutagen; (b) exposing the population of bacteria exposed to the mutagen in (a) to a diazotrophic growth inhibitor in a microbial composition; (c) co-culturing the microbial composition with a biosensor, wherein the biosensor comprises a bacterium expressing a reporter protein; (d) exposing the co-cultured composition to a stimulus sufficient to activate the reporter molecule, wherein the bacterium expresses the reporter molecule in the absence of ammonium; and (e) identifying bacterial mutants capable of fixing atmospheric nitrogen as those that result in decreased or no reporter molecule output as compared to a control. The control can be a co-culture comprising the biosensor comprising bacterium and a bacterial strain known to be capable of fixing atmospheric nitrogen. The control can be a co-culture comprising the biosensor comprising bacterium and a bacterial strain known to be incapable of fixing atmospheric nitrogen. In some cases, the method further comprises isolating the bacterial mutants capable of fixing atmospheric nitrogen identified in (e). The diazotrophic growth inhibitor can be ethylenediamine (EDA) or methylammonium.

Any of the methods provided herein that utilize a biosensor as provided herein can be high-throughput in nature.

In one embodiment, the method for identification of bacterial mutants capable of fixing atmospheric nitrogen is high-throughput and comprises: (a) exposing a population of bacteria to a mutagen; (b) transferring the population of bacteria in (a) into one or more samples comprising a medium; (c) co-culturing a biosensor within each of the one or more samples in (b), wherein the biosensor comprises a bacterium expressing a reporter protein, wherein the bacterium expresses the reporter molecule in the absence of ammonium; (d) exposing each of the one or more samples in (c) to a stimulus sufficient to activate the reporter molecule; and (e) identifying from the one or more samples in (d) one or more bacterial mutants capable of fixing atmospheric nitrogen as those that result in decreased output of the reporter molecule as compared to a control. The control can be a co-culture comprising the biosensor comprising bacterium and a bacterial strain known to be capable of fixing atmospheric nitrogen. The control can be a co-culture comprising the biosensor comprising bacterium and a bacterial strain known to be incapable of fixing atmospheric nitrogen. In some cases, the method further comprises isolating the bacterial mutants capable of fixing atmospheric nitrogen identified in (e).

Further to any of the above methods utilizing a biosensor as provided herein, the output of the reporter protein can be measured or detected following exposure of compositions or co-cultures comprising the biosensor comprising bacterium to the stimulus sufficient to activate the reporter protein as compared to a control composition. The control composition can comprise microbes that do not express the reporter protein. The control composition can comprise microbes that express a functionally deleted variant of the reporter protein.

In some aspects, provided herein are methods of utilizing a biosensor as provided herein to identify a genetic variation introduced into at least one gene, or non-coding polynucleotide, of the nitrogen fixation or assimilation genetic regulatory network of a mutant bacterial cell. The at least one genetic variation can be introduced via the random mutagenesis methods described herein. In some cases, further to any of the above embodiments for identifying bacterial mutants capable of fixing atmospheric nitrogen, said methods further comprise sequencing the genome(s) of the bacteria identified as capable of fixing atmospheric nitrogen following isolation of said identified bacteria; and identifying genes, pathways, and/or regulatory elements that contain mutations from the sequenced genomes. In some cases, the methods further comprise determining whether the genes, pathways, and/or regulatory elements contain mutations known to be associated with the fixation of atmospheric nitrogen.

In one embodiment, the biosensor for use in any of the methods employing said biosensor comprises a bacterium comprising: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein, wherein the bacterium expresses the reporter molecule in the absence of ammonium. The promoter or fragment thereof for use in the biosensor can be selected from the nifHDK operon. In one embodiment, the promoter is a nifH promoter. The inhibitory nitrogen fixation regulatory protein can be NifL. The positive nitrogen fixation regulatory protein can be NifA.

The population of bacteria for use in any of the methods provided herein can be a population of any bacteria known in the art and/or provided herein. In one embodiment, the population of bacteria is selected from wild-type bacteria, transgenic mutant bacteria, non-intergeneric mutant bacteria and intergeneric mutant bacteria.

In one embodiment, the stimulus is selected from the group consisting of a chemical stimulus, a physical stimulus, a genetic stimulus and an energy stimulus. In one embodiment, the stimulus is light.

Further to any of the above embodiments, the reporter protein or molecule can be any reporter protein known in the art and/or provided herein. In some aspects, the reporter can be an enzyme that is adapted to produce a luminescent or fluorescent signal. In some aspects, the reporter protein can be an enzyme such as luciferase or alkaline phosphatase that yields a luminescent or fluorescent signal respectively. In some aspects, the reporter can also be a fluorescent protein or can include fluorescent, charged, or magnetic nanoparticles, nanodots, or quantum dots. In some aspects, the reporter can be a dye that has fluorescent, ultraviolet, or visible properties, wherein the fluorescent, ultraviolet, or visible properties undergo a detectable change in response to the activation of the biosensor circuit. In one embodiment, the reporter protein or molecule is a fluorescent protein, functional fragment, and/or fusions thereof. The fluorescent protein can be any fluorescent protein known in the art and/or provided herein such as, for example, GFP, RFP, YFP, CFP, or functional variants or fragments thereof. In one embodiment, the fluorescent protein is GFP. In one embodiment, the GFP is a superfolder GFP. In one embodiment, the reporter protein is a fluorescent protein and the stimulus is light such that exposing the co-cultures comprising biosensor comprising bacterium entails exposing said co-cultures to light excitation sufficient to fluoresce the fluorescent protein, functional fragment, and/or fusions thereof. The fluorescence output (e.g., intensity) can then be detected and/or measured with a flow cytometer, a plate reader, or fluorescence-activated droplet sorting.

The mutagen used in any of the above embodiments can be any mutagen known in the art and/or provided herein. The mutagen can be selected from mitomycin C (MMC), N-methyl-N-nitrosourea (MNU), nitrous acid (NA), diepoxybutane (DEB), 1, 2, 7, 8-diepoxyoctane (DEO), ethyl methane sulfonate (EMS), methyl methane sulfonate (MMS), N-methyl-N'-nitro-N-nitrosoguanidine (MNNG), 4-nitroquinoline 1-oxide (4-NQO), 2-methyloxy-6-chloro-9 (3-[ethyl-2-chloroethyl]-aminopropylamin)-acridinedihydrochloride (ICR-170), 2-amino purine (2AP), and hydroxylamine (HA). In one embodiment, the mutagen is EMS.

High-Throughput Method

In some aspects, the high-throughput method is capable of performing the method on at least 100, at least 1,000, at least 10,000, at least 100,000, at least 1,000,000, or at least 10,000,000 bacteria. In some aspects, the high-throughput method is capable of being performed in less than 1 hour, less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 24 hours, less than 36 hours, less than 48 hours, less than 60 hours, or less than 72 hours. In some aspects, the high-throughput method is capable of being performed in less than 1 day, less than 2 days, less than 3 days, less than 4 days, less than 5 days, less than 6 days, or less than 7 days.

In some aspects, the high-throughput method is capable of performing the method on at least 100, at least 1,000, at least 10,000, at least 100,000, at least 1,000,000, or at least 10,000,000 bacteria in less than 1 hour, less than 2 hours, less than 3 hours, less than 4 hours, less than 5 hours, less than 6 hours, less than 7 hours, less than 8 hours, less than 9 hours, less than 10 hours, less than 11 hours, less than 12 hours, less than 24 hours, less than 36 hours, less than 48 hours, less than 60 hours, or less than 72 hours.

In some aspects, the methods of the disclosure include the use of minute volumes of media or another liquid, in which mutagenized microbes can be placed along with a biosensor. These small volumes of liquid amount to microdroplets that can be utilized with the biosensor strain to rapidly screen random microbial mutants and sort and collect the droplets via fluorescence-activated droplet sorting in embodiments where the reporter protein is a fluorescent protein.

In some aspects, the microdroplets comprise less than 2 µL, less than 3 µL, less than 4 µL, less than 5 µL, less than 6 µL, less than 7 µL, less than 8 µL, less than 9 µL, less than 10 µL, less than 11 µL, less than 12 µL, less than 13 µL, less than 14 µL, less than 15 µL, less than 16 µL, less than 17 µL, less than 18 µL, less than 19 µL, less than 20 µL, less than 21 µL, less than 22 µL, less than 23 µL, less than 24 µL, less than 25 µL, less than 30 µL, less than 35 µL, less than 40 µL, less than 45 µL, less than 50 µL, less than 55 µL, less than 60 µL, less than 65 µL, less than 70 µL, less than 75 µL, less than 80 µL, less than 85 µL, less than 90 µL, less than 95 µL, less than 100 µL, less than 125 µL, less than 150 µL, less than 175 µL, less than 200 µL, less than 225 µL, less than 250 µL, less than 275 µL, less than 300 µL, less than 325 µL, less than 350 µL, less than 375 µL, less than 400 µL, less than 425 µL, less than 450 µL, less than 475 µL, or less than 500 µL of liquid.

In some aspects, the microdroplets are less than 1 µM, less than 2 µM, less than 3 µM, less than 4 µM, less than 5 M, less than 6 µM, less than 7 µM, less than 8 µM, less than 9 M, less than 10 µM, less than 15 µM, less than 20 µM, less than 25 µM, less than 30 µM, less than 35 µM, less than 40 µM, less than 45 µM, less than 50 µM, less than 55 µM, less than 60 µM, less than 65 µM, less than 70 µM, less than 75 µM, less than 80 µM, less than 85 µM, less than 90 µM, less than 95 µM, less than 100 IM, less than 125 M, less than 150 µM, less than 175 µM, less than 200 µM, less than 225 µM, less than 250 µM, less than 275 µM, less than 300 µM, less than 350 µM, less than 400 µM, less than 450 µM, less than 500 µM, less than 550 µM, less than 600 µM, less than 650 M, less than 700 µM, less than 750 µM, less than 800 µM, less than 850 µM, less than 900 µM, less than 950 µM, or less than 1000 µM in diameter.

The sorted droplets may be subjected to sequencing to identify genetic modifications that are responsible for improve ammonium excretion. The high-throughput methods provide for a method to target genetic engineering to enhance nitrogen fixing and ammonium excreting microbes.

Following cultivation of a mutant library under the nitrogen-fixing conditions, the level of excreted ammonium in the media is quantitatively measured or detected by analyzing GFP from the biosensor by flow cytometer, plate-reader, or other fluorescent output detection method. As the biosensor harbors an antibiotic selection marker, we can lyse the nitrogen fixing microbes with application of antibiotics to which the biosensor is resistant, further enabling the analysis of intracellular levels of nitrogen fixed by the mutated microbes using the biosensor.

In some aspects, the mutants are pooled together prior to the addition of the one or more biosensor microbes or prior to dilution of the medium. In some aspects, the pooled mutants comprise at least 2, at least 3, at least 4, at least 5, at least 6, at least 7, at least 8, at least 9, at least 10, at least 20, at least 25, at least 30, at least 35, at least 40, at least 45, at least 50, at least 55, at least 60, at least 65, at least 70, at least 75, at least 80, at least 85, at least 90, at least 95, or at least 100 different mutants.

Examples

Example 1. Biosensor Assay for *Klebsiella, Kosakonia*, and *Metakosakonia*

Day 1—Cultures for ammonium excretion assay are initiated by inoculating a single colony into a 96-deep well plate containing 1 ml of rich medium (e.g., Lennox LB or SOB). Incubate the cultures with shaking at 900 rpm at 30° C. overnight.

Day 2—The overnight cultures are diluted 100-fold in ARA minimal medium containing 17.1 mM ammonium acetate into 96-well plates. The dilution may be 2 µL of the overnight culture to 200 µL of fresh minimal medium. The ammonium acetate may be substituted with other nitrogen sources. The 96-well plates are incubated with shaking at 900 rpm at 30° C. for 24 hours. Cultures for biosensor strains are initiated by inoculating a single colony into 1 ml of LB medium supplemented with 15 µg/ml gentamicin in a 15 ml culture tube for plasmid and incubated at 250 rpm at 37° C. overnight.

Day 3—The cultures for the ammonium excretion assay are diluted by adding 50 µL of the overnight culture into 450 µL of ammonium-free ARA minimal medium in a 96-deep well plate. The 96-well plate is transferred into an anaerobic Coy chamber and grown with shaking at 900 rpm at 30° C. for 24 hours (the incubation time can be adjusted). The biosensor cultures are diluted into ARA minimal medium containing 17.1 mM ammonium acetate supplemented with 15 µg/mL gentamicin in a 15 mL culture tube by 100-fold and incubated at 250 rpm at 37° C. for ~24 hours.

Day 4—Add 20 µL of 10×ARA salt medium supplemented with 150 µg/ml gentamicin and 20 µL of the overnight grown biosensor into a new 96-well reaction plate. The cultures for the ammonium excretion assay are retrieved from the chamber and centrifuged at 4,000 g for 20 minutes to separate the cell pellets. Add 160 µL of the supernatant into the reaction plate to make 200 µL total. The dilution can be adjusted for supernatant based on the levels of ammonium excretion. If less than 160 µL of the supernatant is used, fill 1×ARA buffer to the remainder of the reaction to bring volume to 200 µL. The 96-well plate is transferred into an anaerobic Coy chamber and grown with shaking at 900 rpm at 30° C. for 15-18 hours.

Day 5—The plate is removed from the anaerobic chamber and incubated at room temperature for approximately one hour for GFP maturation before reading. The fluorescence signals can be analyzed either by a plate reader or a flow cytometer. Translation of the biosensor can be arrested by diluting cells in ice-cold phosphate-buffered saline (PBS) supplemented with 2 mg/ml kanamycin, but the fluorescent signals are stable over 12 hours at room temperature, and for several days at 4° C.

The inclusion of both positive and negative controls is necessary. This experiment utilizes *Klebsiella variicola* strains 137-2084 and 138-1590 as a positive and a negative control, respectively. Strains 137-2084 and 138-1590 are derived from the *Klebsiella variicola* 137. A standard curve for fixed nitrogen (e.g., ammonium or glutamine) can be generated by differing fixed nitrogen sources in the $4^{th}$ day reaction plate in which the supernatant containing excreted ammonium is replaced with 1× ammonium-free ARA buffer.

TABLE 1

| 10× ARA Salt Medium (per L) |
| --- |
| 200 g sucrose |
| 0.25 g MgSO$_4$•7H$_2$0 |
| 10 g NaCl |
| 1 g CaCl$_2$•2H$_2$O |
| 29 mg FeCl$_3$ |
| 2.5 mg Na$_2$MoO$_4$•2H$_2$O |
| If adding nitrogen: 6 µL/mL of 22% |
| ammonium acetate (final 17.1 mM) |

TABLE 2

| ARA Buffer (per L) |
| --- |
| 25 g Na$_2$HPO$_4$ |
| 3 g KH$_2$PO$_4$ |
| If adding nitrogen: 6 µL/mL of 22% |
| ammonium acetate (final 17.1 mM) |

Example 2: Biosensor Assay for *Paraburkholderia* and *Herbaspirillum*

Day 1—Cultures for ammonium excretion assay are initiated by inoculating a single colony into a 96-deep well plate containing 1 ml of rich medium (e.g., Lennox LB or SOB). Incubate the cultures with shaking at 900 rpm at 30° C. overnight.

Day 2—The overnight cultures are diluted 100-fold in JMV minimal medium containing 10 mM ammonium chloride into 96-well plates. The dilution may be 2 µL of the overnight culture to 200 µL of fresh minimal medium. The ammonium chloride may be substituted with other nitrogen sources. The 96-well plates are incubated with shaking at 900 rpm at 30° C. for 24 hours.

Day 3—The cultures for the ammonium excretion assay are diluted by adding 50 µL of the overnight culture into 450 µL of ammonium-free JMV minimal medium in a 96-deep well plate. The 96-well plate is transferred into a hypoxic Coy chamber and grown with shaking at 900 rpm at 30° C. for 48 hours (the incubation time can be adjusted) under hypoxic conditions (1-3% oxygen). Cultures for biosensor strains are initiated by inoculating a single colony into 1 ml of LB medium supplemented with 15 µg/ml gentamicin in a 15 ml culture tube for plasmid and incubated at 250 rpm at 37° C. overnight.

Day 4—The biosensor cultures are diluted into ARA minimal medium containing 17.1 mM ammonium acetate supplemented with 15 µg/mL gentamicin in a 15 mL culture tube by 100-fold and incubated at 250 rpm at 37° C. for ~24 hours.

Day 5—Add 20 µL of 10×ARA salt medium supplemented with 150 µg/ml gentamicin and 20 µL of the overnight grown biosensor into a new 96-well reaction plate. The cultures for the ammonium excretion assay are retrieved from the chamber and centrifuged at 4,000 g for 20 minutes to separate the cell pellets. Add 160 µL of the supernatant into the reaction plate to make 200 µL total. The dilution can be adjusted for supernatant based on the levels of ammonium excretion. If less than 160 µL of the supernatant is used, fill 1×JMV buffer to the remainder of the reaction to bring volume to 200 µL. The 96-well plate is transferred into an anaerobic Coy chamber and grown with shaking at 900 rpm at 30° C. for 15-18 hours.

Day 6—The plate is removed from the anaerobic chamber and incubated at room temperature for approximately one hour for GFP maturation before reading. The fluorescence signals can be analyzed either by a plate reader or a flow cytometer. Translation of the biosensor can be arrested by diluting cells in ice-cold phosphate-buffered saline (PBS) supplemented with 2 mg/ml kanamycin, but the fluorescent signals are stable over 12 hours at room temperature, and for several days at 4° C.

The inclusion of both positive and negative controls is necessary. This experiment utilizes *Paraburkholderia tropica* wild-type and *Paraburkholderia tropica* 8-4752 as a negative control and a positive control, respectively. Strains 1374752 is derived from the *Paraburkholderia tropica* 8. A standard curve for fixed nitrogen (e.g., ammonium or glutamine) can be generated by differing fixed nitrogen sources in the $5^{th}$ day reaction plate in which the supernatant containing excreted ammonium is replaced with 1× ammonium-free JMV buffer.

TABLE 3

| 10× JMV Salt Medium (per L) |
| --- |
| 50 g mannitol |
| 18.02 g glucose |
| 2 g MgSO$_4$•7H$_2$0 |
| 1 g NaCl |
| 1 g CaCl$_2$•2H$_2$O |
| 0.65 g Fe-EDTA |
| 10 ml of Trace element |
| If adding nitrogen: 10 µL/mL of |
| 1M ammonium chloride (final 10 mM) |

TABLE 4

| Trace element (per L) |
| --- |
| 0.04 g CuSO$_4$•5H$_2$O |
| 0.12 g ZnSO$_4$•7H$_2$O |
| 1.4 g H$_3$BO$_3$ |
| 1 g Na$_2$MoO$_4$•2H$_2$O |
| 1.175 g MnSO$_4$•H$_2$O |

TABLE 5

| JMV Buffer (per L) |
| --- |
| 0.6 g K$_2$HPO$_4$ |
| 1.8 g KH$_2$PO$_4$ |
| Adjust pH to 7.0 using KOH |

Example 3: Joint EDA-2AP Selection Assay

Figures 3A, 3B:
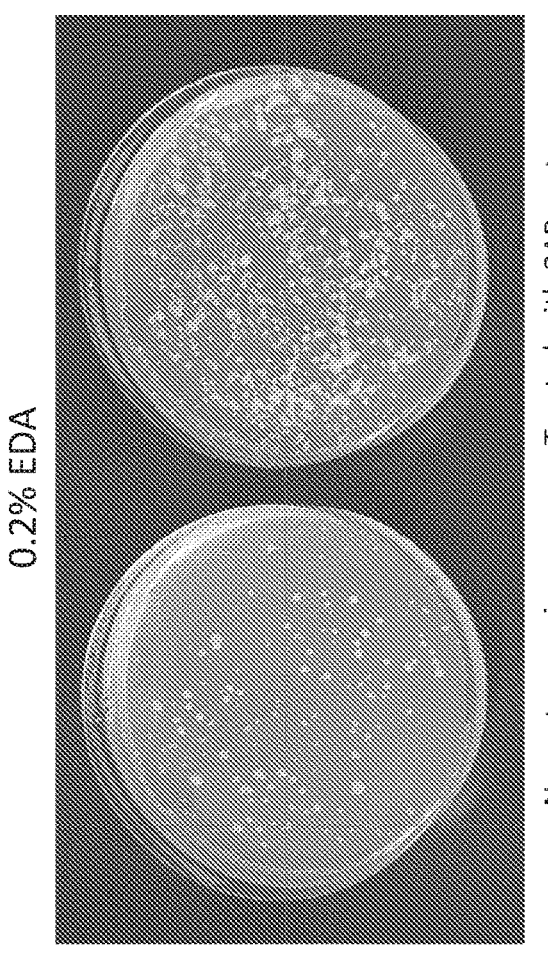
FIGS. 3A-B depict *Klebsiella variicola* 137 strains grown on solid media with 0.2% EDA (FIG. 3A) and *Paraburkholderia tropica* 8 strains grown on solid media with 100 mM methylammonium (FIG. 3B). Within each of FIG. 3A and FIG. 3B, the left plate was plated with *Klebsiella* 137 or *Paraburkholderia* 8 incubated without the mutagen such as 2-aminopurine (2AP) or EMS, and the right plate was plated with *Klebsiella variicola* 137 or *Paraburkholderia* 8 treated with the mutagen 2AP or EMS. The chemically mutagenized strains by 2AP or EMS that grew in the presence of ammonium analogues such as 0.2% EDA or 100 mM methylammonium exhibited higher survival rates on the plate

Single colonies of *Klebsiella, Kosakonia, Metakosakonia, Paraburkholderia,* or *Herbaspirillum* were inoculated into rich media and grown overnight at 30° C. Aliquots (5 μL) of overnight cultures were diluted into 1 mL of rich media supplemented with between 0.5 and 1 mg/mL 2-aminopurine and grown for 24 h at 30° C. At the conclusion of the 24 h period the cultures were washed with PBS twice and plated on ammonium-free minimal medium supplemented with EDA from about 0.1% EDA to about 0.2% EDA or methylammonium from about 25 mM to about 200 mM methylammonium, and the plates were incubated at 30° C. under anaerobic conditions or hypoxic conditions for facultative anaerobes such as *Klebsiella* and obligate aerobes such as *Paraburkholderia,* respectively (FIG. 3A). The resulting individual colonies were indicated as resistant mutants to EDA or methylammonium and selected, grown in liquid media, and stored.

Figure 4:
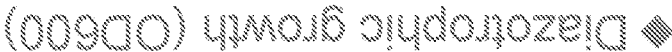
FIG. 4 depicts the fluorescence output of biosensor strains cultured with the supernatants of the EDA mutants, indicating that the EDA mutants excreted ammonium into the medium.
Figure 5B:
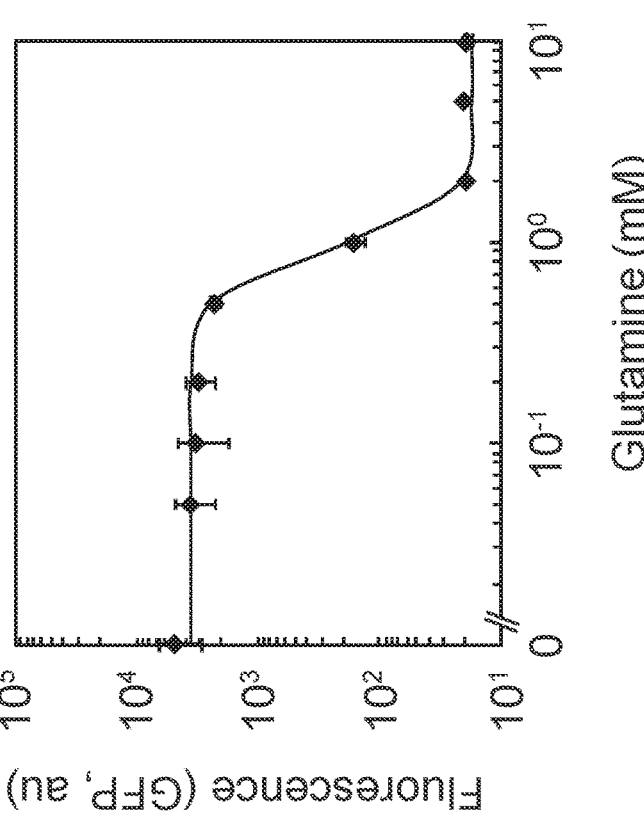
FIGS. 5A-B depicts a standardized response curve for the biosensor strain in the presence of varying concentrations of free ammonium (FIG. 5A) and glutamine (FIG. 5B) and the corresponding fluorescent output. The dissociation constant (Km) for ammonium and glutamine is ~0.5 mM and ~0.6 mM, respectively.
Figure 5A:
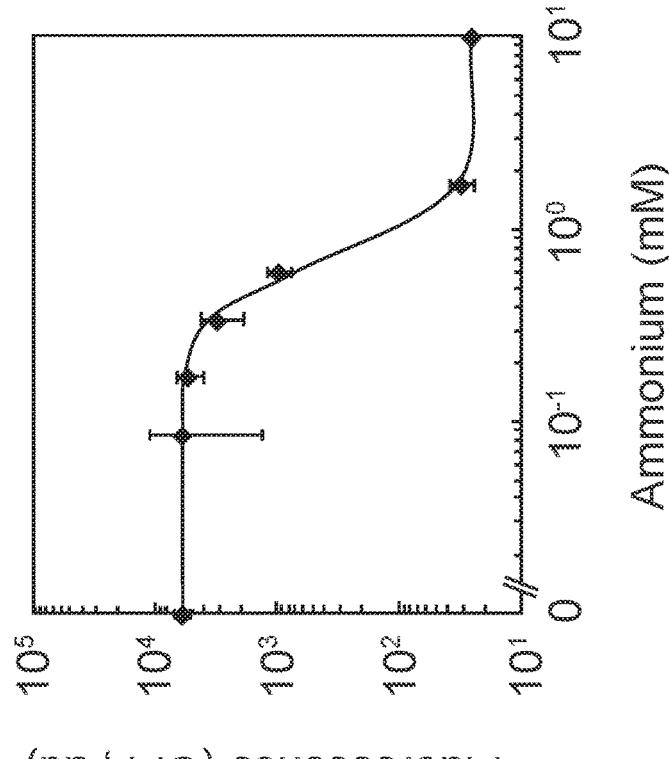
Figure 6:
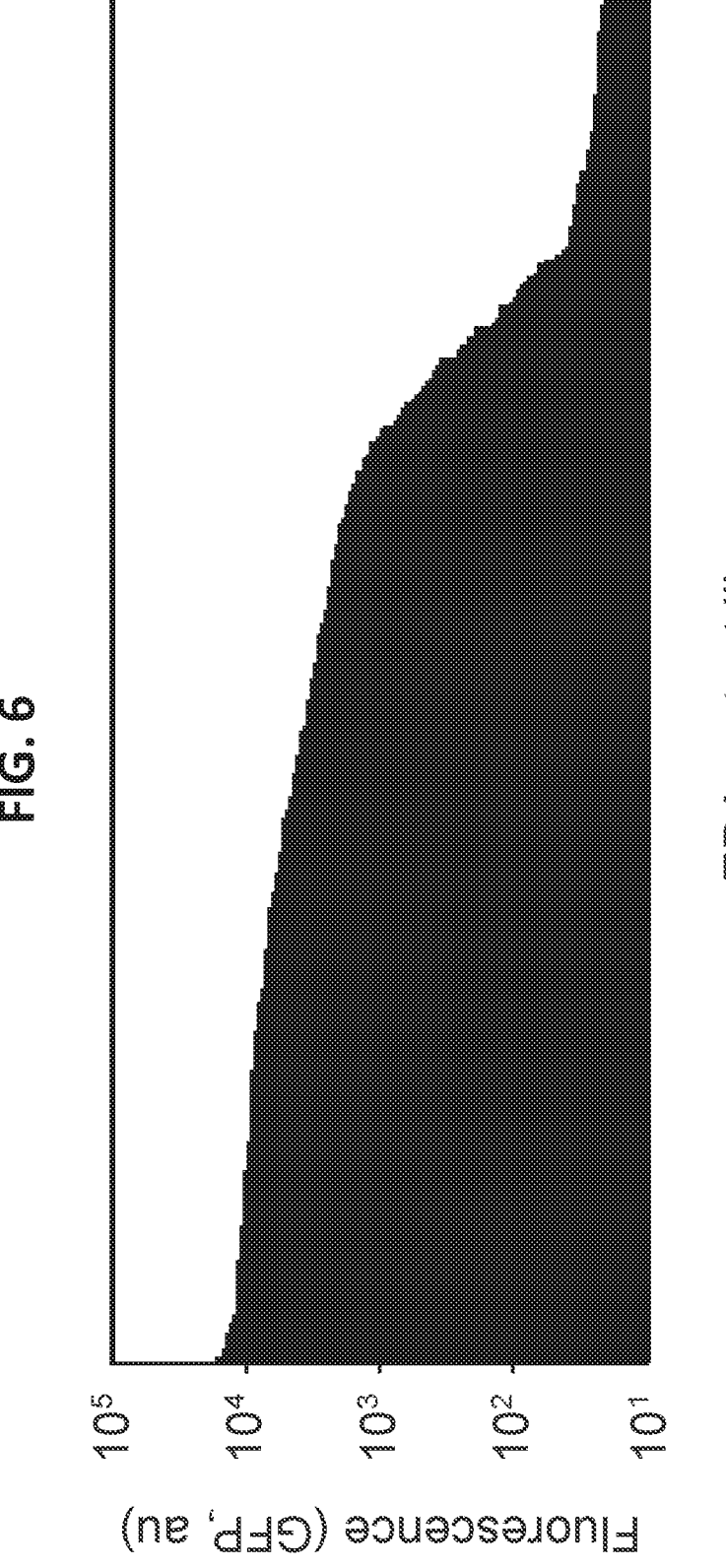
FIG. 6 depicts the range of fluorescence, in fluorescence arbitrary units (au), as a result of GFP expression and fluorescence, for an EDA resistant mutant library comprising 327 mutant *Klebsiella variicola* strains, indicating that approximately ⅓ of the EDA resistant mutant library comprises mutants capable of excreting fixed nitrogen at levels greater than the 137 wild-type strain does.
Figure 7:
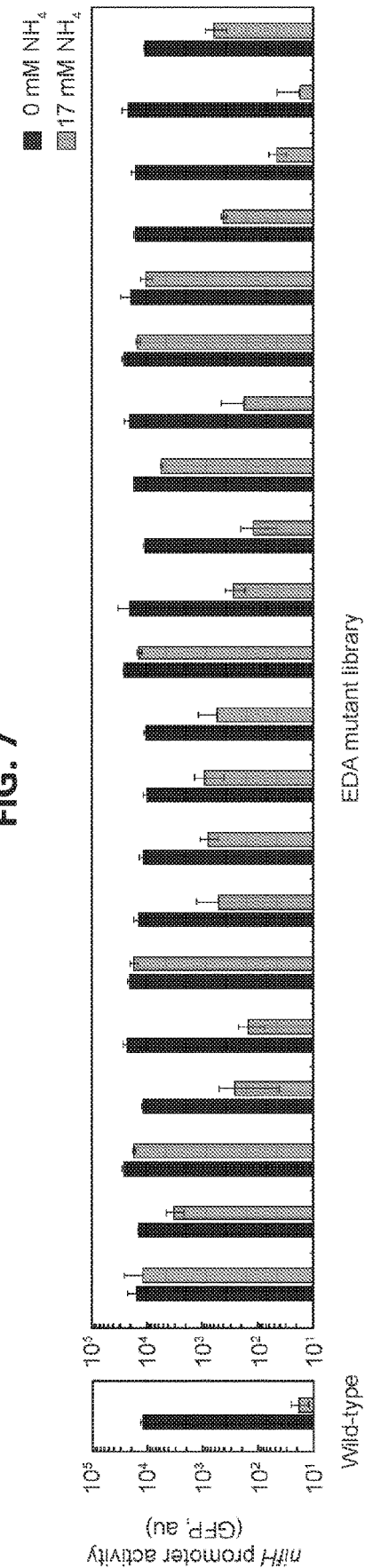
FIG. 7 depicts the nifH promoter activity in fluorescence arbitrary units (au), as a result of GFP expression and fluorescence, for 21 *Klebsiella variicola* EDA resistant mutant strains co-cultured with the biosensor. The black bars indicate the absence of ammonium and the gray bars indicate the presence of ammonium. In the 137 wild-type (left panel), the nifH promoter in the biosensor is repressed in the presence of ammonium, whereas many of the nifH promoters in the EDA resistant mutants are active or de-repressed in the presence of ammonium (right panel).
Figure 8:
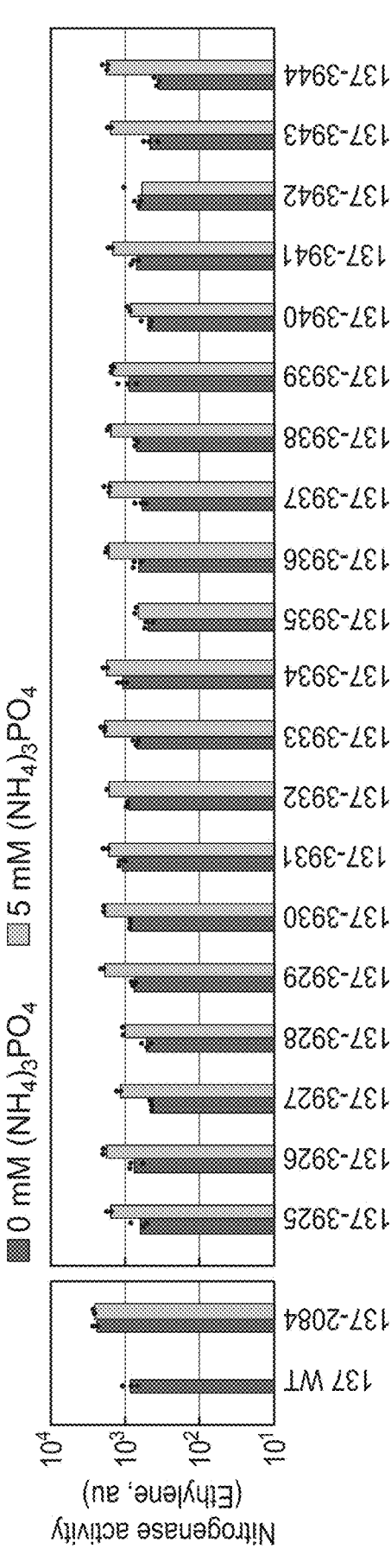
FIG. 8 depicts nitrogenase activity of 20 *Klebsiella variicola* EDA resistant mutant strains assessed by acetylene reduction assay. Ethylene production is used as a proxy for nitrogenase activity. All 20 mutant strains showed nitrogenase activity in the presence of 5 mM ammonium phosphate.
Figure 9:
FIG. 9 depicts the amounts of ammonium excreted from 19 *Klebsiella variicola* EDA resistant mutant strains after 72 hr of incubation. Twelve (12) of *Klebsiella variicola* EDA resistant mutant strains excreted more than 20 mM ammonium.
Figure 10A:
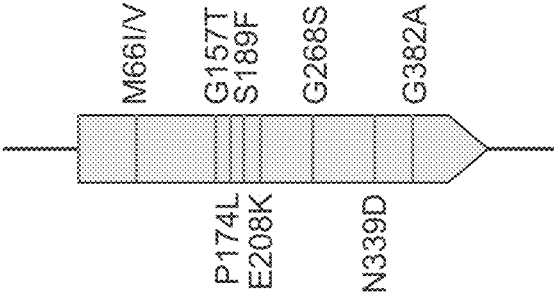
FIGS. 10A-B depict ammonium excretion mutants in four different species identified by random mutagenesis and selection using ammonium analogues such as EDA and methylammonium along with the approximate positions of the mutations in GlnA in the four different species identified by genome-wide sequencing (FIG. 10A).
Figure 10A:
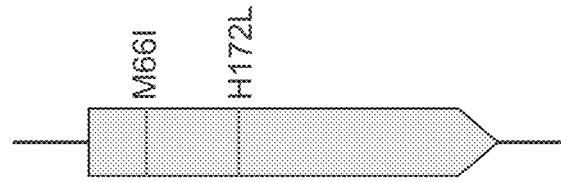
Figure 10A:
Figure 10A:
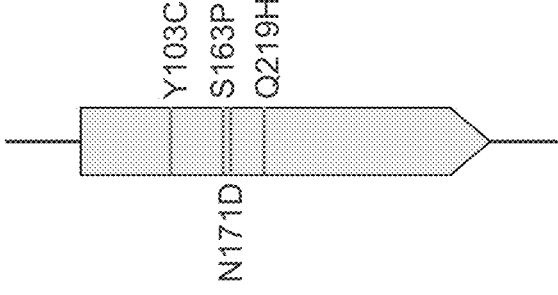
Figure 10B:
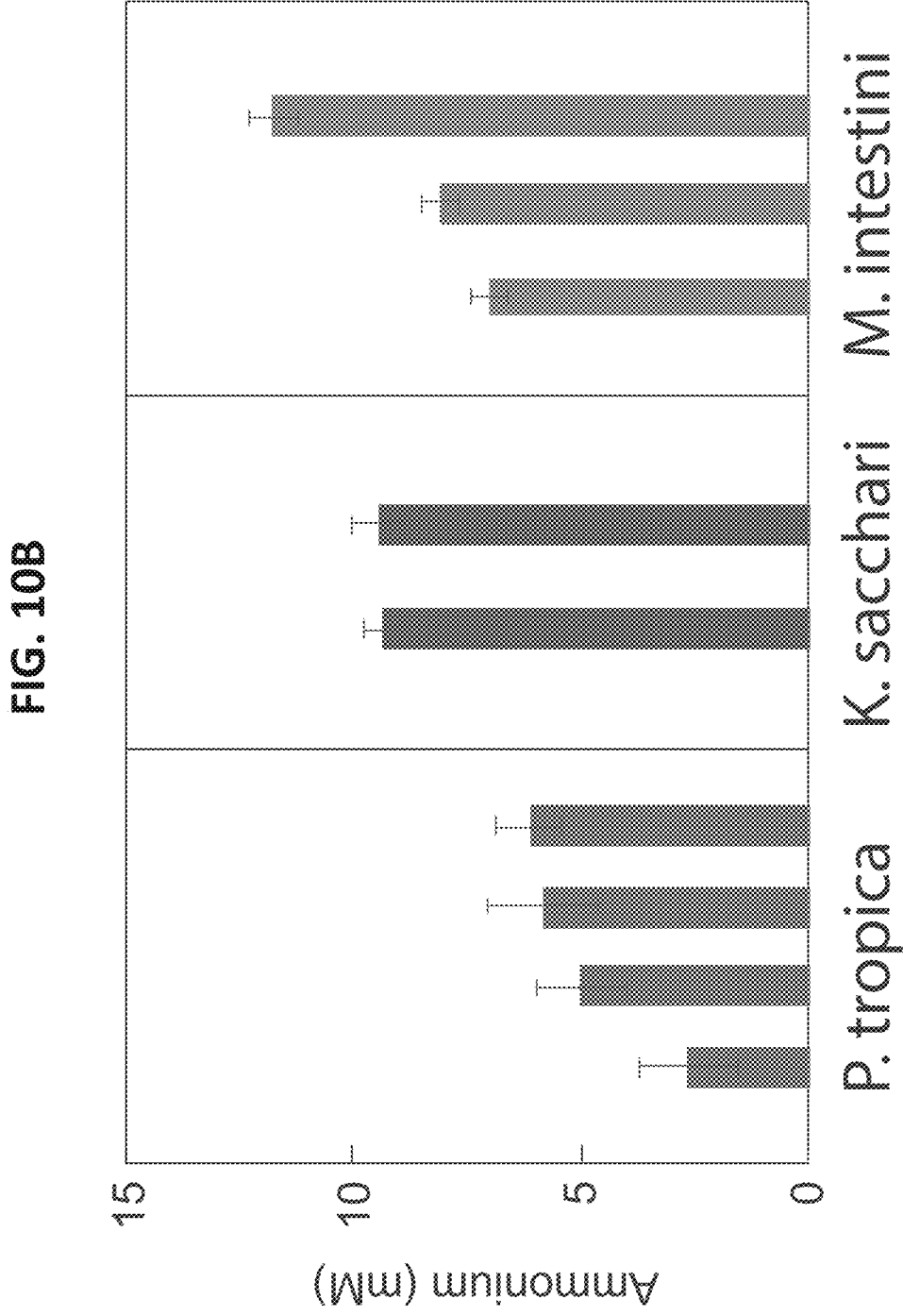

Combining the biosensor strain with the EDA- or methylammonium-resistant mutants for co-culture of the biosensor strain with the individual resistant mutants and various control strains allowed for a determination of the degree of ammonium excretion from nitrogen fixation activity of the resistant mutants as determined by the presence/absence, or the degree thereof, of GFP fluorescence from the biosensor strain. The biosensor can detect higher ammonium excretion from the 5 selected EDA-resistant mutants than from the 137 wild-type and its derivatives remodeled by targeted engineering (FIG. 4). In addition, the biosensor can detect higher ammonium excretion from the selected methylammonium-resistant mutants than from their own wild-type as ammonium excretion from the wild-type strains is undetectable (FIG. 10A-B). These methods provide low false positive rates. The library composed of 327 mutants and 20% of EDA-resistant mutants from *Klebsiella variicola* showed improved ammonium excretion. (FIG. 6). Additionally, we can detect nitrogenase expression when mutants are exposed to ammonium. We introduced a plasmid containing GFP under the regulation of the nifH promoter. In the wild-type background, the nifH expression is repressed by 17 mM ammonium acetate, whereas some of the mutants exhibited the nifH expression even in the presence of 17 mM ammonium acetate, indicating ammonium repression of nitrogenase expression is relieved in those mutants (FIG. 7). These mutants also showed nitrogenase activity in the presence of ammonium (FIG. 8) and higher ammonium excretion up to 22.7 mM ammonium after 72 hr of incubation (FIG. 9).

Example 4: Joint Methylammonium-EMS Selection Assay

Single colonies of *Klebsiella, Kosakonia, Metakosakonia, Paraburkholderia,* or *Herbaspirillum* were inoculated into rich media and grown overnight at 30° C. Aliquots (10 μL) of the overnight cultures were diluted into 1 mL of rich media and grown for 5 hr at 30° C. to an optical density of about 1. The cell pellets collected by centrifugation were washed twice with 1 mL of ARA minimal medium. The cell pellets were resuspended in 1 mL of ARA minimal medium plus 14 μl of EMS and incubated for 2 hr at 30° C. The cell pellets collected by centrifugation were washed twice with 1 mL of ARA minimal medium and resuspended in 1 mL of ARA minimal medium. Aliquots (50 μl) of the cells were diluted into 950 μL of rich media, incubated for overnight at 30° C. and plated on ammonium-free minimal medium supplemented with EDA from about 0.1% EDA to about 0.2% EDA or methylammonium from about 25 mM to about 200 mM methylammonium, and the plates were incubated at 30° C. under anaerobic conditions or hypoxic conditions for facultative anaerobes such as *Klebsiella* and obligate aerobes such as *Paraburkholderia,* respectively (FIG. 3B). The resulting individual colonies were indicated as resistant mutants to EDA or methylammonium and selected, grown in liquid media, and stored.

Combining the biosensor strain with the EDA- or methylammonium-resistant mutants for co-culture of the biosensor strain with the individual resistant mutants and various control strains allowed for a determination of the degree of ammonium excretion from nitrogen fixation activity of the resistant mutants as determined by the presence/absence, or the degree thereof, of GFP fluorescence from the biosensor strain. The biosensor can detect higher ammonium excretion from the selected EDA-resistant mutants than from their wild-type (FIG. 4).

Example 5: Identification of Single Nucleotide Polymorphism (SNP)

In order to identify mutations in the ammonium excreting mutants generated from *Klebsiella variicola, Kosakonia sacchari, Metakosakonia intestini* and *Paraburkholderia tropica* their genome sequences were analyzed using whole-genome sequencing. The genomic DNAs were isolated from each mutant and sequenced with an Illumina MiSeq® (next-generation sequencing (NGS)) v3. The sequence reads were aligned to reference sequences using Bowtie 2. (FIG. 10A and Table 6). Changes in the protein sequences and ammonium excretion levels from each mutant across four species were listed in Table 6 and depicted in FIG. 10B. Most of the SNPs were identified in glnA that encodes glutamine synthetase across four species. In addition, we also identified mutations in glnE of *Klebsiella variicola* that affects glutamine synthetase activity by regulating adenylylation of glutamine synthetase. It is noted that the mutagenized microbes with the edits in Table 6 have been deposited as illustrated in Table 7.

TABLE 6

SNPs in ammonium excreting mutants and their levels of ammonium excretion.

| Gene | Species | Amino acid substitution | Ammonium excretion (mM) | Nucleic Acid SEQ ID NO: | Amino Acid Seq ID NO: |
| --- | --- | --- | --- | --- | --- |
| glnA | *Klebsiella variicola* CI3296 | M66I | 18.58 ± 1.58 | 6 | 29 |
| glnA | *Klebsiella variicola* CI3936 | M66V | 19.98 ± 2.04 | 7 | 30 |
| glnA | *Klebsiella variicola* CI3933 | G157C | 20.12 ± 1.49 | 8 | 31 |
| glnA | *Klebsiella variicola* CI3927 | P174L | 18.59 ± 1.01 | 9 | 32 |

TABLE 6-continued

SNPs in ammonium excreting mutants and their levels of
ammonium excretion.

| Gene | Species | Amino acid substitution | Ammonium excretion (mM) | Nucleic Acid SEQ ID NO: | Amino Acid Seq ID NO: |
|---|---|---|---|---|---|
| glnA | Klebsiella variicola CI3925 | S189F | 21.26 ± 1.42 | 10 | 33 |
| glnA | Klebsiella variicola CI3943 | E208K | 22.73 ± 0.97 | 11 | 34 |
| glnA | Klebsiella variicola CI3940 | G268S | 19.98 ± 1.40 | 12 | 35 |
| glnA | Klebsiella variicola CI3938 | N339D | 22.19 ± 1.01 | 13 | 36 |
| glnE | Klebsiella variicola CI4874 | G322E/ G746D | 2.34 ± 0.34 | 14 | 37 |
| glnA | Kosakonia sacchari CI4065 | M66I | 9.30 ± 0.18 | 15 | 38 |
| glnA | Metakosakonia intestini CI4875 | H172L | 10.01 ± 1.21 | 16 | 39 |
| glnA | Metakosakonia intestini CI4876 | G218S | 11.76 ± 0.54 | 17 | 40 |
| glnA | Metakosakonia intestini CI4877 | T255I | 10.28 ± 0.25 | 18 | 41 |
| glnA | Metakosakonia intestini CI4878 | A329V | 10.33 ± 0.19 | 19 | 42 |
| glnA | Paraburkholderia tropica CI4751 | Y103C | 6.16 ± 0.71 | 20 | 43 |
| glnA | Paraburkholderia tropica CI4753 | S163P | 5.03 ± 0.99 | 21 | 44 |
| glnA | Paraburkholderia tropica CI4879 | N171D | 5.86 ± 1.22 | 22 | 45 |
| glnA | Paraburkholderia tropica CI4752 | Q219H | 2.65 ± 1.09 | 23 | 46 |

Example 6: Determining Relative Abundance of Microbial Strains

In order to determine the colonization capacity of some of the strains identified and isolated as described in the Examples provided herein, the percent relative abundance was calculated for a series of bacterial strains derived from *K. variicola* parental strain 137 using the cocoseq assay as described in PCT/US2020/012564, filed on Jan. 7, 2020.

In particular, unique naturally occurring cocoseq barcodes were inserted into the following strains: 137, 137-1036, 137-3933, 137-3944, 137-4073, 137-4074, 137-2285. All resulting barcoded strains were pooled in equal ratio to create an inoculum (final optical density of 1.0) which was then applied to ten seedlings (1 mL of inoculum per seedlings) in sterile sand. Successfully germinated plants were harvested three weeks after inoculation and processed similarly to previous colonization experiments to result in purified gDNA of the root rhizosphere. Purified gDNA was used as template (3 ul of gDNA per reaction) for cocoseq PCR as described in PCT/US2020/012564, filed on Jan. 7, 2020, which is incorporated by reference herein. Subsequent PCR products were sequenced on the Illumina MiSeq® (next-generation sequencing (NGS)) platform (2×75 bp) and resulting data was analyzed via in-house software to identify and enumerate cocoseq barcodes.

Figure 11:
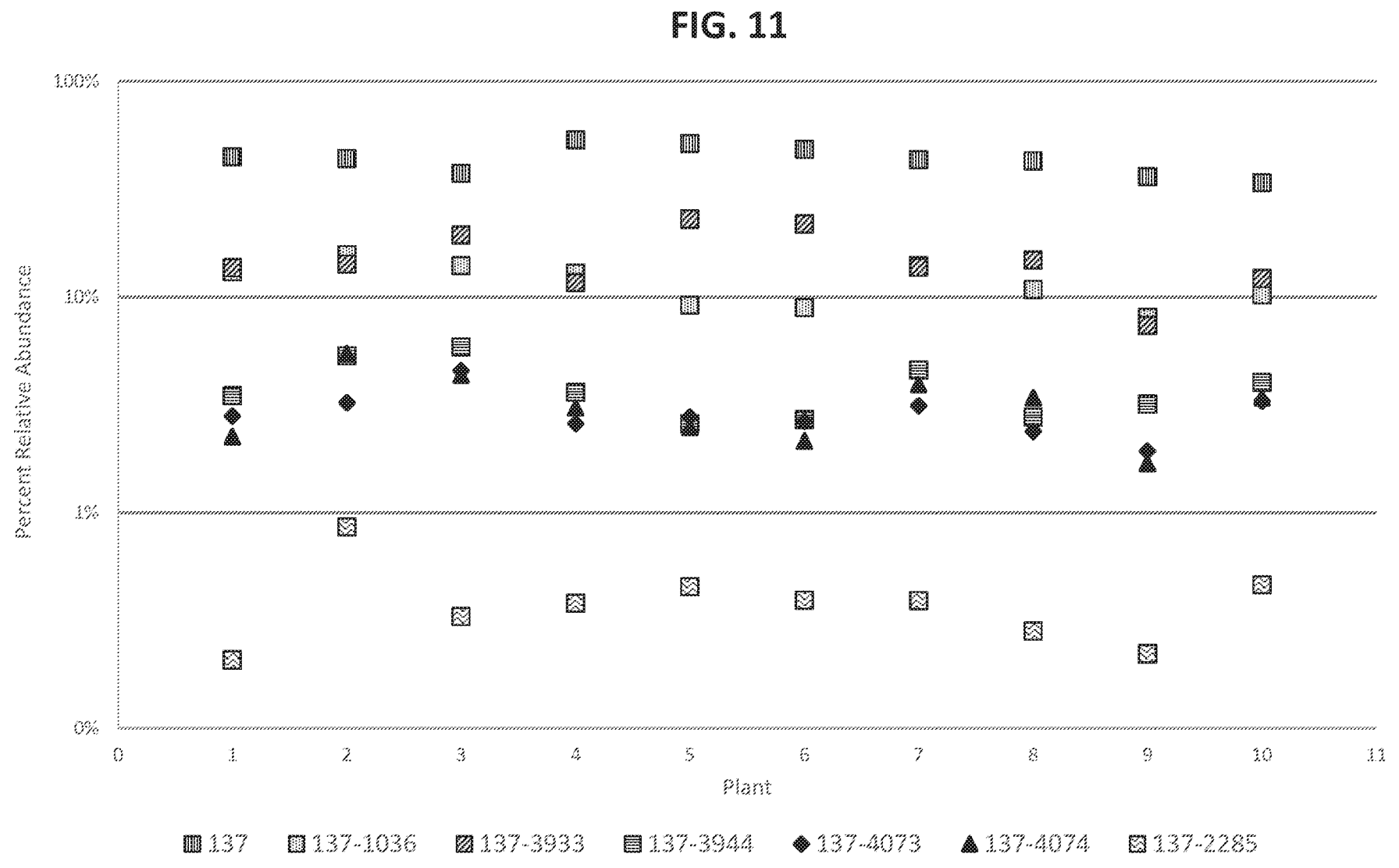

As can be seen in FIG. 11, strains identified in the Examples provided herein (e.g., 137-3933), had colonization capacities similar to the parental 137 strain.

Example 7: Trials with Mutagenized Strains of the Disclosure

An experiment will be conducted utilizing each of the deposited mutant microbes described in Table 6 and their corresponding parental strain in order to evaluate the ability of the mutant microbes to fix nitrogen. The mutant microbe and respective parental strain will be added to a liquid composition comprising an agriculturally acceptable carrier and applied to a plant, a plant part (e.g., seed), or a locus in which the plant is located, or a locus in which the plant will be grown. The plants to be tested will include corn, soybean, canola, *sorghum*, potato, rice, vegetables, cereals (e.g., barley, rye, *sorghum*), pseudocereals (e.g., breadnut, buckwheat, sesame), and oilseeds.

In one set of experiments, the microbial compositions will be applied in furrow at a concentration of about $1\times10^6$ to about $1\times10^{11}$ cfu of bacterial cells per milliliter or at a concentration per acre of between about $1\times10^6$ to about $3\times10^{12}$ cfu per acre for each plant to be tested.

In another set of experiments, the microbial compositions will be applied by coating a seed of the specific plant at a concentration of about $1\times10^4$ to about $1\times10^8$ cfu per seed.

The relative and/or absolute abundance of each microbe will be assessed using the cocoseq assay as described in PCT/US2020/012564, filed on Jan. 7, 2020. The N-fixation activity of each of the microbes tested in this Example (i.e., microbes from Table 6 and their respective parental strains) will be assessed using an in vitro ARA assay at 5 mM glutamine or ammonium phosphate.

NUMBERED EMBODIMENTS OF THE DISCLOSURE

Other subject matter contemplated by the present disclosure is set out in the following numbered embodiments:

1) A biosensor capable of detecting the presence of ammonium in a composition, the biosensor comprising: a bacterium comprising: (a) a nucleic acid sequence encoding a reporter molecule, (b) a promoter or fragment thereof selected from the Nif regulon operably linked to the nucleic acid sequence of (a), (c) a nucleic acid sequence encoding an inhibitory nitrogen fixation regulatory protein, and (d) a nucleic acid sequence encoding a positive nitrogen fixation regulatory protein; wherein the bacterium expresses the reporter molecule in the absence of ammonium.

2) The biosensor of embodiment 1, wherein the reporter molecule is a fluorescent protein, functional fragment, and/or fusions thereof.

3) The biosensor of embodiment 2, wherein the fluorescent protein is a GFP, RFP, YFP, CFP, or functional variant or fragment thereof.

4) The biosensor of embodiment 3, wherein the fluorescent protein is GFP.

5) The biosensor of embodiment 4, wherein the GFP is a superfolder GFP.

6) The biosensor of any one of the above embodiments, wherein the promoter or fragment thereof is selected from the nifHDK operon.

7) The biosensor of any one of the above embodiments, wherein the promoter is a nifH promoter.

8) The biosensor of any one of the above embodiments, wherein the inhibitory nitrogen fixation regulatory protein is NifL.

9) The biosensor of any one of the above embodiments, wherein the positive nitrogen fixation regulatory protein is NifA.

10) The biosensor of any one of the above embodiments, wherein the bacterium in *Escherichia coli.*

11) A method of detecting the presence of ammonium in a composition, the method comprising: (a) inoculating a composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein; wherein the bacterium expresses the reporter molecule in the absence of ammonium; (b) exposing the inoculated composition to a stimulus sufficient to activate the reporter molecule; and (c) detecting reporter molecule output of the inoculated composition following (b), as compared to a control composition.

12) The method of embodiment 11, further comprising quantifying the amount of ammonium in the composition based upon the detected reporter molecule output.

13) The method of embodiment 11 or 12, wherein the stimulus is selected from the group consisting of a chemical stimulus, a physical stimulus, a genetic stimulus and an energy stimulus.

14) The method of any one of embodiments 11-13, wherein the stimulus is light.

15) The method of embodiment 14, wherein the reporter molecule is a fluorescent protein, functional fragment, and/ or fusions thereof.

16) The method of embodiment 15, wherein the fluorescent protein is a GFP, RFP, YFP, CFP, or functional variant or fragment thereof.

17) The method of embodiment 15 or 16, wherein the fluorescent protein is GFP.

18) The method of embodiment 17, wherein the GFP is a superfolder GFP.

19) The method of any one of embodiments 15-18, wherein step (b) entails exposing the inoculated composition to light excitation sufficient to fluoresce the fluorescent protein, functional fragment, and/or fusions thereof.

20) The method of any one of embodiments 15-19, wherein step (c) entails detecting intensity of fluorescent output of the inoculated composition following (b), as compared to the control composition.

21) The method of any one of embodiments 15-20, wherein the fluorescence is detected with a flow cytometer, a plate reader, or fluorescence-activated droplet sorting.

22) A method for identification of bacterial mutants capable of fixing atmospheric nitrogen, the method comprising: (a) exposing a population of bacteria to a mutagen in a microbial composition; (b) co-culturing the microbial composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein, wherein the bacterium expresses the reporter molecule in the absence of ammonium; (c) exposing the co-cultured composition to a stimulus sufficient to activate the reporter molecule; and (d) identifying bacterial mutants capable of fixing atmospheric nitrogen as those that result in decreased or no reporter molecule output as compared to a control.

23) The method of embodiment 22, wherein the reporter molecule output of the co-cultured composition is detected following (c), as compared to a control composition.

24) The method of embodiment 23, wherein the control composition comprises microbes that do not express the reporter molecule.

25) The method of embodiment 23, wherein the control composition comprises microbes that express a functionally deleted variant of the reporter molecule.

26) The method of any one of embodiment 22-25, wherein the stimulus is selected from the group consisting of a chemical stimulus, a physical stimulus, a genetic stimulus and an energy stimulus.

27) The method of any one of embodiments 22-25, wherein the stimulus is light.

28) The method of embodiment 27, wherein the reporter molecule is a fluorescent protein, functional fragment, and/ or fusions thereof.

29) The method of embodiment 28, wherein the fluorescent protein is a GFP, RFP, YFP, CFP, or functional variant or fragment thereof.

30) The method of embodiment 28 or 29, wherein the fluorescent protein is GFP.

31) The method of embodiment 30, wherein the GFP is a superfolder GFP.

32) The method of any one of embodiments 28-31, wherein step (c) entails exposing the inoculated composition to light excitation sufficient to fluoresce the fluorescent protein, functional fragment, and/or fusions thereof.

33) The method of any one of embodiments 28-32, wherein the fluorescence is detected with a flow cytometer, a plate reader, or fluorescence-activated droplet sorting.

34) The method of any one of embodiments 22-33, further comprising isolating the bacterial mutants capable of fixing atmospheric nitrogen identified in (d).

35) The method of embodiment 34, wherein the isolated bacterial mutants are comprise a bacterium selected from a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof.

36) The method of embodiment 34, wherein the isolated bacterial mutants comprise a bacterium comprising at least one genetic variation introduced into a member selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH nifD, nifK, nifY, nifF, nifN, nifU, nifS, nifV, nifW, nifZ, nifM, nifF, nifB, nifQ, a gene associated with biosynthesis of a nitrogenase enzyme, or combinations thereof.

37) The method of embodiment 34 or 36, wherein the isolated bacterial mutants comprise a bacterium comprising at least one genetic variation in glnA.

38) The method of embodiment 37, wherein the at least one genetic variation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof.

39) The method of embodiment 38, wherein the *Klebsiella* glnA gene comprises a nucleic acid sequence of SEQ ID NO: 1.

40) The method of embodiment 38, wherein the homolog of the *Klebsiella* glnA gene is a *Kosakonia* glnA gene.

41) The method of embodiment 38 or 40, wherein the homolog of the *Klebsiella* glnA gene comprises a nucleic acid sequence of SEQ ID NO: 2.

42) The method of embodiment 38, wherein the homolog of the *Klebsiella* glnA gene is a *Metakosakonia* glnA gene.

43) The method of embodiment 38 or 42, wherein the homolog of the *Klebsiella* glnA gene comprises a nucleic acid sequence of SEQ ID NO: 3.

44) The method of any one of embodiments 37-43, wherein the glnA gene comprising the at least one genetic variation comprises a nucleic acid sequence selected from the group consisting of SEQ ID NOs 6-13 and 15-19.

45) The method of any one of embodiments 37-44, wherein expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof.

46) The method of any one of embodiments 37-44, wherein expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof.

47) The method of embodiment 45 or 46, wherein the *Klebsiella* GlnA protein comprises an amino acid sequence of SEQ ID NO: 24.

48) The method of embodiment 45 or 46, wherein the homolog of the *Klebsiella* GlnA protein is a *Kosakonia* GlnA protein.

49) The method of any one of embodiment 45, 46 or 48, wherein the homolog of the *Klebsiella* GlnA protein comprises an amino acid sequence of SEQ ID NO: 25.

50) The method of embodiment 45 or 46, wherein the homolog of the *Klebsiella* GlnA protein is a *Metakosakonia* GlnA protein.

51) The method of any one of embodiment 45, 46 or 50, wherein the homolog of the *Klebsiella* GlnA protein comprises an amino acid sequence of SEQ ID NO: 26.

52) The method of any one of embodiments 45-51, wherein the GlnA protein comprises an amino acid sequence selected from the group consisting of SEQ ID NOs 29-36 and 38-42.

53) The method of embodiment 37, wherein the at least one genetic variation in glnA comprises at least one nucleotide substitution at nucleotide position 308, 487, 511 and/or 657 of a *Paraburkholderia* glnA gene or in a homologous nucleotide position in a homolog thereof.

54) The method of embodiment 53, wherein the *Paraburkholderia* glnA gene comprises a nucleic acid sequence of SEQ ID NO: 4.

55) The method of any one of embodiments 37, 53 or 54, wherein the glnA gene comprising the at least one genetic variation comprises a nucleic acid sequence selected from the group consisting of SEQ ID NOs 20-23.

56) The method of any one of embodiments 37 or 53-55, wherein expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof.

57) The method of any one of embodiments 37 or 53-55, wherein expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof.

58) The method of embodiment 56 or 57, wherein the *Paraburkholderia* GlnA protein comprises an amino acid sequence of SEQ ID NO: 27.

59) The method of any one of embodiments 56-58, wherein the GlnA protein comprises an amino acid sequence selected from the group consisting of SEQ ID NOs 43-46.

60) The method of embodiment 34 or 36, wherein the isolated bacterial mutants comprise a bacterium comprising at least one genetic variation in glnE.

61) The method of embodiment 60, wherein the at least one genetic variation in glnE comprises at least one nucleotide substitution at nucleotide position 965 and/or 2838 of a *Klebsiella* glnE gene or at a homologous nucleotide position in a homolog thereof.

62) The method of embodiment 60 or 61, wherein the at least one genetic variation in glnE comprises at least one nucleotide substitution at nucleotide position 965 and 2838 of a *Klebsiella* glnE gene or at a homologous nucleotide position in a homolog thereof.

63) The method of embodiment 61 or 62, wherein the *Klebsiella* glnE gene comprises a nucleic acid sequence of SEQ ID NO: 5.

64) The method of any one of embodiments 60-63, wherein the glnE gene comprising the at least one genetic variation comprises a nucleic acid sequence of SEQ ID NO: 14.

65) The method of any one of embodiments 60-64, wherein expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof.

66) The method of any one of embodiments 60-64, wherein expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof.

67) The method of embodiment 65 or 66, wherein the amino acid substitution at position 322 or the homologous amino acid position is a G to E substitution.

68) The method of any one of embodiments 65-67, wherein the amino acid substitution at position 746 or the homologous amino acid position is a G to D substitution.

69) The method of any one of embodiments 65-68, wherein the *Klebsiella* GlnE protein comprises an amino acid sequence of SEQ ID NO: 28.

70) The method of any one of embodiments 65-69, wherein the GlnE protein comprises an amino acid sequence of SEQ ID NO: 37.

71) A method for high-throughput identification of one or more bacterial mutants capable of fixing atmospheric nitrogen, the method comprising. (a) exposing a population of bacteria to a mutagen; (b) transferring the population of bacteria in (a) into one or more samples comprising a medium; (c) co-culturing a biosensor within each of the one or more samples in (b), wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and(iv) a nucleic acid sequence encoding a positive nitrogen fixation regulatory protein; wherein the bacterium expresses the reporter molecule in the absence of ammonium; (d) exposing each of the one or more samples in (c) to a stimulus sufficient to activate the reporter molecule; and (e) identifying from the one or more samples in (d) one or more bacterial mutants capable of fixing atmospheric nitrogen as those that result in decreased output of the reporter molecule as compared to a control.

72) The method of embodiment 71, wherein the output of the reporter molecule of the one or more samples in (d) is measured following (d), as compared to a control composition.

73) The method of embodiment 72, wherein the control composition comprises microbes that do not express the reporter molecule.

74) The method of embodiment 72, wherein the control composition comprises microbes that express a functionally deleted variant of the reporter molecule.

75) The method of any one of embodiments 71-74, wherein the stimulus is selected from the group consisting of a chemical stimulus, a physical stimulus, a genetic stimulus and an energy stimulus.

76) The method of any one of embodiments 71-75, wherein the stimulus is light.

77) The method of embodiment 76, wherein the reporter molecule is a fluorescent protein, functional fragment, and/ or fusions thereof.

78) The method of embodiment 77, wherein the fluorescent protein is a GFP, RFP, YFP, CFP, or functional variant or fragment thereof.

79) The method of embodiment 77 or 78, wherein the fluorescent protein is GFP.

80) The method of embodiment 79, wherein the GFP is a superfolder GFP.

81) The method of any one of embodiments 77-80, wherein step (d) entails exposing the inoculated composition to light excitation sufficient to fluoresce the fluorescent protein, functional fragment, and/or fusions thereof.

82) The method of any one of embodiments 77-81, wherein the fluorescence is detected with a flow cytometer, a plate reader, or fluorescence-activated droplet sorting.

83) The method of any one of embodiments 71-80, further comprising isolating the bacterial mutants capable of fixing atmospheric nitrogen.

84) The method of embodiment 83, wherein the isolated bacterial mutants comprise a bacterium are selected from a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof.

85) The method of embodiment 83, wherein the isolated bacterial mutants comprise a bacterium comprising at least one genetic variation introduced into a member selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifF, nifN, nifU, nifS, nifV, nifW, nifZ, nifM, nifF, nifB, nifQ, a gene associated with biosynthesis of a nitrogenase enzyme, or combinations thereof.

86) The method of embodiment 83 or 85, wherein the isolated bacterial mutants comprise a bacterium comprising at least one genetic variation in glnA.

87) The method of embodiment 86, wherein the at least one genetic variation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof.

88) The method of embodiment 87, wherein the *Klebsiella* glnA gene comprises a nucleic acid sequence of SEQ ID NO: 1.

89) The method of embodiment 87, wherein the homolog of the *Klebsiella* glnA gene is a *Kosakonia* glnA gene.

90) The method of embodiment 87 or 89, wherein the homolog of the *Klebsiella* glnA gene comprises a nucleic acid sequence of SEQ ID NO: 2.

91) The method of embodiment 87, wherein the homolog of the *Klebsiella* glnA gene is a *Metakosakonia* glnA gene.

92) The method of embodiment 87 or 91, wherein the homolog of the *Klebsiella* glnA gene comprises a nucleic acid sequence of SEQ ID NO: 3.

93) The method of any one of embodiments 86-92, wherein the glnA gene comprising the at least one genetic variation comprises a nucleic acid sequence selected from the group consisting of SEQ ID NOs 6-13 and 15-19.

94) The method of any one of embodiments 86-93, wherein expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof.

95) The method of any one of embodiments 86-93, wherein expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof.

96) The method of embodiment 94 or 95, wherein the *Klebsiella* GlnA protein comprises an amino acid sequence of SEQ ID NO: 24.

97) The method of embodiment 94 or 95, wherein the homolog of the *Klebsiella* GlnA protein is a *Kosakonia* GlnA protein.

98) The method of any one of embodiment 94, 95 or 97, wherein the homolog of the *Klebsiella* GlnA protein comprises an amino acid sequence of SEQ ID NO: 25.

99) The method of embodiment 94 or 95, wherein the homolog of the *Klebsiella* GlnA protein is a *Metakosakonia* GlnA protein.

100) The method of any one of embodiment 94, 95 or 99, wherein the homolog of the *Klebsiella* GlnA protein comprises an amino acid sequence of SEQ ID NO: 26.

101) The method of any one of embodiments 94-100, wherein the GlnA protein comprises an amino acid sequence selected from the group consisting of SEQ ID NOs 29-36 and 38-42.

102) The method of embodiment 86, wherein the at least one genetic variation in glnA comprises at least one nucleotide substitution at nucleotide position 308, 487, 511 and/or 657 of a *Paraburkholderia* glnA gene or in a homologous nucleotide position in a homolog thereof.

103) The method of embodiment 102, wherein the *Paraburkholderia* glnA gene comprises a nucleic acid sequence of SEQ ID NO: 4.

104) The method of any one of embodiments 86, 102 or 103, wherein the glnA gene comprising the at least one genetic variation comprises a nucleic acid sequence selected from the group consisting of SEQ ID NOs 20-23.

105) The method of any one of embodiments 86 or 102-104, wherein expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof.

106) The method of any one of embodiments 86 or 102-104, wherein expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof.

107) The method of embodiment 105 or 106, wherein the *Paraburkholderia* GlnA protein comprises an amino acid sequence of SEQ ID NO: 27.

108) The method of any one of embodiments 105-107, wherein the GlnA protein comprises an amino acid sequence selected from the group consisting of SEQ ID NOs 43-46.

109) The method of embodiment 83 or 85, wherein the isolated bacterial mutants comprise at least one genetic variation in glnE.

110) The method of embodiment 109, wherein the at least one genetic variation in glnE comprises at least one nucleotide substitution at nucleotide position 965 and/or 2838 of a *Klebsiella* glnE gene or at a homologous nucleotide position in a homolog thereof.

111) The method of embodiment 109 or 110, wherein the at least one genetic variation in glnE comprises at least one nucleotide substitution at nucleotide position 965 and 2838 of a *Klebsiella* glnE gene or at a homologous nucleotide position in a homolog thereof.

112) The method of embodiment 110 or 111, wherein the *Klebsiella* glnE gene comprises a nucleic acid sequence of SEQ ID NO: 5.

113) The method of any one of embodiments 109-112, wherein the glnE gene comprising the at least one genetic variation comprises a nucleic acid sequence of SEQ ID NO: 14.

114) The method of any one of embodiments 109-113, wherein expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof.

115) The method of any one of embodiments 109-113, wherein expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof.

116) The method of embodiment 114 or 115, wherein the amino acid substitution at position 322 or the homologous amino acid position is a G to E substitution.

117) The method of any one of embodiments 114-116, wherein the amino acid substitution at position 746 or the homologous amino acid position is a G to D substitution.

118) The method of any one of embodiments 114-117, wherein the *Klebsiella* GlnE protein comprises an amino acid sequence of SEQ ID NO: 28.

119) The method of any one of embodiments 114-118, wherein the GlnE protein comprises an amino acid sequence of SEQ ID NO: 37.

120) The method of any one of embodiments 71-119, wherein the population of bacteria comprises at least 100,000 bacteria, and wherein the method for high-throughput identification is completed in less than four hours.

121) A method for identifying novel bacterial genes, pathways, and/or regulatory elements involved in fixing atmospheric nitrogen, the method comprising: (a) exposing a population of bacteria to a mutagen in a microbial composition; (b) inoculating the microbial composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein; wherein the bacterium expresses the reporter molecule in the absence of ammonium; (c) exposing the inoculated composition to a stimulus sufficient to activate the reporter molecule, (d) measuring the output of the reporter molecule of the inoculated composition following (c), as compared to a control composition; (e) isolating bacteria from inoculated compositions that exhibit a decreased output of the reporter molecule as compared to the control composition as bacteria capable of fixing atmospheric nitrogen; (f) sequencing the genome(s) of the bacteria capable of fixing atmospheric nitrogen from (e); and (g) identifying genes, pathways, and/or regulatory elements that contain mutations from the sequenced genomes.

122) The method of embodiment 121, wherein the control composition comprises microbes that do not express the reporter molecule.

123) The method of embodiment 121, wherein the control composition comprises microbes that express a functionally deleted variant of the reporter molecule.

124) The method of any one of embodiments 121-123, wherein the stimulus is selected from the group consisting of a chemical stimulus, a physical stimulus, a genetic stimulus and an energy stimulus.

125) The method of any one of embodiments 121-124, wherein the stimulus is light.

126) The method of embodiment 125, wherein the reporter molecule is a fluorescent protein, functional fragment, and/or fusions thereof.

127) The method of embodiment 126, wherein the fluorescent protein is a GFP, RFP, YFP, CFP, or functional variant or fragment thereof.

128) The method of embodiment 126 or 127, wherein the fluorescent protein is GFP.

129) The method of embodiment 128, wherein the GFP is a superfolder GFP.

130) The method of any one of embodiments 126-129, wherein step (c) entails exposing the inoculated composition to light excitation sufficient to fluoresce the fluorescent protein, functional fragment, and/or fusions thereof.

131) The method of any one of embodiments 126-129, wherein the fluorescence is detected with a flow cytometer, a plate reader, or fluorescence-activated droplet sorting.

132) The method of any one of embodiments 121-131, further comprising determining whether the genes, pathways, and/or regulatory elements contain mutations known to be associated with the fixation of atmospheric nitrogen.

133) The method of any one of embodiments 121-132, wherein the identified mutations comprise at least one mutation in glnA or glnE.

134) The method of embodiment 133, wherein the at least one mutation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof.

135) The method of embodiment 134, wherein the *Klebsiella* glnA gene comprises a nucleic acid sequence of SEQ ID NO: 1.

136) The method of embodiment 134, wherein the homolog of the *Klebsiella* glnA gene is a *Kosakonia* glnA gene.

137) The method of embodiment 134 or 136, wherein the homolog of the *Klebsiella* glnA gene comprises a nucleic acid sequence of SEQ ID NO: 2.

138) The method of embodiment 134, wherein the homolog of the *Klebsiella* glnA gene is a *Metakosakonia* glnA gene.

139) The method of embodiment 134 or 138, wherein the homolog of the *Klebsiella* glnA gene comprises a nucleic acid sequence of SEQ ID NO: 3.

140) The method of any one of embodiments 133-139, wherein the glnA gene comprising the at least one genetic variation comprises a nucleic acid sequence selected from the group consisting of SEQ ID NOs 6-13 and 15-19.

141) The method of any one of embodiments 133-140, wherein expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof.

142) The method of any one of embodiments 133-140, wherein expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof.

143) The method of embodiment 141 or 142, wherein the *Klebsiella* GlnA protein comprises an amino acid sequence of SEQ ID NO: 24.

144) The method of embodiment 141 or 142, wherein the homolog of the *Klebsiella* GlnA protein is a *Kosakonia* GlnA protein.

145) The method of any one of embodiment 141, 142 or 144, wherein the homolog of the *Klebsiella* GlnA protein comprises an amino acid sequence of SEQ ID NO: 25.

146) The method of embodiment 141 or 142, wherein the homolog of the *Klebsiella* GlnA protein is a *Metakosakonia* GlnA protein.

147) The method of any one of embodiment 141, 142 or 146, wherein the homolog of the *Klebsiella* GlnA protein comprises an amino acid sequence of SEQ ID NO: 26.

148) The method of any one of embodiments 141-147, wherein the GlnA protein comprises an amino acid sequence selected from the group consisting of SEQ ID NOs 29-36 and 38-42.

149) The method of embodiment 133, wherein the at least one genetic variation in glnA comprises at least one nucleotide substitution at nucleotide position 308, 487, 511 and/or 657 of a *Paraburkholderia* glnA gene or in a homologous nucleotide position in a homolog thereof.

150) The method of embodiment 149, wherein the *Paraburkholderia* glnA gene comprises a nucleic acid sequence of SEQ ID NO: 4.

151) The method of any one of embodiments 133, 149 or 150, wherein the glnA gene comprising the at least one genetic variation comprises a nucleic acid sequence selected from the group consisting of SEQ ID NOs 20-23.

152) The method of any one of embodiments 133 or 147-151, wherein expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof.

153) The method of any one of embodiments 133 or 147-151, wherein expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof.

154) The method of embodiment 152 or 153, wherein the *Paraburkholderia* GlnA protein comprises an amino acid sequence of SEQ ID NO: 27.

155) The method of any one of embodiments 152-154, wherein the GlnA protein comprises an amino acid sequence selected from the group consisting of SEQ ID NOs 43-46.

156) The method of embodiment 133, wherein the at least one genetic variation in glnE comprises at least one nucleotide substitution at nucleotide position 965 and/or 2838 of a *Klebsiella* glnE gene or at a homologous nucleotide position in a homolog thereof.

157) The method of embodiment 133 or 156, wherein the at least one genetic variation in glnE comprises at least one nucleotide substitution at nucleotide position 965 and 2838 of a *Klebsiella* glnE gene or at a homologous nucleotide position in a homolog thereof.

158) The method of embodiment 156 or 157, wherein the *Klebsiella* glnE gene comprises a nucleic acid sequence of SEQ ID NO: 5.

159) The method of any one of embodiments 133 or 156-158, wherein the glnE gene comprising the at least one genetic variation comprises a nucleic acid sequence of SEQ ID NO: 14.

160) The method of any one of embodiments 133 or 156-159, wherein expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof.

161) The method of any one of embodiments 133 or 156-159, wherein expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof.

162) The method of embodiment 160 or 161, wherein the amino acid substitution at position 322 or the homologous amino acid position is a G to E substitution.

163) The method of any one of embodiments 160-162, wherein the amino acid substitution at position 746 or the homologous amino acid position is a G to D substitution.

164) The method of any one of embodiments 160-163, wherein the *Klebsiella* GlnE protein comprises an amino acid sequence of SEQ ID NO: 28.

165) The method of any one of embodiments 160-164, wherein the GlnE protein comprises an amino acid sequence of SEQ ID NO: 37.

166) A method for identification of bacterial mutants capable of fixing atmospheric nitrogen, the method comprising: (a) exposing a population of bacteria to a mutagen; (b) exposing the population of bacteria exposed to the mutagen in (a) to a diazotrophic growth inhibitor in a microbial composition; (c) co-culturing the microbial composition with a biosensor, wherein the biosensor comprises a bacterium, which comprises: (i) a nucleic acid sequence encoding a reporter molecule, (ii) a promoter or fragment thereof selected from the Nif regulon operably linked to the nucleic acid sequence of (i), (iii) a nucleic acid sequence encoding an inhibitory nitrogen fixation regulatory protein, and (iv) a nucleic acid sequence encoding a positive nitrogen fixation regulatory protein, wherein the bacterium expresses the reporter molecule in the absence of ammonium; (d) exposing the co-cultured composition to a stimulus sufficient to activate the reporter molecule; and (e) identifying bacterial mutants capable of fixing atmospheric nitrogen as those that result in decreased or no output of the reporter molecule, as compared to a control.

167) The method of embodiment 166, wherein the diazotrophic growth inhibitor is ethylenediamine (EDA) or methylammonium.

168) The method of embodiment 166 or 167, wherein the output of the reporter molecule of the one or more samples in (d) is measured following (d), as compared to a control composition.

169) The method of embodiment 168, wherein the control composition comprises microbes that do not express the reporter molecule.

170) The method of embodiment 168, wherein the control composition comprises microbes that express a functionally deleted variant of the reporter molecule.

171) The method of any one of embodiments 166-170, wherein the stimulus is selected from the group consisting of a chemical stimulus, a physical stimulus, a genetic stimulus and an energy stimulus.

172) The method of any one of embodiments 166-171, wherein the stimulus is light.

173) The method of embodiment 172, wherein the reporter molecule is a fluorescent protein, functional fragment, and/or fusions thereof.

174) The method of embodiment 173, wherein the fluorescent protein is a GFP, RFP, YFP, CFP, or functional variant or fragment thereof.

175) The method of embodiment 173 or 174, wherein the fluorescent protein is GFP.

176) The method of embodiment 175, wherein the GFP is a superfolder GFP.

177) The method of any one of embodiments 173-176, wherein step (d) entails exposing the inoculated composition to light excitation sufficient to fluoresce the fluorescent protein, functional fragment, and/or fusions thereof.

178) The method of any one of embodiments 173-177, wherein the fluorescence is detected with a flow cytometer, a plate reader, or fluorescence-activated droplet sorting.

179) The method of any one of embodiments 166-178, further comprising isolating the bacterial mutants identified as capable of fixing atmospheric nitrogen.

180) The method of embodiment 179, wherein the isolated bacterial mutants are comprise a bacterium selected from a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725, a bacterium deposited as PTA-126726 and combinations thereof.

181) The method of embodiment 179, wherein the isolated bacterial mutants comprise bacteria which comprise at least one genetic variation introduced into a member selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifW, nifZ, nifM, nifF, nifB, nifQ, a gene associated with biosynthesis of a nitrogenase enzyme, or combinations thereof.

182) The method of embodiment 179 or 181, wherein the isolated bacterial mutants comprise a bacterium comprising a genetic variation in glnA.

183) The method of embodiment 182, wherein the at least one genetic variation in glnA comprises at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof.

184) The method of embodiment 183, wherein the *Klebsiella* glnA gene comprises a nucleic acid sequence of SEQ ID NO: 1.

185) The method of embodiment 183, wherein the homolog of the *Klebsiella* glnA gene is a *Kosakonia* glnA gene.

186) The method of embodiment 183 or 185, wherein the homolog of the *Klebsiella* glnA gene comprises a nucleic acid sequence of SEQ ID NO: 2.

187) The method of embodiment 183, wherein the homolog of the *Klebsiella* glnA gene is a *Metakosakonia* glnA gene.

188) The method of embodiment 183 or 187, wherein the homolog of the *Klebsiella* glnA gene comprises a nucleic acid sequence of SEQ ID NO: 3.

189) The method of any one of embodiments 182-188, wherein the glnA gene comprising the at least one genetic variation comprises a nucleic acid sequence selected from the group consisting of SEQ ID NOs 6-13 and 15-19.

190) The method of any one of embodiments 182-189, wherein expression of the glnA gene comprising the at least one genetic variation produces a GlnA protein comprising at least one amino acid substitution at amino acid position 66, 157, 172, 174, 189, 208, 218, 255, 268, 329 and/or 339 of a *Klebsiella* GlnA protein or at a homologous amino acid position in a homolog thereof.

191) The method of any one of embodiments 182-189, wherein expression of the glnA gene comprising the at least one genetic variation produces a GlnA protein comprising at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof.

192) The method of embodiment 190 or 191, wherein the *Klebsiella* GlnA protein comprises an amino acid sequence of SEQ ID NO: 24.

193) The method of embodiment 190 or 191, wherein the homolog of the *Klebsiella* GlnA protein is a *Kosakonia* GlnA protein.

194) The method of any one of embodiment 190, 191 or 193, wherein the homolog of the *Klebsiella* GlnA protein comprises an amino acid sequence of SEQ ID NO: 25.

195) The method of embodiment 190 or 191, wherein the homolog of the *Klebsiella* GlnA protein is a *Metakosakonia* GlnA protein.

196) The method of any one of embodiment 190, 191 or 195, wherein the homolog of the *Klebsiella* GlnA protein comprises an amino acid sequence of SEQ ID NO: 26.

197) The method of any one of embodiments 190-196, wherein the GlnA protein comprises an amino acid sequence selected from the group consisting of SEQ ID NOs 29-36 and 38-42.

198) The method of embodiment 182, wherein the at least one genetic variation in glnA comprises at least one nucleotide substitution at nucleotide position 308, 487, 511 and/or 657 of a *Paraburkholderia* glnA gene or in a homologous nucleotide position in a homolog thereof.

199) The method of embodiment 198, wherein the *Paraburkholderia* glnA gene comprises a nucleic acid sequence of SEQ ID NO: 4.

200) The method of any one of embodiments 182, 198 or 199, wherein the glnA gene comprising the at least one genetic variation comprises a nucleic acid sequence selected from the group consisting of SEQ ID NOs 20-23.

201) The method of any one of embodiments 182 or 198-200, wherein expression of the glnA gene comprising the at least one genetic variation produces a GlnA protein comprising at least one amino acid substitution at amino acid position 103, 163, 171 and/or 219 of a *Paraburkholderia* GlnA protein or in a homologous position in a homolog thereof.

202) The method of any one of embodiments 182 or 198-200, wherein expression of the glnA gene comprising the at least one genetic variation produces a GlnA protein comprising at least one amino acid substitution selected from the group consisting of Y103C, S163P, N171D and/or Q219H of a *Paraburkholderia* GlnA protein and identical amino acid substitutions in homologous amino acid positions in a homolog thereof.

203) The method of embodiment 201 or 202, wherein the *Paraburkholderia* GlnA protein comprises an amino acid sequence of SEQ ID NO: 27.

204) The method of any one of embodiments 201-203, wherein the GlnA protein comprises an amino acid sequence selected from the group consisting of SEQ ID NOs 43-46.

205) The method of embodiment 179 or 181, wherein the isolated bacterial mutants comprise at least one genetic variation in glnE.

206) The method of embodiment 205, wherein the at least one genetic variation in glnE comprises at least one nucleotide substitution at nucleotide position 965 and/or 2838 of a *Klebsiella* glnE gene or at a homologous nucleotide position in a homolog thereof.

207) The method of embodiment 205 or 206, wherein the at least one genetic variation in glnE comprises at least one nucleotide substitution at nucleotide position 965 and 2838 of a *Klebsiella* glnE gene or at a homologous nucleotide position in a homolog thereof.

208) The method of embodiment 206 or 207, wherein the *Klebsiella* glnE gene comprises a nucleic acid sequence of SEQ ID NO: 5.

209) The method any one of embodiments 205-208, wherein the glnE gene comprising the at least one genetic variation comprises a nucleic acid sequence of SEQ ID NO: 14.

210) The method of any one of embodiments 205-209, wherein expression of the glnE gene comprising the at least one genetic variation produces a GlnE protein comprising at least one amino acid substitution at amino acid position 322 and/or 746 of a *Klebsiella* GlnE protein or at a homologous amino acid position in a homolog thereof.

211) The method of any one of embodiments 205-209, wherein expression of the glnE gene comprising the at least one genetic variation produces a GlnE protein comprising at least one amino acid substitution at amino acid position 322 and 746 of a *Klebsiella* GlnE protein or at a homologous amino acid position in a homolog thereof.

212) The method of embodiment 210 or 211, wherein the amino acid substitution at position 322 or the homologous amino acid position is a G to E substitution.

213) The method of any one of embodiments 210-212, wherein the amino acid substitution at position 746 or the homologous amino acid position is a G to D substitution.

214) The method of any one of embodiments 210-213, wherein the *Klebsiella* GlnE protein comprises an amino acid sequence of SEQ ID NO: 28.

215) The method of any one of embodiments 210-214, wherein the GlnE protein comprises an amino acid sequence of SEQ ID NO: 37.

216) The method of any one of embodiments 11-215, wherein the promoter or fragment thereof is selected from the nifHDK operon.

217) The method of any one of embodiments 11-216, wherein the promoter is a nifH promoter.

218) The method of any one of embodiments 11-217, wherein the inhibitory nitrogen fixation regulatory protein is NifL.

219) The method of any one of embodiments 11-218, wherein the positive nitrogen fixation regulatory protein is NifA.

220) The method of any one of embodiments 22-219, wherein the population of bacteria is selected from wild-type bacteria, transgenic mutant bacteria, non-intergeneric mutant bacteria and intergeneric mutant bacteria.

221) The method of any one of embodiments 22-220, wherein the mutagen is selected from mitomycin C (MMC), N-methyl-N-nitrosourea (MNU), nitrous acid (NA), diepoxybutane (DEB), 1, 2, 7, 8-diepoxyoctane (DEO), ethyl methane sulfonate (EMS), methyl methane sulfonate (MMS), N-methyl-N'-nitro-N-nitrosoguanidine (MNNG), 4-nitroquinoline 1-oxide (4-NQO), 2-methyloxy-6-chloro-9 (3-[ethyl-2-chloroethyl]-aminopropylamin)-acridinedihydrochloride (ICR-170), 2-amino purine (2AP), and hydroxylamine (HA).

222) The method of embodiment 95221, wherein the mutagen is EMS.

223) A microbial composition, comprising: one or more isolated bacteria selected from the group consisting of a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725 and a bacterium deposited as PTA-126726.

224) The microbial composition of embodiment 223, further comprising an agriculturally acceptable carrier.

225) The microbial composition of embodiment 223, wherein the one or more isolated bacteria fix atmospheric nitrogen at a rate higher than a wild type parental lineage bacteria.

226) A nitrogen fixing bacterium comprising a mutant glnE gene comprising at least one nucleotide substitution at nucleotide position 965 and/or 2838 of a *Klebsiella* glnE gene or at a homologous nucleotide position in a homolog thereof.

227) The nitrogen fixing bacterium of embodiment 226, wherein the mutant glnE gene comprises a nucleotide substitution at nucleotide position 965 and 2838 of the *Klebsiella* glnE gene or in homologous nucleotide positions in the homolog thereof.

228) The nitrogen fixing bacterium of embodiment 226 or 227, wherein the mutant glnE gene shares at least 85%, 86%, 87%, 88%, 89%, 90%, 91%, 92%, 93%, 94%, 95%, 96%, 97%, 98%, or 99% identity with the *Klebsiella* glnE gene or the homolog thereof.

229) The nitrogen fixing bacterium of embodiment 226, wherein expression of the mutant glnE gene produces a mutant GlnE protein with at least one amino acid substitution at amino acid position 322 and/or 746 of a *Klebsiella* GlnE protein or at a homologous amino acid position in a homolog thereof.

230) The nitrogen fixing bacterium of embodiment 227, wherein expression of the mutant glnE gene produces a mutant GlnE protein with amino acid substitutions at amino acid positions 322 and 746 of the *Klebsiella* GlnE protein or at homologous amino acid positions in the homolog thereof.

231) The nitrogen fixing bacterium of embodiment 229 or 230, wherein the amino acid substitution at position 322 or the homologous amino acid position is a G to E substitution.

232) The nitrogen fixing bacterium of any one of embodiments 229-231, wherein the amino acid substitution at position 746 or the homologous amino acid position is a G to D substitution.

233) The nitrogen fixing bacterium of any one of embodiments 229-232, wherein the mutant GlnE protein shares at least 90%, 91%, 92%, 93%, 94%, 95%, 96%, 97%, 98%, or 99% identity with the *Klebsiella* GlnE protein or the homolog thereof.

234) The nitrogen fixing bacterium of any one of embodiments 226-233, wherein the *Klebsiella* glnE gene comprises a nucleic acid sequence of SEQ ID NO: 5.

235) The nitrogen fixing bacterium of any one of embodiments 226-234, wherein the mutant glnE gene comprises a nucleic acid sequence of SEQ ID NO: 14.

236) The nitrogen fixing bacterium of any one of embodiments 226-235, wherein the *Klebsiella* GlnE protein comprises an amino acid sequence of SEQ ID NO: 28.

237) The nitrogen fixing bacterium of any one of embodiments 229-236, wherein the mutant GlnE protein comprises an amino acid sequence of SEQ ID NO: 37.

238) A nitrogen fixing bacterium comprising a mutant glnE gene encoding a GlnE protein comprising an amino acid sequence with at least one amino acid substitution at amino acid positions 322 and/or 746 of a *Klebsiella* GlnE protein or at a homologous amino acid position in a homolog thereof.

239) The nitrogen fixing bacterium of embodiment 238, wherein the GlnE protein comprises amino acid substitutions at amino acid positions 322 and 746 of the *Klebsiella* GlnE protein or at homologous amino acid positions in the homolog thereof.

240) The nitrogen fixing bacterium of embodiment 238 or 239, wherein the amino acid substitution at position 322 or the homologous amino acid position is a G to E substitution.

241) The nitrogen fixing bacterium of any one of embodiments 238-240, wherein the amino acid substitution at position 746 or the homologous amino acid position is a G746D substitution.

242) The nitrogen fixing bacterium of any one of embodiments 238-241, wherein the GlnE protein shares at least 90%, 91%, 92%, 93%, 94%, 95%, 96%, 97%, 98%, or 99% identity with the *Klebsiella* GlnE protein or the homolog thereof.

243) The nitrogen fixing bacterium of any one of embodiments 238-242, wherein the *Klebsiella* GlnE protein comprises an amino acid sequence of SEQ ID NO: 28.

244) The nitrogen fixing bacterium of any one of embodiments 238-243, wherein the mutant GlnE protein comprises an amino acid sequence of SEQ ID NO: 37.

245) A nitrogen fixing bacterium comprising a mutant GlnE protein comprising an amino acid sequence with at least one amino acid substitution at amino acid positions 322 and/or 746 of a *Klebsiella* GlnE protein or at a homologous amino acid position in a homolog thereof.

246) The nitrogen fixing bacterium of embodiment 245, wherein the GlnE protein comprises amino acid substitutions at amino acid positions 322 and 746 of the *Klebsiella* GlnE protein or at homologous amino acid positions in the homolog thereof.

247) The nitrogen fixing bacterium of embodiment 245 or 246, wherein the amino acid substitution at position 322 or the homologous amino acid position is a G to E substitution.

248) The nitrogen fixing bacterium of any one of embodiments 245-247, wherein the amino acid substitution at position 746 or the homologous amino acid position is a G to D substitution.

249) The nitrogen fixing bacterium of any one of embodiments 245-248, wherein the GlnE protein shares at least 90%, 91%, 92%, 93%, 94%, 95%, 96%, 97%, 98%, or 99% identity with the *Klebsiella* GlnE protein or the homolog thereof.

250) The nitrogen fixing bacterium of any one of embodiments 245-249, wherein the *Klebsiella* GlnE protein comprises an amino acid sequence of SEQ ID NO: 28.

251) The nitrogen fixing bacterium of any one of embodiments 245-250, wherein the mutant GlnE protein comprises an amino acid sequence of SEQ ID NO: 37.

252) The nitrogen fixing bacterium of any one of embodiments 226-251, wherein the nitrogen fixing bacterium is *Klebsiella variicola* CI4874.

253) A nitrogen fixing bacterium comprising a mutant glnA gene comprising at least one nucleotide substitution at nucleotide position 198, 469, 515, 521, 566, 622, 652, 764, 802, 986 and/or 1015 of a *Klebsiella* glnA gene or at a homologous nucleotide position in a homolog thereof.

254) The nitrogen fixing bacterium of embodiment 253, wherein the mutant glnA gene shares at least 85%, 86%, 87%, 88%, 89%, 90%, 91%, 92%, 93%, 94%, 95%, 96%, 97%, 98%, or 99% identity with the *Klebsiella* glnA gene or the homolog thereof.

255) The nitrogen fixing bacterium of embodiment 253 or 254, wherein expression of the mutant glnA gene produces a mutant GlnA protein with at least one amino acid substitution at amino acid position 66, 157, 172, 174, 189, 208, 218, 255, 268, 329 and/or 339 of a *Klebsiella* GlnA protein or at a homologous amino acid position in a homolog thereof.

256) The nitrogen fixing bacterium of embodiment 253 or 254, wherein expression of the mutant glnA gene produces a mutant GlnA protein with at least one amino acid substitution selected from the group consisting of M66I, M66V, G157C, H172L, P174L, S189F, E208K, G218S, T255I, G268S, A329V and/or N339D of a *Klebsiella* GlnA protein and identical amino acid substitutions at homologous amino acid positions in a homolog thereof.

257) The nitrogen fixing bacterium of embodiment 255 or 256, wherein the mutant GlnA protein shares at least 90%, 91%, 92%, 93%, 94%, 95%, 96%, 97%, 98%, or 99% identity with the *Klebsiella* GlnA protein or the homolog thereof.

258) The nitrogen fixing bacterium of any one of embodiments 253-257, wherein the *Klebsiella* glnA gene comprises a nucleic acid sequence of SEQ ID NO: 1.

259) The nitrogen fixing bacterium of any one of embodiments 253-257, wherein the homolog of the *Klebsiella* glnA gene is a *Kosakonia* glnA gene.

260) The nitrogen fixing bacterium of any one of embodiments 253-257 or 259, wherein the homolog of the *Klebsiella* glnA gene comprises a nucleic acid sequence of SEQ ID NO: 2.

261) The nitrogen fixing bacterium of any one of embodiments 253-257, wherein the homolog of the *Klebsiella* glnA gene is a *Metakosakonia* glnA gene.

262) The nitrogen fixing bacterium of any one of embodiments 253-257 or 261, wherein the homolog of the *Klebsiella* glnA gene comprises a nucleic acid sequence of SEQ ID NO: 3.

263) The nitrogen fixing bacterium of any one of embodiments 253-262, wherein the mutant glnA gene comprises a nucleic acid sequence selected from the group consisting of SEQ ID NOs 6-13 and 15-19.

264) The nitrogen fixing bacterium of any one of embodiments 255-258, wherein the *Klebsiella* GlnA protein comprises an amino acid sequence of SEQ ID NO: 24.

265) The nitrogen fixing bacterium of any one of embodiments 255-257, 259-260 or 263, wherein the homolog of the *Klebsiella* GlnA protein comprises an amino acid sequence of SEQ ID NO: 25.

266) The nitrogen fixing bacterium of any one of embodiments 255-257 or 261-263, wherein the homolog of the *Klebsiella* GlnA protein comprises an amino acid sequence of SEQ ID NO: 26.

267) The nitrogen fixing bacterium of any one of embodiments 255-266, wherein the mutant GlnA protein comprises an amino acid sequence selected from the group consisting of SEQ ID NOs 29-36 and 38-42.

268) A nitrogen fixing bacterium comprising a mutant glnA gene encoding a GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof.

269) The nitrogen fixing bacterium of embodiment 268, wherein the least one amino acid substitution is selected from the group consisting of M66I, M66V, G157C, H172L, P174L, S189F, E208K, G218S, T255I, G268S, A329V and N339D of the *Klebsiella* GlnA protein and identical amino acid substitutions at homologous positions in the homolog thereof.

270) The nitrogen fixing bacterium of embodiment 268 or 269, wherein the mutant GlnA protein shares at least 90%, 91%, 92%, 93%, 94%, 95%, 96%, 97%, 98%, or 99% identity with the *Klebsiella* GlnA protein or the homolog thereof.

271) The nitrogen fixing bacterium of any one of embodiments 268-270, wherein the *Klebsiella* GlnA protein comprises an amino acid sequence of SEQ ID NO: 24.

272) The nitrogen fixing bacterium of any one of embodiments 268-270, wherein the homolog of the *Klebsiella* GlnA protein is a *Kosakonia* GlnA protein.

273) The nitrogen fixing bacterium of any one of embodiments 268-270 or 272, wherein the homolog of the *Klebsiella* GlnA protein comprises an amino acid sequence of SEQ ID NO: 25.

274) The nitrogen fixing bacterium of any one of embodiments 268-270, wherein the homolog of the *Klebsiella* GlnA protein is a *Metakosakonia* GlnA protein.

275) The nitrogen fixing bacterium of any one of embodiments 268-270 or 274, wherein the homolog of the *Klebsiella* GlnA protein comprises an amino acid sequence of SEQ ID NO: 26.

276) The nitrogen fixing bacterium of any one of embodiments 268-275, wherein the GlnA protein comprises an amino acid sequence selected from the group consisting of SEQ ID NOs 29-36 and 38-42.

277) A nitrogen fixing bacterium comprising a mutant GlnA protein comprising an amino acid sequence with at least one amino acid substitution at amino acid positions 66, 157, 172, 174, 189, 208, 218, 255, 268, 329 and/or 339 of a *Klebsiella* GlnA protein or at a homologous amino acid position in a homolog thereof.

278) The nitrogen fixing bacterium of embodiment 277, wherein the least one amino acid substitution is selected from the group consisting of M66I, M66V, G157C, H172L, P174L, S189F, E208K, G218S, T255I, G268S, A329V and N339D of the *Klebsiella* GlnA protein and identical amino acid substitutions in homologous amino acid positions in the homolog thereof.

279) The nitrogen fixing bacterium of embodiment 277 or 278, wherein the mutant GlnA protein shares at least 90%, 91%, 92%, 93%, 94%, 95%, 96%, 97%, 98%, or 99% identity with the *Klebsiella* GlnA protein or the homolog thereof.

280) The nitrogen fixing bacterium of any one of embodiments 277-279, wherein the *Klebsiella* GlnA protein comprises an amino acid sequence of SEQ ID NO: 24.

281) The nitrogen fixing bacterium of any one of embodiments 277-279, wherein the homolog of the *Klebsiella* GlnA protein is a *Kosakonia* GlnA protein.

282) The nitrogen fixing bacterium of any one of embodiments 277-279 or 281, wherein the homolog of the *Klebsiella* GlnA protein comprises an amino acid sequence of SEQ ID NO: 25.

283) The nitrogen fixing bacterium of any one of embodiments 277-279, wherein the homolog of the *Klebsiella* GlnA protein is a *Metakosakonia* GlnA protein.

284) The nitrogen fixing bacterium of any one of embodiments 277-279 or 283, wherein the homolog of the *Klebsiella* GlnA protein comprises an amino acid sequence of SEQ ID NO: 26.

285) The nitrogen fixing bacterium of any one of embodiments 277-284, wherein the GlnA protein comprises an amino acid sequence selected from the group consisting of SEQ ID NOs 29-36 and 38-42.

286) The nitrogen fixing bacterium of any one of embodiments 253-285, wherein the nitrogen fixing bacterium is selected from the group consisting of *Klebsiella variicola* CI3296, *Klebsiella variicola* CI3936, *Klebsiella variicola* CI3933, *Klebsiella variicola* CI3927, *Klebsiella variicola* CI3925. *Klebsiella variicola* CI3943, *Klebsiella variicola* 013940, *Klebsiella variicola* CI3938, *Kosakonia sacchari* CI4065, *Metakosakonia intestini* CI4875, *Metakosakonia intestini* CI4876, *Metakosakonia intestini* CI4877 and *Metakosakonia intestini* CI4878.

287) A nitrogen fixing bacterium comprising a mutant glnA gene comprising at least one nucleotide substitution at nucleotide position 308, 487, 511 and/or 657 of a *Paraburkholderia* glnA gene or in a homologous nucleotide position in a homolog thereof.

288) The nitrogen fixing bacterium of embodiment 287, wherein the mutant glnA gene shares at least 85%, 86%, 87%, 88%, 89%, 90%, 91%, 92%, 93%, 94%, 95%, 96%, 97%, 98%, or 99% identity with the *Paraburkholderia* glnA gene or the homolog thereof.

289) The nitrogen fixing bacterium of embodiment 287 or 288, wherein expression of the mutant glnA gene produces a mutant GlnA protein with at least one amino acid substitution at amino acid position 103, 163, 171 and/or 219 of a *Paraburkholderia* GlnA protein or in a homologous position in a homolog thereof.

290) The nitrogen fixing bacterium of embodiment 287 or 288, wherein expression of the mutant glnA gene produces a mutant GlnA protein with at least one amino acid substitution selected from the group consisting of Y103C, S163P, N171D and/or Q219H of a *Paraburkholderia* GlnA protein and identical amino acid substitutions in homologous amino acid positions in a homolog thereof.

291) The nitrogen fixing bacterium of embodiment 289 or 290, wherein the mutant GlnA protein shares at least 90%, 91%, 92%, 93%, 94%, 95%, 96%, 97%, 98%, or 99% identity with the *Paraburkholderia* GlnA protein or the homolog thereof.

292) The nitrogen fixing bacterium of any one of embodiments 287-291, wherein the *Paraburkholderia* glnA gene comprises a nucleic acid sequence of SEQ ID NO: 4.

293) The nitrogen fixing bacterium of any one of embodiments 287-292, wherein the mutant glnA gene comprises a nucleic acid sequence selected from the group consisting of SEQ ID NOs 20-23.

294) The nitrogen fixing bacterium of any one of embodiments 289-293, wherein the *Paraburkholderia* GlnA protein comprises an amino acid sequence of SEQ ID NO: 27.

295) The nitrogen fixing bacterium of any one of embodiments 289-294, wherein the mutant GlnA protein comprises an amino acid sequence selected from the group consisting of SEQ ID NOs 43-46.

296) A nitrogen fixing bacterium comprising a mutant glnA gene encoding a GlnA protein comprising an amino acid sequence with at least one amino acid substitution at amino acid positions 103, 163, 171 and/or 219 of a *Paraburkholderia* GlnA protein or in a homologous amino acid position in a homolog thereof.

297) The nitrogen fixing bacterium of embodiment 296, wherein the least one amino acid substitution is selected from the group consisting of Y103C, S163P, N171D and Q219H of the *Paraburkholderia* GlnA protein and identical amino acid substitutions in homologous amino acid positions in the homolog thereof.

298) The nitrogen fixing bacterium of embodiment 296 or 297, wherein the mutant GlnA protein shares at least 90%, 91%, 92%, 93%, 94%, 95%, 96%, 97%, 98%, or 99% identity with the *Paraburkholderia* GlnA protein or the homolog thereof.

299) The nitrogen fixing bacterium of any one of embodiments 296-298, wherein the *Paraburkholderia* GlnA protein comprises an amino acid sequence of SEQ ID NO: 27.

300) The nitrogen fixing bacterium of any one of embodiments 296-299, wherein the GlnA protein comprises an amino acid sequence selected from the group consisting of SEQ ID NOs 43-46.

301) A nitrogen fixing bacterium comprising a mutant GlnA protein comprising an amino acid sequence with at least one amino acid substitution at amino acid positions 103, 163, 171 and/or 219 of a *Paraburkholderia* GlnA protein or in homologous amino acid positions in a homolog thereof.

302) The nitrogen fixing bacterium of embodiment 301, wherein the least one amino acid substitution is selected from the group consisting of Y103C, S163P, N171D and Q219H of the *Paraburkholderia* GlnA protein and identical amino acid substitutions in homologous amino acid positions in the homolog thereof.

303) The nitrogen fixing bacterium of embodiment 301 or 302, wherein the mutant GlnA protein shares at least 90%, 91%, 92%, 93%, 94%, 95%, 96%, 97%, 98%, or 99% identity with the *Paraburkholderia* GlnA protein or the homolog thereof.

304) The nitrogen fixing bacterium of any one of embodiments 301-303, wherein the *Paraburkholderia* GlnA protein comprises an amino acid sequence of SEQ ID NO: 27.

305) The nitrogen fixing bacterium of any one of embodiments 301-304, wherein the GlnA protein comprises an amino acid sequence selected from the group consisting of SEQ ID NOs 43-46.

306) The nitrogen fixing bacterium of any one of embodiments 287-305, wherein the nitrogen fixing bacterium is selected from the group consisting of *Paraburkholderia tropica* CI4751, *Paraburkholderia tropica* (14753, *Paraburkholderia tropica* 714879 and *Paraburkholderia tropica* (C4752.

307) The nitrogen fixing bacterium of any one of embodiments 226-306, wherein the bacterium is genetically engineered.

308) A microbial composition comprising the nitrogen fixing bacterium of any one of embodiments 226-307 and a carrier.

309) A method of providing fixed nitrogen to a plant comprising applying a microbial composition to a plant, a plant part, or a locus in which the plant is located, or a locus in which the plant will be grown, wherein the microbial composition comprises at least one nitrogen fixing bacterium of any one of embodiments 226-306.

310) The method of embodiment 309, wherein the microbial composition produces 1% or more of fixed nitrogen in the plant.

311) The method of any one of embodiments 309-310, wherein the composition is a solid.

312) The method of any one of embodiments 309-310, wherein the composition is a liquid.

313) The method of any one of embodiments 309-312, wherein the applying comprises coating a seed or other plant propagation member with the microbial composition.

314) The method of embodiment 313, wherein the at least one nitrogen fixing bacterium in the microbial composition has an average colonization ability per unit of plant root tissue of at least about $1.0\times10^4$ cfu per gram of fresh weight of plant root tissue and produce fixed N of at least about $1\times10^5$ mmol N per bacterial cell per hour.

315) The method of embodiment 313, wherein the applying comprises performing in-furrow treatment of the microbial composition.

316) The method of embodiment 315, wherein the in-furrow treatment comprises applying the microbial composition at a concentration per acre of between about $1\times10^6$ to about $3\times10^{12}$ cfu per acre.

317) The method of embodiment 315 or 316, wherein the microbial composition is a liquid formulation comprising about $1\times10^6$ to about $1\times10^{11}$ cfu of bacterial cells per milliliter.

SEQUENCES OF THE DISCLOSURE WITH SEQ ID NO IDENTIFIERS

| Gene Name | Nucleic Acid SEQ ID NO. | Amino Acid SEQ ID NO: | Strain |
|---|---|---|---|
| glnA | 1 | 24 | K. variicola CI137, 137 |
| glnA | 2 | 25 | K. sacchari 6 |
| glnA | 3 | 26 | M. intestini 910 |
| glnA | 4 | 27 | P. tropica 8 |
| glnE | 5 | 28 | K. variicola CI137, 137 |
| glnA | 6 | 29 | K. variicola CI3296, 137-3296 |

-continued

SEQUENCES OF THE DISCLOSURE WITH SEQ ID NO IDENTIFIERS

| Gene Name | Nucleic Acid SEQ ID NO. | Amino Acid SEQ ID NO: | Strain |
|---|---|---|---|
| glnA | 7 | 30 | K. variicola CI3936, 137-3936 |
| glnA | 8 | 31 | K. variicola CI3933, 137-3933 |
| glnA | 9 | 32 | K. variicola CI3927, 137-3927 |
| glnA | 10 | 33 | K. variicola CI3925, 137-3925 |
| glnA | 11 | 34 | K. variicola CI3943, 137-3943 |
| glnA | 12 | 35 | K. variicola CI3940, 137-3940 |
| glnA | 13 | 36 | K. variicola CI3938, 137-3938 |
| glnE | 14 | 37 | K. variicola CI4874, 137-4874 |
| glnA | 15 | 38 | K. sacchari CI4065, 6-4065 |
| glnA | 16 | 39 | M. intestini CI4875, 910-4875 |
| glnA | 17 | 40 | M. intestini CI4876, 910-4876 |
| glnA | 18 | 41 | M. intestini CI4877, 910-4877 |
| glnA | 19 | 42 | M. intestini CI4878, 910-4878 |
| glnA | 20 | 43 | P. tropica CI4751, 8-4751 |
| glnA | 21 | 44 | P. tropica CI4753, 8-4753 |
| glnA | 22 | 45 | P. tropica CI4879, 8-4879 |
| glnA | 23 | 46 | P. tropica CI4752, 8-4752 |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed:

1. A nitrogen fixing bacterium comprising a mutant GlnA protein comprising an amino acid sequence with an N339D amino acid substitution at amino acid position 339 of a *Klebsiella* GlnA protein with SEQ ID NO: 24, wherein the nitrogen fixing bacterium is *Klebsiella variicola*.

2. The nitrogen fixing bacterium of claim 1, wherein the mutant GlnA protein is SEQ ID NO: 36.

3. A nitrogen fixing bacterium comprising a mutant glnA gene comprising a nucleotide substitution at nucleotide position 1015 of a *Klebsiella* glnA gene with SEQ ID NO: 1 that encodes a mutant GlnA protein comprising an amino acid sequence with an N339D amino acid substitution at amino acid position 339 of a *Klebsiella* GlnA protein with SEQ ID NO: 24, wherein the nitrogen fixing bacterium is *Klebsiella variicola*.

4. The nitrogen fixing bacterium of claim 3, wherein the mutant glnA gene is SEQ ID NO: 13.

5. The nitrogen fixing bacterium of claim 3, wherein the bacterium is genetically engineered.

6. A microbial composition comprising the nitrogen fixing bacterium of claim 3 and a carrier.

7. A method of providing fixed nitrogen to a plant comprising applying a microbial composition to a plant, a plant part or a locus in which the plant is located, or a locus in which the plant will be grown, wherein the microbial composition comprises at least one nitrogen fixing bacterium of claim 3.

8. A nitrogen fixing bacterium comprising a mutant glnA gene comprising a nucleotide substitution at nucleotide position 1015 of a *Klebsiella* glnA gene with SEQ ID NO: 1 or at a homologous nucleotide position in a homolog thereof, wherein the nitrogen fixing bacterium is *Klebsiella variicola* CI3938 deposited as PTA-126716.

9. A microbial composition, comprising: one or more isolated bacteria selected from the group consisting of a bacterium deposited as PTA-126709, a bacterium deposited as PTA-126710, a bacterium deposited as PTA-126711, a bacterium deposited as PTA-126712, a bacterium deposited as PTA-126713, a bacterium deposited as PTA-126714, a bacterium deposited as PTA-126715, a bacterium deposited as PTA-126716, a bacterium deposited as PTA-126717, a bacterium deposited as PTA-126718, a bacterium deposited as PTA-126719, a bacterium deposited as PTA-126720, a bacterium deposited as PTA-126721, a bacterium deposited as PTA-126722, a bacterium deposited as PTA-126723, a bacterium deposited as PTA-126724, a bacterium deposited as PTA-126725 and a bacterium deposited as PTA-126726.

\* \* \* \* \*